US011807888B2

(12) United States Patent
Olsson et al.

(10) Patent No.: US 11,807,888 B2
(45) Date of Patent: Nov. 7, 2023

(54) PRODUCTION OF STEVIOL GLYCOSIDE IN RECOMBINANT HOSTS

(71) Applicant: EVOLVA SA, Reinach (CH)

(72) Inventors: Kim Olsson, Frederiksberg (DK); Ernesto Simon, Copenhagen (DK); Michael Dalgaard Mikkelsen, Vaerlose (DK); Simon Carlsen, Reinach (CH); Veronique Douchin, Frederiksberg (DK); Swee Chuang Lim, Vallensbaek Strand (DK); Louis During, Copenhagen (DK)

(73) Assignee: EVOLVA SA, Reinach (CH)

( * ) Notice: Subject to any disclaimer, the term of this patent is extended or adjusted under 35 U.S.C. 154(b) by 212 days.

(21) Appl. No.: 17/243,904

(22) Filed: Apr. 29, 2021

(65) Prior Publication Data
US 2023/0033436 A1 Feb. 2, 2023

Related U.S. Application Data

(60) Continuation of application No. 16/434,202, filed on Jun. 7, 2019, now Pat. No. 11,041,183, which is a division of application No. 15/541,686, filed as application No. PCT/EP2016/052007 on Jan. 29, 2016, now Pat. No. 10,364,450.

(60) Provisional application No. 62/110,207, filed on Jan. 30, 2015.

(51) Int. Cl.
| C12P 19/56 | (2006.01) |
| C12N 9/10 | (2006.01) |
| C12P 15/00 | (2006.01) |
| C07H 15/256 | (2006.01) |

(52) U.S. Cl.
CPC .......... C12P 19/56 (2013.01); C07H 15/256 (2013.01); C12N 9/1051 (2013.01); C12P 15/00 (2013.01); C12Y 204/01 (2013.01)

(58) Field of Classification Search
CPC ...... C07H 15/256; C12N 9/1051; C12P 15/00
See application file for complete search history.

(56) References Cited

U.S. PATENT DOCUMENTS

| 4,590,160 A | 5/1986 | Nishihashi et al. |
| 5,198,360 A | 3/1993 | Ballou |
| 5,204,253 A | 4/1993 | Sanford et al. |
| 5,306,862 A | 4/1994 | Chappell et al. |
| 5,460,949 A | 10/1995 | Saunders et al. |
| 5,538,880 A | 7/1996 | Lundquist et al. |
| 6,013,863 A | 1/2000 | Lundquist et al. |
| 6,215,051 B1 | 4/2001 | Yu et al. |
| 6,255,557 B1 | 7/2001 | Brandle |
| 6,284,493 B1 | 9/2001 | Roth |
| 6,284,506 B1 | 9/2001 | Hoshino et al. |
| 6,329,571 B1 | 12/2001 | Hiei |
| 6,586,202 B2 | 7/2003 | Hoshino et al. |
| 6,660,507 B2 | 12/2003 | Cheng et al. |
| 6,806,076 B1 | 10/2004 | Miyake et al. |
| 6,969,595 B2 | 11/2005 | Brzostowicz et al. |
| 7,034,140 B2 | 4/2006 | Bramucci et al. |
| 7,056,717 B2 | 6/2006 | Cheng et al. |
| 7,098,000 B2 | 8/2006 | Cheng et al. |
| 7,129,392 B2 | 10/2006 | Hahn et al. |
| 7,132,268 B2 | 11/2006 | Miyake et al. |
| 7,172,886 B2 | 2/2007 | Keasling et al. |
| 7,183,089 B2 | 2/2007 | Keasling et al. |
| 7,186,891 B1 | 3/2007 | Chappell et al. |
| 7,208,298 B2 | 4/2007 | Miyake et al. |
| 7,335,815 B2 | 2/2008 | Boronat et al. |
| 7,364,885 B2 | 4/2008 | Miyake et al. |
| 7,422,884 B2 | 9/2008 | Bai et al. |
| 7,514,597 B2 | 4/2009 | Nakamura et al. |
| 7,569,389 B2 | 9/2009 | Feldmann et al. |
| 7,692,065 B2 | 4/2010 | Harper et al. |
| 7,838,287 B2 | 11/2010 | Goldsmith et al. |
| 7,923,541 B2 | 4/2011 | Yang et al. |
| 7,927,851 B2 | 4/2011 | Brandle et al. |
| 7,981,647 B2 | 7/2011 | Berry et al. |
| 9,562,251 B2 | 2/2017 | Kishore et al. |
| 9,957,540 B2 | 5/2018 | Mikkelsen et al. |
| 10,010,099 B2 * | 7/2018 | Mao ............... C12Y 204/01013 |
| 10,017,804 B2 | 7/2018 | Simon et al. |
| 10,364,450 B2 | 7/2019 | Olsson et al. |
| 10,947,515 B2 | 3/2021 | Boer et al. |
| 2002/0142408 A1 | 10/2002 | DiCosimo et al. |
| 2003/0033626 A1 | 2/2003 | Hahn et al. |
| 2003/0148416 A1 | 8/2003 | Berry et al. |
| 2003/0148479 A1 | 8/2003 | Keasling et al. |

(Continued)

FOREIGN PATENT DOCUMENTS

| CN | 101720910 | 6/2010 |
| CN | 102216313 | 10/2011 |

(Continued)

OTHER PUBLICATIONS

Garber et al., "Computational methods for transcriptome annotation and quantification using RNA-seq," Nat Methods 8(6):469-77 (2011).
Kawai et al., "Transformation of *Saccharomyces cerevisiae* and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320(5881 ): 1344-9 (2008).
Nikko & Pelham, "Arrestin-mediated endocytosis of yeast plasma membrane transporters," Traffic 10(12):1856-67 (2009).

(Continued)

*Primary Examiner* — Tekchand Saidha
(74) *Attorney, Agent, or Firm* — McDonnell Boehnen Hulbert & Berghoff LLP

(57) ABSTRACT

The invention relates to recombinant microorganisms and methods for producing steviol glycosides, glycosylated ent-kaurenol, and glycosylated ent-kaurenoic acid.

1 Claim, 70 Drawing Sheets
Specification includes a Sequence Listing.

(56) References Cited

U.S. PATENT DOCUMENTS

| | | |
|---|---|---|
| 2003/0190734 A1 | 10/2003 | Hoshino et al. |
| 2003/0219798 A1 | 11/2003 | Gokarn et al. |
| 2004/0010815 A1 | 1/2004 | Lange et al. |
| 2004/0072311 A1 | 4/2004 | DiCosimo et al. |
| 2004/0078846 A1 | 4/2004 | Desouza et al. |
| 2004/0176570 A1 | 9/2004 | Bacher et al. |
| 2004/0194162 A1 | 9/2004 | Hahn et al. |
| 2005/0003474 A1 | 1/2005 | Desouza et al. |
| 2005/0032169 A1 | 2/2005 | Miyake et al. |
| 2006/0014264 A1 | 1/2006 | Sauer et al. |
| 2006/0079476 A1 | 4/2006 | Keasling et al. |
| 2006/0083838 A1 | 4/2006 | Jackson et al. |
| 2007/0004000 A1 | 1/2007 | Miyake et al. |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 11/2007 | Millis et al. |
| 2007/0269857 A1 | 11/2007 | Miyake et al. |
| 2007/0286850 A1 | 12/2007 | Bai et al. |
| 2008/0064063 A1 | 3/2008 | Brandle et al. |
| 2008/0081358 A1 | 4/2008 | Vittanen et al. |
| 2008/0131926 A1 | 6/2008 | Miyake et al. |
| 2008/0216397 A1 | 9/2008 | Busby et al. |
| 2008/0261280 A1 | 10/2008 | Hahn et al. |
| 2008/0271205 A1 | 10/2008 | Yamaguchi et al. |
| 2008/0286870 A1 | 11/2008 | Vittanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0143308 A1 | 6/2009 | Monk et al. |
| 2009/0286262 A1 | 11/2009 | Slack |
| 2009/0298706 A1 | 12/2009 | Lee et al. |
| 2010/0112156 A1 | 5/2010 | Abelyan et al. |
| 2010/0120096 A1 | 5/2010 | Kitaoka et al. |
| 2010/0221801 A1 | 9/2010 | Van Dyk |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Abelyan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0137138 A1 | 5/2013 | Hansen |
| 2013/0171328 A1 | 7/2013 | Kishore et al. |
| 2014/0329281 A1 | 11/2014 | Houghton-Larsen et al. |
| 2015/0159188 A1 | 6/2015 | Ono et al. |
| 2015/0342234 A1 | 12/2015 | Hicks et al. |
| 2015/0361476 A1 | 12/2015 | Simon et al. |
| 2021/0147815 A1 | 5/2021 | Boer et al. |

FOREIGN PATENT DOCUMENTS

| | | |
|---|---|---|
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 59101408 | 6/1984 |
| JP | 3-277275 | 12/1991 |
| JP | 05-115298 | 5/1993 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2008/091547 | 7/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/021261 | 5/2013 |
| WO | WO 2013/076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | 2015/011209 | 1/2015 |
| WO | WO 2015/007748 | 1/2015 |
| WO | 2015/014959 | 2/2015 |
| WO | 2015/016393 | 2/2015 |
| WO | WO 2015/014969 | 2/2015 |
| WO | WO 2015/028324 | 3/2015 |
| WO | WO 2015051454 | 4/2015 |
| WO | WO 2015/132411 | 9/2015 |
| WO | 2016/023844 | 2/2016 |

(56) References Cited

FOREIGN PATENT DOCUMENTS

| WO | WO 2016/038095 | 3/2016 |
|---|---|---|
| WO | WO2016054544 A1 | 4/2016 |
| WO | WO 2016/100689 | 6/2016 |
| WO | WO 2016/156616 | 10/2016 |
| WO | 2017/025362 | 2/2017 |
| WO | WO 2017/095932 | 6/2017 |

OTHER PUBLICATIONS

Nikko et al. "Arrestin-like proteins mediate ubiquitination and endocytosis of the yeast metal transporter Smf1," EMBO Rep. 9(12):1216-21 (2008).
Ohta et al., MassBank Accession No. FU000299 (May 2016).
Ohta et al., MassBank Accession No. FU000332 (May 2016).
Olsson et al., "Microbial production of next-generation stevia sweeteners," Microbial Cell Factories, 15:11-14 (2016).
Partow et al., "Characterization of different promoters for designing a new expression vector in Saccharomyces cerevisiae," Yeast 27:955-64 (2010).
Robinson & Oshlack et al., "A scaling normalization method for differential expression analysis of RNA-seq data," Genome Biol. 11(3):R25 (2010).
Saier Jr. et al., "The transporter classification database," Nucl. Acids Res., 42(1):D251-258 (2014).
Song et al., "The Aspergillus fumigatus 1-29 damage resistance protein family coordinately regulates ergosterol biosynthesis and azole susceptibility," MBIO, 7:1-13 (2016).
Wang et al., "RNA-Seq: a revolutionary tool for transcriptomics," Nat Rev Genet. 10(1):57-63 (2009).
Wilhelm et al., "Defining transcribed regions using RNA-seq," Nature Protocols 5:255-66 (2010).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Non-Final Office Action for U.S. Appl. No. 14/761,629, dated Mar. 21, 2017 (pp. 1-19).
Final Office Action for U.S. Appl. No. 14/761,629, dated Aug. 11, 2017 (pp. 1-16).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 22, 2013 (238 pages).
Extended European Search Report and Opinion issued by the European Patent Office for European Application No. 11790428.4, dated Dec. 20, 2013.
Search Report issued by the Intellectual Property Office of Singapore for Singaporean Application No. 201208854-8, dated Nov. 3, 2014.
Non-Final Office Action for U.S. Appl. No. 14/237,540, dated Dec. 30, 2015 (pp. 1-19).
Final Office Action issued in U.S. Appl. No. 14/237,540; dated Jul. 8, 2017, pp. 1-19.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.

Extended European Search Report issued in EP 15193074.0; dated Feb. 12, 2016, pp. 1-9.
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015. (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Third Party Submission in U.S. Appl. No. 14/648,747; dated Mar. 28, 2016, pp. 1-231.
Invitation to Pay Additional Fees and, Where Applicable, Protest Fee by the International Searching Authority for International Application No. PCT/EP2015/070620, mailed Nov. 27, 2015 (pp. 1-14).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Search Report and Written Opinion of the International Searching Authority for International Application No. PCT/EP2015/052007; dated Jul. 4, 2016, pp. 1-24.
Liu et al., "Functional and Biochemical Characteritzation of Escherichia coli Sugar Efflux Transporters," JBC, 274(33):22977-22984 (Aug. 1999).
Sun et al., "Regulation and Function of Escherichia coli Sugar Efflux Transporter A (Set A) during Glucose-Phosphate Stress," J of Bacteriology, 193(1):143-153 (Jan. 2011).
International Search Report and Written Opinion of the International Searching Authority for International Application No. PCT/EP2016/068259; dated Jan. 24, 2017, pp. 1-18.
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).

(56) References Cited

OTHER PUBLICATIONS

Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathwayin Stevia rebaudiana (Bertoni)" Gene 492:276-84 (Epub Oct. 20, 2011).
Kusama et al., "Transglucosylation into stevioside by the enzyme system from *Streptomyces* sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast Rhodosporidium toruloides Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1(3):267-86 (2010).
Madhav et al., "Functional and structural variation of uridine diphosphate glycosyltransferase (UGT) gene of Stevia rebaudiana-UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from Scoparia dulcis L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).

Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial *Saccharomyces* sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol. 143(3):212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Hallstrom & Moye-Rowley, "Divergent transcriptional control of multidrug resistance genes in *Saccharomyces cerevisiae*," J. Biol. Chem. 273(4):2098-104 (Jan. 1998).
Katzmann et al., "Expression of an ATP-binding cassette transporter-encoding gene (YOR1) is required for oligomycin resistance in *Saccharomyces cerevisiae*," Mol. Cell Biol. 15(12):6875-83 (Dec. 1995).

(56) References Cited

OTHER PUBLICATIONS

Li et al., "Phylogenetic analysis of the UDP-glycosyltransferase multigene family of *Arabidopsis thaliana*," J. Biol. Chem. 276(6):4338-43 (Oct. 2000).
Masada et al., "An efficient chemoenzymatic production of small molecule glucosides with in situ UDP-glucose recycling," FEBS Lett. 581(13):2562-6 (May 2007).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).
Nagy et al., "Role of the yeast ABC transporter Yor1p in cadmium detoxification," Biochimie 88(11):1665-71 (Jun. 2006).
Nikaido & Takatsuk, "Mechanisms of RND multidrug efflux pumps," Biochim. Biophys. Acta. 1794(5):769-81 (May 2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).
Osmani et al., "Substrate specificity of plant UDP-dependent glycosyltransferases predicted from crystal structures and homology modeling," Phytochemistry 70(3):325-47 (Feb. 2009).
Richman et al., "Functional genomics uncovers three glucosyltransferases involved in the synthesis of the major sweet glucosides of Stevia rebaudiana," Plant J. 41(1):56-67 (Jan. 2005).
Riesmeier et al., "Isolation and characterization of a sucrose carrier cDNA from spinach by functional expression in yeast," EMBO J. 11(13):4705-13 (Dec. 1992).
Rodríguez-Concepción & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).
Saier Jr et al., "The major facilitator superfamily," J. Mol. Microbiol. Biotechnol. 1(2):257-79 (Nov. 1999).
Saier Jr et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coli*," J. Biol. Chem. 279(8):6613-9 (Dec. 2003).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J. Biol. Chem. 280(2):899-906 (Jan. 2005).
Shao et al., "Enhanced production of alpha-galactosyl epitopes by metabolically engineered Pichia pastoris," Appl. Environ. Microbiol. 69(9):5238-42 (Sep. 2003).
Son et al., "Production of flavonoid O-glucoside using sucrose synthase and flavonoid O-glucosyltransferase fusion protein," J. Microbiol. Biotechnol. 19(7):709-12 (Jul. 2009).
Sonnhammer et al., "Pfam: a comprehensive database of protein domain families based on seed alignments," Proteins 28(3):405-20 (Jul. 1997).
Sonnhammer et al., "Pfam: multiple sequence alignments and HMM-profiles of protein domains," Nucleic Acids Res. 26(1):320-2 (Jan. 1998).
Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
Non-Final Office Action for U.S. Appl. No. 14/648,747, dated Mar. 23, 2017 (pp. 1-20).
International Preliminary Report on Patentability from the International Bureau for International Application No. PCT/EP2015/068314, dated Feb. 14, 2017 (pp. 1-10).
International Search Report and Written Opinion of the International Searching Authority for International Application No. PCT/EP2016/080516; dated Mar. 15, 2017, pp. 1-22.
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Communication of a Notice of Opposition issued by the European Patent Office for European Application No. 12750513.9, dated Mar. 6, 2017 (pp. 1-8).
Mahe et al., "The ATP Binding Cassette Transporters Pdr5 and Snq2 of *Saccharomyces cerevisiae* Can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Sequence alignment between the sequence of Uniprot database entry Q75183 version 31, updated Jul. 22, 2008 and Seq ID No. 152 (from European Patent No. 2742142) as cited in Notice of Opposition against EP Application No. 12750513.9; mailed Mar. 6, 2017; pp. 1-2.
Statement of fact and arguments in support of opposition, dated Feb. 28, 2017 (pp. 1-24).
Uniprot Accession No. Q75183, dated Jul. 5, 2004 (pp. 1-2).
Uniprot Accession No. Q75183, dated Jul. 22, 2008 (pp. 1-4).
Third Party Observation in EP Application No. 13801569.8; mailed Apr. 26, 2017. pp. 1-5.
International Search Report and Written Opinion of International Search Authority for International Application No. PCTEP2017/059028; dated Jun. 27, 2017, pp. 1-15.
Arnold, F. H. "Combinatorial and computational challenges for biocatalyst design," Nature 409(6817):253-257 (2001).
Bruyn et al., "Metabolic engineering of *Escherichia coli* into a versatile glycosylation platform: production of bio-active quercetin glycosides," Microb Cell Fact., 14:138 (2015).
Bruyn et al., "Development of an in vivo glucosylation platform by coupling production to growth: production of phenolic glucosides by a glycosyltransferase of Vitis vinifera," Biotechnol Bioeng., 112(8):1594-603 (2015).
Duetz, "Microtiter plates as mini-bioreactors: miniaturization of fermentation methods," Trends Microbiol 15(10):469-75 (2007).
François et al., "Reserve carbohydrates metabolism in the yeast *Saccharomyces cerevisiae*," FEMS Microbiol Rev., 25(1):125-45 (2001).
Non-Final Office Action for U.S. Appl. No. 15/541,686, dated Nov. 7, 2018 (pp. 1-24).
Mikayama et al., "Molecular cloning and functional expression of a cDNA encoding glycosylation-inhibiting factor," Proc Natl Acad Sci U S A. 90(21):10056-60 (1993).
Rudinger et al., "Characteristics of the amino acids as components of a peptide hormone sequence," Peptide Hormones. Biol. Council. pp. 5-7 (1976).
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide Seq ID No. 4723" (1 page), dated Jun. 2, 2005.
Shao et al., "Crystal structures of a multifunctional triterpene/flavonoid glycosyltransferase from Medicago truncatula," Plant Cell 17(11):3141-54 (2005).
Shibata et al., "Glucosylation of Steviol and Steviol-Glucosides in Extracts from Stevia rebaudiana Bertoni" Plant Physiol. 95(1):152-56 (1991).
Singh et al., "Compendium of Transgenic Crop Plants: Transgenic Sugar, Tuber and Fiber," Ed. Kole & Hall, Blackwell Publishing Ltd. pp. 97-115 (2008).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of

(56) References Cited

OTHER PUBLICATIONS

RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast Kluyveromyces lactis," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA, pp. 1-5 (2004).
Wallin, "Steviol Glycosides," Chem. Tech Assessment—69th JECFA, pp. 1-7 (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20):3303-9 (2009).
Xu et al., "Generation of hepatitis B virus PreS2-S antigen in Hansenula polymorpha," Virol Sin. 29(6):403-9 (Dec. 2014).
Yadav et al., "A review on the improvement of stevia [Stevia rebaudiana (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast Rhodosporidium toruloides," Nature Commun. 3:1112 (Oct. 2012).
GenBank Accession No. AAF61439.1, dated Sep. 25, 2000 (2 pages).
GenBank Accession No. AAM53963.1, dated Jun. 17, 2002 (2 pages).
GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454.4, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP81B1" (1 page).
EBI Accession No. ABM86477, "Rice abiotic stress responsive polypeptide Seq ID No. 4723" (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Jones et al., "UGT73C6 and UGT78D1, Glycosyltransferases Involved in Flavonol Glycoside Biosynthesis in *Arabidopsis thaliana*\*," J. Biol. Chem., vol. 278, No. 45, pp. 43910-43918 (2003).
Popenberger et al., Heterologous Expression of *Arabidopsis* UDP-Glucosyltransferases in *Saccharomyces cerevisiae* for Production ofZearalenone-4-0-Glucoside, Appl. Environ. Microbial., vol. 72, pp. 4404-4410 (2006).
Wang et al., "Glycosylation and Glycosyltransferase of Small Molecular Compounds of Plant," China Academic Journal, vol. 44-5, 997-1003 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).
GenBank Accession No. AAS07253.1, dated Jan. 31, 2004 (3 pages).
Gloster, "Advances in understanding glycosyltransferases from a structural perspective," Curr Opin Struct Biol. 28:131-41 (2014).
Guo et al., "Protein tolerance to random amino acid change", Proceedings of the National Academy of Sciences USA, vol. 101, No. 25, pp. 9205-9210 (2004).
Ni et al., "Outer membrane mutation effects on UDP-glucose permeability and whole cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Stevoil Glycoside Biosynthesis and Its Key Enzymes," Biotechnology Bulletin, Feb. 2008 (English Abstract translation).
GenBank Accession No. AZF53544, dated Apr. 14, 2011 (2 pages).
UniProt Accession No. B5MEX6, Nov. 4, 2008 (1 page).
UniProt Accession No. E4MVV7, Feb. 8, 2011 (1 page).
UniProt Accession No. F6KWJ2, Jul. 27, 2011 (1 page).
UniProt Accession No. H9BYK3, May 16, 2012 (1 page).
International Preliminary Report on Patentability from the International Bureau for International Application PCT/EP2015/052007; dated Aug. 1, 2017 (pp. 1-16).
Chen, "Summary on Study of Stevioside," China Pharmacist, 10(6):598-599 (2007).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from *Saccharomyces cerevisiae*," Eur J Biochem. 233(2):520-30 (Jul. 1995).
Husar et al., "Overexpression of the UGT73C6 alters brassinosteriod glucoside formation in *Arabidopsis thaliana*", BMC Plant Biology, 11:1-14 (2011).
Malonek et al., "The NADPH-cytochrome P450 Reductase Gene from Gibberalla fujikuroi is Essential for Gibberellin Biosynthesis", J Bio Chem. 279(24):25075-84 (Jun. 2004).
Mao et al., "Produce steviol glycosides in engineered yeast", 2015 Synthetic Biology: Engineering, Evolution & Design (SEED), Poster Abstract (Jun. 2015).
Nagatoshi et al., "UGT75L6 and UGT94E5 mediate sequential glucosylation of crocetin to crocin in Gardenia iasminoides", FEBS Letters, 586:1055-1061 (2012).

(56) References Cited

OTHER PUBLICATIONS

Tiwari et al., "Plant secondary metabolism linked glycosyltransferases: An update on expanding knowledge and scopes", Biotechnology Advances, 34:714-739 (May 2016).
Wang et al., "Pathway mining-based integration of critical enzyme parts for de novo biosynthesis of steviol glycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "Design and construction of artificial biological systems for complex natural products biosynthesis", Chinese Journal of Biotechnology, 29:114-1160, (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Yang et al., "Base substitution mutations in uridinediphosphate-dependent glycosyltransferase 76G1 gene of Stevia rebaudioside A; Mustation in UGT76G1, a key gene of steviol glycoside synthesis", Plant Physiology and Biochemistry, 80:220-225 (2014).
Examination Report issued by the European Patent Office for European Application No. 12750513.9, dated Nov. 26, 2014.
Non-Final Office Action for U.S. Appl. No. 14/764,898, dated Mar. 30, 2017, pp. 1-17.
Final Office Action for U.S. Appl. No. 14/648,747, dated Sep. 6, 2017, pp. 1-19.
Third Party Observation in EP Application No. 13801569.8; mailed Oct. 23, 2017. pp. 1-6.
International Search Report and Written Opinion of International Search Authority for International Application No. PCT/EP2017/055589; dated May 12, 2017, pp. 1-18.
International Search Report of the International Searching Authority for International Application No. PCT/EP2017/061774; dated Aug. 30, 2017, pp. 1-20.
Written Opinion of the International Searching Authority for International Application No. PCT/EP2017/061774; dated Aug. 30, 2017, pp. 1-13.
International Search Report and Written Opinion of the International Searching Authority for International Application No. PCT/EP2017/061775; dated Sep. 6, 2017, pp. 1-17.
Abraham & Bhat, "Permeabilization of baker's yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthsis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).
Carretero-Paulet et al., "Expression and Molecular Analysis of the *Arabidopsis* DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in *Saccharomyces cerevisiae*," Microb Cell Fact. 5:20 (2006).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol. 16(4):378-84 (2005).
Chow & Palecek, "Enzyme encapsulation in permeabilized *Saccharomyces cerevisiae* cells," Biotechnol Prog. 20(2):449-56 (2004).
Correa et al., "Genetic mapping of 1,3-beta-glucanase-encoding genes in *Saccharomyces cerevisiae*," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "*Arabidopsis* ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
EMBOSS Needle results for Pairwise Sequence Alignment of UGT91D1 and UGT91D2; dated Apr. 4, 2016, 2 pages.
Emmerstorfer et al., "Over-expression of ICE2 stabilizes cytochrome P450 reductase in *Saccharomyces cerevisiae* and Pichia pastoris," Biotechnol J. 10(4):623-35 (Apr. 2015).
Estrada De Martin et al., "Ice2p is important for the distribution and structure of the cortical ER network in *Saccharomyces cerevisiae*," J Cell Sci. 118(Pt 1):65-77 (Oct. 2006).
Fernandez et al., "Activation of chitin synthetase in permeabilized cells of a *Saccharomyces cerevisiae* mutant lacking proteinase B," J Bacteriol. 152(3):1255-64 (1982).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).

(56) References Cited

OTHER PUBLICATIONS

Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast Schizosaccharomyces Pombe," Biotechnol. & Biotechnol. Eq. 20(3):76-82 (2006).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Andolino et al., "High-Quality RNA, cDNA, and Derived EST Libraries From Grapevine (*Vitis vinifera* L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosynthesis: baxane 13 alpha-hydroxylase is a cytochrome P450-dependent monooxygenase," Proc Natl Acad Sci U S A 98(24):13595-600 (2001).
Bateman et al., "Pfam 3.1: 1313 multiple alignments and profile HMMs match the majority of proteins," Nucleic Acids Res. 27(1):260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from *Saccharomyces cerevisiae* S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31(13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. AEE36246, dated Oct. 6, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ398871.3, dated May 28, 2008 (2 pages).
GenBank Accession No. EDY51667, dated Sep. 2, 2008 (2 pages).
GenBank Accession No. EU263989, dated Jun. 11, 2008 (2 pages).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
Broun et al., "Catalytic plasticity of fatty acid modification enzymes underlying chemical diversity of plant lipids," Science, vol. 282: 1315-1317 (1998).
Cheng, "Food Biotechnology," Inner Mongolia Science and Technology Press (2008).
Devos et al., "Practical limits of function prediction," Proteins: Structure, Function, and Genetics, vol. 41: 98-107 (2000).
Seffernick et al., "Melamine deaminase and Atrazine chlorohydrolase: 98 percent identical but functionally different," J. Bacteriol., vol. 183 (8): 2405-2410 (2001).
Whisstock et al., "Prediction of protein function from protein sequence," Q. Rev. Biophysics., vol. 36 (3): 307-340 (2003).
Witkowski et al., "Conversion of b-ketoacyl synthase to a Malonyl Decarboxylase by replacement of the active cysteine with glutamine," Biochemistry, vol. 38: 11643-11650 (1999).
Extended Search Report in European Patent Application No. 22189583.2 dated Feb. 15, 2023 (15 pages).
Adari, et al., "Synthesis of rebaudioside-A by enzymatic transglycosylation of stevioside present in the leaves of Stevia rebaudiana Bertoni", Food Chemistry 200:154-158 (2016).

* cited by examiner

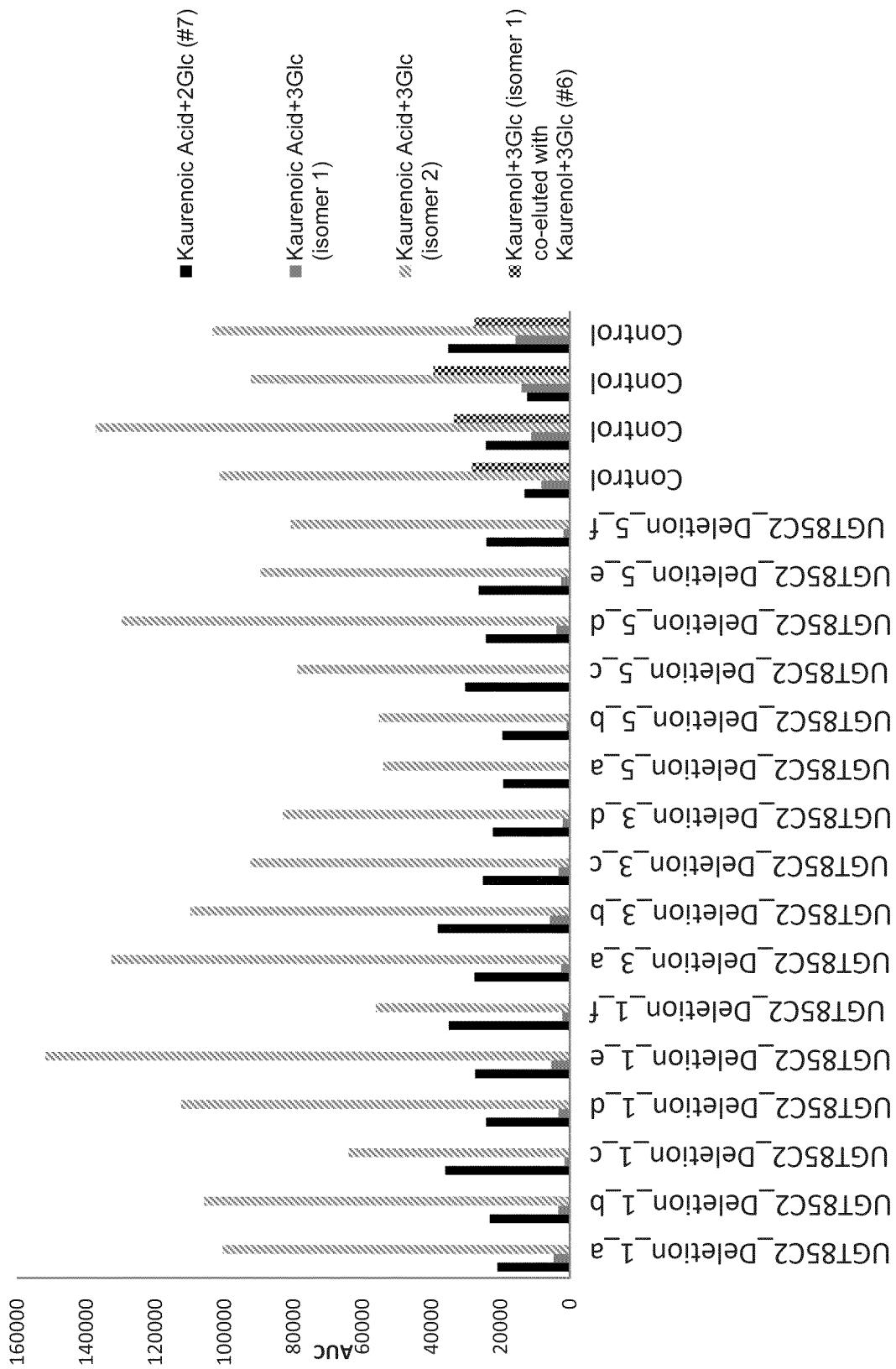

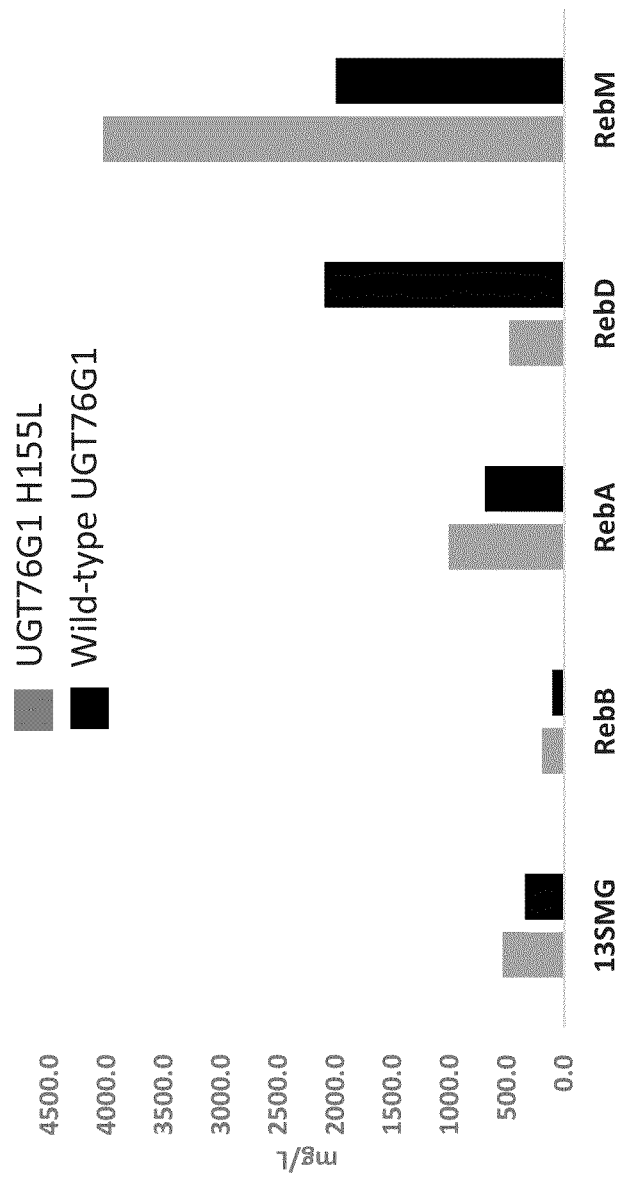

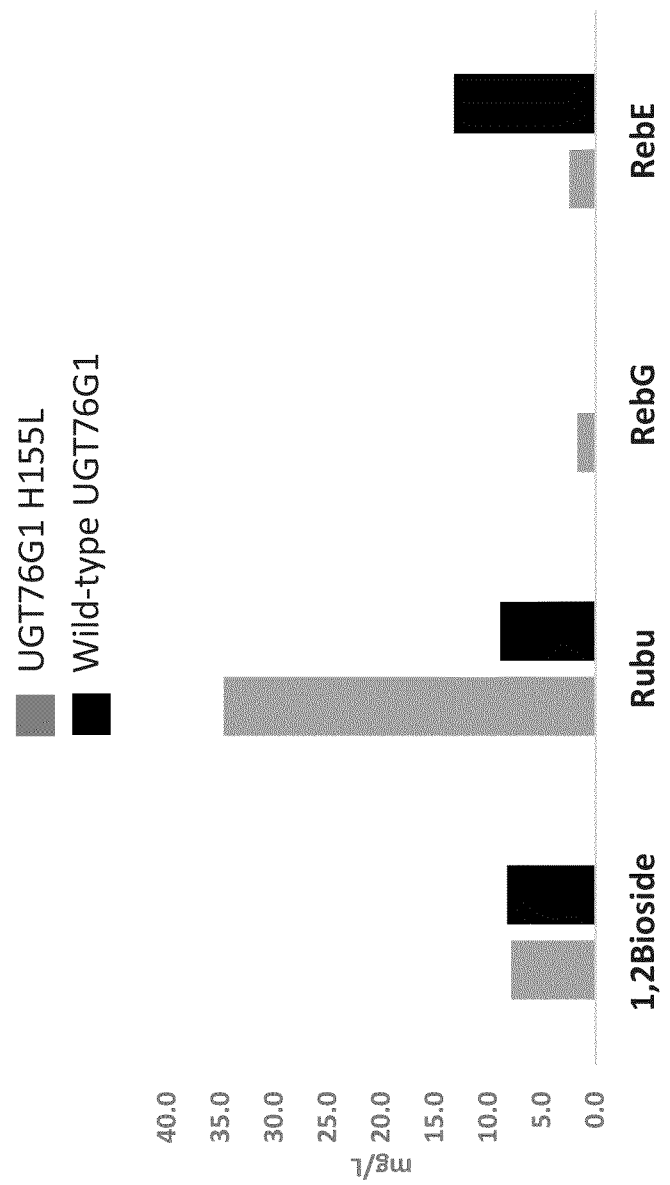

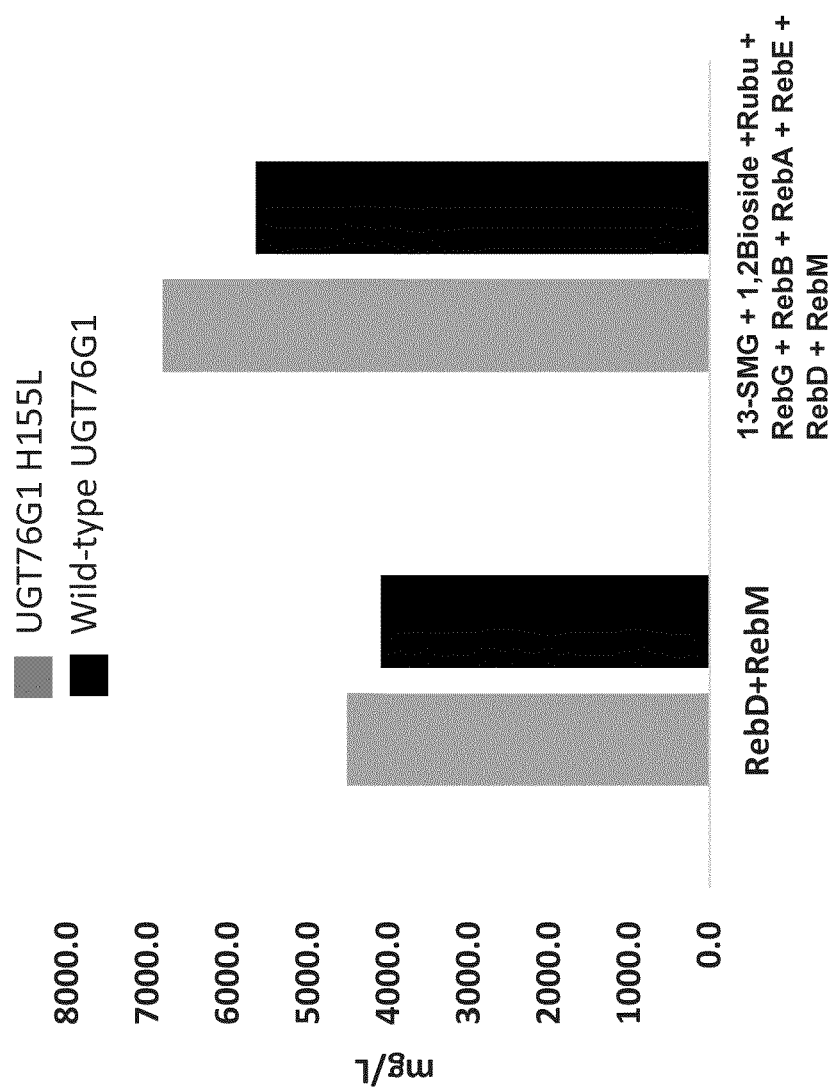

Figure 7A
Kaurenoic acid+3Glc (isomer 2)
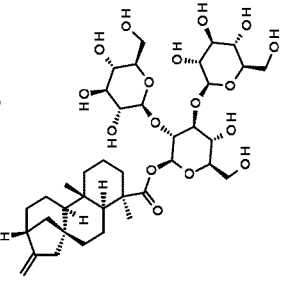
Formula Weight : 788.87(3)
Exact Mass : 788.38305050(3)
Formula : $C_{38}H_{60}O_{17}$
Kaurenol+3Glc (isomer 1)
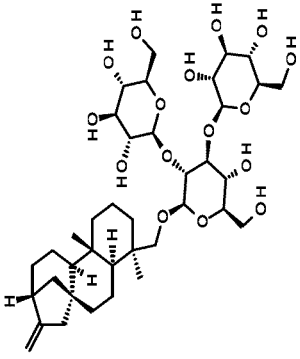
Formula Weight : 774.89(3)
Exact Mass : 774.40378594(3)
Formula : $C_{38}H_{62}O_{16}$
Kaurenoic acid+3Glc (isomer 1)
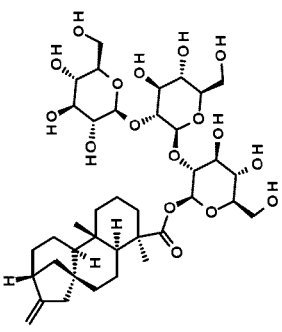
Formula Weight : 788.87(3)
Exact Mass : 788.38305050(3)
Formula : $C_{38}H_{60}O_{17}$
Kaurenoic acid+2Glc+1GlcNAc
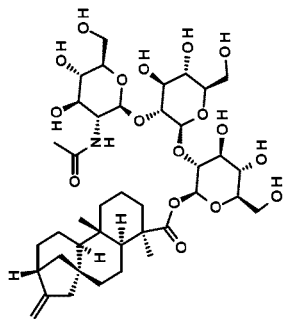
Formula Weight : 829.92(3)
Exact Mass : 829.40959960(4)
Formula : $C_{40}H_{63}NO_{17}$ Figure 7B
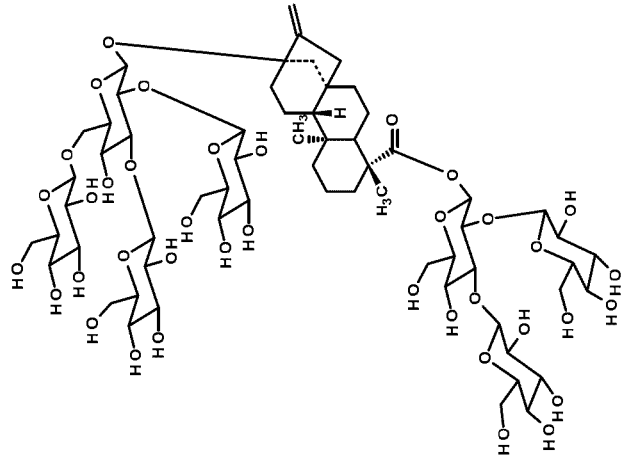
Steviol+7Glc (isomer 2)
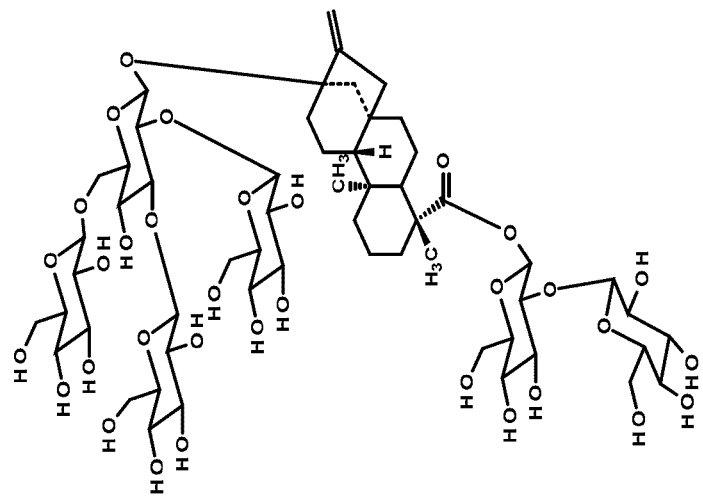
Steviol+6Glc (isomer 1)

Figure 7C
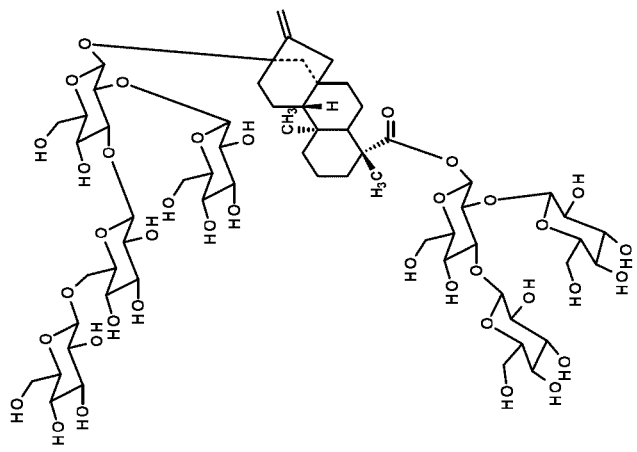
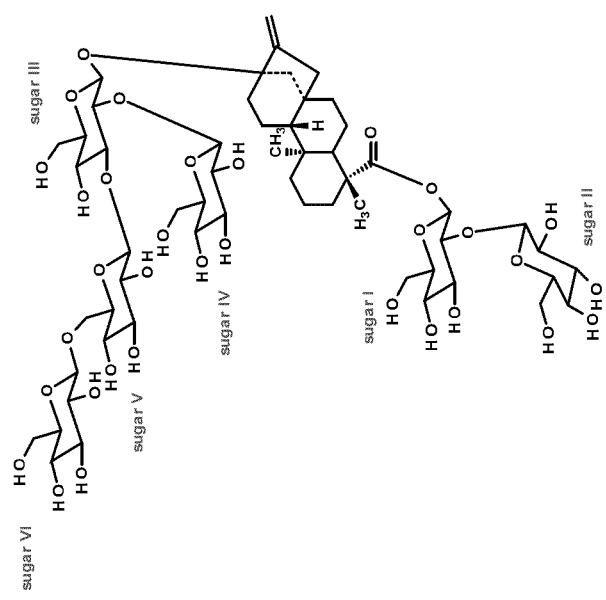

Figure 7E
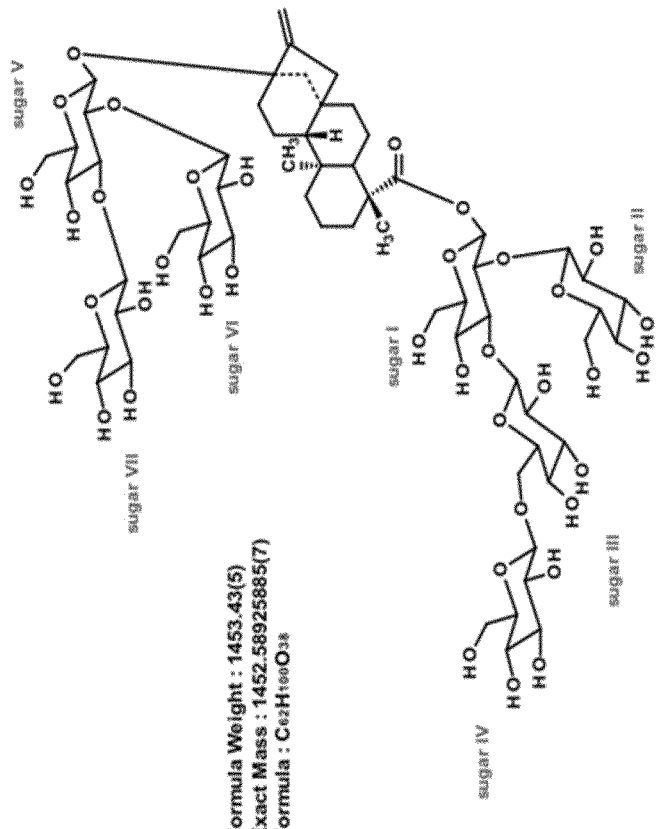
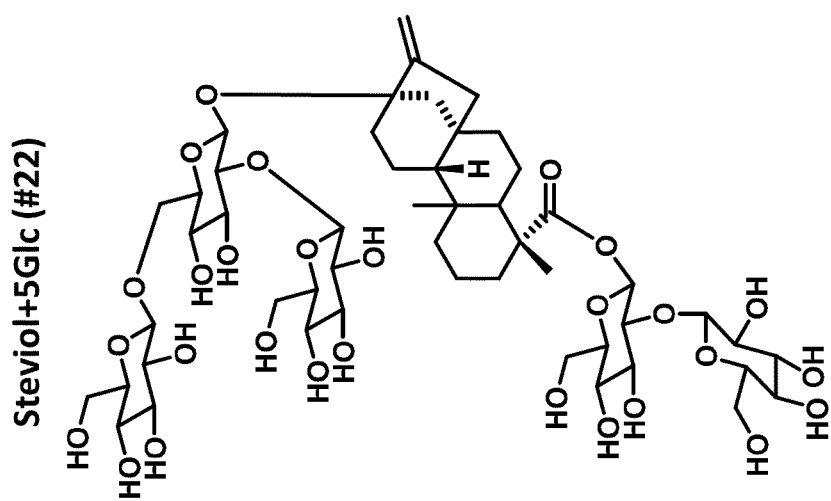

Figure 8B

Kaurenoic Acid+3Glc (isomer 1)

| Atom1 | Shift1 (ppm) | H's | Type | J (Hz) | Multiplet1 | (ppm) |
|---|---|---|---|---|---|---|
| 55<''> | 0.78 | 1 | m | - | M34 | [0.74 .. 0.81] |
| 57 | 0.86 | 3 | m | - | M33 | [0.83 .. 0.90] |
| 53<''> | 0.97 | 1 | td | 13.33, 4.16 | M32 | [0.92 .. 1.00] |
| 13a, 2a, 10<''> | 1.07 | 3 | m | - | M31 | [1.02 .. 1.10] |
| 52 | 1.15 | 3 | s | - | M30 | [1.12 .. 1.18] |
| 11<''>, 4<''>, 54<''> | 1.38 | 3 | m | - | M29 | [1.30 .. 1.44] |
| 11<''> | 1.47 | 1 | m | - | M28 | [1.44 .. 1.50] |
| 4<''>, 3 | 1.56 | 3 | m | - | M27 | [1.50 .. 1.62] |
| 55<''>, 12, 54<''> | 1.79 | 4 | m | - | M26 | [1.72 .. 1.87] |
| 10<''>, 8<''> | 1.95 | 2 | m | - | M25 | [1.91 .. 1.99] |
| 8<''> | 2.06 | 1 | d | 17.12 | M24 | [2.02 .. 2.08] |
| 53<''> | 2.16 | 1 | d | 12.72 | M23 | [2.12 .. 2.19] |
| 5a | 2.59 | 1 | br. s. | - | M22 | [2.57 .. 2.61] |
| 38<ax>, 26<ax> | 3.02 | 2 | m | - | M14 | [2.98 .. 3.06] |
| 30<ax>, 40<ax>, 28<ax>, 32<ax> | 3.10 | 4 | m | - | M15 | [3.07 .. 3.15] |
| 46<ax>, 23<ax>, 48<ax> | 3.22 | 3 | m | - | M16 | [3.16 .. 3.26] |
| 36<ax> | 3.32 | 1 | m | - | M21 | [3.30 .. 3.33] |
| 33<''> | 3.42 | 1 | dd | 11.00, 5.14 | M35 | [3.41 .. 3.43] |
| 49<''> | 3.46 | 1 | m | - | M20 | [3.44 .. 3.49] |
| 41<''> | 3.52 | 1 | m | - | M19 | [3.50 .. 3.55] |
| 44<ax>, 49<''> | 3.64 | 2 | m | - | M18 | [3.60 .. 3.67] |
| 41<''>, 33<''>, 20<ax> | 3.71 | 3 | m | - | M17 | [3.68 .. 3.75] |
| 25<ax> | 4.31 | 1 | d | 7.82 | M11 | [4.28 .. 4.33] |
| 50 | 4.35 | 1 | m | - | M10 | [4.34 .. 4.37] |
| 42 | 4.41 | 1 | t | 5.38 | M09 | [4.39 .. 4.43] |
| 34 | 4.48 | 1 | t | 5.62 | M08 | [4.45 .. 4.51] |
| 58<a> | 4.72 | 1 | s | - | M07 | [4.69 .. 4.74] |
| 58<b> | 4.78 | 1 | br. s. | - | M06 | [4.76 .. 4.81] |
| 31 | 4.93 | 1 | d | 5.38 | M13 | [4.91 .. 4.95] |
| 27, 39, 29 | 4.99 | 3 | m | - | M12 | [4.96 .. 5.02] |
| 22<ax> | 5.04 | 1 | d | 7.83 | M05 | [5.02 .. 5.06] |
| 47 | 5.12 | 1 | d | 5.38 | M04 | [5.09 .. 5.14] |
| 45 | 5.18 | 1 | d | 2.45 | M03 | [5.15 .. 5.21] |
| 19<ax> | 5.43 | 1 | d | 7.83 | M02 | [5.40 .. 5.46] |
| 37 | 5.52 | 1 | d | 2.45 | M01 | [5.49 .. 5.54] |

$^1$H NMR (800 MHz, DMSO $d_6$) δ ppm 0.74 - 0.81 (m, 1 H) 0.83 - 0.90 (m, 3 H) 0.97 (td, J=13.33, 4.16 Hz, 1 H) 1.02 - 1.10 (m, 3 H) 1.15 (s, 3 H) 1.30 - 1.44 (m, 3 H) 1.44 - 1.50 (m, 1 H) 1.50 - 1.62 (m, 3 H) 1.72 - 1.87 (m, 4 H) 1.91 - 1.99 (m, 2 H) 2.06 (d, J=17.12 Hz, 1 H) 2.16 (d, J=12.72 Hz, 1 H) 2.59 (br. s., 1 H) 2.98 - 3.06 (m, 2 H) 3.07 - 3.15 (m, 4 H) 3.16 - 3.26 (m, 3 H) 3.30 - 3.33 (m, 1 H) 3.42 (dd, J=11.00, 5.14 Hz, 1 H) 3.44 - 3.49 (m, 1 H) 3.50 - 3.55 (m, 1 H) 3.60 - 3.67 (m, 2 H) 3.68 - 3.75 (m, 3 H) 4.31 (d, J=7.82 Hz, 1 H) 4.34 - 4.37 (m, 1 H) 4.41 (t, J=5.38 Hz, 1 H) 4.48 (t, J=5.62 Hz, 1 H) 4.72 (s, 1 H) 4.78 (br. s., 1 H) 4.93 (d, J=5.38 Hz, 1 H) 4.96 - 5.02 (m, 3 H) 5.04 (d, J=7.83 Hz, 1 H) 5.12 (d, J=5.38 Hz, 1 H) 5.18 (d, J=2.45 Hz, 1 H) 5.43 (d, J=7.83 Hz, 1 H) 5.52 (d, J=2.45 Hz, 1 H)

$^{13}$C NMR (201.21 MHz, DMSO $d_6$) δ ppm 175.4 (1C), 155.3 (1C), 104.6 (1C), 103.6 (1C), 99.8 (1C), 92.4 (1C), 83.4 (1C), 77.6 (1C), 77.5 (1C), 77.2 (1C), 76.9 (1C), 76.2 (1C), 76.1 (1C), 75.8 (1C), 75.2 (1C), 70.8 (1C), 70.0 (1C), 69.8 (1C), 61.5 (1C), 61.4 (1C), 60.6 (1C), 56.7 (1C), 54.6 (1C), 48.7 (1C), 43.9 (1C), 43.4 (1C), 43.3 (1C), 41.2 (1C), 40.4 (1C), 40.0 (1C), 39.4 (1C), 37.8 (1C), 32.9 (1C), 28.5 (1C), 21.6 (1C), 19.1 (1C), 18.5 (1C), 16.1 (1C)

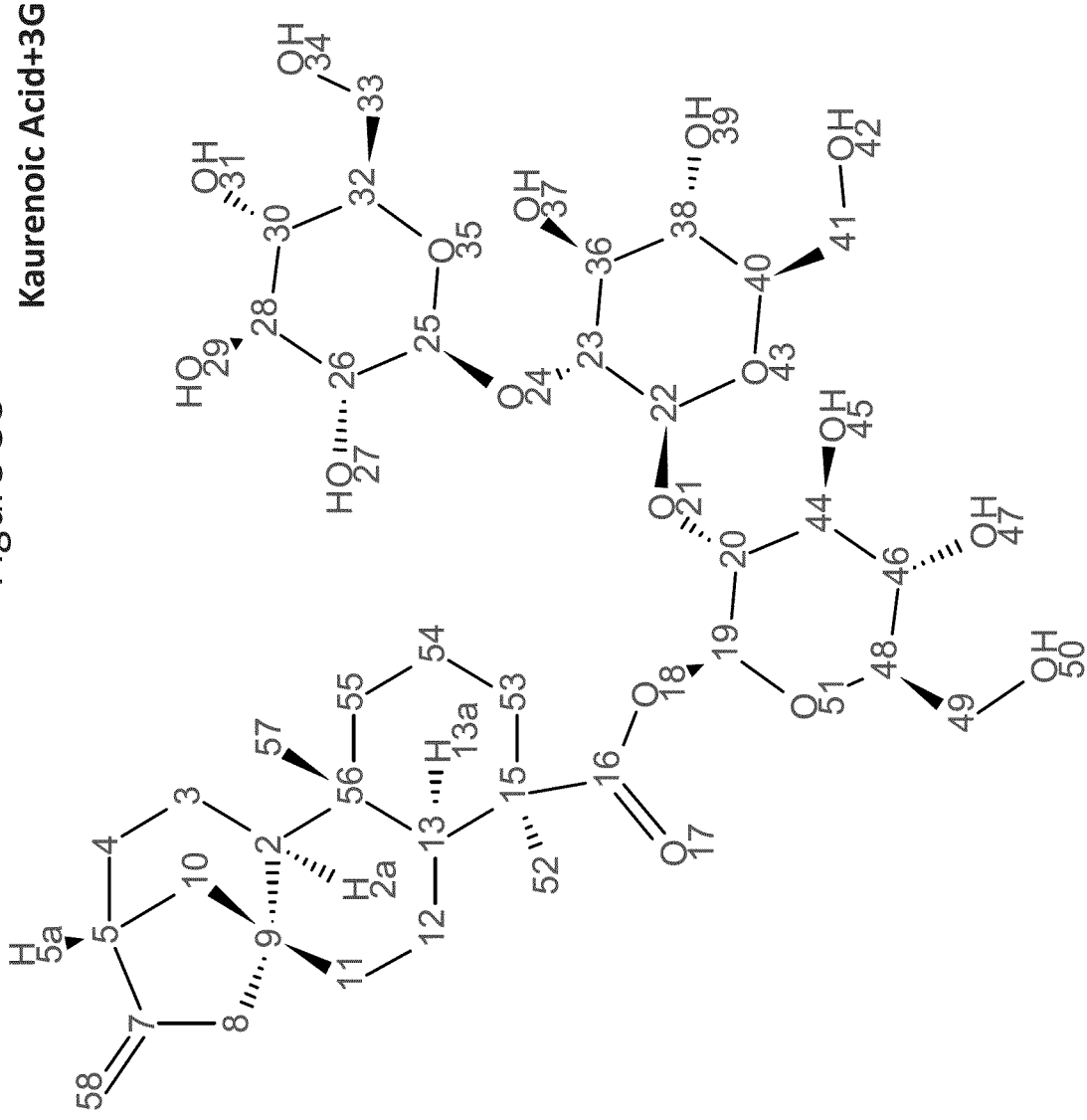
Figure 8C  Kaurenoic Acid+3Glc (isomer 1)

Kaurenoic Acid+3Glc (isomer 2)

Figure 8E

Kaurenoic Acid+3Glc (isomer 2)

| Atom1 | Shift1 (ppm) | H's | Type | J (Hz) | Multiplet1 | (ppm) |
|---|---|---|---|---|---|---|
| 46<'> | 0.77 | 1 | m | - | M40 | [0.73 .. 0.80] |
| 61 | 0.83 | 3 | s | - | M07 | [0.81 .. 0.85] |
| 44<'> | 0.92 | 1 | td | 13.33, 4.16 | M39 | [0.89 .. 0.96] |
| 2a | 1.03 | 1 | m | - | M38 | [1.00 .. 1.04] |
| 57<'>, 48a | 1.07 | 2 | m | - | M37 | [1.04 .. 1.10] |
| 43 | 1.17 | 3 | s | - | M06 | [1.13 .. 1.21] |
| 45<'> | 1.36 | 1 | m | - | M36 | [1.33 .. 1.38] |
| 51<'>, 58<'> | 1.40 | 2 | m | - | M35 | |
| 58<''> | 1.49 | 1 | d | 12.72 | M34 | |
| 50, 51<''> | 1.54 | 3 | m | - | M33 | |
| 46<''>, 45<''>, 59 | 1.78 | 4 | m | - | M32 | |
| 57<''> | 1.90 | 1 | m | - | M05 | |
| 55<'> | 1.95 | 1 | m | - | M04 | |
| 55<''> | 2.06 | 1 | m | - | M03 | |
| 44<''> | 2.31 | 1 | m | - | M02 | |
| 52a | 2.58 | 1 | br. s. | - | M01 | |
| 19<ax> | 2.86 | 1 | m | - | M31 | |
| 15<ax> | 2.92 | 1 | m | - | M30 | |
| 31<ax>, 24<ax> | 3.07 | 2 | m | - | M29 | |
| 17<ax>, 12<ax>, 29<ax> | 3.16 | 4 | m | - | M28 | |
| 33<ax> | 3.21 | 1 | m | - | M27 | |
| 39<ax>, 37<ax> | 3.32 | 2 | m | - | M26 | |
| 34<'>, 13<'> | 3.41 | 2 | m | - | M25 | |
| 40<'> | 3.50 | 1 | m | - | M24 | |
| 40<''> | 3.64 | 1 | dd | 10.51, 4.16 | M23 | |
| 34<''>, 13<''>, 21<ax> | 3.73 | 3 | d | 7.83 | M22 | |
| 8<ax> | 3.78 | 1 | s | - | M21 | |
| 25 | 4.12 | 1 | m | - | M41 | |
| 14 | 4.34 | 1 | t | 5.14 | M20 | |
| 23<ax> | 4.48 | 1 | d | 7.83 | M08 | |
| 41 | 4.56 | 1 | t | 5.62 | M19 | |
| 35 | 4.66 | 1 | t | 4.89 | M18 | |
| 20 | 4.69 | 1 | d | 2.45 | M17 | |
| 60<a> | 4.72 | 1 | s | - | M16 | |
| 60<b> | 4.79 | 1 | br. s. | - | M15 | |
| 10<ax> | 4.86 | 1 | d | 7.83 | M09 | [4.84 .. 4.88] |
| 38, 30 | 4.95 | 2 | br. s. | - | M14 | [4.93 .. 4.99] |
| 18 | 5.04 | 1 | d | 4.89 | M13 | [5.02 .. 5.06] |
| 32 | 5.11 | 1 | br. s. | - | M12 | [5.09 .. 5.13] |
| 16 | 5.16 | 1 | d | 6.36 | M11 | [5.14 .. 5.18] |
| 7<ax> | 5.49 | 2 | d | 8.31 | M10 | [5.46 .. 5.53] |

$^1$H NMR (800 MHz, DMSO $d_6$) δ ppm 0.73 - 0.80 (m, 1 H) 0.83 (s, 3 H) 0.92 (td, J=13.33, 4.16 Hz, 1 H) 1.00 - 1.04 (m, 1 H) 1.04 - 1.10 (m, 2 H) 1.17 (s, 3 H) 1.33 - 1.38 (m, 1 H) 1.38 - 1.44 (m, 2 H) 1.49 (d, J=12.72 Hz, 1 H) 1.51 - 1.59 (m, 3 H) 1.75 - 1.83 (m, 4 H) 1.88 - 1.93 (m, 1 H) 1.93 - 1.98 (m, 1 H) 2.03 - 2.09 (m, 1 H) 2.27 - 2.34 (m, 1 H) 2.58 (br. s., 1 H) 2.83 - 2.88 (m, 1 H) 2.89 - 2.95 (m, 1 H) 3.04 - 3.10 (m, 2 H) 3.12 - 3.19 (m, 4 H) 3.19 - 3.23 (m, 1 H) 3.30 - 3.35 (m, 2 H) 3.39 - 3.44 (m, 2 H) 3.4 - 3.53 (m, 1 H) 3.64 (dd, J=10.51, 4.16 Hz, 1 H) 3.73 (d, J=7.83 Hz, 3 H) 3.78 (s, 1 H) 4.09 - 4.14 (m, 1 H) 4.34 (t, J=5.14 Hz, 1 H) 4.48 (d, J=7.83 Hz, 1 H) 4.56 (t, J=5.62 Hz, 1 H) 4.66 (t, J=4.89 Hz, 1 H) 4.69 (d, J=2.45 Hz, 1 H) 4.72 (s, 1 H) 4.79 (br. s., 1 H) 4.86 (d, J=7.83 Hz, 1 H) 4.95 (br. s., 2 H) 5.04 (d, J=4.89 Hz, 1 H) 5.11 (br. s., 1 H) 5.16 (d, J=6.36 Hz, 1 H) 5.49 (d, J=8.31 Hz, 2 H)

$^{13}$C NMR (201.21 MHz, DMSO $d_6$) δ ppm 175.1 (1C), 155.4 (1C), 103.7 (1C), 103.2 (1C), 101.5 (1C), 92.1 (1C), 86.8 (1C), 77.9 (1C), 77.3 (1C), 77.1 (1C), 77.0 (1C), 76.8 (1C), 76.7 (1C), 74.4 (1C), 73.9 (1C), 71.2 (1C), 70.2 (1C), 68.2 (1C), 61.8 (1C), 61.1 (1C), 60.6 (1C), 56.7 (1C), 54.6 (1C), 48.8 (1C), 44.0 (1C), 43.6 (1C), 43.4 (1C), 41.1 (1C), 40.0 (1C), 39.5 (1C), 39.4 (1C), 37.1 (1C), 32.8 (1C), 28.4 (1C), 21.6 (1C), 19.3 (1C), 18.2 (1C), 16.2 (1C)

Kaurenoic Acid+2Glc+1GlcNAc

Figure 8H

Kaurenoic Acid+2Glc+1GlcNAc

¹H NMR (800 MHz, DMSO $d_6$) δ ppm 0.77 (br. s., 1 H) 0.87 (s, 3 H) 0.93 - 1.00 (m, 1 H) 1.01 - 1.08 (m, 3 H) 1.15 (s, 3 H) 1.33 - 1.43 (m, 3 H) 1.47 (d, $J$=13.20 Hz, 1 H) 1.53 (d, $J$=10.27 Hz, 1 H) 1.57 (d, $J$=11.74 Hz, 2 H) 1.76 (br. s., 1 H) 1.77 - 1.87 (m, 6 H) 1.95 (d, $J$=14.18 Hz, 2 H) 2.05 (d, $J$=17.12 Hz, 1 H) 2.18 (d, $J$=12.23 Hz, 1 H) 2.57 (br. s., 1 H) 3.00 (br. s., 1 H) 3.04 - 3.12 (m, 2 H) 3.13 - 3.19 (m, 2 H) 3.20 - 3.31 (m, 4 H) 3.38 - 3.43 (m, 2 H) 3.43 - 3.49 (m, 1 H) 3.53 - 3.60 (m, 1 H) 3.60 - 3.67 (m, 2 H) 3.67 - 3.77 (m, 3 H) 4.33 (t, $J$=5.38 Hz, 1 H) 4.43 - 4.49 (m, 3 H) 4.53 (d, $J$=8.31 Hz, 1 H) 4.72 (br. s., 1 H) 4.78 (br. s., 1 H) 4.89 (d, $J$=5.38 Hz, 1 H) 4.95 (d, $J$=7.83 Hz, 1 H) 4.97 - 5.05 (m, 3 H) 5.08 (d, $J$=5.38 Hz, 1 H) 5.46 (d, $J$=7.82 Hz, 1 H) 7.79 - 7.84 (m, 1 H)

¹³C NMR (201.21 MHz, DMSO $d_6$) δ ppm 175.6 (1C), 171.6 (1C), 155.5 (1C), 103.6 (1C), 101.9 (1C), 99.9 (1C), 92.5 (1C), 82.1 (1C), 77.6 (1C), 77.3 (1C), 77.0 (1C), 77.0 (1C), 76.1 (1C), 75.9 (1C), 74.0 (1C), 70.5 (1C), 70.3 (1C), 69.9 (1C), 61.8 (1C), 61.0 (1C), 60.9 (1C), 57.2 (1C), 56.7 (1C), 54.6 (1C), 48.8 (1C), 44.1 (1C), 43.8 (1C), 43.4 (1C), 41.3 (1C), 40.4 (1C), 39.9 (1C), 39.5 (1C), 37.6 (1C), 32.9 (1C), 28.5 (1C), 23.4 (1C), 21.6 (1C), 19.2 (1C), 18.4 (1C), 16.2 (1C)

| Atom1 | Shift1 (ppm) | H's | Type | J (Hz) | Multiplet1 | (ppm) |
|---|---|---|---|---|---|---|
| 55<'> | 0.77 | 1 | br. s. | - | M12 | [0.75 .. 0.80] |
| 57 | 0.87 | 3 | s | - | M14 | [0.86 .. 0.88] |
| 53<'> | 0.96 | 1 | m | - | M13 | [0.93 .. 1.00] |
| 2a, 13a, 10<'> | 1.05 | 3 | m | - | M15 | [1.01 .. 1.08] |
| 52 | 1.15 | 3 | s | - | M16 | [1.13 .. 1.17] |
| 54<'>, 4<'>, 11<'> | 1.38 | 3 | m | - | M17 | [1.33 .. 1.43] |
| 11<"> | 1.47 | 1 | d | 13.20 | M18 | [1.45 .. 1.49] |
| 3<'> | 1.53 | 1 | d | 10.27 | M19 | [1.50 .. 1.55] |
| 3<"'>, 4<"> | 1.57 | 2 | d | 11.74 | M20 | [1.55 .. 1.62] |
| 12<'> | 1.76 | 1 | br. s. | - | M21 | [1.72 .. 1.77] |
| 12<"'>, 55<">, 54<"'>, 3 | 1.82 | 6 | m | - | M37 | [1.77 .. 1.87] |
| 10<'>, 8<'> | 1.95 | 2 | d | 14.18 | M22 | [1.93 .. 2.00] |
| 8<"> | 2.05 | 1 | d | 17.12 | M23 | [2.03 .. 2.08] |
| 53<"> | 2.18 | 1 | d | 12.23 | M24 | [2.14 .. 2.20] |
| 5a | 2.57 | 1 | br. s. | - | M25 | [2.56 .. 2.59] |
| 38<ax> | 3.00 | 1 | br. s. | - | M28 | [2.98 .. 3.03] |
| 48<ax>, 23<ax> | 3.08 | 2 | m | - | M29 | [3.04 .. 3.12] |
| 32<ax>, 30 | 3.15 | 2 | m | - | M30 | [3.13 .. 3.19] |
| 40, 46, 36, 28 | 3.24 | 4 | m | - | M31 | [3.20 .. 3.31] |
| 41<'>, 26 | 3.41 | 2 | m | - | M36 | [3.38 .. 3.43] |
| 49<'> | 3.46 | 1 | m | - | M35 | [3.43 .. 3.49] |
| 33<'> | 3.56 | 1 | m | - | M34 | [3.53 .. 3.60] |
| 33<">, 44<ax> | 3.65 | 2 | m | - | M33 | [3.60 .. 3.67] |
| 41<'''>, 49<">, 20<ax> | 3.72 | 3 | m | - | M32 | [3.67 .. 3.77] |
| 50 | 4.33 | 1 | t | 5.38 | M03 | [4.31 .. 4.35] |
| 37, 34, 42 | 4.47 | 3 | m | - | M04 | [4.43 .. 4.49] |
| 25<ax> | 4.53 | 1 | d | 8.31 | M05 | [4.51 .. 4.54] |
| 58<a> | 4.72 | 1 | br. s. | - | M06 | [4.71 .. 4.73] |
| 58<b> | 4.78 | 1 | br. s. | - | M07 | [4.78 .. 4.79] |
| 29 | 4.89 | 1 | d | 5.38 | M08 | [4.86 .. 4.90] |
| 22<ax> | 4.95 | 1 | d | 7.83 | M09 | [4.93 .. 4.97] |
| 31, 39, 45 | 5.01 | 3 | m | - | M10 | [4.97 .. 5.05] |
| 47 | 5.08 | 1 | d | 5.38 | M11 | [5.05 .. 5.10] |
| 19<ax> | 5.46 | 1 | d | 7.82 | M02 | [5.43 .. 5.49] |
| 27 | 7.82 | 1 | m | - | M01 | [7.79 .. 7.84] |

Kaurenol+3Glc (isomer 1)

| Atom1 | Shift1 (ppm) | H's | Type | J (Hz) | Multiplet1 | (ppm) |
|---|---|---|---|---|---|---|
| 46<"> | 0.74 | 1 | m | - | M32 | [0.70 .. 0.76] |
| 44<">, 2a | 0.84 | 2 | m | - | M25 | [0.79 .. 0.89] |
| 61 | 0.93 | 3 | s | - | M08 | [0.91 .. 0.96] |
| 43 | 0.98 | 3 | s | - | M07 | [0.96 .. 1.00] |
| 48a, 57<'> | 1.04 | 2 | m | - | M28 | [1.01 .. 1.08] |
| 45 | 1.32 | 3 | m | - | M27 | [1.28 .. 1.34] |
| 59<'> | 1.36 | 1 | m | - | M36 | [1.34 .. 1.39] |
| 51<'>, 58<'> | 1.41 | 2 | m | - | M35 | [1.39 .. 1.44] |
| 58<"> | 1.46 | 1 | m | - | M26 | [1.44 .. 1.48] |
| 59<">, 50, 51<"> | 1.56 | 4 | m | - | M34 | [1.48 .. 1.65] |
| 44<">, 46<'> | 1.78 | 2 | m | - | M09 | [1.74 .. 1.82] |
| 57<">, 55<'> | 1.94 | 2 | m | - | M29 | [1.88 .. 2.00] |
| 55<"> | 2.06 | 1 | m | - | M06 | [2.02 .. 2.09] |
| 52a | 2.59 | 1 | m | - | M05 | [2.57 .. 2.62] |
| 19<ax> | 2.94 | 1 | m | - | M24 | [2.91 .. 2.97] |
| 37<ax> | 3.02 | 1 | m | - | M23 | [2.99 .. 3.04] |
| 31<ax>, 24<ax> | 3.07 | 2 | m | - | M30 | [3.04 .. 3.11] |
| 15<ax> | 3.13 | 1 | t | 9.05 | M11 | [3.11 .. 3.15] |
| 17<ax>, 29<ax>, 12<ax>, 33<ax>, 39<ax> | 3.19 | 5 | m | - | M31 | [3.15 .. 3.23] |
| 4<'> | 3.24 | 1 | m | - | M33 | [3.23 .. 3.28] |
| 8<ax>, 21<ax> | 3.46 | 2 | m | - | M22 | [3.44 .. 3.48] |
| 13<'>, 34<'>, 40<"'> | 3.51 | 3 | dd | 11.74, 7.82 | M21 | [3.48 .. 3.56] |
| 13<">, 34<">, 40<'> | 3.67 | 3 | br. s. | - | M12 | [3.60 .. 3.72] |
| 4<"> | 3.86 | 1 | m | - | M04 | [3.83 .. 3.89] |
| 14, 10<ax> | 4.25 | 2 | d | 7.34 | M03 | [4.21 .. 4.30] |
| 23<ax> | 4.42 | 1 | d | 7.83 | M14 | [4.39 .. 4.45] |
| 35 | 4.51 | 1 | br. s. | - | M15 | [4.49 .. 4.54] |
| 38 | 4.59 | 1 | s | - | M16 | [4.56 .. 4.61] |
| 20, 7<ax> | 4.63 | 2 | d | 8.31 | M17 | [4.62 .. 4.66] |
| 60<a> | 4.71 | 1 | s | - | M18 | [4.69 .. 4.73] |
| 60<b> | 4.78 | 1 | br. s. | - | M01 | [4.75 .. 4.81] |
| 30, 41 | 4.92 | 2 | br. s. | - | M19 | [4.86 .. 4.96] |
| 18, 16, 32 | 5.07 | 3 | m | - | M20 | [5.01 .. 5.17] |
| 25 | 5.57 | 1 | m | - | M02 | [5.52 .. 5.62] |

Figure 8L

Kaurenol+3Glc (isomer 1)

$^1$H NMR (800 MHz, DMSO $d_6$) δ ppm 0.70 - 0.76 (m, 1 H) 0.79 - 0.89 (m, 2 H) 0.93 (s, 3 H) 0.98 (s, 3 H) 1.01 - 1.08 (m, 2 H) 1.28 - 1.34 (m, 1 H) 1.34 - 1.39 (m, 1 H) 1.39 - 1.44 (m, 2 H) 1.44 - 1.48 (m, 1 H) 1.48 - 1.65 (m, 4 H) 1.74 - 1.82 (m, 2 H) 1.88 - 2.00 (m, 2 H) 2.02 - 2.09 (m, 1 H) 2.57 - 2.62 (m, 1 H) 2.91 - 2.97 (m, 1 H) 2.99 - 3.04 (m, 1 H) 3.04 - 3.11 (m, 2 H) 3.13 (t, $J$=9.05 Hz, 1 H) 3.15 - 3.23 (m, 5 H) 3.23 - 3.28 (m, 1 H) 3.44 - 3.48 (m, 2 H) 3.51 (dd, $J$=11.74, 7.82 Hz, 3 H) 3.67 (br. s., 3 H) 3.83 - 3.89 (m, 1 H) 4.25 (d, $J$=7.34 Hz, 2 H) 4.42 (d, $J$=7.83 Hz, 1 H) 4.51 (br. s., 1 H) 4.59 (s, 1 H) 4.63 (d, $J$=8.31 Hz, 2 H) 4.71 (s, 1 H) 4.78 (br. s., 1 H) 4.92 (br. s., 2 H) 5.01 - 5.17 (m, 3 H) 5.52 - 5.62 (m, 1 H)

$^{13}$C NMR (201.21 MHz, DMSO $d_6$) δ ppm 155.8 (1C), 103.6 (1C), 103.4 (1C), 102.3 (1C), 102.1 (1C), 86.7 (1C), 78.6 (1C), 77.1 (1C), 77.0 (1C), 76.5 (1C), 76.4 (1C), 76.2 (1C), 74.7 (1C), 73.8 (1C), 72.2 (1C), 70.5 (1C), 70.2 (1C), 68.8 (1C), 61.5 (1C), 61.3 (1C), 61.1 (1C), 56.7 (1C), 55.9 (1C), 48.9 (1C), 44.1 (1C), 43.6 (1C), 41.4 (1C), 40.4 (1C), 39.4 (1C), 39.1 (1C), 37.7 (1C), 36.4 (1C), 33.1 (1C), 28.0 (1C), 20.4 (1C), 18.4 (1C), 18.2 (1C), 18.1 (1C)

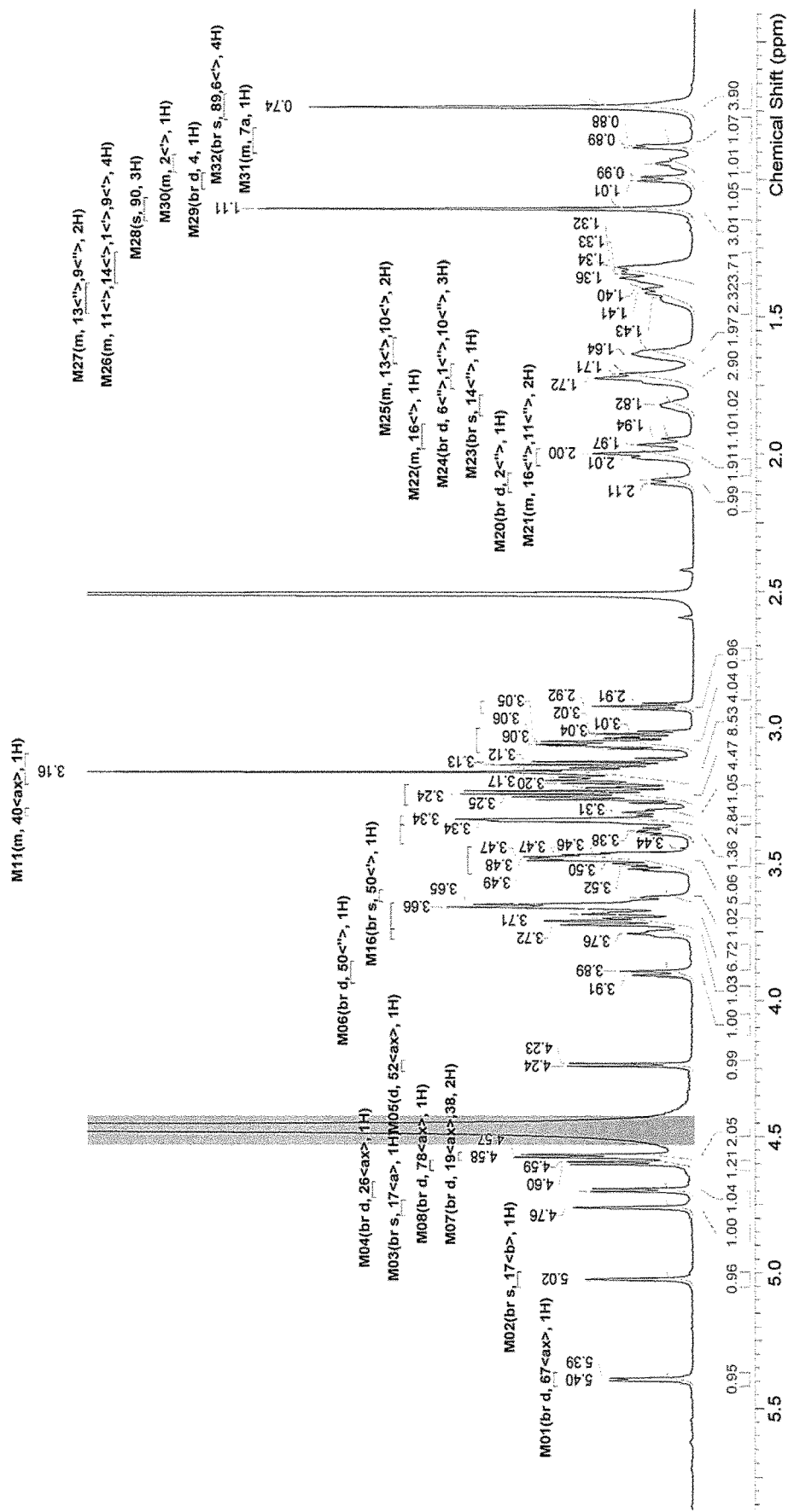

Figure 8N

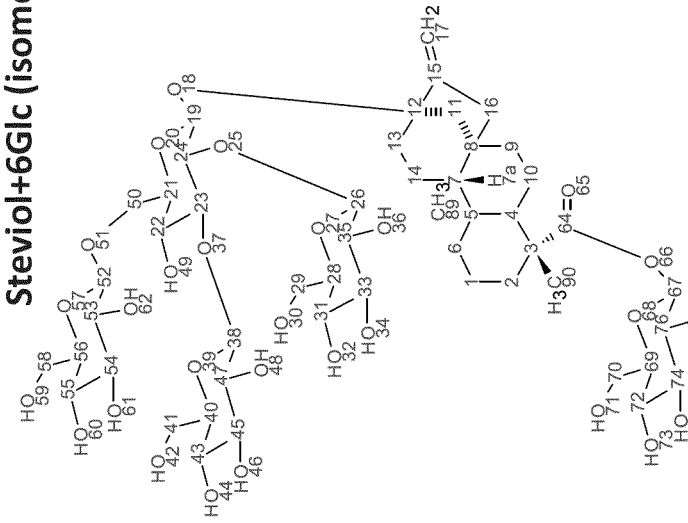

Steviol+6Glc (isomer 1)

| No. | Atom1 | Shift1 (ppm) | H's | Type | J (Hz) | Multiplet1 | (ppm) |
|---|---|---|---|---|---|---|---|
| 1 | 89, 6<'> | 0.74 | 4 | br s | - | M32 | [0.69 .. 0.78] |
| 2 | 7a | 0.88 | 1 | m | - | M31 | [0.81 .. 0.91] |
| 3 | 2<'> | 0.94 | 1 | m | - | M30 | [0.91 .. 0.98] |
| 4 | 4 | 1.00 | 1 | br d | 12.72 | M29 | [0.98 .. 1.04] |
| 5 | 90 | 1.11 | 3 | s | - | M28 | [1.07 .. 1.15] |
| 6 | 11<'>, 14<'>, 1<'>, 9<'> | 1.34 | 4 | m | - | M26 | [1.27 .. 1.38] |
| 7 | 13<''>, 9<''> | 1.42 | 2 | m | - | M27 | [1.38 .. 1.49] |
| 8 | 13<'>, 10<'> | 1.64 | 2 | m | - | M25 | [1.58 .. 1.67] |
| 9 | 6<''>, 1<''>, 10<''> | 1.72 | 3 | br d | 12.23 | M24 | [1.67 .. 1.76] |
| 10 | 14<''> | 1.82 | 1 | br s | - | M23 | [1.79 .. 1.86] |
| 11 | 16<'> | 1.96 | 1 | m | - | M22 | [1.89 .. 1.98] |
| 12 | 16<''>, 11<''> | 2.00 | 2 | m | - | M21 | [1.98 .. 2.04] |
| 13 | 2<''> | 2.10 | 1 | br d | 11.49 | M20 | [2.07 .. 2.14] |
| 14 | 31<ax> | 2.92 | 1 | m | - | M15 | [2.90 .. 2.95] |
| 15 | 85<ax>, 87<ax>, 35<ax>, 53<ax> | 3.05 | 4 | m | - | M14 | [3.00 .. 3.09] |
| 16 | 80<ax>, 83<ax>, 43<ax>, 55<ax>, 56<ax>, 28<ax>, 47<ax>, 33<ax> | 3.16 | 8 | m | - | M13 | [3.10 .. 3.21] |
| 17 | 45<ax>, 54<ax>, 74<ax>, 72<ax> | 3.25 | 4 | br dd | 17.24, 8.93 | M19 | [3.21 .. 3.28] |
| 18 | 40<ax> | 3.31 | 1 | m | - | M11 | [3.30 .. 3.32] |
| 19 | 69<ax>, 21<ax>, 22<ax> | 3.34 | 3 | br d | 4.65 | M18 | [3.32 .. 3.35] |
| 20 | 29<'> | 3.38 | 1 | m | - | M12 | [3.36 .. 3.43] |
| 21 | 81<'>, 41<'>, 58<'>, 70<'>, 24<ax> | 3.48 | 5 | br s | - | M10 | [3.44 .. 3.54] |
| 22 | 50<'> | 3.62 | 1 | m | - | M16 | [3.59 .. 3.64] |
| 23 | 81<''>, 41<''>, 58<''>, 76<ax>, 70<''>, 29<''> | 3.68 | 6 | m | - | M09 | [3.64 .. 3.74] |
| 24 | 23<ax> | 3.75 | 1 | br d | 8.56 | M17 | [3.74 .. 3.78] |
| 25 | 50<''> | 3.90 | 1 | br d | 11.25 | M06 | [3.86 .. 3.94] |
| 26 | 52<ax> | 4.24 | 1 | d | 7.82 | M05 | [4.22 .. 4.26] |
| 27 | 19<ax>, 38 | 4.57 | 2 | br d | 7.83 | M07 | [4.56 .. 4.59] |
| 28 | 78<ax> | 4.60 | 1 | br d | 7.58 | M08 | [4.59 .. 4.63] |
| 29 | 26<ax> | 4.70 | 1 | br d | 7.82 | M04 | [4.67 .. 4.72] |
| 30 | 17<a> | 4.76 | 1 | br s | - | M03 | [4.73 .. 4.79] |
| 31 | 17<b> | 5.02 | 1 | br s | - | M02 | [5.00 .. 5.05] |
| 32 | 67<ax> | 5.39 | 1 | br d | 7.34 | M01 | [5.37 .. 5.42] |

$^1$H NMR (800 MHz, *DMSO-d₆*) δ ppm 0.74 (br s, 4 H) 0.81 - 0.91 (m, 1 H) 0.91 - 0.98 (m, 1 H) 1.00 (br d, *J*=12.72 Hz, 1 H) 1.11 (s, 3 H) 1.27 - 1.38 (m, 4 H) 1.38 - 1.49 (m, 2 H) 1.58 - 1.67 (m, 2 H) 1.72 (br d, *J*=12.23 Hz, 3 H) 1.82 (br s, 1 H) 1.89 - 1.98 (m, 1 H) 1.98 - 2.04 (m, 2 H) 2.10 (br d, *J*=11.49 Hz, 1 H) 2.90 - 2.95 (m, 1 H) 3.00 - 3.09 (m, 4 H) 3.10 - 3.21 (m, 8 H) 3.25 (br dd, *J*=17.24, 8.93 Hz, 4 H) 3.30 - 3.32 (m, 1 H) 3.34 (br d, *J*=4.65 Hz, 3 H) 3.36 - 3.43 (m, 1 H) 3.44 - 3.54 (m, 5 H) 3.62 (br s, 1 H) 3.64 - 3.74 (m, 6 H) 3.75 (br d, *J*=8.56 Hz, 1 H) 3.90 (br d, *J*=11.25 Hz, 1 H) 4.24 (d, *J*=7.82 Hz, 1 H) 4.57 (br d, *J*=7.83 Hz, 2 H) 4.60 (br d, *J*=7.58 Hz, 1 H) 4.70 (br d, *J*=7.82 Hz, 1 H) 4.76 (br s, 1 H) 5.02 (br s, 1 H) 5.39 (br d, *J*=7.34 Hz, 1 H)

Steviol+6Glc (isomer 1) — ACD numbering

| F2 Atom | F2 (ppm) | F2 (ppm) | | F1 Atom | F1 (ppm) | | F1 Atom | F1 (ppm) |
|---|---|---|---|---|---|---|---|---|
| 1<'> | 1.71 | 2.91 | | 1 | 19.9 | | 31 | 71.5 |
| 1<> | 1.31 | 3.18 | | | | | 33 | 77.2 |
| 2<'> | 2.09 | 3.01 | | 2 | 37.7 | | 35 | 75.4 |
| 2<> | 0.93 | 4.56 | | | | | 38 | 103.3 |
| | | 3.33 | | 3 | 44.8 | | 40 | 77.8 |
| 4 | 0.99 | 3.69 | | 4 | 57.4 | | 41 | 61.9 |
| 4 | | 3.46 | | 5 | 40.3 | | | |
| 6<'> | 1.71 | 3.24 | | 6 | 40.8 | | 43 | 70.3 |
| 6<> | 0.73 | 3.23 | | | | | 45 | 76.9 |
| 7a | 0.87 | 3.12 | | 7 | 54 | | 47 | 74.4 |
| | | 3.89 | | 8 | 42.2 | | 50 | 69.3 |
| 9<'> | 1.39 | 3.62 | | 9 | 42.1 | | | |
| 9<> | 1.31 | 4.23 | | | | | 52 | 103.9 |
| 10<'> | 1.72 | 3.04 | | 10 | 22.7 | | 53 | 74.2 |
| 10<> | 1.62 | 3.18 | | | | | 54 | 77.2 |
| 11<'> | 2 | 3.33 | | 11 | 44.4 | | 55 | 69.1 |
| 11<> | 1.34 | 3.3 | | | | | 56 | 77.2 |
| 13<'> | 1.81 | 3.68 | | 12 | 88.4 | | 58 | 62 |
| 13<> | 1.36 | 3.46 | | 13 | 38.3 | | | |
| 14<'> | 1.62 | 5.38 | | 14 | 20.6 | | 64 | 178 |
| 14<> | 1.43 | 3.23 | | | | | 67 | 93.6 |
| | | 3.64 | | 15 | 153.2 | | 69 | 76.9 |
| 16<'> | 1.99 | 3.5 | | 16 | 47.4 | | 70 | 61.6 |
| 16<> | 1.94 | 3.15 | | | | | | |
| 17<a> | 4.75 | 3.65 | | 17 | 105.8 | | 72 | 70.8 |
| 17<b> | 5.02 | 3.65 | | | | | 74 | 77.2 |
| 19<ax> | 4.57 | 4.59 | | 19 | 96.4 | | 76 | 78.4 |
| 21<ax> | 3.15 | 3.33 | | 21 | 77.6 | | 78 | 103.3 |
| 22<ax> | 3.12 | 3.66 | | 22 | 70.8 | | 80 | 75.6 |
| 23<ax> | 3.75 | 3.37 | | 23 | 86.5 | | 81 | 62.7 |
| 24<ax> | 3.48 | 3.06 | | 24 | 79.6 | | | |
| 26<ax> | 4.69 | 3.18 | | 26 | 103 | | 83 | 71.3 |
| 28<ax> | 3.3 | 3.05 | | 28 | 77.2 | | 85 | 77.2 |
| 29<'> | 3.71 | 0.73 | | 29 | 62.1 | | 87 | 75.1 |
| 29<> | 3.69 | 1.1 | | | | | 89 | 17.1 |
| | | | | | | | 90 | 29.2 |

$^{13}$C NMR (201 MHz, DMSO-$d_6$) δ ppm 17.1, 19.9, 20.6, 22.7, 29.2, 37.7, 38.3, 40.3, 40.8, 42.1, 42.2, 44.4, 44.8, 47.4, 54.0, 57.4, 61.6, 61.9, 62.0, 62.1, 62.7, 69.1, 69.3, 70.3, 70.8, 70.8, 71.3, 71.5, 74.2, 74.4, 75.1, 75.4, 75.6, 76.9, 77.2, 77.2, 77.2, 77.2, 77.2, 77.2, 77.6, 77.8, 78.4, 79.6, 86.5, 88.4, 93.6, 96.4, 103.0, 103.3, 103.3, 103.9, 105.8, 153.2, 178.0

Figure 8R

Steviol+7Glc (isomer 2)

| No. | Atom1 | Shift1 (ppm) | H's | Type | J (Hz) | Multiplet1 | (ppm) |
|---|---|---|---|---|---|---|---|
| 1 | 100, 6<'> | 0.87 | 4 | s | - | M17 | [0.80 .. 0.93] |
| 2 | 7a | 0.99 | 1 | m | - | M18 | [0.96 .. 1.02] |
| 3 | 2<'> | 1.06 | 1 | m | - | M19 | [1.02 .. 1.09] |
| 4 | 4 | 1.12 | 1 | m | - | M20 | [1.09 .. 1.15] |
| 5 | 101 | 1.24 | 3 | s | - | M21 | [1.17 .. 1.30] |
| 6 | 1<'>, 9<'> | 1.44 | 2 | br s | - | M22 | [1.38 .. 1.47] |
| 7 | 9<''>, 14<'>, 13<'>, 11<'> | 1.56 | 4 | m | - | M23 | [1.47 .. 1.65] |
| 8 | 10<'> | 1.70 | 1 | m | - | M24 | [1.65 .. 1.75] |
| 9 | 14<''>, 1<''>, 6<''>, 13<''>, 10<''> | 1.88 | 5 | br d | 10.51 | M25 | [1.76 .. 1.99] |
| 10 | 16<'> | 2.05 | 1 | m | - | M26 | [2.00 .. 2.09] |
| 11 | 16<''>, 11<''> | 2.16 | 2 | m | - | M27 | [2.10 .. 2.22] |
| 12 | 2<'> | 2.26 | 1 | m | - | M28 | [2.23 .. 2.30] |
| 13 | 31<ax> | 3.14 | 1 | br t | 9.41 | M16 | [3.10 .. 3.17] |
| 14 | 98<ax>, 35<ax>, 94<ax>, 53<ax> | 3.24 | 4 | m | - | M15 | [3.19 .. 3.30] |
| 15 | 40<ax>, 81<ax>, 78<ax>, 47<ax>, 85<ax>, 55<ax>, 91<ax>, 28<ax>, 56<ax>, 33<ax>, 96<ax>, 54< | 3.40 | 12 | m | - | M14 | [3.32 .. 3.47] |
| 16 | 45<ax>, 69<ax>, 21<ax>, 83<ax>, 43<ax> | 3.50 | 5 | m | - | M13 | [3.47 .. 3.54] |
| 17 | 29<'>, 72<ax>, 22<ax>, 58<'> | 3.58 | 4 | m | - | M12 | [3.54 .. 3.63] |
| 18 | 92<''>, 70<'>, 79<'>, 41<'>, 24<ax> | 3.69 | 5 | m | - | M11 | [3.63 .. 3.74] |
| 19 | 92<''>, 29<''>, 70<''>, 50<'>, 23<ax>, 79<''>, 41<''>, 58<''> | 3.86 | 8 | m | - | M10 | [3.77 .. 3.95] |
| 20 | 74<ax>, 87<ax>, 50<''> | 4.09 | 3 | m | - | M09 | [4.04 .. 4.16] |
| 21 | 52<ax> | 4.45 | 1 | d | 7.82 | M03 | [4.42 .. 4.49] |
| 22 | 19<ax> | 4.77 | 1 | br d | 8.07 | M08 | [4.76 .. 4.77] |
| 23 | 38<ax> | 4.78 | 1 | br d | 8.07 | M07 | [4.78 .. 4.79] |
| 24 | 76<ax> | 4.80 | 1 | br d | 8.07 | M06 | [4.79 .. 4.81] |
| 25 | 26<ax> | 4.83 | 1 | br d | 7.83 | M05 | [4.81 .. 4.85] |
| 26 | 17<a>, 89<ax> | 4.91 | 2 | m | - | M04 | [4.88 .. 4.95] |
| 27 | 17<b> | 5.13 | 1 | br s | - | M02 | [5.09 .. 5.17] |
| 28 | 67<ax> | 5.61 | 1 | d | 7.83 | M01 | [5.58 .. 5.63] |

$^1$H NMR (800 MHz, *DEUTERIUM OXIDE*) δ ppm 0.87 (s, 4 H) 0.96 - 1.02 (m, 1 H) 1.02 - 1.09 (m, 1 H) 1.09 - 1.15 (m, 1 H) 1.24 (s, 3 H) 1.44 (br s, 2 H) 1.47 - 1.65 (m, 4 H) 1.65 - 1.75 (m, 1 H) 1.88 (br d, *J*=10.51 Hz, 5 H) 2.00 - 2.09 (m, 1 H) 2.10 - 2.22 (m, 2 H) 2.23 - 2.30 (m, 1 H) 3.14 (br t, *J*=9.41 Hz, 1 H) 3.19 - 3.30 (m, 4 H) 3.32 - 3.47 (m, 12 H) 3.47 - 3.54 (m, 5 H) 3.54 - 3.63 (m, 4 H) 3.63 - 3.74 (m, 5 H) 3.77 - 3.95 (m, 8 H) 4.04 - 4.16 (m, 3 H) 4.45 (d, *J*=7.82 Hz, 1 H) 4.77 (br d, *J*=8.07 Hz, 1 H) 4.78 (br d, *J*=8.07 Hz, 1 H) 4.80 (br d, *J*=8.07 Hz, 1 H) 4.83 (br d, *J*=7.83 Hz, 1 H) 4.88 - 4.95 (m, 2 H) 5.13 (br s, 1 H) 5.61 (d, *J*=7.83 Hz, 1 H)

Steviol+7Glc (isomer 2)

ACD numbering

| F2 Atom | F2 (ppm) | F1 Atom | F1 (ppm) | F2 Atom | F2 (ppm) | F1 Atom | F1 (ppm) |
|---|---|---|---|---|---|---|---|
| 1<"> | 1.87 | 1 | 19.3 | 40<ax> | 3.44 | 40 | 76.2 |
| 1<> | 1.45 | | | 41<"> | 3.89 | 41 | 61.1 |
| 2<"> | 2.27 | 2 | 37.1 | 41<> | 3.7 | | |
| 2<> | 1.06 | | | 43<ax> | 3.51 | 43 | 69.9 |
| | | 3 | 44.3 | 45<ax> | 3.51 | 45 | 76.3 |
| 4 | 1.12 | 4 | 57.1 | 47<ax> | 3.35 | 47 | 73.8 |
| | | 5 | 39.8 | 50<"> | 4.1 | 50 | 68.9 |
| 6<"> | 1.88 | 6 | 40.3 | 50<> | 3.83 | | |
| 6<> | 0.84 | | | 52<ax> | 4.46 | 52 | 103.1 |
| 7a | 0.99 | 7 | 53.5 | 53<ax> | 3.28 | 53 | 73.5 |
| | | | 42 | 54<ax> | 3.44 | 54 | 76.2 |
| 9<"> | 1.55 | 8 | 41.5 | 55<ax> | 3.39 | 55 | 69.9 |
| 9<> | 1.44 | 9 | | 56<ax> | 3.44 | 56 | 76.2 |
| 10<"> | 1.91 | 10 | 22.1 | 58<"> | 3.89 | 58 | 61.1 |
| 10<> | 1.7 | | | 58<> | 3.7 | | |
| 11<"> | 2.15 | 11 | 44 | | | 64 | 178.8 |
| 11<> | 1.5 | | | 67<ax> | 5.62 | 67 | 92.9 |
| | | 12 | 88.6 | 69<ax> | 3.51 | 69 | 76.3 |
| 13<"> | 1.96 | 13 | 37.5 | 70<"> | 3.89 | 70 | 61.1 |
| 13<> | 1.52 | | | 70<> | 3.7 | | |
| 14<"> | 1.81 | 14 | 20.3 | 72<ax> | 3.54 | 72 | 68.5 |
| 14<> | 1.6 | | | 74<ax> | 4.13 | 74 | 85.1 |
| | | 15 | 153.1 | 76<ax> | 4.8 | 76 | 102.4 |
| 16<"> | 2.19 | 16 | 47 | 78<ax> | 3.39 | 78 | 76.6 |
| 16<> | 2.06 | | | 79<"> | 3.89 | 79 | 61.1 |
| 17<a> | 4.91 | 17 | 104.9 | 79<> | 3.7 | | |
| 17<b> | 5.14 | | | 81<ax> | 3.39 | 81 | 69.9 |
| 19<ax> | 4.77 | 19 | 95.7 | 83<ax> | 3.51 | 83 | 76.3 |
| 21<ax> | 3.54 | 21 | 74.8 | 85<ax> | 3.37 | 85 | 73.8 |
| 22<ax> | 3.57 | 22 | 68.5 | 87<ax> | 4.07 | 87 | 76.3 |
| 23<ax> | 3.92 | 23 | 85.4 | 89<ax> | 4.92 | 89 | 101.9 |
| 24<ax> | 3.68 | 24 | 78.9 | 91<ax> | 3.39 | 91 | 76.6 |
| 26<ax> | 4.84 | 26 | 102.4 | 92<> | 3.92 | 92 | 62 |
| 28<ax> | 3.39 | 28 | 76.6 | 92<> | 3.67 | | |
| 29<"> | 3.87 | 29 | 62 | 94<ax> | 3.26 | 94 | 70.9 |
| 29<> | 3.6 | | | 96<ax> | 3.44 | 96 | 76.2 |
| 31<ax> | 3.15 | 31 | 70.9 | 98<ax> | 3.22 | 98 | 74.2 |
| 33<ax> | 3.44 | 33 | 76.2 | 100 | 0.87 | 100 | 16.4 |
| 35<ax> | 3.25 | 35 | 74.6 | 101 | 1.25 | 101 | 28.6 |
| 38<ax> | 4.79 | 38 | 102.4 | | | | |

$^{13}$C NMR (201 MHz, DEUTERIUM OXIDE) δ ppm 16.4, 19.3, 20.3, 22.1, 28.6, 37.1, 37.5, 39.8, 40.3, 41.5, 42.0, 44.0, 44.3, 47.0, 53.5, 57.1, 61.1, 61.1, 61.1, 61.1, 62.0, 62.0, 68.5, 68.5, 68.9, 69.9, 69.9, 70.9, 70.9, 73.5, 73.8, 73.8, 74.2, 74.6, 74.8, 76.2, 76.2, 76.2, 76.3, 76.3, 76.3, 76.6, 76.6, 76.6, 78.9, 85.1, 85.4, 88.6, 92.9, 95.7, 101.9, 102.4, 102.4, 102.4, 103.1, 104.9, 153.1, 178.8

Figure 8V

Steviol+6Glc (isomer 4)

| Multiplet1 | Shift1 (ppm) | Atom1 | H's | Type | J (Hz) | (ppm) |
|---|---|---|---|---|---|---|
| M01 | 0.90 | 89, 6<'> | 4 | m | - | [0.85 .. 0.93] |
| M02 | 1.04 | 7a | 1 | br d | 8.07 | [1.02 .. 1.06] |
| M03 | 1.11 | 2<'> | 1 | m | - | [1.08 .. 1.14] |
| M04 | 1.17 | 4 | 1 | br d | 12.47 | [1.15 .. 1.20] |
| M05 | 1.28 | 90 | 3 | s | - | [1.25 .. 1.30] |
| M06 | 1.49 | 11<'>, 9<'>, 1<'> | 3 | m | - | [1.45 .. 1.54] |
| M51 | 1.57 | 13<'>, 9<''> | 2 | m | - | [1.54 .. 1.61] |
| M07 | 1.64 | 14<'> | 1 | m | - | [1.61 .. 1.67] |
| M08 | 1.74 | 10<'> | 1 | m | - | [1.71 .. 1.78] |
| M35 | 1.85 | 14<''> | 1 | m | - | [1.83 .. 1.87] |
| M09 | 1.89 | 6<''>, 10<''>, 1<''> | 3 | m | - | [1.83 .. 1.94] |
| M10 | 1.98 | 13<''> | 1 | td | 12.10, 6.11 | [1.95 .. 2.01] |
| M11 | 2.10 | 16<'> | 1 | br d | 17.12 | [2.08 .. 2.13] |
| M12 | 2.20 | 11<''>, 16<''> | 2 | m | - | [2.18 .. 2.24] |
| M13 | 2.30 | 2<''> | 1 | m | - | [2.28 .. 2.33] |
| M42 | 3.24 | 31<ax> | 1 | m | - | [3.23 .. 3.26] |
| M30 | 3.27 | 35<ax> | 1 | m | - | [3.26 .. 3.29] |
| M14 | 3.32 | 87<ax>, 52<ax> | 2 | m | - | [3.29 .. 3.34] |
| M28 | 3.36 | 83<ax> | 1 | m | - | [3.34 .. 3.38] |
| M44 | 3.41 | 50<ax>, 40<ax> | 2 | m | - | [3.39 .. 3.43] |
| M32 | 3.42 | 22<ax>, 58<ax> | 2 | m | - | [3.38 .. 3.46] |
| M43 | 3.45 | 45<ax> | 3 | m | - | [3.44 .. 3.46] |
| M33 | 3.47 | 33<ax>, 28<ax> | 2 | m | - | [3.46 .. 3.48] |
| M27 | 3.48 | 48<ax>, 85<ax> | 3 | m | - | [3.38 .. 3.57] |
| M31 | 3.51 | 72<ax> | 1 | m | - | [3.49 .. 3.53] |
| M36 | 3.53 | 54<ax> | 1 | m | - | [3.51 .. 3.55] |
| M34 | 3.55 | 80<ax> | 1 | m | - | [3.53 .. 3.56] |
| M26 | 3.59 | 69<ax> | 1 | ddd | 9.72, 5.07, 2.32 | [3.57 .. 3.61] |
| M25 | 3.66 | 29<'> | 1 | dd | 12.23, 7.09 | [3.64 .. 3.68] |
| M18 | 3.73 | 24<ax>, 70<'>, 56<ax>, 81<'> | 4 | m | - | [3.68 .. 3.79] |
| M47 | 3.74 | 46<'> | 1 | m | - | [3.71 .. 3.77] |
| M49 | 3.76 | 61<'> | 1 | m | - | [3.74 .. 3.78] |
| M37 | 3.85 | 74<ax> | 1 | m | - | [3.83 .. 3.87] |
| M15 | 3.89 | 41<'>, 76<ax> | 2 | m | - | [3.82 .. 3.96] |
| M40 | 3.90 | 23<ax>, 29<''> | 2 | m | - | [3.85 .. 3.94] |
| M39 | 3.90 | 46<''>, 61<''> | 2 | m | - | [3.85 .. 3.94] |
| M41 | 3.90 | 81<''> | 1 | m | - | [3.85 .. 3.94] |
| M38 | 3.91 | 70<''> | 1 | m | - | [3.87 .. 3.94] |
| M16 | 4.22 | 41<''> | 1 | br d | 9.54 | [4.20 .. 4.24] |
| M17 | 4.50 | 43<ax> | 1 | d | 7.83 | [4.49 .. 4.53] |
| M29 | 4.77 | 38<ax> | 1 | m | - | [4.75 .. 4.78] |
| M19 | 4.79 | 19<ax> | 1 | d | 7.83 | [4.78 .. 4.80] |
| M24 | 4.79 | 78<ax> | 1 | m | - | [4.78 .. 4.80] |
| M20 | 4.88 | 26<ax> | 1 | d | 8.07 | [4.86 .. 4.90] |
| M21 | 4.95 | 17<a> | 1 | s | - | [4.94 .. 4.97] |
| M22 | 5.16 | 17<b> | 1 | br s | - | [5.14 .. 5.18] |
| M23 | 5.61 | 67<ax> | 1 | d | 7.82 | [5.60 .. 5.62] |

Steviol+6Glc (isomer 4)

1H NMR (800 MHz, DEUTERIUM OXIDE) δ ppm 0.85 - 0.93 (m, 4 H) 1.04 (br d, $J$=8.07 Hz, 1 H) 1.08 - 1.14 (m, 1 H) 1.17 (br d, $J$=12.47 Hz, 1 H) 1.28 (s, 3 H) 1.45 - 1.54 (m, 3 H) 1.54 - 1.61 (m, 2 H) 1.61 - 1.67 (m, 1 H) 1.71 - 1.78 (m, 1 H) 1.83 - 1.87 (m, 1 H) 1.83 - 1.94 (m, 3 H) 1.98 (td, $J$=12.10, 6.11 Hz, 1 H) 2.10 (br d, $J$=17.12 Hz, 1 H) 2.18 - 2.24 (m, 2 H) 2.28 - 2.33 (m, 1 H) 3.23 - 3.26 (m, 1 H) 3.26 - 3.29 (m, 1 H) 3.29 - 3.34 (m, 2 H) 3.34 - 3.38 (m, 1 H) 3.38 - 3.46 (m, 3 H) 3.39 - 3.43 (m, 2 H) 3.44 - 3.46 (m, 1 H) 3.46 - 3.48 (m, 2 H) 3.49 - 3.53 (m, 1 H) 3.51 - 3.55 (m, 1 H) 3.53 - 3.56 (m, 1 H) 3.59 (ddd, $J$=9.72, 5.07, 2.32 Hz, 1 H) 3.66 (dd, $J$=12.23, 7.09 Hz, 1 H) 3.68 - 3.79 (m, 4 H) 3.71 - 3.77 (m, 1 H) 3.74 - 3.78 (m, 1 H) 3.82 - 3.96 (m, 2 H) 3.83 - 3.87 (m, 1 H) 3.85 - 3.94 (m, 2 H) 3.85 - 3.94 (m, 2 H) 3.87 - 3.94 (m, 1 H) 4.22 (br d, $J$=9.54 Hz, 1 H) 4.50 (d, $J$=7.83 Hz, 1 H) 4.75 - 4.78 (m, 1 H) 4.79 (d, $J$=7.83 Hz, 1 H) 4.78 - 4.80 (m, 1 H) 4.88 (d, $J$=8.07 Hz, 1 H) 4.95 (s, 1 H) 5.16 (br s, 1 H) 5.61 (d, $J$=7.82 Hz, 1 H)

13C NMR (201 MHz, DEUTERIUM OXIDE) δ ppm 18.8, 21.8, 22.6, 24.2, 31.1, 39.6, 39.6, 42.0, 42.7, 43.7, 44.1, 46.8, 46.8, 49.5, 55.8, 59.5, 63.3, 63.7, 64.3, 71.3, 71.5, 72.2, 72.3, 72.5, 72.8, 73.3, 75.9, 76.1, 77.0, 77.5, 78.0, 78.4, 78.4, 78.5, 78.6, 78.7, 78.7, 78.8, 79.0, 79.0, 79.3, 80.8, 81.3, 89.0, 90.5, 95.4, 98.4, 104.8, 105.2, 105.3, 105.3, 107.1, 155.9, 181.1

Steviol+6Glc (isomer 4)

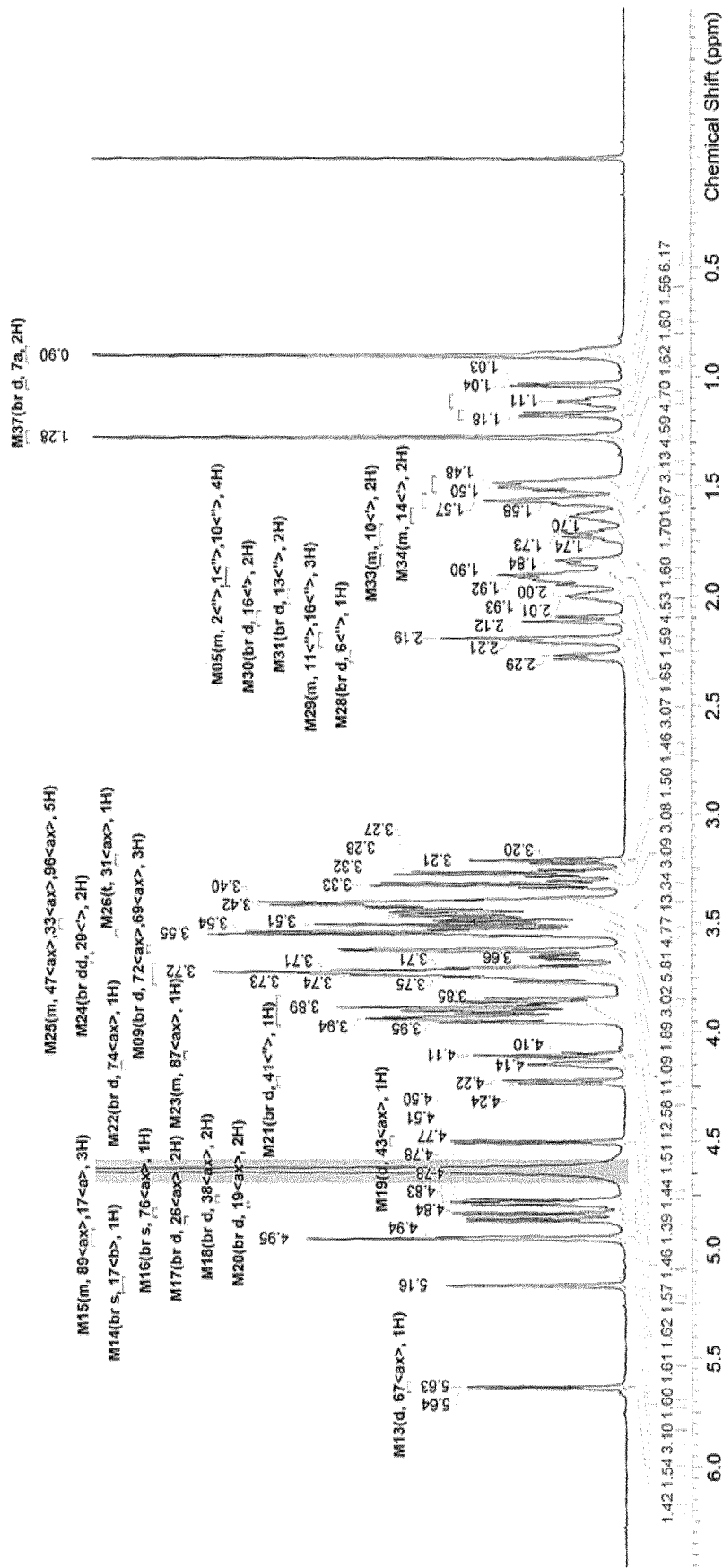

Figure 8Z

Steviol+7Glc (isomer 5)

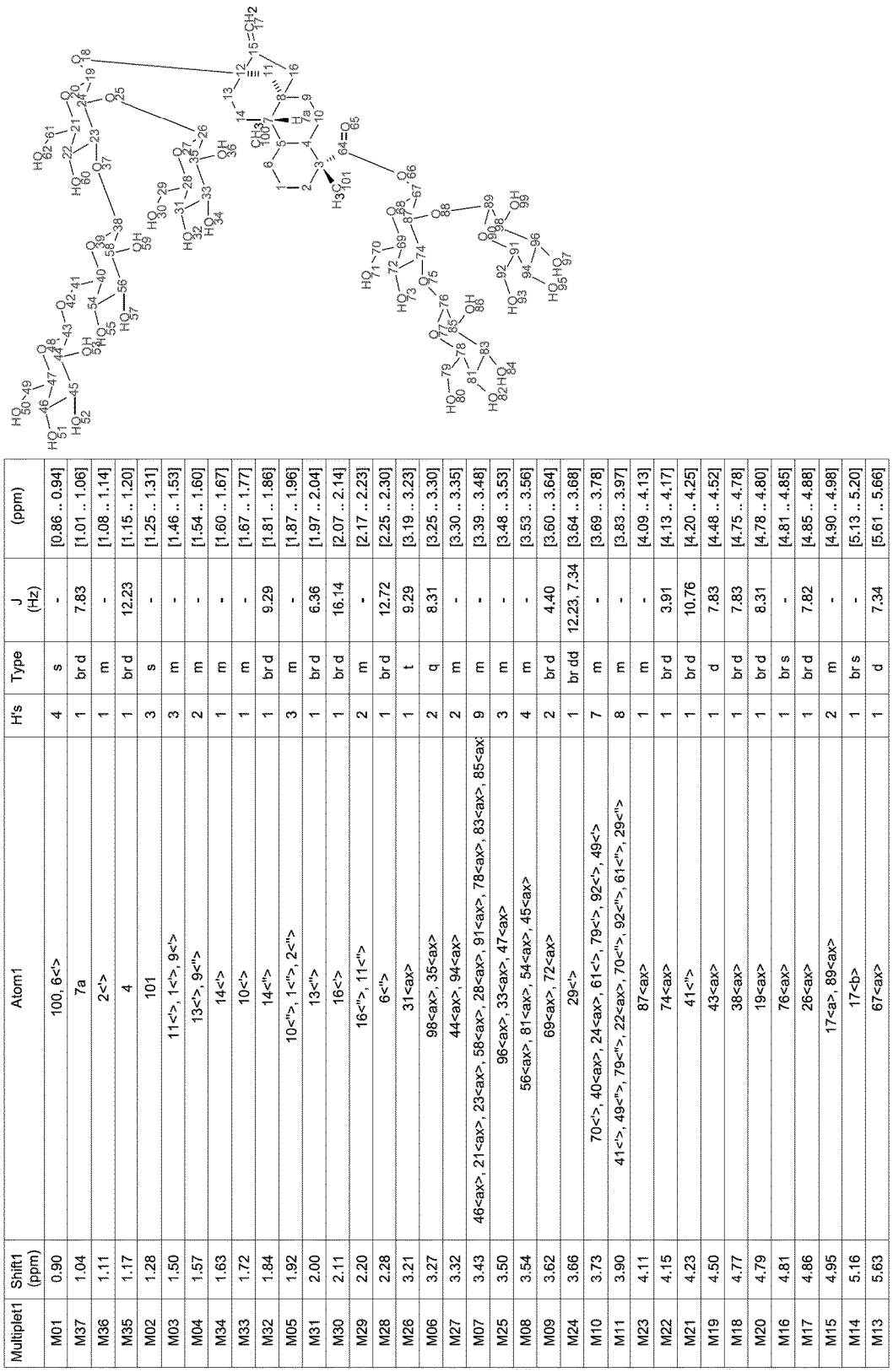

| Multiplet1 | Shift1 (ppm) | Atom1 | H's | Type | J (Hz) | (ppm) |
|---|---|---|---|---|---|---|
| M01 | 0.90 | 100, 6<''> | 4 | s | - | [0.86 .. 0.94] |
| M37 | 1.04 | 7a | 1 | br d | 7.83 | [1.01 .. 1.06] |
| M36 | 1.11 | 2<''> | 1 | m | - | [1.08 .. 1.14] |
| M35 | 1.17 | 4 | 1 | br d | 12.23 | [1.15 .. 1.20] |
| M02 | 1.28 | 101 | 3 | s | - | [1.25 .. 1.31] |
| M03 | 1.50 | 11<''>, 1<''>, 9<''> | 3 | m | - | [1.46 .. 1.53] |
| M04 | 1.57 | 13<''>, 9<''''> | 2 | m | - | [1.54 .. 1.60] |
| M34 | 1.63 | 14<''> | 1 | m | - | [1.60 .. 1.67] |
| M33 | 1.72 | 10<''> | 1 | m | - | [1.67 .. 1.77] |
| M32 | 1.84 | 14<''''> | 1 | br d | 9.29 | [1.81 .. 1.86] |
| M05 | 1.92 | 10<''>, 1<''''>, 2<''> | 3 | m | - | [1.87 .. 1.96] |
| M31 | 2.00 | 13<''> | 1 | br d | 6.36 | [1.97 .. 2.04] |
| M30 | 2.11 | 16<''> | 1 | br d | 16.14 | [2.07 .. 2.14] |
| M29 | 2.20 | 16<''''>, 11<''''> | 2 | m | - | [2.17 .. 2.23] |
| M28 | 2.28 | 6<''''> | 1 | br d | 12.72 | [2.25 .. 2.30] |
| M26 | 3.21 | 31<ax> | 1 | t | 9.29 | [3.19 .. 3.23] |
| M06 | 3.27 | 98<ax>, 35<ax> | 2 | q | 8.31 | [3.25 .. 3.30] |
| M27 | 3.32 | 44<ax>, 94<ax> | 2 | m | - | [3.30 .. 3.35] |
| M07 | 3.43 | 46<ax>, 21<ax>, 23<ax>, 58<ax>, 28<ax>, 91<ax>, 78<ax>, 83<ax>, 85<ax> | 9 | m | - | [3.39 .. 3.48] |
| M25 | 3.50 | 96<ax>, 33<ax>, 47<ax> | 3 | m | - | [3.48 .. 3.53] |
| M08 | 3.54 | 56<ax>, 81<ax>, 54<ax>, 45<ax> | 4 | m | - | [3.53 .. 3.56] |
| M09 | 3.62 | 69<ax>, 72<ax> | 2 | br d | 4.40 | [3.60 .. 3.64] |
| M24 | 3.66 | 29<''> | 1 | br dd | 12.23, 7.34 | [3.64 .. 3.68] |
| M10 | 3.73 | 70<''>, 40<ax>, 24<ax>, 61<''>, 79<''>, 92<''>, 49<''> | 7 | m | - | [3.69 .. 3.78] |
| M11 | 3.90 | 41<''>, 49<''>, 79<''''>, 22<ax>, 70<ax>, 92<''''>, 61<''''>, 29<''''> | 8 | m | - | [3.83 .. 3.97] |
| M23 | 4.11 | 87<ax> | 1 | m | - | [4.09 .. 4.13] |
| M22 | 4.15 | 74<ax> | 1 | br d | 3.91 | [4.13 .. 4.17] |
| M21 | 4.23 | 41<''''> | 1 | br d | 10.76 | [4.20 .. 4.25] |
| M19 | 4.50 | 43<ax> | 1 | d | 7.83 | [4.48 .. 4.52] |
| M18 | 4.77 | 38<ax> | 1 | br d | 7.83 | [4.75 .. 4.78] |
| M20 | 4.79 | 19<ax> | 1 | br d | 8.31 | [4.78 .. 4.80] |
| M16 | 4.81 | 76<ax> | 1 | br s | - | [4.81 .. 4.85] |
| M17 | 4.86 | 26<ax> | 1 | br d | 7.82 | [4.85 .. 4.88] |
| M15 | 4.95 | 17<a>, 89<ax> | 2 | m | - | [4.90 .. 4.98] |
| M14 | 5.16 | 17<b> | 1 | br s | - | [5.13 .. 5.20] |
| M13 | 5.63 | 67<ax> | 1 | d | 7.34 | [5.61 .. 5.66] |

Figure 8AA

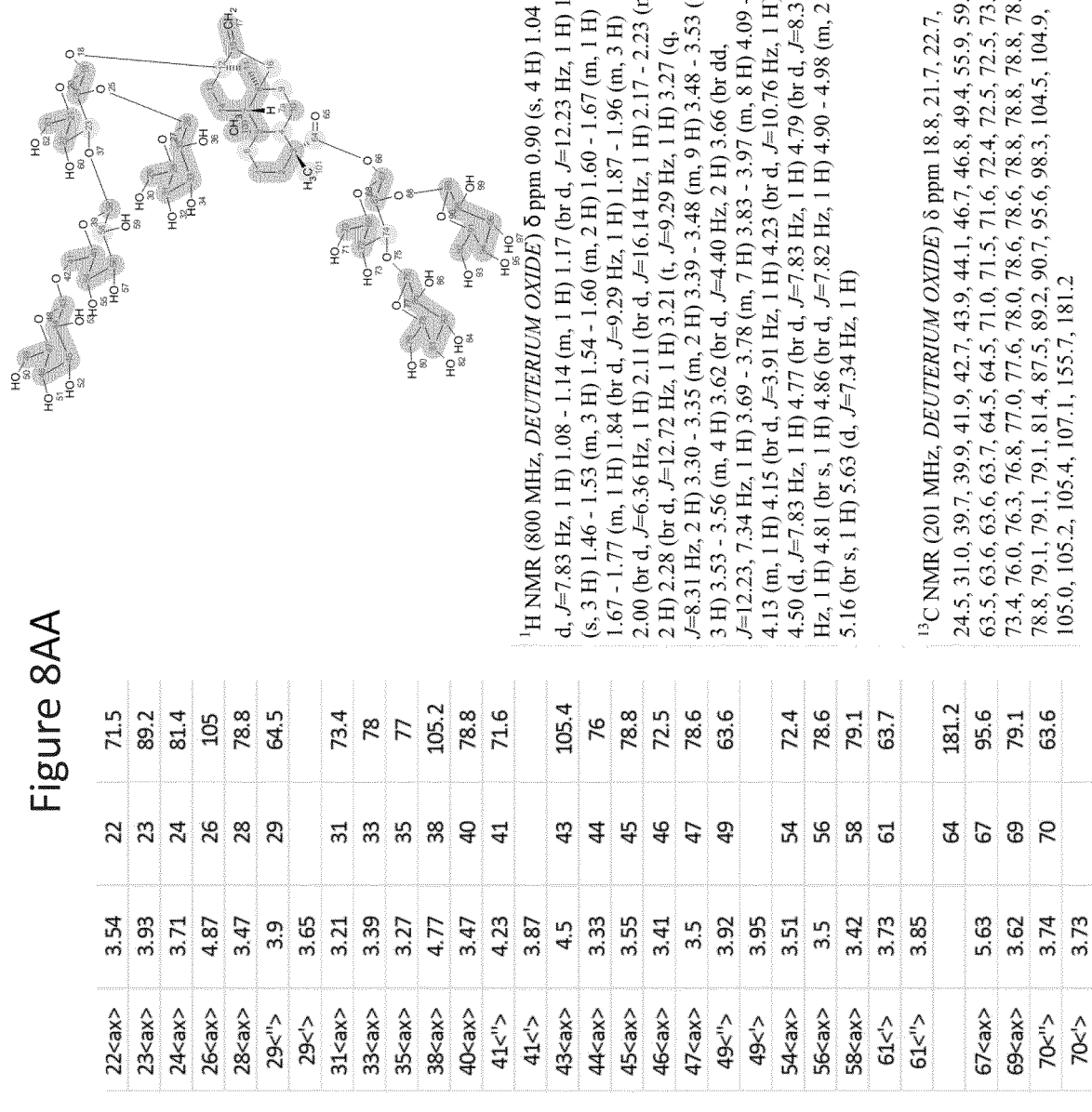

Steviol+7Glc (isomer 5)

| F2 Atom | F2 (ppm) | F1 Atom | F1 (ppm) |     |         |      |
|---------|----------|---------|----------|-----|---------|------|
| 1<'>    | 1.9      | 1       | 21.7     |     | 22<ax>  | 71.5 |
| 1<>     | 1.49     |         |          |     | 23<ax>  | 89.2 |
| 2<'>    | 2.28     | 2       | 39.7     |     | 24<ax>  | 81.4 |
| 2<>     | 1.11     |         |          |     | 26<ax>  | 105  |
|         |          | 3       | 46.8     |     | 28<ax>  | 78.8 |
| 4       | 1.17     | 4       | 59.5     |     | 29<'>   | 64.5 |
|         |          | 5       | 41.9     |     | 29<>    | 3.9  |
| 6<'>    | 1.91     | 6       | 42.7     |     | 31<ax>  | 73.4 |
| 6<>     | 0.89     |         |          |     | 33<ax>  | 78   |
| 7a      | 1.04     | 7       | 55.9     |     | 35<ax>  | 77   |
|         |          | 8       | 44.1     |     | 38<ax>  | 105.2 |
| 9<'>    | 1.57     | 9       | 43.9     |     | 40<ax>  | 78.8 |
| 9<>     | 1.48     |         |          |     | 41<''>  | 71.6 |
| 10<''>  | 1.94     | 10      | 24.5     |     | 41<>    | 3.87 |
| 10<'>   | 1.72     |         |          |     | 43<ax>  | 105.4 |
| 11<'>   | 2.2      | 11      | 46.7     |     | 44<ax>  | 76   |
| 11<>    | 1.51     |         |          |     | 45<ax>  | 78.8 |
|         |          | 12      | 90.7     |     | 46<ax>  | 72.5 |
| 13<'>   | 2        | 13      | 39.9     |     | 47<ax>  | 78.6 |
| 13<>    | 1.56     |         |          |     | 49<'>   | 63.6 |
| 14<''>  | 1.84     | 14      | 22.7     |     | 49<>    | 3.95 |
| 14<'>   | 1.63     |         |          |     | 54<ax>  | 72.4 |
|         |          | 15      | 155.7    |     | 56<ax>  | 78.6 |
| 16<'>   | 2.2      | 16      | 49.4     |     | 58<ax>  | 79.1 |
| 16<>    | 2.11     |         |          |     | 61<'>   | 63.7 |
| 17<a>   | 4.95     | 17      | 107.1    |     | 61<''>  | 3.85 |
| 17<b>   | 5.16     |         |          |     | 64      | 181.2 |
| 19<ax>  | 4.79     | 19      | 98.3     |     | 67<ax>  | 95.6 |
| 21<ax>  | 3.72     | 21      | 77.6     |     | 69<ax>  | 79.1 |
|         |          |         |          |     | 70<''>  | 63.6 |
|         |          |         |          |     | 70<>    |      |

$^1$H NMR (800 MHz, DEUTERIUM OXIDE) δ ppm 0.90 (s, 4 H) 1.04 (br d, J=7.83 Hz, 1 H) 1.08 - 1.14 (m, 1 H) 1.17 (br d, J=12.23 Hz, 1 H) 1.28 (s, 3 H) 1.46 - 1.53 (m, 3 H) 1.54 - 1.60 (m, 2 H) 1.60 - 1.67 (m, 1 H) 1.67 - 1.77 (m, 1 H) 1.84 (br d, J=9.29 Hz, 1 H) 1.87 - 1.96 (m, 3 H) 2.00 (br d, J=6.36 Hz, 1 H) 2.11 (br d, J=16.14 Hz, 1 H) 2.17 - 2.23 (m, 2 H) 2.28 (br d, J=12.72 Hz, 1 H) 3.21 (t, J=9.29 Hz, 1 H) 3.27 (q, J=8.31 Hz, 2 H) 3.30 - 3.35 (m, 2 H) 3.39 - 3.48 (m, 9 H) 3.48 - 3.53 (m, 3 H) 3.53 - 3.56 (m, 4 H) 3.62 (br d, J=4.40 Hz, 2 H) 3.66 (br dd, J=12.23, 7.34 Hz, 1 H) 3.69 - 3.78 (m, 7 H) 3.83 - 3.97 (m, 8 H) 4.09 - 4.13 (m, 1 H) 4.15 (br d, J=3.91 Hz, 1 H) 4.23 (br d, J=10.76 Hz, 1 H) 4.50 (d, J=7.83 Hz, 1 H) 4.77 (br d, J=7.83 Hz, 1 H) 4.79 (br d, J=8.31 Hz, 1 H) 4.81 (br s, 1 H) 4.86 (br d, J=7.82 Hz, 1 H) 4.90 - 4.98 (m, 2 H) 5.16 (br s, 1 H) 5.63 (d, J=7.34 Hz, 1 H)

$^{13}$C NMR (201 MHz, DEUTERIUM OXIDE) δ ppm 18.8, 21.7, 22.7, 24.5, 31.0, 39.7, 39.9, 41.9, 42.7, 43.9, 44.1, 46.7, 46.8, 49.4, 55.9, 59.5, 63.5, 63.6, 63.6, 63.7, 64.5, 64.5, 71.0, 71.5, 71.6, 72.4, 72.5, 73.4, 73.4, 76.0, 76.3, 76.8, 77.0, 77.6, 78.0, 78.6, 78.8, 78.8, 78.8, 78.8, 79.1, 79.1, 81.4, 87.5, 89.2, 90.7, 95.6, 98.3, 104.5, 104.9, 105.0, 105.2, 105.4, 107.1, 155.7, 181.2

Figure 8AD

Steviol+4Glc+1GlcNAc (#11)

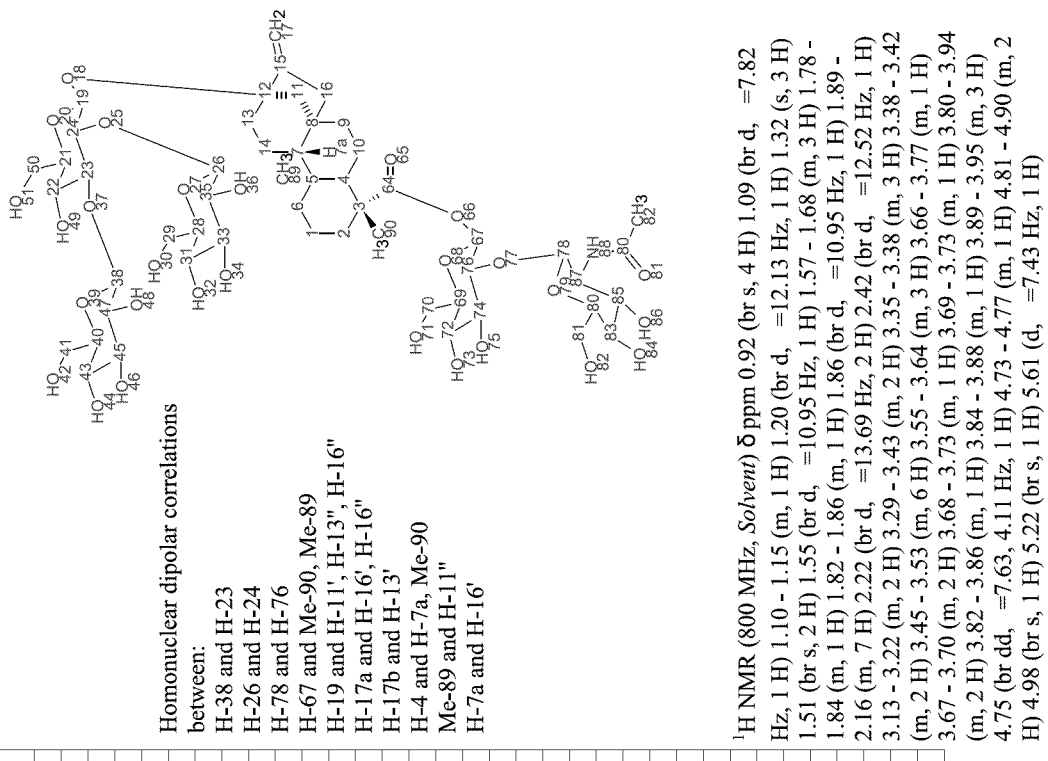

| Multiplet1 | Shift1 (ppm) | Atom1 | H's | Type | J (Hz) | (ppm) |
|---|---|---|---|---|---|---|
| M25 | 5.61 | 67<ax> | 1 | d | 7.43 | [5.60...5.62] |
| M24 | 5.22 | 17<b> | 1 | br s | - | [5.21...5.24] |
| M23 | 4.98 | 17<a> | 1 | br s | - | [4.96...4.99] |
| M22 | 4.86 | 26<ax>, 78 | 2 | m | - | [4.81...4.90] |
| M26 | 4.75 | 19<ax> | 1 | m | - | [4.73...4.77] |
| M21 | 4.75 | 38<ax> | 1 | br dd | 7.63, 4.11 | [4.73...4.77] |
| M27 | 3.92 | 41<">, 50<">, 81<"> | 3 | m | - | [3.89...3.95] |
| M20 | 3.86 | 23<ax>, 76 | 2 | m | - | [3.80...3.94] |
| M28 | 3.86 | 29<"> | 1 | m | - | [3.84...3.88] |
| M30 | 3.84 | 70<"> | 1 | m | - | [3.82...3.86] |
| M32 | 3.71 | 70<"> | 1 | m | - | [3.69...3.73] |
| M29 | 3.71 | 41<'> | 1 | m | - | [3.68...3.73] |
| M19 | 3.70 | 24<ax> | 1 | m | - | [3.66...3.77] |
| M31 | 3.68 | 50<'>, 81<'> | 2 | m | - | [3.67...3.70] |
| M18 | 3.61 | 29<'>, 74, 87<ax> | 3 | m | - | [3.55...3.64] |
| M17 | 3.48 | 21<ax>, 40<ax>, 85<ax>, 72<ax>, 69<ax>, 22 | 6 | m | - | [3.45...3.53] |
| M34 | 3.40 | 80<ax>, 33<ax> | 2 | m | - | [3.38...3.42] |
| M33 | 3.36 | 28<ax>, 45<ax>, 43<ax> | 3 | m | - | [3.35...3.38] |
| M16 | 3.36 | 83<ax>, 47<ax> | 2 | m | - | [3.29...3.43] |
| M15 | 3.19 | 31<ax>, 35<ax> | 2 | m | - | [3.13...3.22] |
| M13 | 2.42 | 2<'> | 1 | br d | 12.52 | [2.38...2.45] |
| M12 | 2.22 | 11<">, 16<'> | 2 | br d | 13.69 | [2.18...2.25] |
| M11 | 2.03 | 10<">, 13<'>, 16<'>, 6<'>, 82 | 7 | m | - | [1.89...2.16] |
| M10 | 1.86 | 14<'> | 1 | br d | 10.95 | [1.85...1.89] |
| M35 | 1.84 | 1<'> | 1 | m | - | [1.82...1.86] |
| M09 | 1.81 | 10<'> | 1 | m | - | [1.78...1.84] |
| M08 | 1.62 | 14<'>, 13<'>, 9<"> | 3 | m | - | [1.57...1.68] |
| M07 | 1.55 | 11<'> | 1 | br d | 10.95 | [1.53...1.57] |
| M06 | 1.51 | 1<'>, 9<'> | 2 | br s | - | [1.47...1.53] |
| M05 | 1.32 | 90 | 3 | s | - | [1.29...1.34] |
| M04 | 1.20 | 4 | 1 | br d | 12.13 | [1.17...1.22] |
| M03 | 1.12 | 2<'> | 1 | m | - | [1.10...1.15] |
| M02 | 1.09 | 7a | 1 | br d | 7.82 | [1.07...1.10] |
| M01 | 0.92 | 6<'>, 89 | 4 | br s | - | [0.90...0.95] |

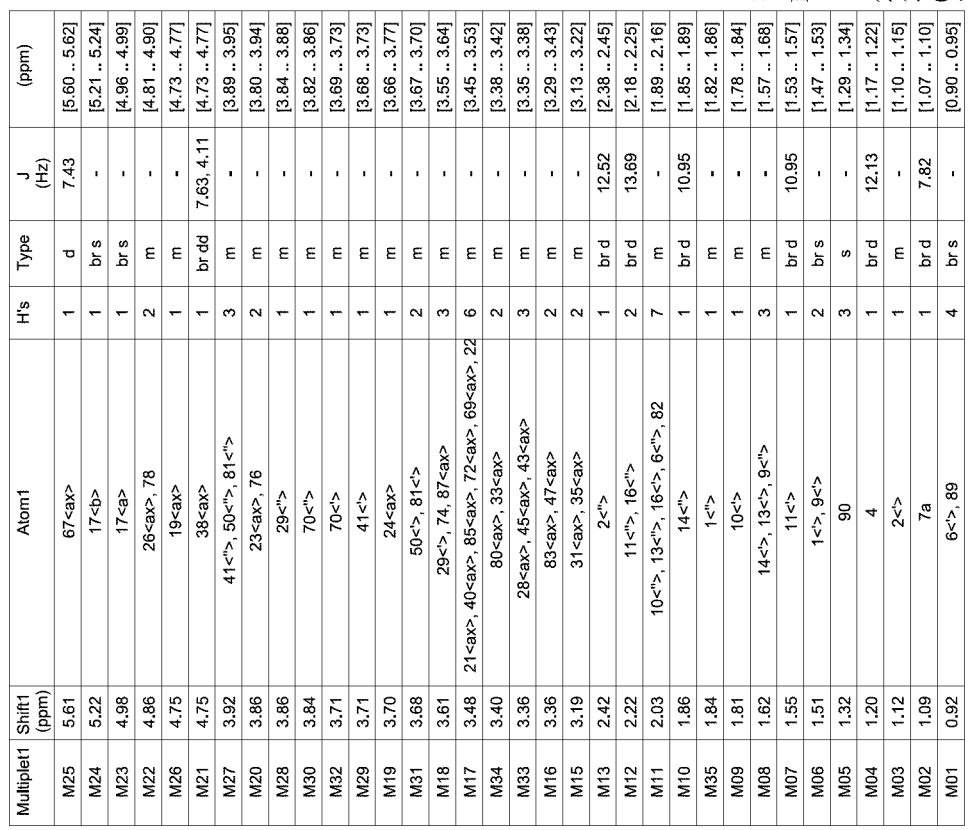

Homonuclear dipolar correlations between:
H-38 and H-23
H-26 and H-24
H-78 and H-76
H-67 and Me-90, Me-89
H-19 and H-11', H-13", H-16"
H-17a and H-16, H-16"
H-17b and H-13'
H-4 and H-7a, Me-90
Me-89 and H-11"
H-7a and H-16'

$^1$H NMR (800 MHz, Solvent) δ ppm 0.92 (br s, 4 H) 1.09 (br d, =7.82 Hz, 1 H) 1.10 - 1.15 (m, 1 H) 1.20 (br d, =12.13 Hz, 1 H) 1.32 (s, 3 H) 1.51 (br s, 2 H) 1.55 (br d, =10.95 Hz, 1 H) 1.57 - 1.68 (m, 3 H) 1.78 - 1.84 (m, 1 H) 1.82 - 1.86 (m, 1 H) 1.86 (br d, =10.95 Hz, 1 H) 1.89 - 2.16 (m, 7 H) 2.22 (br d, =13.69 Hz, 2 H) 2.42 (br d, =12.52 Hz, 1 H) 3.13 - 3.22 (m, 2 H) 3.29 - 3.43 (m, 2 H) 3.35 - 3.38 (m, 3 H) 3.38 - 3.42 (m, 2 H) 3.45 - 3.53 (m, 6 H) 3.55 - 3.64 (m, 3 H) 3.66 - 3.77 (m, 1 H) 3.67 - 3.70 (m, 2 H) 3.68 - 3.73 (m, 1 H) 3.69 - 3.73 (m, 1 H) 3.80 - 3.94 (m, 2 H) 3.82 - 3.86 (m, 1 H) 3.84 - 3.88 (m, 1 H) 3.89 - 3.95 (m, 3 H) 4.75 (br dd, =7.63, 4.11 Hz, 1 H) 4.73 - 4.77 (m, 1 H) 4.81 - 4.90 (m, 2 H) 4.98 (br s, 1 H) 5.22 (br s, 1 H) 5.61 (d, =7.43 Hz, 1 H)

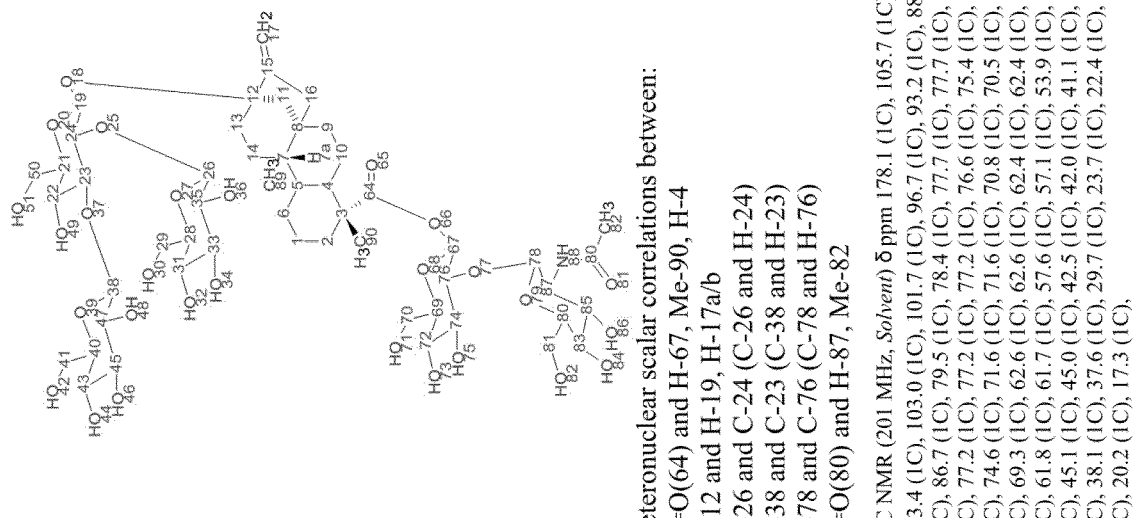

Figure 8AE

Heteronuclear scalar correlations between:
C=O(64) and H-67, Me-90, H-4
C-12 and H-19, H-17a/b
H-26 and C-24 (C-26 and H-24)
H-38 and C-23 (C-38 and H-23)
H-78 and C-76 (C-78 and H-76)
C=O(80) and H-87, Me-82

$^{13}$C NMR (201 MHz, Solvent) δ ppm 178.1 (1C), 105.7 (1C), 103.4 (1C), 103.0 (1C), 101.7 (1C), 96.7 (1C), 93.2 (1C), 88.4 (1C), 86.7 (1C), 79.5 (1C), 78.4 (1C), 77.7 (1C), 77.7 (1C), 77.6 (1C), 77.2 (1C), 77.2 (1C), 77.2 (1C), 76.6 (1C), 75.4 (1C), 75.2 (1C), 74.6 (1C), 71.6 (1C), 71.6 (1C), 70.8 (1C), 70.5 (1C), 70.5 (1C), 69.3 (1C), 62.6 (1C), 62.6 (1C), 62.4 (1C), 62.4 (1C), 61.8 (1C), 61.8 (1C), 61.7 (1C), 57.6 (1C), 57.1 (1C), 53.9 (1C), 47.9 (1C), 45.1 (1C), 45.0 (1C), 42.5 (1C), 42.0 (1C), 41.1 (1C), 40.1 (1C), 38.1 (1C), 37.6 (1C), 29.7 (1C), 23.7 (1C), 22.4 (1C), 21.0 (1C), 20.2 (1C), 17.3 (1C).

Steviol+4Glc+1GlcNAc (#11)

| F2 Atom | δ(1H) (ppm) | F1 Atom | δ(13C) (ppm) | F2 Atom | δ(1H) (ppm) | F1 Atom | δ(13C) (ppm) |
|---|---|---|---|---|---|---|---|
| 1<"> | 1.84 | 1 | 20.2 | 22 | 3.49 | 22 | 69.3 |
| 1<> | 1.51 | | | 23<ax> | 3.86 | 23 | 86.7 |
| 2<"> | 2.42 | 2 | 37.6 | 24<ax> | 3.72 | 24 | 79.5 |
| 2<> | 1.12 | | | 26<ax> | 4.89 | 26 | 103 |
| | | | | 28<ax> | 3.37 | 28 | 77.7 |
| 3 | | 3 | 45.1 | 29<"> | 3.86 | 29 | 62.6 |
| 4 | 1.2 | 4 | 57.6 | 29<> | 3.58 | 29 | 62.6 |
| 5 | | 5 | 40.1 | 31<ax> | 3.17 | 31 | 71.6 |
| 6<"> | 1.91 | 6 | 41.1 | 33<ax> | 3.41 | 33 | 77.2 |
| 6<> | 0.92 | | | 35<ax> | 3.2 | 35 | 75.4 |
| | | | | 38<ax> | 4.75 | 38 | 103.4 |
| 7a | 1.08 | 7 | 53.9 | 40<ax> | 3.47 | 40 | 77.2 |
| 8 | | 8 | 42.5 | 41<"> | 3.93 | 41 | 62.4 |
| 9<"> | 1.62 | 9 | 42 | 41<> | 3.71 | 41 | 62.4 |
| 9<> | 1.51 | | | 43<ax> | 3.37 | 43 | 70.8 |
| 10<"> | 1.93 | 10 | 22.4 | 45<ax> | 3.36 | 45 | 76.6 |
| 10<> | 1.81 | | | 47<ax> | 3.33 | 47 | 74.6 |
| 11<"> | 2.22 | 11 | 45 | 50<"> | 3.92 | 50 | 61.8 |
| 11<> | 1.55 | | | 50<> | 3.69 | | |
| | | | | | | 64 | 178.1 |
| 12 | | 12 | 88.4 | 67<ax> | 5.61 | 67 | 93.2 |
| 13<"> | 1.96 | 13 | 38.1 | 69<ax> | 3.52 | 69 | 77.7 |
| 13<> | 1.59 | | | 70<"> | 3.84 | 70 | 61.7 |
| 14<"> | 1.86 | 14 | 21 | 70<> | 3.71 | | |
| 14<> | 1.65 | | | 72<ax> | 3.46 | 72 | 70.5 |
| 16<"> | 2.22 | 16 | 47.9 | 74 | 3.63 | 74 | 77.6 |
| 16<> | 2.14 | | | 76 | 3.82 | 76 | 78.4 |
| 17<a> | 4.98 | 17 | 105.7 | 78 | 4.83 | 78 | 101.7 |
| 17<b> | 5.22 | | | 80<ax> | 3.41 | 80 | 77.2 |
| 19<ax> | 4.75 | 19 | 96.7 | 81<"> | 3.92 | 81 | 61.8 |
| 21<ax> | 3.5 | 21 | 75.2 | 81<> | 3.69 | | |
| | | | | 82 | 2.06 | 82 | 23.7 |

$^{13}$C NMR (201 MHz, DMSO $d_6$) δ ppm 174.9 (1C), 152.6 (1C), 104.8 (1C), 103.3 (1C), 101.8 (1C), 98.1 (1C), 91.9 (1C), 87.0 (1C), 85.8 (1C), 77.8 (1C), 77.3 (2C), 77.0 (3C), 76.9 (1C), 75.5 (1C), 74.3 (1C), 74.0 (2C), 71.4 (1C), 70.5 (1C), 70.3 (1C), 68.3 (1C), 62.0 (1C), 61.4 (1C), 61.3 (1C), 60.7 (1C), 56.7 (1C), 53.4 (1C), 47.8 (1C), 43.6 (2C), 41.6 (1C), 41.3 (1C), 40.2 (1C), 39.1 (1C), 37.9 (1C), 36.6 (1C), 28.5 (1C), 21.4 (1C), 20.1 (1C), 19.5 (1C), 16.4 (1C)

Steviol+4Glc (#26)

| F2 Atom | δ(1H) (ppm) | F1 Atom | δ(13C) (ppm) | | | |
|---|---|---|---|---|---|---|
| 2<ax> | 5.52 | 2 | 91.9 | 35<> | 1.5 | |
| 3<ax> | 3.73 | 3 | 75.5 | 36<¹> | 2.4 | 36 | 36.6 |
| 4<ax> | 3.69 | 4 | 87 | 36<> | 0.89 | | |
| 5<ax> | 3.34 | 5 | 68.3 | 37<¹> | 1.74 | 37 | 19.5 |
| 6<ax> | 3.33 | 6 | 77.8 | 37<> | 1.35 | | |
| | | 8 | 174.9 | 38<¹> | 1.78 | 38 | 40.2 |
| 11<ax> | 4.79 | 11 | 101.8 | 38<> | 0.77 | | |
| 13<ax> | 3.14 | 13 | 77.3 | 39 | 1.78 | 39 | 21.4 |
| 14<ax> | 2.89 | 14 | 71.4 | 40<¹> | 1.49 | 40 | 41.3 |
| 15<ax> | 3.14 | 15 | 77 | 40<> | 1.35 | | |
| 16<ax> | 2.83 | 16 | 74.3 | 41<¹> | 2.06 | 41 | 47.8 |
| 18<ax> | 4.47 | 18 | 103.3 | 41<> | 2 | | |
| 20<ax> | 3.21 | 20 | 77.3 | | | 42 | 152.6 |
| 21<ax> | 3.07 | 21 | 70.3 | 43<¹> | 3.59 | 43 | 61.4 |
| 22<ax> | 3.14 | 22 | 77 | 43<> | 3.39 | | |
| 23<ax> | 3.06 | 23 | 74 | 48<¹> | 3.4 | 48 | 61.3 |
| 25<¹> | 3.65 | 25 | 60.7 | 48<> | 3.71 | | |
| 25<> | 3.5 | | | 53 | 1.17 | 53 | 28.5 |
| | | | | 54 | 0.82 | 54 | 16.4 |
| 28 | 1.01 | 27 | 43.6 | 56<ax> | 4.28 | 56 | 98.1 |
| | | 28 | 56.7 | 58<ax> | 2.98 | 58 | 76.9 |
| | | 29 | 39.1 | 59<ax> | 3.03 | 59 | 70.5 |
| | | 31 | 41.6 | 60<ax> | 3.14 | 60 | 77 |
| 32<¹> | 2 | 32 | 43.6 | 61<ax> | 2.91 | 61 | 74 |
| 32<> | 1.48 | | | 62<a> | 4.77 | 62 | 104.8 |
| | | 33 | 85.8 | 62<b> | 5.15 | | |
| 34<¹> | 1.82 | 34 | 37.9 | 63<¹> | 3.73 | 63 | 62 |
| 34<> | 1.39 | | | 63<> | 3.39 | | |
| 35<¹> | 1.7 | 35 | 20.1 | 68 | 0.94 | 30 | 53.4 |

Steviol+5Glc (#22)

Figure 8AL

Steviol+5Glc (#22)

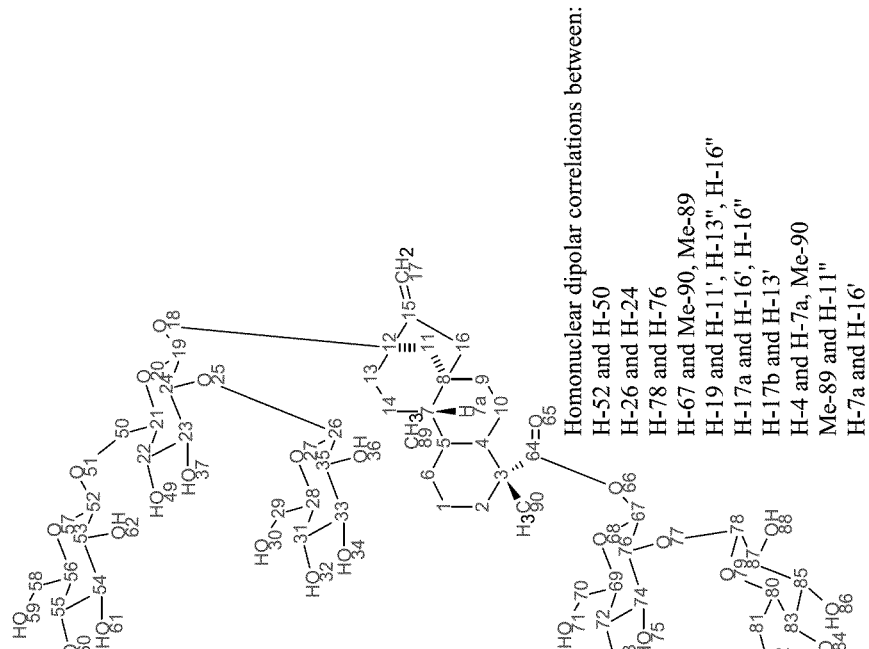

| Multiplet1 | Shift1 (ppm) | Atom1 | Hs | Type | J (Hz) | (ppm) |
|---|---|---|---|---|---|---|
| M22 | 5.50 | 67<ax> | 1 | d | 7.82 | [5.49 .. 5.51] |
| M21 | 5.00 | 17<b> | 1 | br s | - | [4.99 .. 5.01] |
| M20 | 4.79 | 17<a> | 1 | s | - | [4.78 .. 4.81] |
| M19 | 4.65 | 19<ax> | 1 | d | 7.82 | [4.64 .. 4.67] |
| M23 | 4.62 | 78<ax> | 1 | m | - | [4.61 .. 4.64] |
| M32 | 4.59 | 26<ax> | 1 | m | - | [4.58 .. 4.61] |
| M18 | 4.34 | 52<ax> | 1 | d | 8.07 | [4.33 .. 4.35] |
| M17 | 3.97 | 50<'> | 1 | br d | 10.51 | [3.95 .. 3.98] |
| M25 | 3.76 | 81<'>, 58<'>, 29<'> | 3 | m | - | [3.72 .. 3.79] |
| M24 | 3.74 | 70<'>, 76<ax> | 2 | m | - | [3.72 .. 3.76] |
| M16 | 3.73 | 74<ax>, 50<'> | 2 | m | - | [3.66 .. 3.78] |
| M26 | 3.60 | 81<'>, 70<'>, 58<'> | 3 | m | - | [3.58 .. 3.62] |
| M15 | 3.57 | 29<'>, 23<ax> | 2 | m | - | [3.50 .. 3.62] |
| M14 | 3.34 | 85<ax>, 54<ax>, 33<ax>, 72<ax>, 21, 22, 69, 24<ax> | 8 | m | - | [3.24 .. 3.45] |
| M28 | 3.29 | 80<ax>, 56<ax>, 55<ax>, 28<ax> | 4 | m | - | [3.26 .. 3.32] |
| M27 | 3.20 | 83<ax> | 1 | m | - | [3.18 .. 3.21] |
| M13 | 3.16 | 87<ax>, 31<ax>, 53<ax>, 35<ax> | 4 | m | - | [3.11 .. 3.21] |
| M12 | 2.18 | 2<'> | 1 | br d | 13.20 | [2.16 .. 2.20] |
| M11 | 2.06 | 11<'>, 16<'> | 2 | m | - | [2.03 .. 2.09] |
| M10 | 1.93 | 16<'> | 1 | m | - | [1.90 .. 1.96] |
| M09 | 1.78 | 13<'>, 10<'>, 6<'> | 3 | m | - | [1.73 .. 1.84] |
| M29 | 1.71 | 1<'> | 1 | m | - | [1.67 .. 1.74] |
| M08 | 1.70 | 14<'> | 1 | br d | 10.51 | [1.67 .. 1.74] |
| M07 | 1.60 | 10<'> | 1 | m | - | [1.57 .. 1.64] |
| M06 | 1.46 | 13<'>, 9<'>, 14<'> | 3 | m | - | [1.40 .. 1.52] |
| M05 | 1.34 | 11<'>, 9<'>, 1<'> | 3 | m | - | [1.29 .. 1.38] |
| M04 | 1.13 | 90 | 3 | s | - | [1.10 .. 1.15] |
| M03 | 0.98 | 2<'>, 4 | 2 | m | - | [0.92 .. 1.04] |
| M02 | 0.89 | 7a | 1 | br d | 7.83 | [0.87 .. 0.91] |
| M01 | 0.75 | 6<'>, 89 | 4 | m | - | [0.71 .. 0.77] |

Homonuclear dipolar correlations between:
H-52 and H-50
H-26 and H-24
H-78 and H-76
H-67 and Me-90, Me-89
H-19 and H-11', H-13", H-16"
H-17a and H-16', H-16"
H-17b and H-13'
H-4 and H-7a, Me-90
Me-89 and H-11"
H-7a and H-16'

¹H NMR (800 MHz, *DEUTERIUM OXIDE*) δ ppm 0.71 - 0.77 (m, 4 H) 0.89 (br d, J=7.83 Hz, 1 H) 0.92 - 1.04 (m, 2 H) 1.13 (s, 3 H) 1.29 - 1.38 (m, 3 H) 1.40 - 1.52 (m, 3 H) 1.57 - 1.64 (m, 1 H) 1.70 (br d, J=10.51 Hz, 1 H) 1.67 - 1.74 (m, 1 H) 1.73 - 1.84 (m, 3 H) 1.90 - 1.96 (m, 1 H) 2.03 - 2.09 (m, 2 H) 2.18 (br d, J=13.20 Hz, 1 H) 3.11 - 3.21 (m, 4 H) 3.18 - 3.21 (m, 1 H) 3.24 - 3.45 (m, 8 H) 3.26 - 3.32 (m, 4 H) 3.50 - 3.62 (m, 2 H) 3.58 - 3.62 (m, 3 H) 3.66 - 3.78 (m, 2 H) 3.72 - 3.76 (m, 2 H) 3.72 - 3.79 (m, 3 H) 3.97 (br d, J=10.51 Hz, 1 H) 4.34 (d, J=8.07 Hz, 1 H) 4.58 - 4.61 (m, 1 H) 4.61 - 4.64 (m, 1 H) 4.65 (d, J=7.82 Hz, 1 H) 4.79 (s, 1 H) 5.00 (br s, 1 H) 5.50 (d, J=7.82 Hz, 1 H)

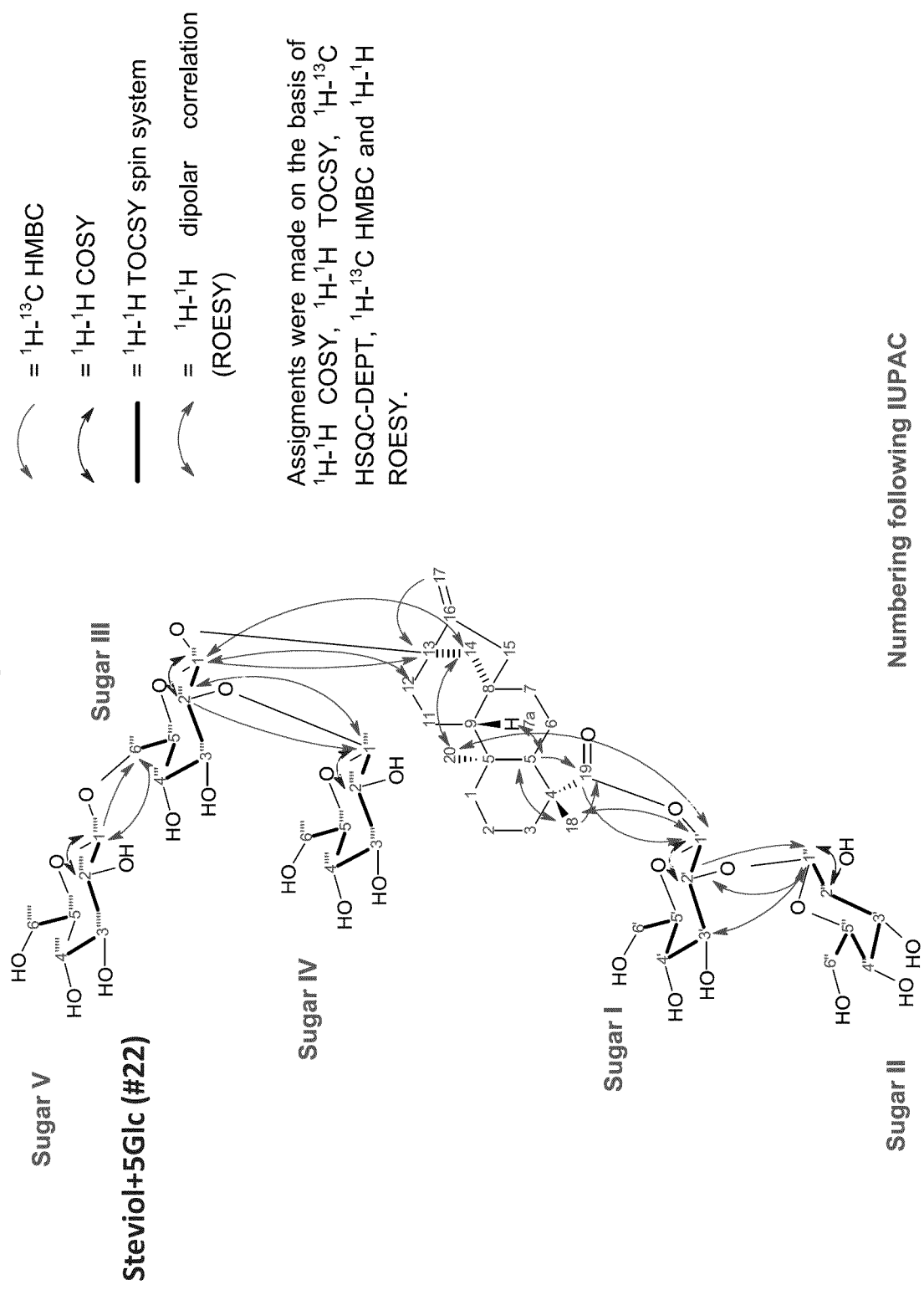
Figure 8AN Steviol+5Glc (#22)

Figure 8AP

Steviol+7Glc (#14)

| Multiplet1 | Shift1 (ppm) | Atom1 | H's | Type | J (Hz) | (ppm) |
|---|---|---|---|---|---|---|
| M29 | 5.62 | 10<ax> | 1 | d | 7.83 | [5.60 .. 5.63] |
| M28 | 5.15 | 73<b> | 1 | br s | - | [5.13 .. 5.17] |
| M27 | 4.93 | 26<ax> | 1 | m | - | [4.91 .. 4.96] |
| M30 | 4.93 | 73<a> | 1 | m | - | [4.92 .. 4.94] |
| M31 | 4.85 | 85<ax> | 1 | br d | 7.83 | [4.83 .. 4.86] |
| M50 | 4.82 | 78<ax> | 1 | m | - | [4.81 .. 4.82] |
| M26 | 4.80 | 2<ax> | 1 | br d | 8.56 | [4.78 .. 4.81] |
| M45 | 4.78 | 67<ax> | 1 | m | - | [4.78 .. 4.79] |
| M25 | 4.51 | 19<ax> | 1 | d | 8.07 | [4.49 .. 4.53] |
| M24 | 4.23 | 17<"> | 1 | br d | 10.03 | [4.20 .. 4.25] |
| M23 | 4.12 | 8<ax>, 9<ax> | 2 | m | - | [4.08 .. 4.17] |
| M22 | 3.89 | 71<ax>, 43<'> | 2 | m | - | [3.81 .. 3.95] |
| M35 | 3.88 | 91<">, 35<"> | 2 | m | - | [3.84 .. 3.93] |
| M33 | 3.88 | 38<">, 17<'> | 2 | m | - | [3.84 .. 3.93] |
| M32 | 3.88 | 96<"> | 1 | m | - | [3.86 .. 3.90] |
| M34 | 3.83 | 74<"> | 1 | m | - | [3.82 .. 3.85] |
| M36 | 3.74 | 35<'> | 1 | m | - | [3.72 .. 3.76] |
| M46 | 3.71 | 91<'>, 74<'>, 38<'> | 3 | m | - | [3.69 .. 3.73] |
| M21 | 3.71 | 72<ax>, 6<ax>, 43<'> | 3 | m | - | [3.67 .. 3.75] |
| M20 | 3.62 | 96<'>, 12<ax>, 13<ax> | 3 | m | - | [3.59 .. 3.65] |
| M19 | 3.49 | 5<ax> | 1 | m | - | [3.44 .. 3.54] |
| M40 | 3.47 | 82<ax>, 70<ax>, 23<ax> | 3 | m | - | [3.39 .. 3.56] |

| | | | | | | |
|---|---|---|---|---|---|---|
| M41 | 3.47 | 89<ax>, 21<ax>, 4<ax>, 30<ax> | 4 | m | - | [3.39 .. 3.55] |
| M42 | 3.42 | 28<ax> | 1 | m | - | [3.41 .. 3.43] |
| M43 | 3.40 | 3<ax>, 87<ax> | 2 | m | - | [3.38 .. 3.43] |
| M37 | 3.40 | 81<ax> | 1 | m | - | [3.37 .. 3.43] |
| M18 | 3.39 | 83<ax>, 22<ax> | 2 | m | - | [3.36 .. 3.43] |
| M38 | 3.39 | 80<ax>, 69<ax> | 2 | m | - | [3.35 .. 3.43] |
| M17 | 3.28 | 24<ax>, 29<ax> | 2 | m | - | [3.23 .. 3.34] |
| M39 | 3.26 | 90<ax>, 31<ax> | 2 | m | - | [3.22 .. 3.29] |
| M16 | 3.18 | 88<ax> | 1 | m | - | [3.16 .. 3.21] |
| M15 | 2.26 | 57<"> | 1 | t | 9.41 | [2.22 .. 2.29] |
| M14 | 2.18 | 53<">, 62<"> | 2 | br d | 12.23 | [2.15 .. 2.21] |
| M13 | 2.09 | 62<'> | 1 | br d | 17.12 | [2.07 .. 2.11] |
| M12 | 1.99 | 55<"> | 1 | m | - | [1.96 .. 2.02] |
| M47 | 1.92 | 60<"> | 1 | m | - | [1.89 .. 1.95] |
| M11 | 1.90 | 58<">, 59<"> | 2 | m | - | [1.86 .. 1.95] |
| M10 | 1.82 | 56<'> | 1 | br d | 9.78 | [1.78 .. 1.86] |
| M09 | 1.70 | 60<'> | 1 | m | - | [1.67 .. 1.73] |
| M08 | 1.61 | 56<'> | 1 | m | - | [1.57 .. 1.65] |
| M07 | 1.54 | 55<'>, 61<"'> | 2 | br s | - | [1.52 .. 1.57] |
| M06 | 1.48 | 58<'>, 61<'>, 53<'> | 3 | m | - | [1.42 .. 1.52] |
| M05 | 1.26 | 64 | 3 | s | - | [1.24 .. 1.28] |
| M04 | 1.16 | 49 | 1 | br d | 12.72 | [1.14 .. 1.20] |
| M03 | 1.10 | 57<'> | 1 | m | - | [1.06 .. 1.14] |
| M02 | 1.02 | 101 | 1 | br d | 7.58 | [0.96 .. 1.05] |
| M01 | 0.88 | 65 | 3 | s | - | [0.83 .. 0.93] |
| M44 | 0.87 | 59<'> | 3 | m | - | [0.84 .. 0.90] |

Homonuclear dipolar correlations between:
H-26 and H-9
H-2 and H-8
H-19 and H-17
H-85 and H-72
H-78 and H-71
H-10 and Me-65, Me-64
H-67 and H-53', H-55''
H-101 and H-49
H-49 and H-59', H-101, Me-64
Me-65 and H-60', H-53'', H-53' (indirect)
Me-64 and H-60''

$^1$H NMR (800 MHz, DEUTERIUM OXIDE) δ ppm 0.88 (s, 3 H) 0.84 - 0.90 (m, 1 H) 1.02 (br d, J=7.58 Hz, 1 H) 1.06 - 1.14 (m, 1 H) 1.16 (br d, J=12.72 Hz, 1 H) 1.26 (s, 3 H) 1.42 - 1.52 (m, 3 H) 1.54 (br s, 2 H) 1.57 - 1.65 (m, 1 H) 1.67 - 1.73 (m, 1 H) 1.82 (br d, J=9.78 Hz, 1 H) 1.86 - 1.95 (m, 2 H) 1.89 - 1.95 (m, 1 H) 1.96 - 2.02 (m, 1 H) 2.09 (br d, J=17.12 Hz, 1 H) 2.15 - 2.21 (m, 2 H) 2.26 (br d, J=12.23 Hz, 1 H) 3.18 (t, J=9.41 Hz, 1 H) 3.22 - 3.29 (m, 2 H) 3.23 - 3.34 (m, 2 H) 3.35 - 3.43 (m, 2 H) 3.36 - 3.43 (m, 2 H) 3.37 - 3.43 (m, 1 H) 3.38 - 3.42 (m, 2 H) 3.39 - 3.56 (m, 3 H) 3.39 - 3.55 (m, 4 H) 3.41 - 3.43 (m, 1 H) 3.44 - 3.54 (m, 1 H) 3.59 - 3.65 (m, 3 H) 3.67 - 3.75 (m, 3 H) 3.69 - 3.73 (m, 3 H) 3.72 - 3.76 (m, 1 H) 3.81 - 3.95 (m, 2 H) 3.82 - 3.85 (m, 1 H) 3.84 - 3.93 (m, 2 H) 3.84 - 3.93 (m, 2 H) 3.86 - 3.90 (m, 1 H) 4.08 - 4.17 (m, 2 H) 4.23 (br d, J=10.03 Hz, 1 H) 4.51 (d, J=8.07 Hz, J=10.03 Hz, 1 H) 4.78 - 4.79 (m, 1 H) 4.80 (br d, J=8.56 Hz, 1 H) 4.81 - 4.82 (m, 1 H) 4.85 (br d, J=7.83 Hz, 1 H) 4.91 - 4.96 (m, 1 H) 4.92 - 4.94 (m, 1 H) 5.15 (br s, 1 H) 5.62 (d, J=7.83 Hz, 1 H)

Figure 8AQ

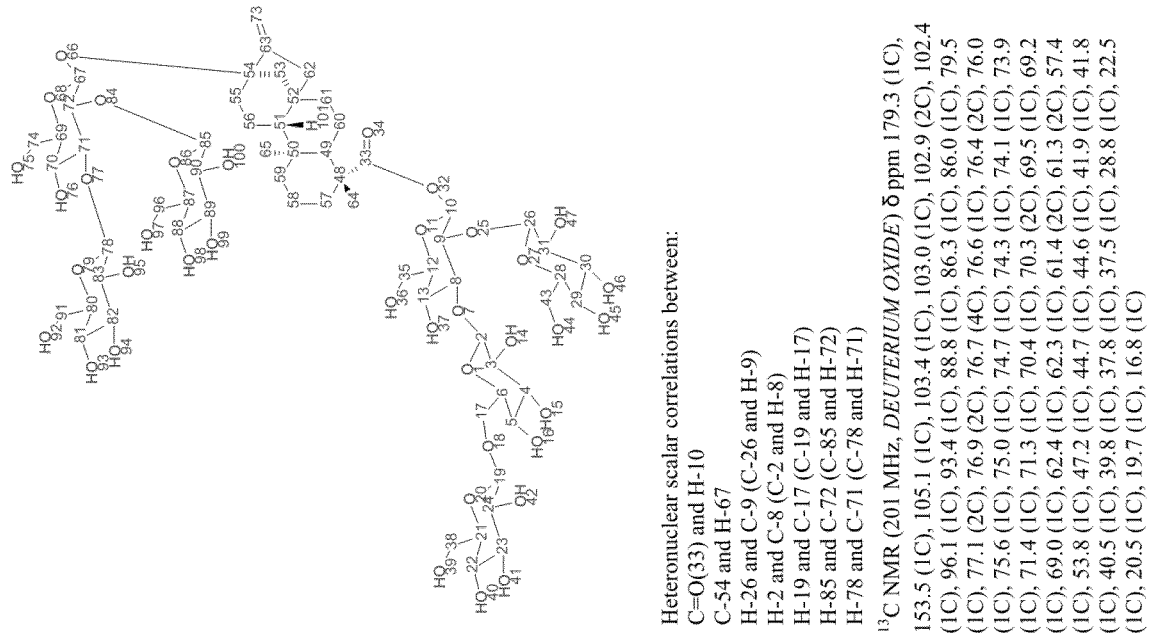

Steviol+7Glc (#14)

| F2 Atom | δ(1H) (ppm) | F1 Atom | δ(13C) (ppm) | | | |
|---|---|---|---|---|---|---|
| 2<ax> | 4.8 | 2 | 102.9 | | 48 | 44.7 |
| 3<ax> | 3.4 | 3 | 77.1 | 49 | 49 | 57.4 |
| 4<ax> | 3.52 | 4 | 76.7 | | 50 | 39.8 |
| 5<ax> | 3.49 | 5 | 70.4 | | 52 | 41.9 |
| 6<ax> | 3.71 | 6 | 75.6 | | 53 | 44.6 |
| 8<ax> | 4.14 | 8 | 86.3 | 53<'> | | |
| 9<ax> | 4.1 | 9 | 76.6 | 53<> | | |
| 10<ax> | 5.62 | 10 | 93.4 | | 54 | 88.8 |
| 12<ax> | 3.61 | 12 | 76.9 | 55<'> | 1.99 | 55 | 37.8 |
| 13<ax> | 3.61 | 13 | 69 | 55<> | 1.54 | | |
| 17<'> | 4.23 | 17 | 69.5 | 56<'> | 1.82 | 56 | 20.5 |
| 17<> | 3.86 | | | 56<> | 1.61 | | |
| 19<ax> | 4.51 | 19 | 103.4 | 57<'> | 2.26 | 57 | 37.5 |
| 21<ax> | 3.45 | 21 | 76.7 | 57<> | 1.1 | | |
| 22<ax> | 3.39 | 22 | 70.3 | 58<'> | 1.88 | 58 | 19.7 |
| 23<ax> | 3.49 | 23 | 76.4 | 58<> | 1.46 | | |
| 24<ax> | 3.32 | 24 | 73.9 | 59<'> | 1.89 | 59 | 40.5 |
| 26<ax> | 4.94 | 26 | 102.4 | 59<> | 0.87 | | |
| 28<ax> | 3.41 | 28 | 76.9 | 60<'> | 1.92 | 60 | 22.5 |
| 29<ax> | 3.29 | 29 | 71.3 | 60<> | 1.7 | | |
| 30<ax> | 3.45 | 30 | 76.7 | 61<'> | 1.55 | 61 | 41.8 |
| 31<ax> | 3.24 | 31 | 74.7 | 61<> | 1.47 | | |
| | | 33 | 179.3 | 62<'> | 2.18 | 62 | 47.2 |
| 35<'> | 3.87 | 35 | 61.3 | 62<> | 2.09 | | |
| 35<> | 3.74 | | | | | 63 | 153.5 |
| 38<'> | 3.91 | | | 64 | 1.26 | 64 | 28.8 |
| 38<> | 3.71 | 38 | 61.4 | 65 | 0.88 | 65 | 16.8 |
| 43<'> | 3.93 | 43 | 62.4 | 67<ax> | 4.78 | 67 | 96.1 |
| 43<> | 3.68 | | | 69<ax> | 3.37 | 69 | 74.3 |
| | | | | 70<ax> | 3.5 | 70 | 69.2 |
| | | | | 71<ax> | 3.93 | 71 | 86 |
| | | | | 72<ax> | 3.68 | 72 | 79.5 |

Heteronuclear scalar correlations between:
C=O(33) and H-10
C-54 and H-67
H-26 and C-9 (C-26 and H-9)
H-2 and C-8 (C-2 and H-8)
H-19 and C-17 (C-19 and H-17)
H-85 and C-72 (C-85 and H-72)
H-78 and C-71 (C-78 and H-71)

$^{13}$C NMR (201 MHz, *DEUTERIUM OXIDE*) δ ppm 179.3 (1C), 153.5 (1C), 105.1 (1C), 103.4 (1C), 103.0 (1C), 102.9 (2C), 102.4 (1C), 96.1 (1C), 93.4 (1C), 88.8 (1C), 86.3 (1C), 86.0 (1C), 79.5 (1C), 77.1 (2C), 76.9 (2C), 76.7 (4C), 76.6 (1C), 76.4 (2C), 76.0 (1C), 75.6 (1C), 75.0 (1C), 74.7 (1C), 74.3 (1C), 74.1 (1C), 73.9 (1C), 71.4 (1C), 71.3 (1C), 70.4 (1C), 70.3 (1C), 69.5 (1C), 69.2 (1C), 69.0 (1C), 62.4 (1C), 62.3 (1C), 61.4 (2C), 61.3 (2C), 57.4 (1C), 53.8 (1C), 47.2 (1C), 44.7 (1C), 44.6 (1C), 41.9 (1C), 41.8 (1C), 40.5 (1C), 39.8 (1C), 37.8 (1C), 37.5 (1C), 28.8 (1C), 22.5 (1C), 20.5 (1C), 19.7 (1C), 16.8 (1C)

Steviol+7Glc (#14)

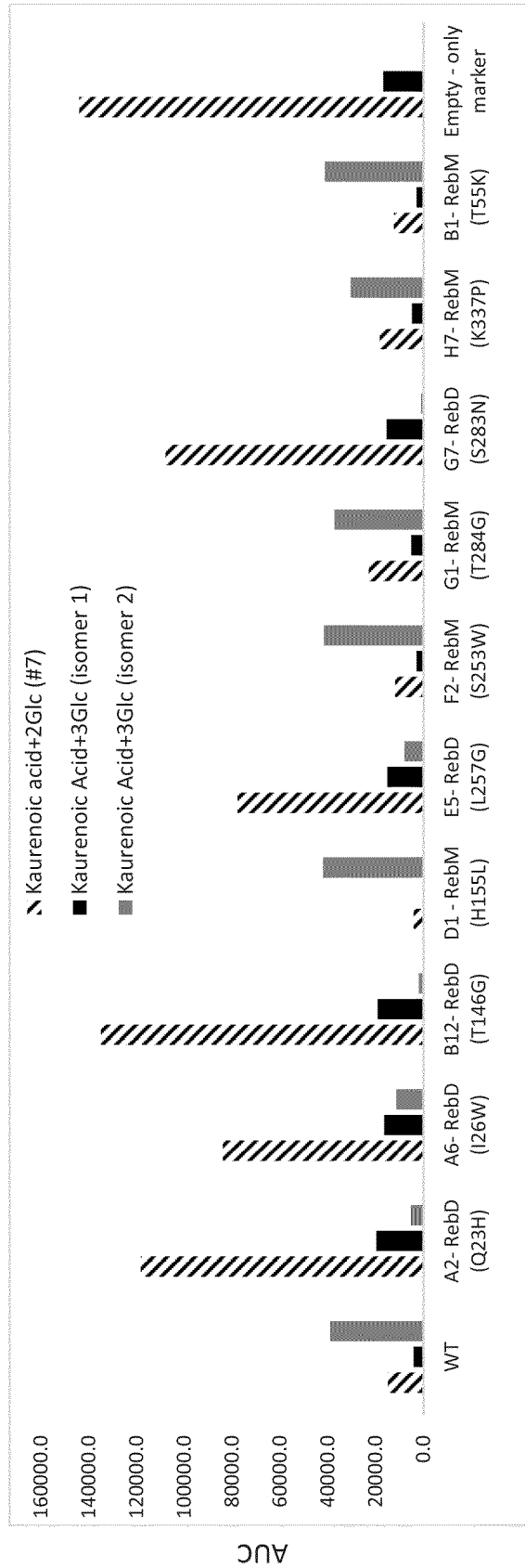

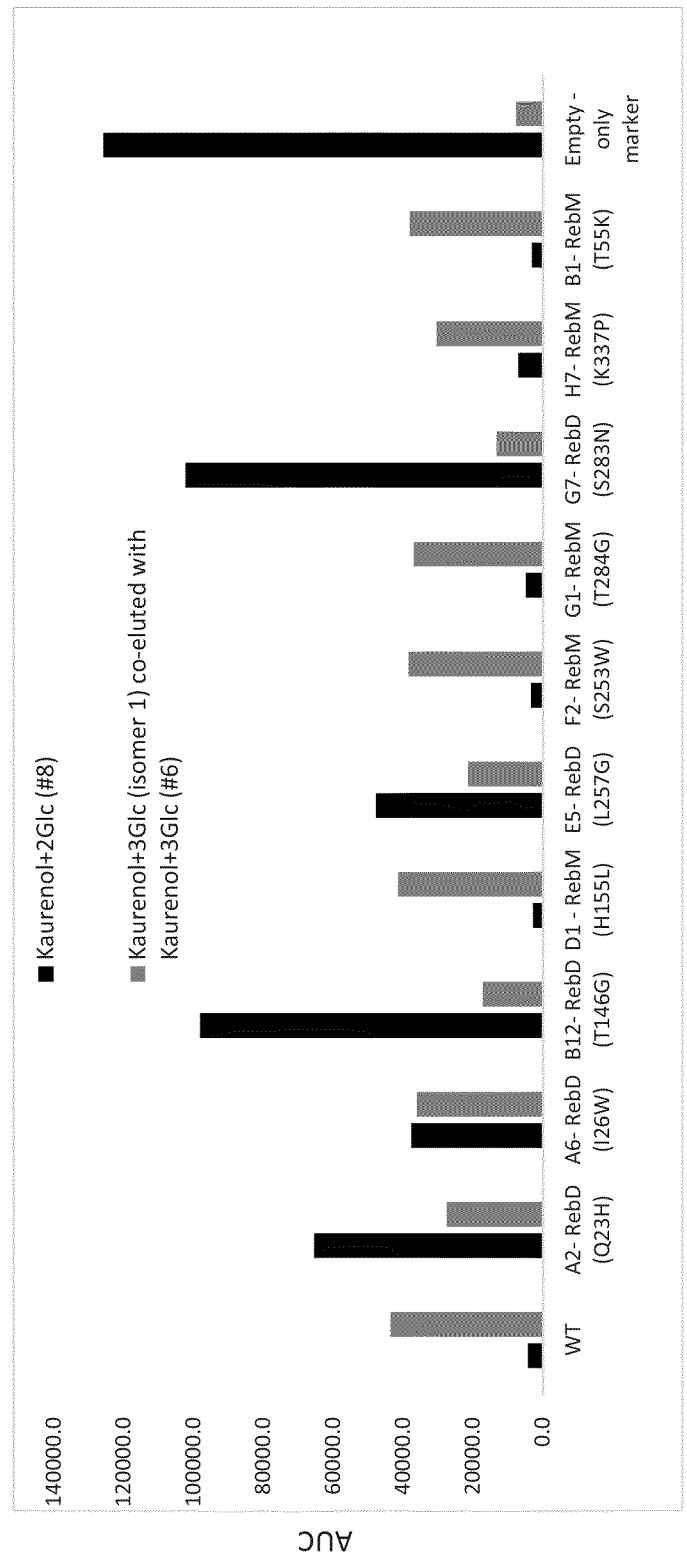

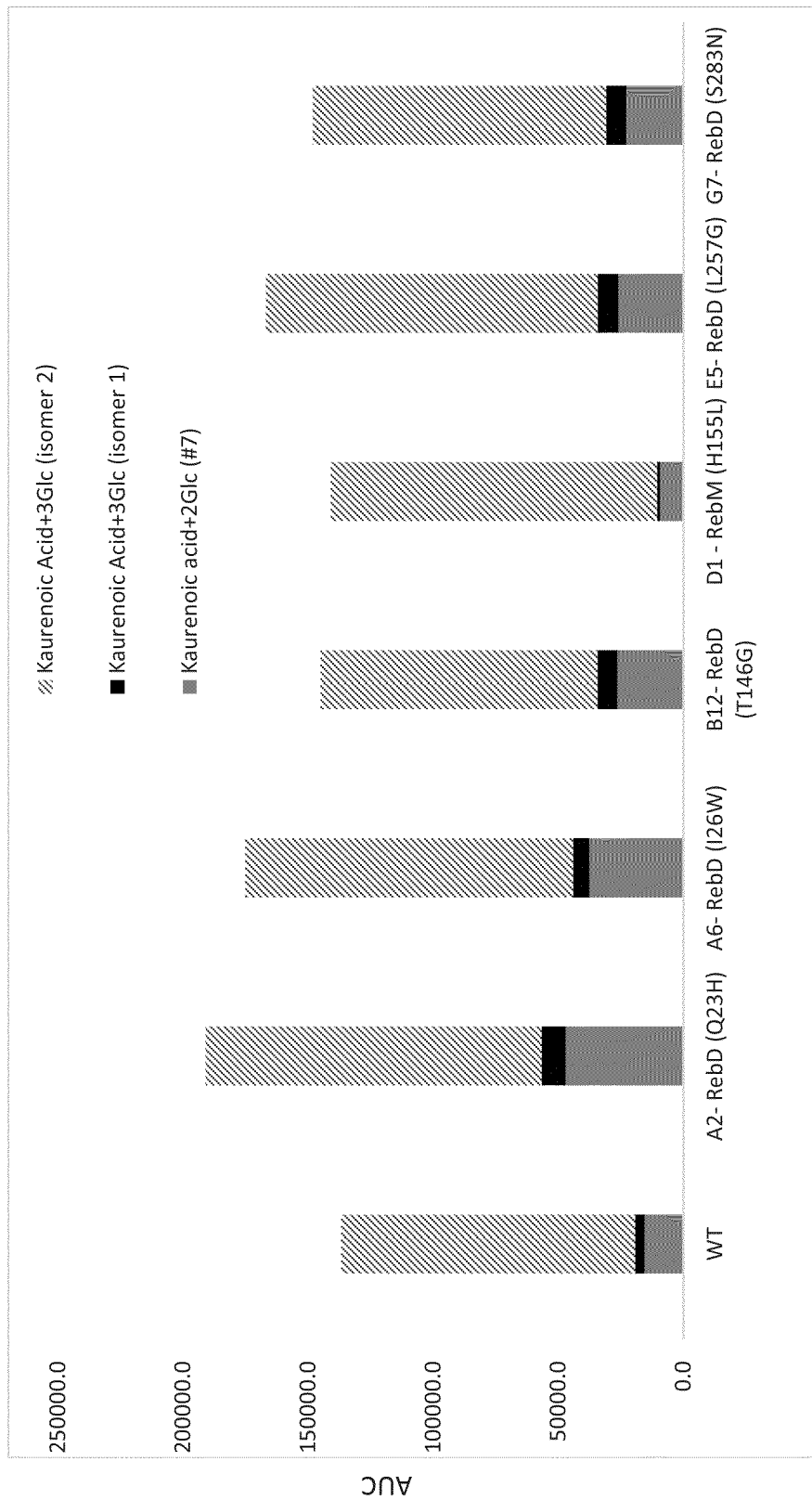

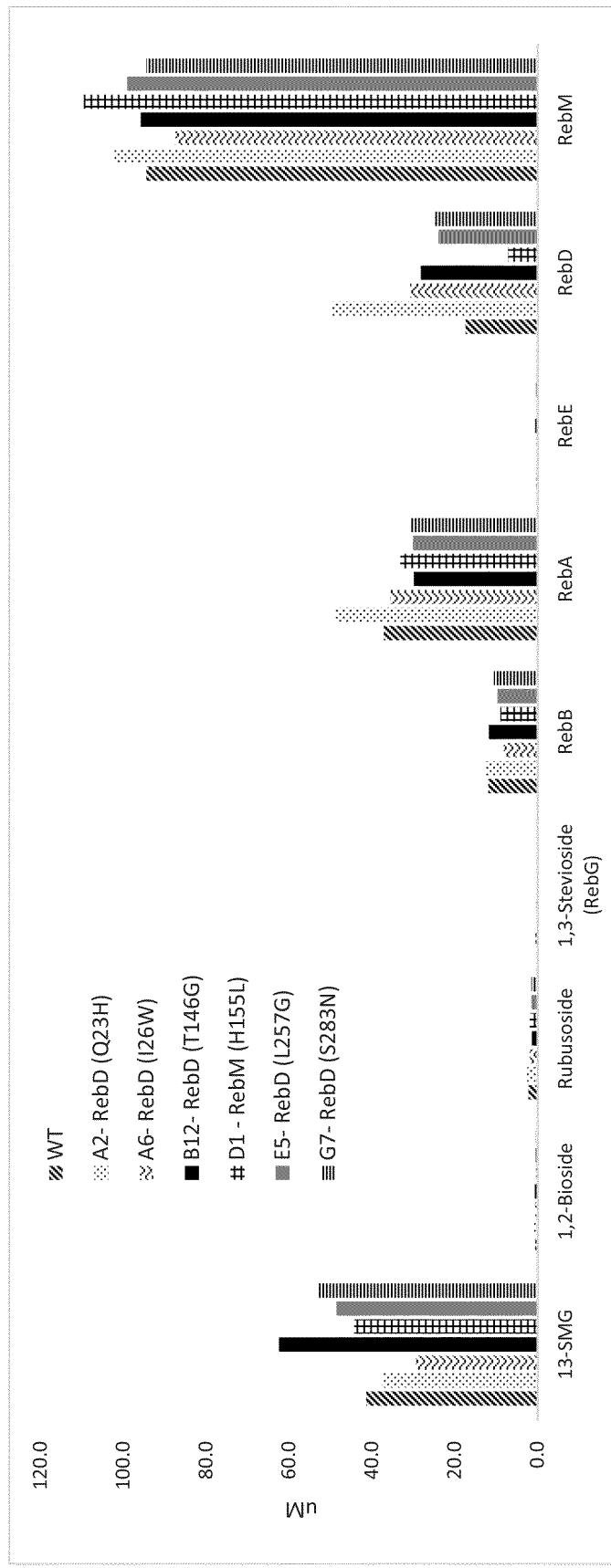

PRODUCTION OF STEVIOL GLYCOSIDE IN RECOMBINANT HOSTS

This application is a continuation of U.S. patent application Ser. No. 16/434,202, filed on Jun. 7, 2019, now U.S. Pat. No. 11,041,183, which is divisional of U.S. patent application Ser. No. 15/541,686, filed on Jul. 5, 2017, now U.S. Pat. No. 10,364,450, which is a U.S. National Phase application under 35 U.S.C. § 371 of PCT/EP2016/052007, filed on Jan. 29, 2016, which claims priority from and the benefit of U.S. Provisional Application No. 62/110,207, filed on Jan. 30, 2015, the specifications of which are hereby incorporated by reference in their entireties.

BACKGROUND OF THE INVENTION

Field of the Invention

This disclosure relates to recombinant production of steviol glycosides and steviol glycoside precursors in recombinant hosts. In particular, this disclosure relates to production of steviol glycosides comprising steviol-13-O-glucoside (13-SMG), steviol-19-O-glucoside (19-SMG), steviol-1,2-bioside, steviol-1,3-bioside, 1,2-stevioside, 1,3-stevioside, rubusoside (Rubu), rebaudioside A (RebA), rebaudioside B (RebB), rebaudioside D (RebD), rebaudioside E (RebE), rebaudioside M (RebM), rebaudioside Q (RebQ), rebaudioside I (RebI), di-glycosylated steviol, tri-glycosylated steviol, tetra-glycosylated steviol, penta-glycosylated steviol, hexa-glycosylated steviol, hepta-glycosylated steviol, glycosylated ent-kaurenol, glycosylated ent-kaurenoic acid, and/or isomers thereof in recombinant hosts.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. Stevia extract is a natural sweetener that can be isolated and extracted from a perennial shrub, Stevia rebaudiana. Stevia is commonly grown in South America and Asia for commercial production of stevia extract. Stevia extract, purified to various degrees, is used commercially as a high intensity sweetener in foods and in blends or alone as a tabletop sweetener.

Chemical structures for several steviol glycosides are shown in FIG. 1, including the diterpene steviol and various steviol glycosides. Extracts of the Stevia plant generally comprise steviol glycosides that contribute to the sweet flavor, although the amount of each steviol glycoside often varies, inter alia, among different production batches.

As recovery and purification of steviol glycosides from the Stevia plant have proven to be labor intensive and inefficient, there remains a need for a recombinant production system that can accumulate high yields of desired steviol glycosides, such as RebD and RebM. There also remains a need for improved production of steviol glycosides in recombinant hosts for commercial uses. As well, there remains a need for identifying enzymes selective towards particular substrates to produce one or more specific steviol glycosides. In some aspects, there remains a need to increase the catalytic capability of enzymes with 19-O glycosylation activity in order to produce higher yields of steviol glycosides.

SUMMARY OF THE INVENTION

It is against the above background that the present invention provides certain advantages and advancements over the prior art.

Although this invention as disclosed herein is not limited to specific advantages or functionalities, the invention provides a recombinant host cell, comprising at least one recombinant gene that is:
  (a) a gene encoding a UGT91D2e polypeptide having at least 90% sequence identity to the amino acid sequence set forth in SEQ ID NO:11;
  (b) a gene encoding a chimeric polypeptide having at least 70% sequence identity to the amino acid sequence set forth in SEQ ID NO:17 or SEQ ID NO:18;
  (c) a gene encoding a UGT85C2 polypeptide having at least 55% sequence identity to the amino acid sequence set forth in SEQ ID NO:7; and/or
  (d) a gene encoding a UGT76G1 polypeptide having at least 50% sequence identity to the amino acid sequence set forth in SEQ ID NO:9;
  wherein the recombinant host cell is capable of producing a steviol glycoside, glycosylated ent-kaurenol compound, and/or a glycosylated ent-kaurenoic acid compound in a cell culture broth.

In one aspect of the recombinant host cell disclosed herein, the UGT91D2e polypeptide comprises a UGT91D2e polypeptide having at least one amino acid substitution at residues 93, 99, 114, 144, 148, 152, 195, 196, 199, 211, 213, 221, 286, 384, 426, 438, or 466 of SEQ ID NO:11.

In one aspect of the recombinant host cell disclosed herein, the UGT85C2 polypeptide comprises a UGT85C2 polypeptide having at least one amino acid substitution at residues 21, 48, 49, 84, 86, 87, 91, 92, 95, 122, 334, or 334 of SEQ ID NO:7.

In one aspect of the recombinant host cell disclosed herein, the UGT76G1 polypeptide comprises a UGT76G1 polypeptide having at least one amino acid substitution at residues 23, 26, 55, 146, 257, 283, and 337 of SEQ ID NO:9.

In one aspect of the recombinant host cell disclosed herein, the UGT91D2e polypeptide comprises one or more of the UGT91D2e polypeptide variants comprising: P93V, S99I, S114F, T144K, T144L, T144M, A148K, M152T, L195G, L195C, L195S, L195N, L195V, V196P, K199C, L211H, L211M, L211I, L211C, L211T, L213E, S221I, V286C, V286N, V286S, G384W, G384K, G384Y, E426G, E438H, 3438M or A466V of SEQ ID NO:11.

In one aspect of the recombinant host cell disclosed herein, the UGT85C2 polypeptide comprises one or more of the UGT85C2 polypeptide variants comprising: Q21L, Q21T, Q21V, F48S, F48H, F48Y, F48R, F48Q, F48W, F48T, I49V, S84G, S84A, S84T, S84C, S84P, S84N, S84V, P86R, P86G, I87H, I87P, I87M, I87Y, L91K, L91R, L91T, L92F, L92I, L92M, I95K, F122S, L334S or L334M of SEQ ID NO:7.

In one aspect of the recombinant host cell disclosed herein, the UGT76G1 polypeptide comprises one or more of the UGT76G1 polypeptide variants comprising: Q23H, I26W, T146G, H155L, L257G, S253W, T284G, S283N, K337P or T55K of SEQ ID NO:9.

In one aspect the recombinant host cell disclosed herein further comprises at least one recombinant gene that is:

(a) a gene encoding a geranylgeranyl diphosphate synthase (GGPPS) polypeptide;
(b) a gene encoding an ent-copalyl diphosphate synthase (CDPS) polypeptide;
(c) a gene encoding an ent-kaurene synthase (KS) polypeptide;
(d) a gene encoding an ent-kaurene oxidase (KO) polypeptide;
(e) a gene encoding a cytochrome P450 reductase (CPR) polypeptide; and
(f) a gene encoding an ent-kaurenoic acid hydroxylase (KAH) polypeptide;
(g) a gene encoding a UGT74G1 polypeptide; and/or
(h) a gene encoding an EUGT11 polypeptide;
wherein the recombinant host cell capable of producing a steviol glycoside, glycosylated ent-kaurenol compound, and/or a glycosylated ent-kaurenoic acid compound in a cell culture broth.

In one aspect of the recombinant host cell disclosed herein,
(a) the GGPPS polypeptide comprises a polypeptide having at least 70% identity to an amino acid sequence set forth in SEQ ID NO:20, SEQ ID NO:22, SEQ ID NO:24, SEQ ID NO:26, SEQ ID NO:28, SEQ ID NO:30, SEQ ID NO:32, or SEQ ID NO:116;
(b) the CDPS polypeptide comprises a polypeptide having at least 70% identity to an amino acid sequence set forth in SEQ ID NO:34, SEQ ID NO:36, SEQ ID NO:38, SEQ ID NO:40, or SEQ ID NO:42;
(c) the KS polypeptide comprises a polypeptide having at least 70% identity to an amino acid sequence set forth in SEQ ID NO:44, SEQ ID NO:46, SEQ ID NO:48, SEQ ID NO:50, or SEQ ID NO:52;
(d) the KO polypeptide comprises a polypeptide having at least 70% identity to an amino acid sequence set forth in SEQ ID NO:60, SEQ ID NO:62, SEQ ID NO:117, SEQ ID NO:66, SEQ ID NO:68, SEQ ID NO:70, SEQ ID NO:72, SEQ ID NO:74, or SEQ ID NO:76;
(e) the CPR polypeptide comprises a polypeptide having at least 70% identity to an amino acid sequence set forth in SEQ ID NO:78, SEQ ID NO:80, SEQ ID NO:82, SEQ ID NO:84, SEQ ID NO:86, SEQ ID NO:88, SEQ ID NO:90, SEQ ID NO:92;
(f) the KAH polypeptide comprises a polypeptide having at least 70% identity to an amino acid sequence set forth in SEQ ID NO:94, SEQ ID NO:97, SEQ ID NO:100, SEQ ID NO:101, SEQ ID NO:102, SEQ ID NO:103, SEQ ID NO:104, SEQ ID NO:106, SEQ ID NO:108, SEQ ID NO:110, SEQ ID NO:112, or SEQ ID NO:114;
(g) the UGT74G1 polypeptide comprises a polypeptide having at least 55% identity to an amino acid sequence set forth in SEQ ID NO:4;
(h) the EUGT11 polypeptide comprises a polypeptide having at least 65% identity to an amino acid sequence set forth in SEQ ID NO:16.

In one aspect of the recombinant host cell disclosed herein, the cell culture broth comprises:
(a) the steviol glycoside, glycosylated ent-kaurenol compound, and/or the glycosylated ent-kaurenoic acid compound produced by the recombinant host cell,
(b) glucose, fructose and/or sucrose; and/or
(c) supplemental nutrients comprising trace metals, vitamins, salts, yeast nitrogen base (YNB), and/or amino acids.

In one aspect of the recombinant host cell disclosed herein, the recombinant host comprises a plant cell, a mammalian cell, an insect cell, a fungal cell, an algal cell, or a bacterial cell.

In one aspect of the recombinant host cell disclosed herein, the bacterial cell comprises *Escherichia* cells, *Lactobacillus* cells, *Lactococcus* cells, *Cornebacterium* cells, *Acetobacter* cells, *Acinetobacter* cells, or *Pseudomonas* cells.

In one aspect of the recombinant host cell disclosed herein, the fungal cell comprises a yeast cell.

In one aspect of the recombinant host cell disclosed herein, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species.

In one aspect of the recombinant host cell disclosed herein, the yeast cell is a *Saccharomyces*.

In one aspect of the recombinant host cell disclosed herein, the yeast cell is a cell from the *Saccharomyces cerevisiae* species.

The invention also provides a method of producing a steviol glycoside, glycosylated ent-kaurenol compound, and/or glycosylated ent-kaurenoic acid compound in a cell culture broth, comprising growing the recombinant host cell disclosed herein in a culture medium, under conditions in which one or more of the genes are expressed;
wherein at least one of the genes is a recombinant gene;
wherein the steviol glycoside, glycosylated ent-kaurenol compound, and/or the glycosylated ent-kaurenoic acid compound is produced by the recombinant host cell.

In one aspect of the methods disclosed herein, one or more of the genes is constitutively expressed and/or expression of one or more of the genes is induced.

The invention also provides a method for producing a steviol glycoside, glycosylated ent-kaurenol compound, and/or the glycosylated ent-kaurenoic acid compound comprising whole-cell bioconversion of plant-derived components or synthetic steviol or steviol glycosides using one or more of:
(a) a UGT91D2e polypeptide having at least 90% sequence identity to the amino acid sequence set forth in SEQ ID NO:11;
(b) a chimeric polypeptide having at least 70% sequence identity to the amino acid sequence set forth in SEQ ID NO:17 or SEQ ID NO:18;
(c) a UGT85C2 polypeptide having at least 55% sequence identity to the amino acid sequence set forth in SEQ ID NO:7; and/or
(d) a UGT76G1 polypeptide having at least 50% sequence identity to the amino acid sequence set forth in SEQ ID NO:9;
wherein at least one of the polypeptides is a recombinant polypeptide.

In one aspect of the methods disclosed herein, the whole cell is the recombinant host cell disclosed herein.

In one aspect of the methods disclosed herein, the recombinant host cell is grown in a fermentor at a temperature for a period of time, wherein the temperature and period of time facilitate the production of the steviol glycoside, glycosylated ent-kaurenol compound, and/or glycosylated ent-kaurenoic acid compound.

The invention also provides an in vitro method for producing a steviol glycoside, glycosylated ent-kaurenol compound, and/or the glycosylated ent-kaurenoic acid compound, comprising adding one or more of:
  (a) a UGT91D2e polypeptide having at least 90% sequence identity to the amino acid sequence set forth in SEQ ID NO:11;
  (b) a chimeric polypeptide having at least 70% sequence identity to the amino acid sequence set forth in SEQ ID NO:17 or SEQ ID NO:18;
  (c) a UGT85C2 polypeptide having at least 55% sequence identity to the amino acid sequence set forth in SEQ ID NO:7; and/or
  (d) a UGT76G1 polypeptide having at least 50% sequence identity to the amino acid sequence set forth in SEQ ID NO:9,
  and plant-derived components or synthetic steviol or steviol glycosides to a reaction mixture;
  wherein at least one of the polypeptides is a recombinant polypeptide; and
  (b) synthesizing steviol glycoside, glycosylated ent-kaurenol compound, and/or the glycosylated ent-kaurenoic acid compound in the reaction mixture.

In one aspect, methods disclosed herein further comprise isolating the steviol glycoside, glycosylated ent-kaurenol compound, and/or the glycosylated ent-kaurenoic acid compound, alone or in combination from the cell culture broth.

In one aspect of the methods disclosed herein, the isolating step comprises:
  (a) providing the cell culture broth comprising the steviol glycoside, glycosylated ent-kaurenol compound, and/or the glycosylated ent-kaurenoic acid compound alone or in combination;
  (b) separating a liquid phase of the cell culture broth from a solid phase of the cell culture broth to obtain a supernatant comprising the steviol glycoside, glycosylated ent-kaurenol compound, and/or the glycosylated ent-kaurenoic acid compound alone or in combination;
  (c) providing one or more adsorbent resins, comprising providing the adsorbent resins in a packed column; and
  (d) contacting the supernatant of step (b) with the one or more adsorbent resins in order to obtain at least a portion of the steviol glycoside, glycosylated ent-kaurenol compound, and/or the glycosylated ent-kaurenoic acid compound alone or in combination thereby isolating the steviol glycoside, glycosylated ent-kaurenol compound, and/or the glycosylated ent-kaurenoic acid compound alone or in combination.

In one aspect, methods disclosed herein further comprise recovering the steviol glycoside, glycosylated ent-kaurenol compound, and/or the glycosylated ent-kaurenoic acid compound alone or a composition comprising the steviol glycoside, glycosylated ent-kaurenol compound, and/or the glycosylated ent-kaurenoic acid compound.

In one aspect of the methods disclosed herein, the recovered composition is enriched for the steviol glycoside, glycosylated ent-kaurenol compound, and/or the glycosylated ent-kaurenoic acid compound relative to a steviol glycoside composition of *Stevia* plant and has a reduced level of non-steviol glycoside *Stevia* plant-derived components relative to a plant-derived stevia extract.

In one aspect of the methods disclosed herein, the cell culture broth comprises:
  (a) one or more steviol glycosides, glycosylated ent-kaurenol compounds, and/or glycosylated ent-kaurenoic acid compounds produced by the recombinant host cell disclosed herein,
  (b) glucose, fructose, and/or sucrose; and/or
  (c) supplemental nutrients comprising trace metals, vitamins, salts, YNB, and/or amino acids.

In one aspect of the methods disclosed herein, the reaction mixture comprising:
  (a) one or more steviol glycosides, glycosylated ent-kaurenol compounds, and/or a glycosylated ent-kaurenoic acid compounds produced in the reaction mixture;
  (b) a UGT polypeptide;
  (c) UDP-glucose, UDP-rhamnose, UDP-xylose, and/or N-acetyl-glucosamine; and/or
  (d) reaction buffer and/or salts.

In one aspect of the methods disclosed herein, the recombinant host cell comprises a plant cell, a mammalian cell, an insect cell, a fungal cell, an algal cell, or a bacterial cell.

In one aspect of the methods disclosed herein, the bacterial cell comprises *Escherichia* cells, *Lactobacillus* cells, *Lactococcus* cells, *Cornebacterium* cells, *Acetobacter* cells, *Acinetobacter* cells, or *Pseudomonas* cells.

In one aspect of the methods disclosed herein, the fungal cell comprises a yeast cell.

In one aspect of the methods disclosed herein, the yeast cell is a cell from *Saccharomyces cerevisiae*, *Schizosaccharomyces pombe*, *Yarrowia lipolytica*, *Candida glabrata*, *Ashbya gossypii*, *Cyberlindnera jadinii*, *Pichia pastoris*, *Kluyveromyces lactis*, *Hansenula polymorpha*, *Candida boidinii*, *Arxula adeninivorans*, *Xanthophyllomyces dendrorhous*, or *Candida albicans* species.

In one aspect of the methods disclosed herein, the yeast cell is a *Saccharomyces*.

In one aspect of the methods disclosed herein, the yeast cell is a cell from the *Saccharomyces cerevisiae* species.

In one aspect of the recombinant hosts and methods disclosed herein,
  (a) the steviol glycoside comprises 13-SMG, 19-SMG, Steviol-1,2-bioside, Steviol-1,3-bioside, 1,2-stevioside, 1,3-stevioside, rubusoside, RebA, RebB, RebD, RebE, RebM, di-glycosylated tri-glycosylated steviol, tetra-glycosylated steviol, penta-glycosylated steviol, hexa-glycosylated steviol, hepta-glycosylated steviol, and/or isomers thereof;
  (b) the glycosylated ent-kaurenol compound comprises di-glycosylated ent-kaurenol, tri-glycosylated ent-kaurenol, and/or isomers thereof; and/or
  (c) the glycosylated ent-kaurenoic acid compound comprises di-glycosylated ent-kaurenoic acid, tri-glycosylated ent-kaurenoic acid, and/or isomers thereof.

In one aspect of the recombinant hosts and methods disclosed herein,
  (a) the di-glycosylated steviol comprises compound 2.23 of Table 1;
  (b) the tri-glycosylated steviol comprises compound 3.1 and/or compound 3.34 of Table 1;
  (c) the tetra-glycosylated steviol comprises compound 4.26 and/or compound 4.33 of Table 1;
  (d) the penta-glycosylated steviol comprises compound 5.22, compound 5.24, and/or compound 5.25 of Table 1;
  (e) the hexa-glycosylated steviol comprises compound 6.1 and/or compound 6.23 of Table 1;
  (f) the hepta-glycosylated steviol comprises compound 7.2, compound 7.5, and/or compound 7.13 of Table 1;
  (g) the glycosylated ent-kaurenoic acid compound comprises compound KA3.1, compound KA3.2, and/or compound KA2.7 of Table 1; and/or
  (h) the glycosylated ent-kaurenol compound comprises compound KL2.8 and/or compound KL3.1 co-eluted with compound KL3.6 of Table 1.

In one aspect of the recombinant hosts and methods disclosed herein,
(a) compound 4.26 has the structure:
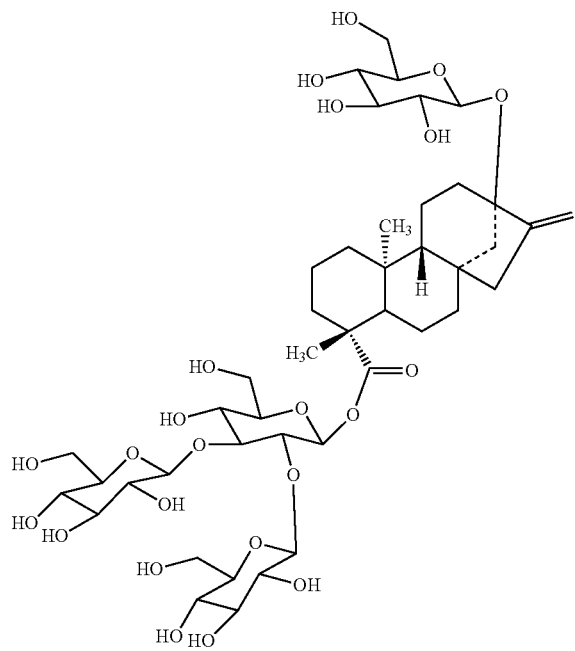
(b) compound 5.22 has the structure:
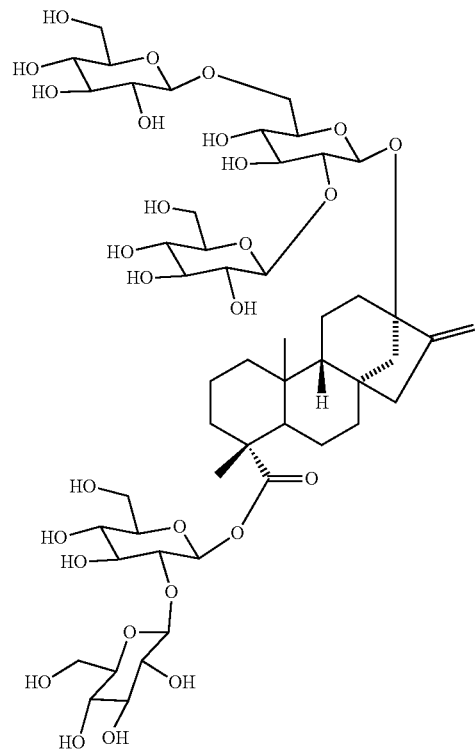
(c) compound 6.1 has the structure:
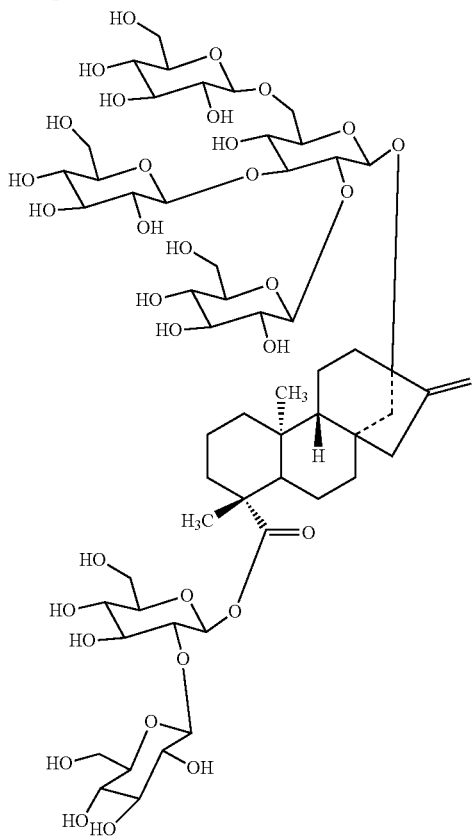
(d) compound 7.2 has the structure:
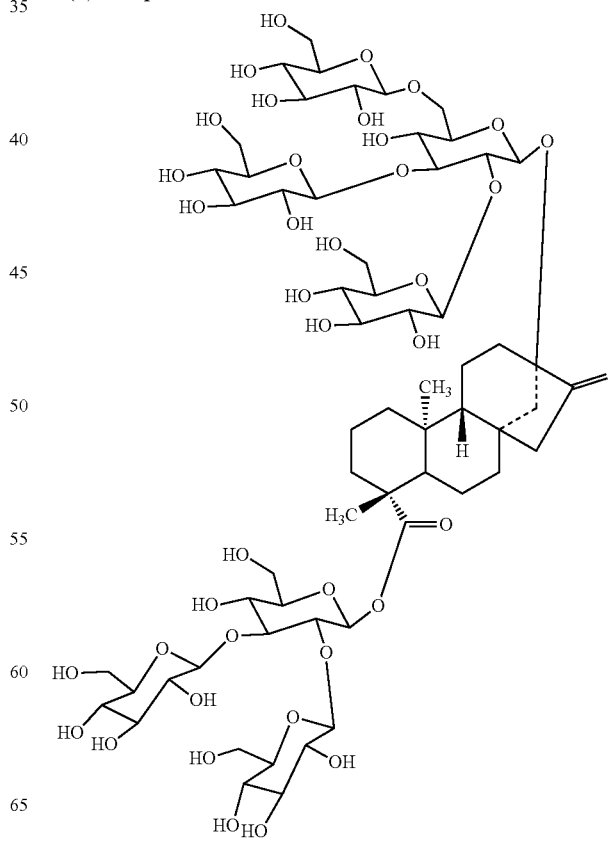

(e) compound 7.5 has the structure:
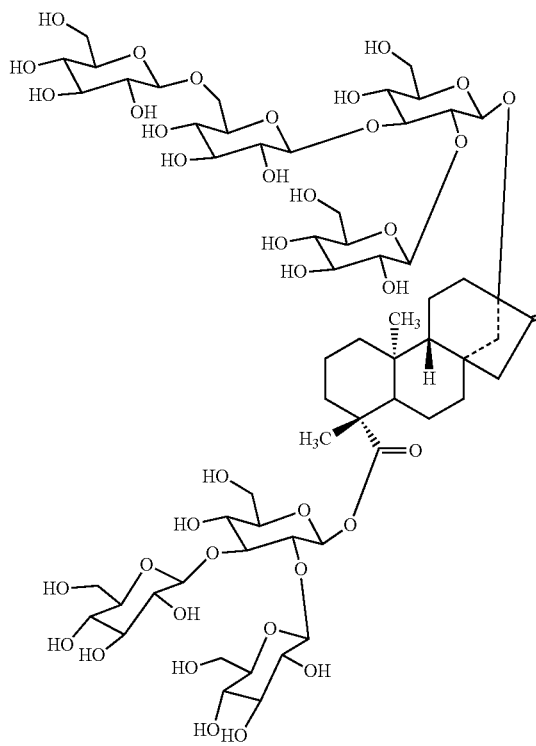
(f) compound KA3.1 has the structure:
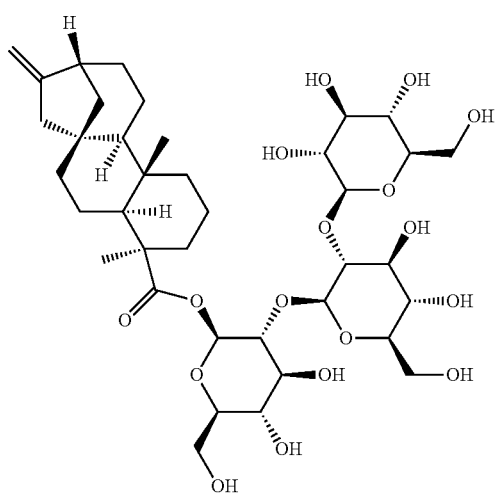
(g) compound KA3.2 has the structure:
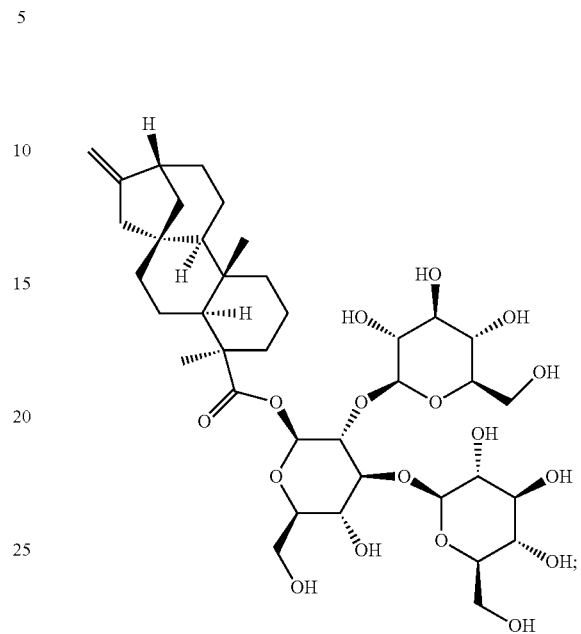
and
(h) compound KL3.1 has the structure:
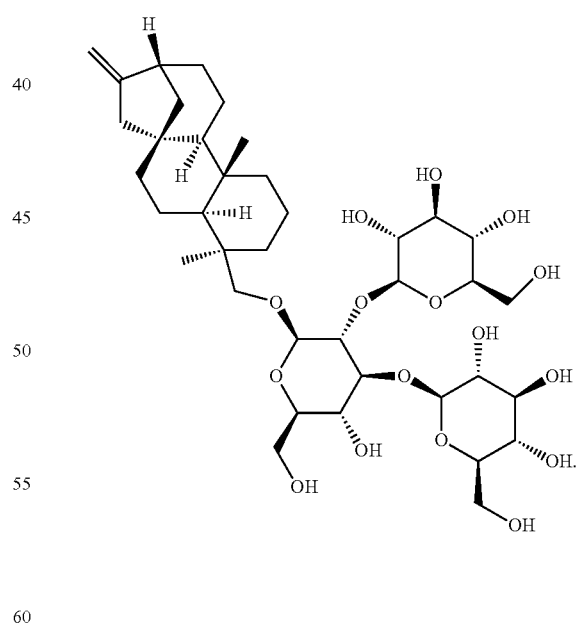
In one aspect of the recombinant hosts and methods disclosed herein,
(a) the tri-glycosylated ent-kaurenoic acid comprises a compound having the structure:

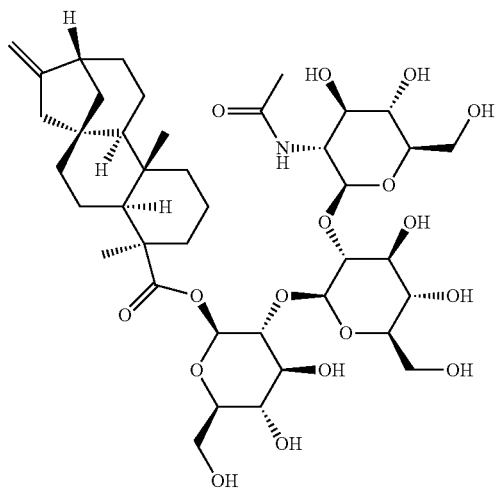

(b) the penta-glycosylated steviol comprises a compound having the structure:

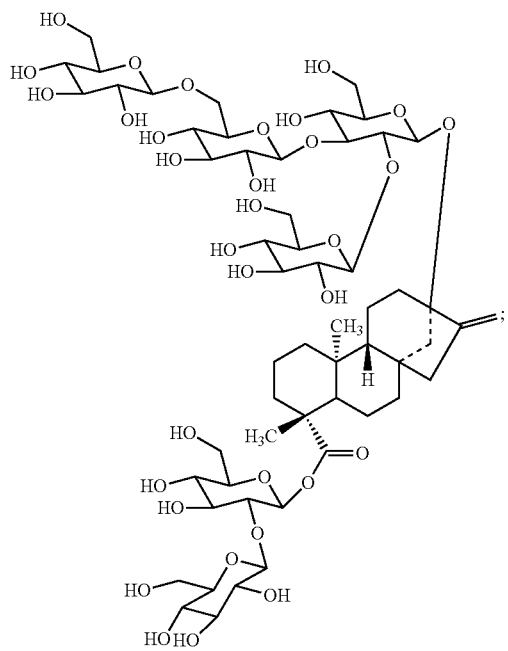

and (d) the hepta-glycosylated steviol comprises a compound having the structure:

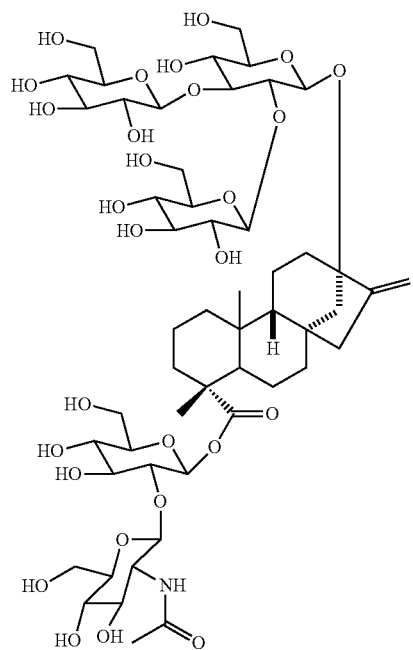

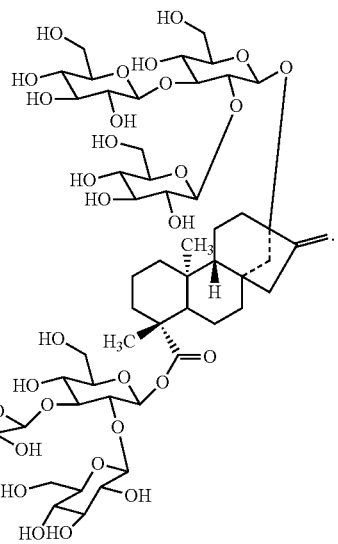

(c) the hexa-glycosylated steviol comprises a compound having the structure:

The invention also provides a steviol glycoside composition produced by the recombinant host cell disclosed herein or the method disclosed herein, wherein the composition has a steviol glycoside composition enriched for RebD, RebM, or isomers thereof relative to a steviol glycoside composition of *Stevia* plant and has a reduced level of non-steviol glycoside *Stevia* plant-derived components relative to a plant-derived stevia extract.

The invention also provides a cell culture broth comprising:
(a) the recombinant host cell disclosed herein; and
(b) one or more steviol glycosides, glycosylated ent-kaurenol compounds, and/or glycosylated ent-kaurenoic acid compounds produced by the recombinant host cell;

wherein one or more steviol glycosides is present at a concentration of at least 1 mg/liter of the culture broth.

The invention also provides a cell culture broth comprising:
(a) one or more steviol glycosides, glycosylated ent-kaurenol compounds, and/or glycosylated ent-kaurenoic acid compounds produced by the recombinant host cell disclosed herein,
(b) glucose, fructose, sucrose, xylose, ethanol, and/or glycerol; and/or
(c) supplemental nutrients comprising trace metals, vitamins, salts, YNB, and/or amino acids.

The invention also provides a cell lysate comprising:
(a) one or more steviol glycosides, glycosylated ent-kaurenol compounds, and/or glycosylated ent-kaurenoic acid compounds produced by the recombinant host cell disclosed herein,
(b) glucose, fructose, sucrose, xylose, ethanol, glycerol, uridine diphosphate (UDP)-glucose, UDP-rhamnose, UDP-xylose, and/or N-acetyl-glucosamine; and/or
(c) supplemental nutrients comprising trace metals, vitamins, salts, YNB, and/or amino acids.

The invention also provides a reaction mixture comprising:
(a) one or more steviol glycosides, glycosylated ent-kaurenol compounds, and/or a glycosylated ent-kaurenoic acid compounds produced in the reaction mixture;
(b) a UGT polypeptide;
(c) glucose, fructose, sucrose, xylose, ethanol, glycerol, uridine diphosphate (UDP)-glucose, UDP-rhamnose, UDP-xylose, and/or N-acetyl-glucosamine; and/or
(d) reaction buffer and/or salts.

These and other features and advantages of the present invention will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which:

FIG. 4A shows accumulation of ent-kaurenoic acid+2Glc (#7), ent-kaurenoic acid+3Glc (isomer 1), and ent-kaurenoic acid+3Glc (isomer 2) by a steviol glycoside-producing S. cerevisiae strain deleted of UGT85C2 (SEQ ID NO:7).

FIG. 6A shows production of RebM, RebD, RebA, RebB, 13-SMG, and rubusoside in a steviol glycoside-producing strain expressing UGT76G1 H155L (gray bars), compared to the control steviol glycoside-producing strain expressing wild-type UGT76G1 (black bars). FIG. 6B shows production of 1,2-bioside, rubusoside (Rubu), RebG, and RebE in a steviol glycoside-producing strain expressing UGT76G1 H155L (gray bars), compared to a control strain expressing wild-type UGT76G1 (black bars). FIG. 6C shows production of quantifiable steviol glycosides (13-SMG+1,2-bioside+Rubu+RebG+RebB+RebA+RebE+RebD+RebM) and RebD plus RebM titers in a steviol glycoside-producing strain expressing UGT76G1 H155L (gray bars), compared to a control strain expressing wild-type UGT76G1 (black bars).

FIG. 7A shows NMR-elucidated structures of tri-glycosylated ent-kaurenoic acid (Ent-Kaurenoic Acid+3Glc (isomers 1 and 2)), ent-kaurenoic acid+2Glc+1GlcNAc, and tri-glycosylated ent-kaurenol (ent-kaurenol+3Glc (isomer 1)). FIG. 7B shows NMR-elucidated structures of steviol+6Glc (isomer 1) and steviol+7Glc (isomer 2). FIG. 7C shows NMR-elucidated structures of steviol+6Glc (isomer 4) and steviol+7Glc (isomer 5). FIG. 7E shows NMR-elucidated structures of steviol+5Glc (#22) and steviol+7Glc (#14). See Examples 6, 8, and 9.

FIGS. 8A, 8B, and 8C show a $^1$H NMR spectrum and $^1$H and $^{13}$C NMR chemical shifts (in ppm) for ent-kaurenoic acid+3Glc (isomer 1). FIGS. 8D, 8E, and 8F show a $^1$H NMR spectrum and $^1$H and $^{13}$C NMR chemical shifts (in ppm) for ent-kaurenoic acid+3Glc (isomer 2). FIGS. 8G, 8H, and 8I show a $^1$H NMR spectrum and $^1$H and $^{13}$C NMR chemical shifts (in ppm) for ent-kaurenoic acid+2Glc+1GlcNAc. FIGS. 8J, 8K, and 8L show a $^1$H NMR spectrum and $^1$H and $^{13}$C NMR chemical shifts (in ppm) for ent-kaurenol+3Glc (isomer 1). FIGS. 8M, 8N, 8O, and 8P show a $^1$H NMR spectrum and $^1$H and $^{13}$C NMR chemical shifts (in ppm) for steviol+6Glc (isomer 1). FIGS. 8Q, 8R, 8S, and 8T show a $^1$H NMR spectrum and $^1$H and $^{13}$C NMR chemical shifts (in ppm) for steviol+7Glc (isomer 2). FIGS.

8U, 8V, 8W, and 8X show a $^1$H NMR spectrum and $^1$H and $^{13}$C NMR chemical shifts (in ppm) for steviol+6Glc (isomer 4). FIGS. 8Y, 8Z, 8AA, and 8AB show a $^1$H NMR spectrum and $^1$H and $^{13}$C NMR chemical shifts (in ppm) for steviol+7Glc (isomer 5). FIGS. 8AC, 8AD, 8AE, and 8AF show a $^1$H NMR spectrum and $^1$H and $^{13}$C NMR chemical shifts (in ppm) for steviol+4Glc+1GlcNAc (#11). FIGS. 8AG, 8AH, 8AI, and 8AJ show a $^1$H NMR spectrum and $^1$H and $^{13}$C NMR chemical shifts (in ppm) for steviol+4Glc (#26). FIGS. 8AK, 8AL, 8AM, and 8AN show a $^1$H NMR spectrum and $^1$H and $^{13}$C NMR chemical shifts (in ppm) for steviol+5Glc (#22). FIGS. 8AO, 8AP, 8AQ, and 8AR show a $^1$H NMR spectrum and $^1$H and $^{13}$C NMR chemical shifts (in ppm) for steviol+7Glc (#14). See Examples 6, 8, and 9.

FIG. 9A shows accumulation of ent-kaurenoic acid+2Glc (#7), ent-kaurenoic acid+3Glc (isomer 1), and ent-kaurenoic acid+3Glc (isomer 2) in *S. cerevisiae* expressing UGT76G1 variants. FIG. 9B shows accumulation of ent-kaurenol+2Glc (#8) and ent-kaurenol+3Glc (isomer 1) co-eluted with ent-kaurenol+3Glc (#6) in *S. cerevisiae* expressing UGT76G1 variants. See Example 8.

FIG. 11B shows total levels of glycosylated ent-kaurenoic acid (ent-kaurenoic acid+2Glc (#7)+ent-kaurenoic acid+3Glc (isomer 1)+ent-kaurenoic acid+3Glc (isomer 2)) in an *S. cerevisiae* steviol glycoside production strain expressing UGT76G1 variants. FIG. 11E shows accumulation of 13-SMG, 1,2-bioside, rubusoside, RebG, RebA, RebB, RebD, RebE, and RebM in an *S. cerevisiae* steviol glycoside production strain expressing UGT76G1 variants. See Example 8.

Figure 1:
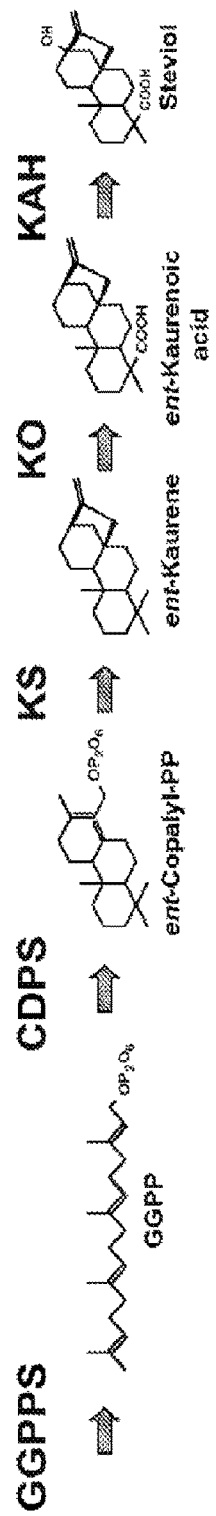
FIG. 1 shows a schematic of the engineered biosynthetic pathway for producing steviol in yeast from geranylgeranyl diphosphate using geranylgeranyl diphosphate synthase (GGPPS), ent-copalyl diphosphate synthase (CDPS), ent-kaurene synthase (KS), ent-kaurene oxidase (KO), and ent-kaurenoic acid hydroxylase (KAH) polypeptides.

Skilled artisans will appreciate that elements in the Figures are illustrated for simplicity and clarity and have not necessarily been drawn to scale. For example, the dimensions of some of the elements in the Figures can be exaggerated relative to other elements to help improve understanding of the embodiment(s) of the present invention.

DETAILED DESCRIPTION OF THE INVENTION

Before describing the present invention in detail, a number of terms will be defined. As used herein, the singular forms "a," "an," and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, CA).

As used herein, the terms "polynucleotide," "nucleotide," "oligonucleotide," and "nucleic acid" can be used interchangeably to refer to nucleic acid comprising DNA, RNA, derivatives thereof, or combinations thereof, in either single-stranded or double-stranded embodiments depending on context as understood by the skilled worker.

As used herein, the terms "microorganism," "microorganism host," "microorganism host cell," "recombinant host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. In some aspects, said recombinant genes are encoded by cDNA. In other embodiments, recombinant genes are synthetic and/or codon-optimized for expression in S. cerevisiae.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast gene. In some embodiments, the gene is endogenous to S. cerevisiae, including, but not limited to S. cerevisiae strain S288C. In some embodiments, an endogenous yeast gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast gene, for example ADH, is deleted. See, e.g., Giaever & Nislow, 2014, Genetics 197(2):451-65. As used herein, the terms "deletion," "deleted," "knockout," and "knocked out" can be used interchangeably to refer to an endogenous gene that has been manipulated to no longer be expressed in an organism, including, but not limited to, S. cerevisiae.

As used herein, the terms "heterologous sequence" and "heterologous coding sequence" are used to describe a sequence derived from a species other than the recombinant host. In some embodiments, the recombinant host is an S. cerevisiae cell, and a heterologous sequence is derived from an organism other than S. cerevisiae. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, Ann. Rev. Genetics 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild-type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

Figure 2:
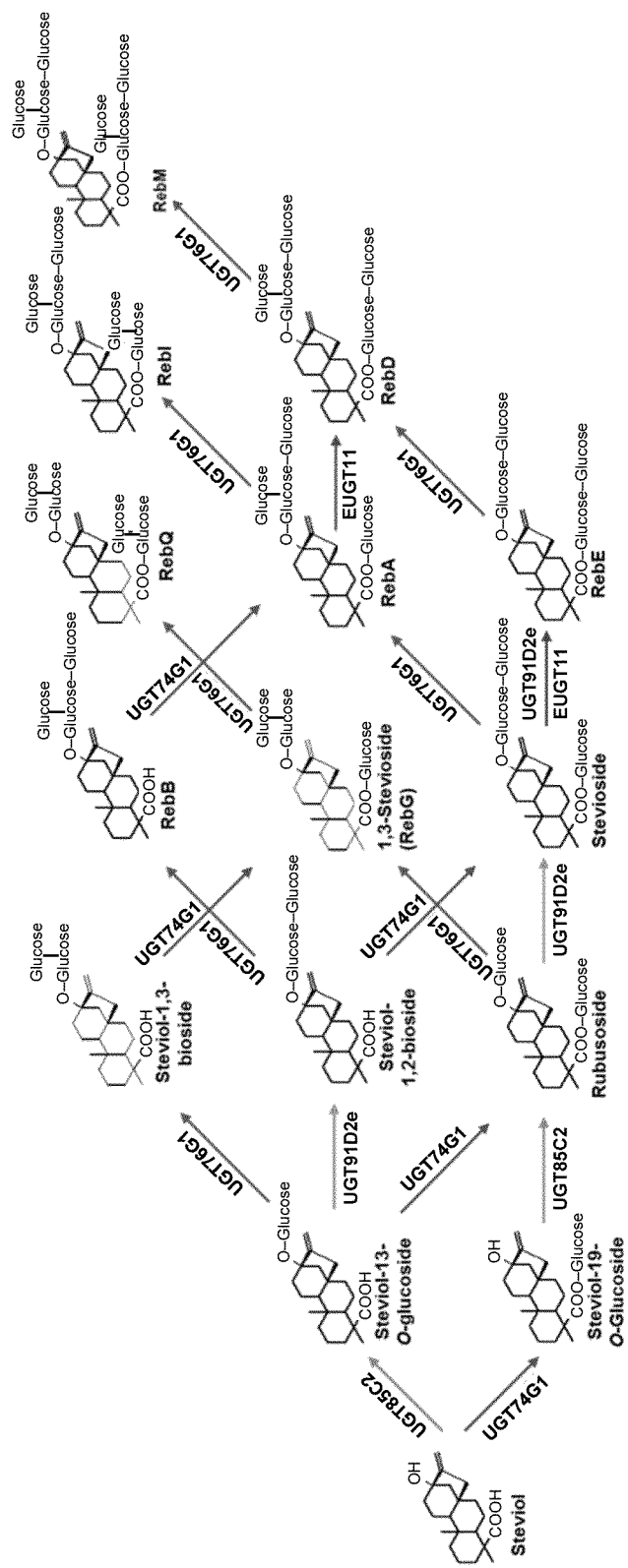
FIG. 2 shows representative steviol glycoside glycosylation reactions catalyzed by suitable uridine 5'-diphospho (UDP) glycosyl transferases (UGT) enzymes and chemical structures for several steviol glycoside compounds.
Figure 7D:
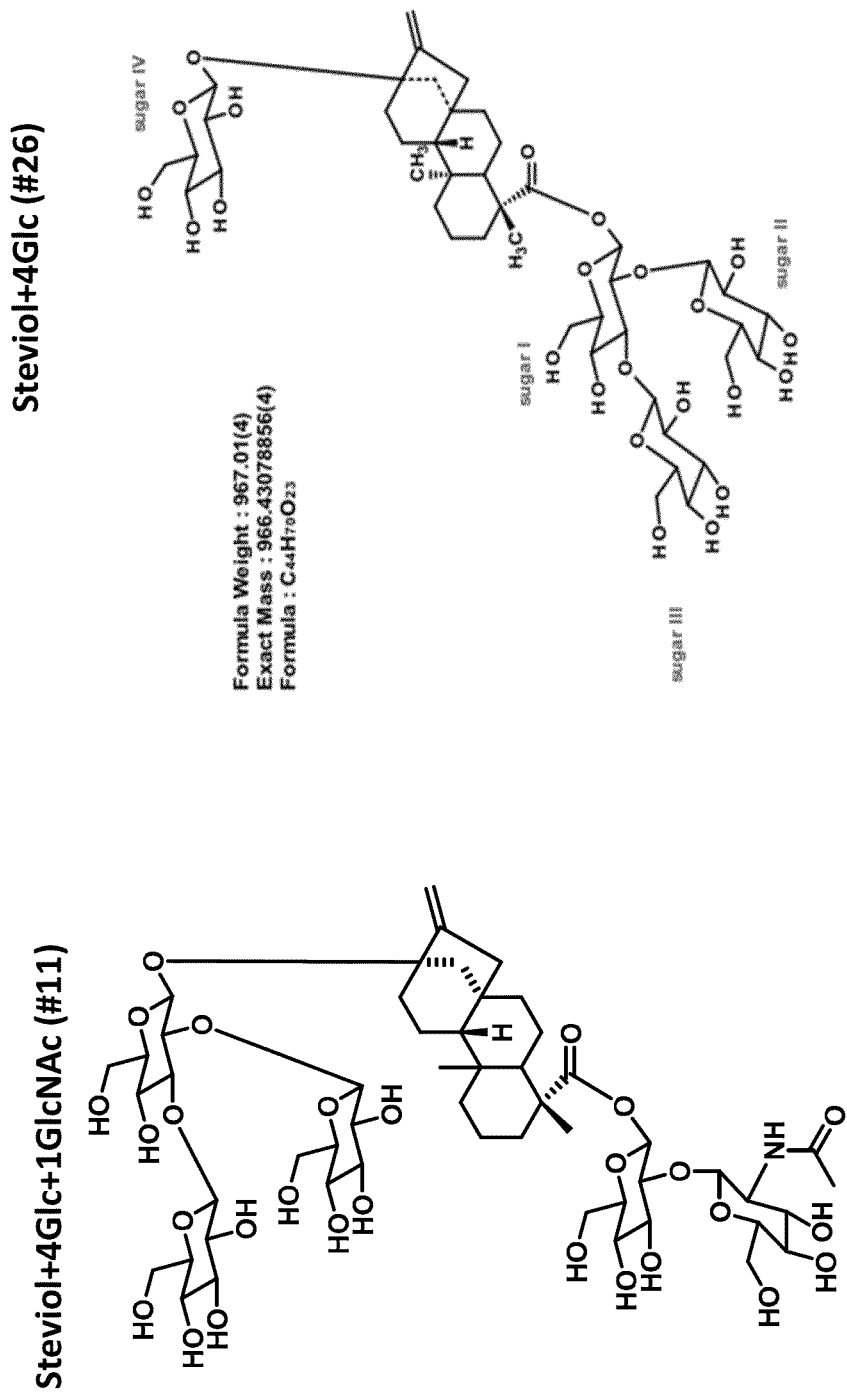
FIG. 7D shows NMR-elucidated structures of steviol+4Glc+1GlcNAc (#11) and steviol+4Glc (#26).
Figure 8A:
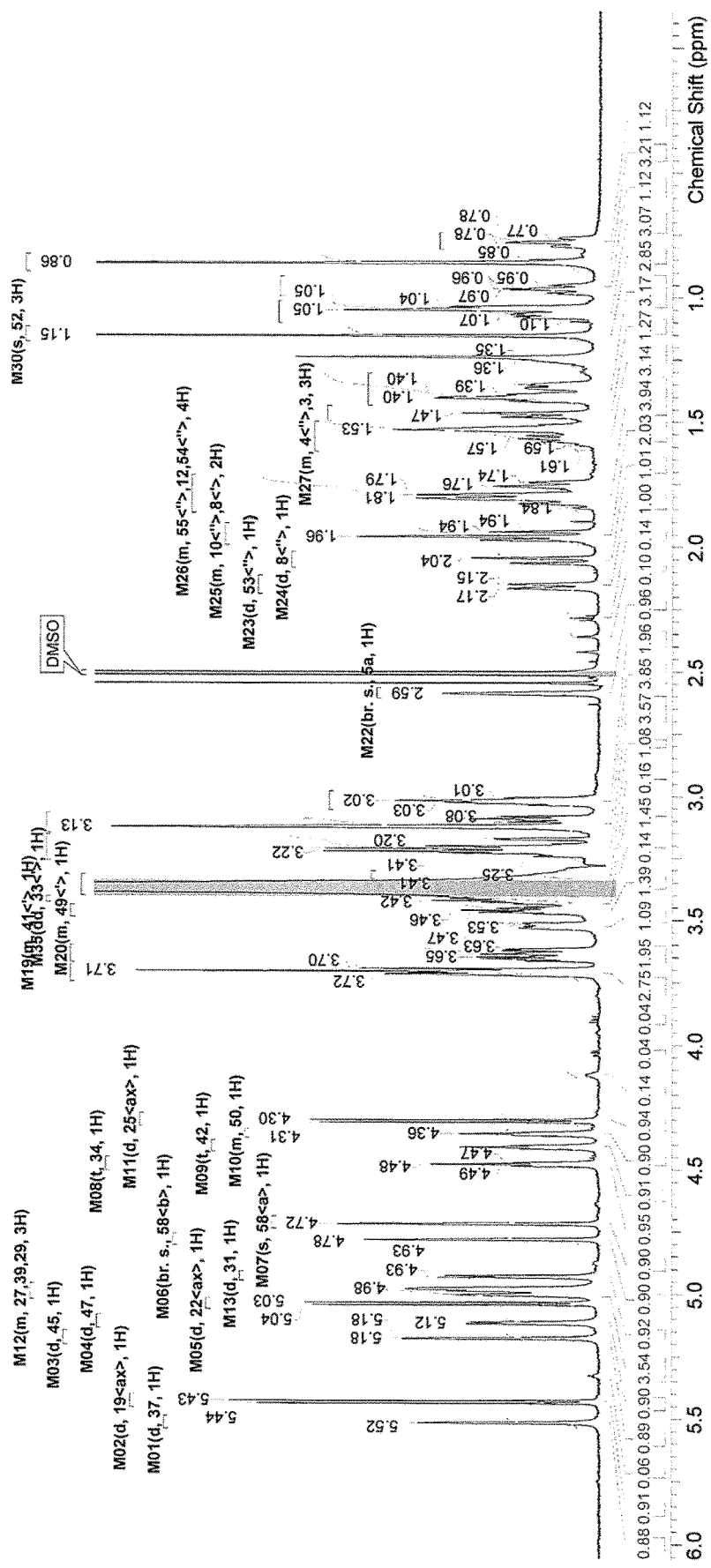
Figure 8D:
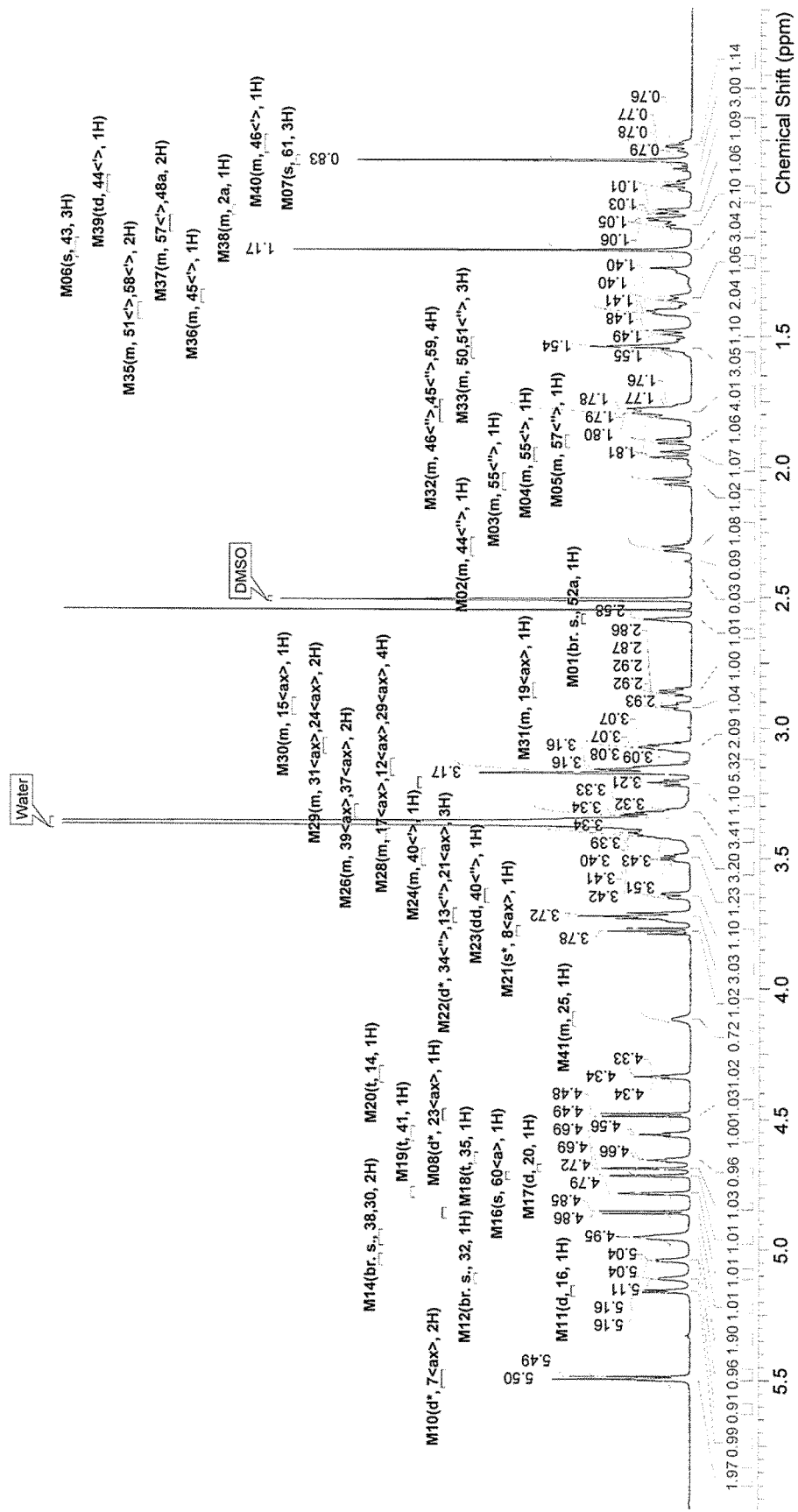
Figure 8F:
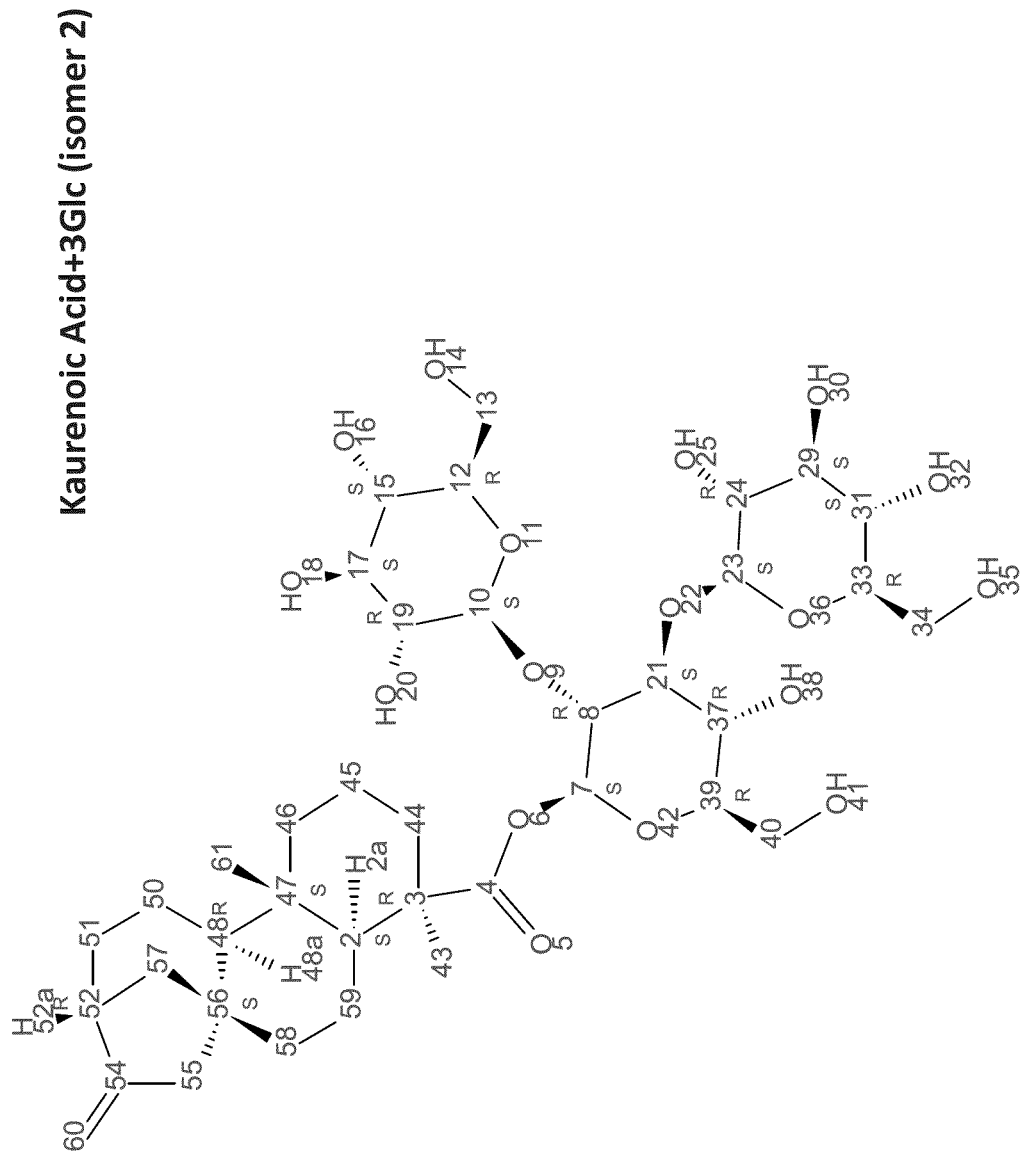
Figure 8G:
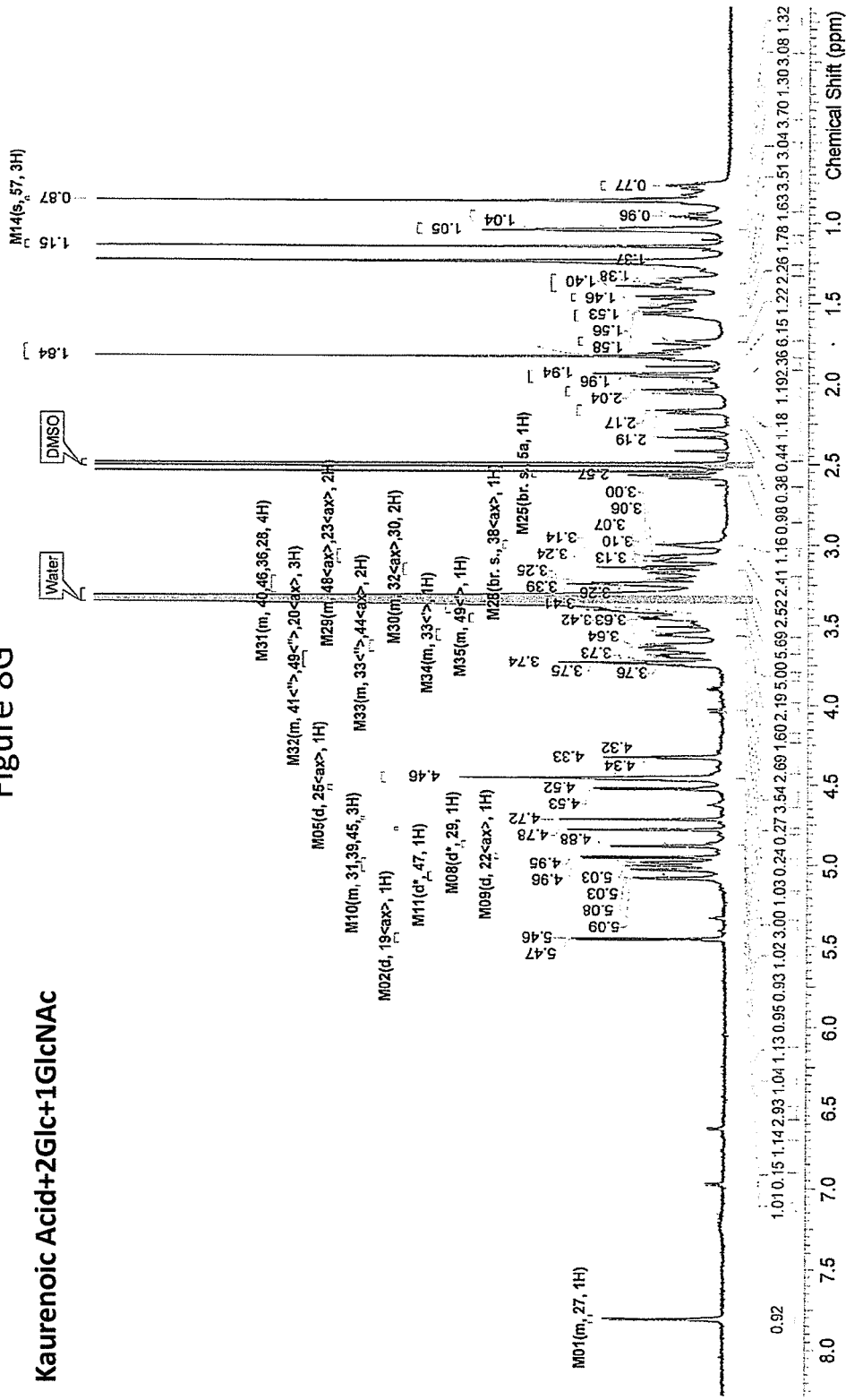
Figure 8I:
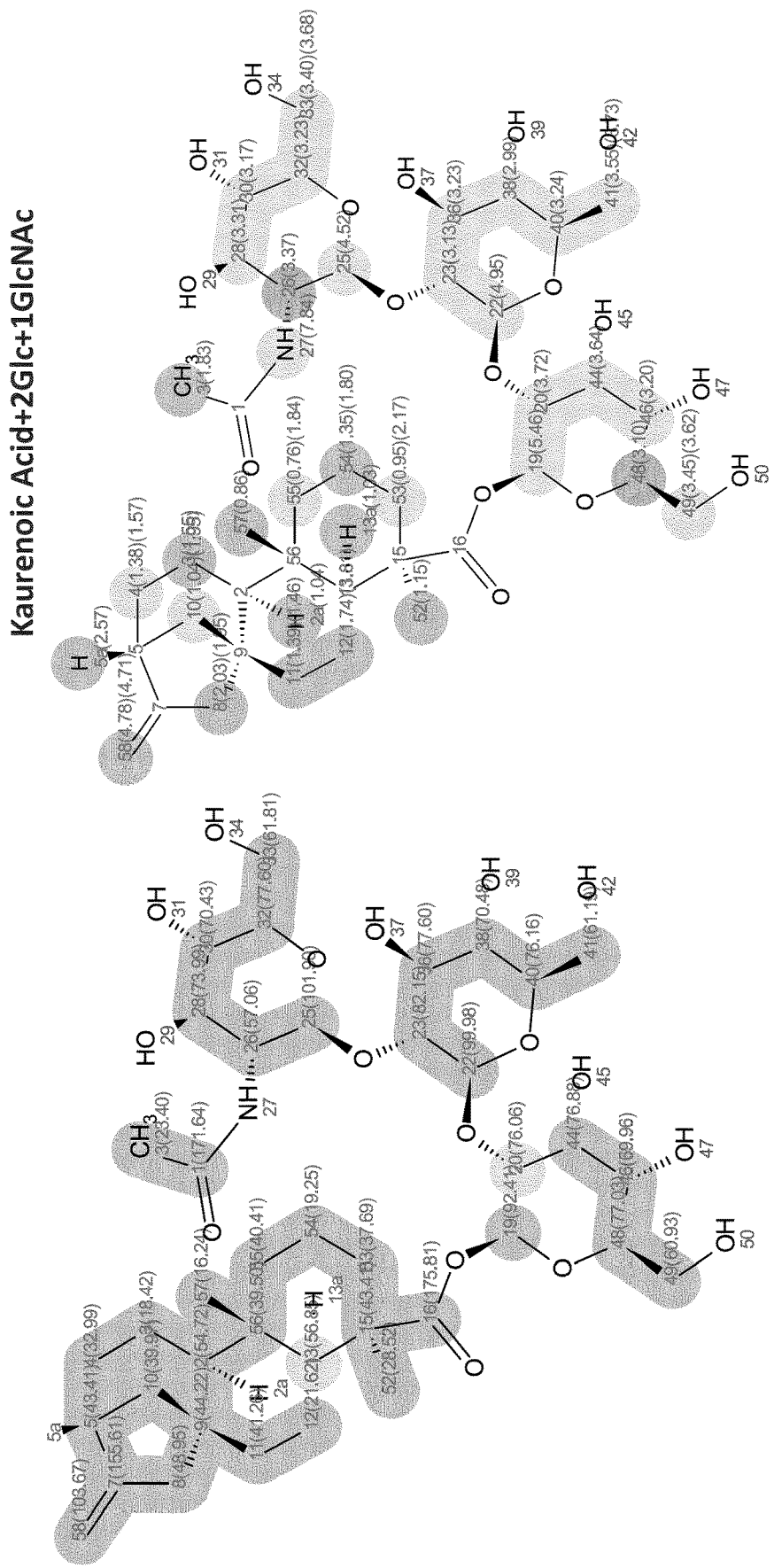
Figure 8J:
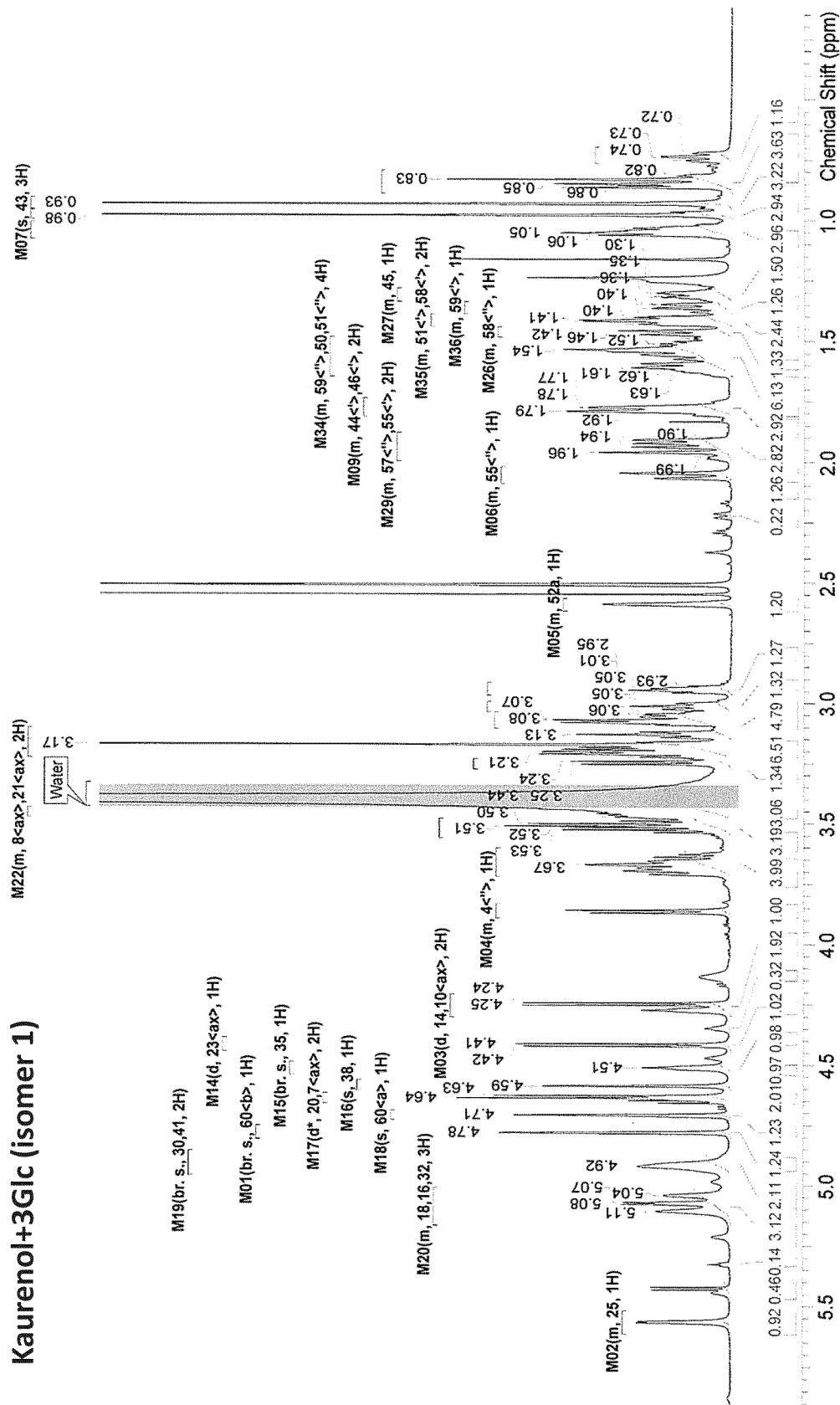
Figure 8K:
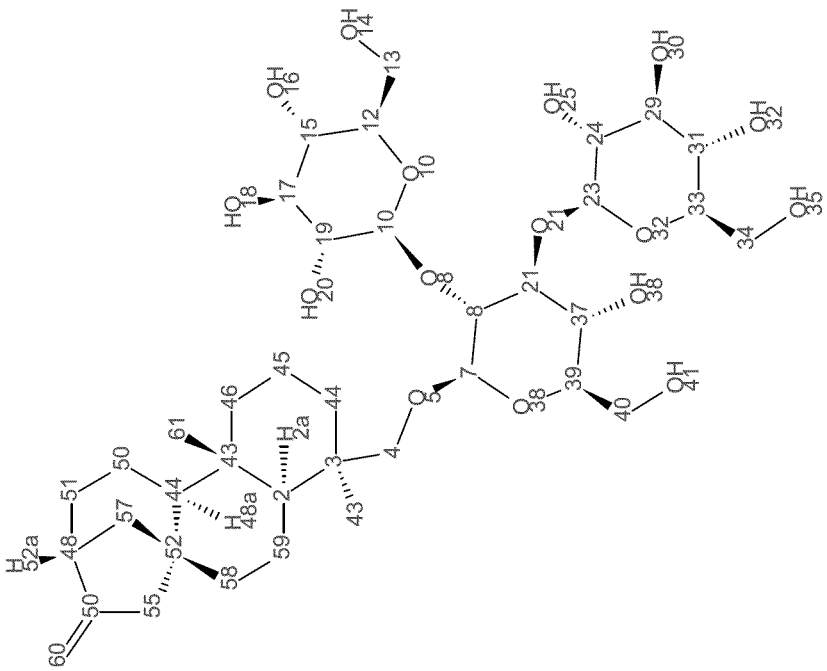
Figure 80:
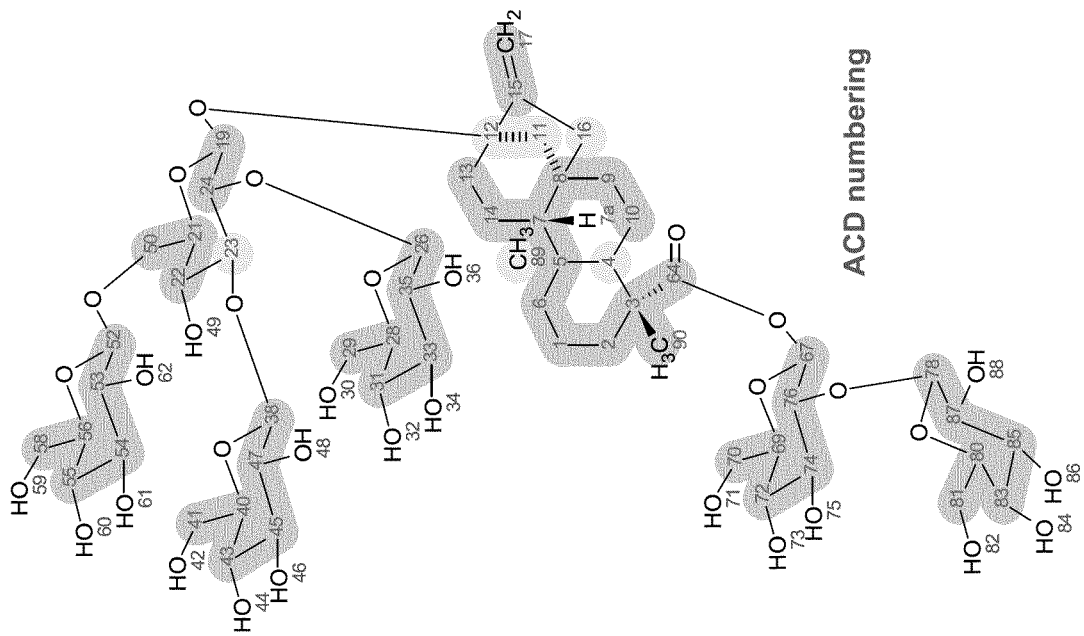
Figure 8P:
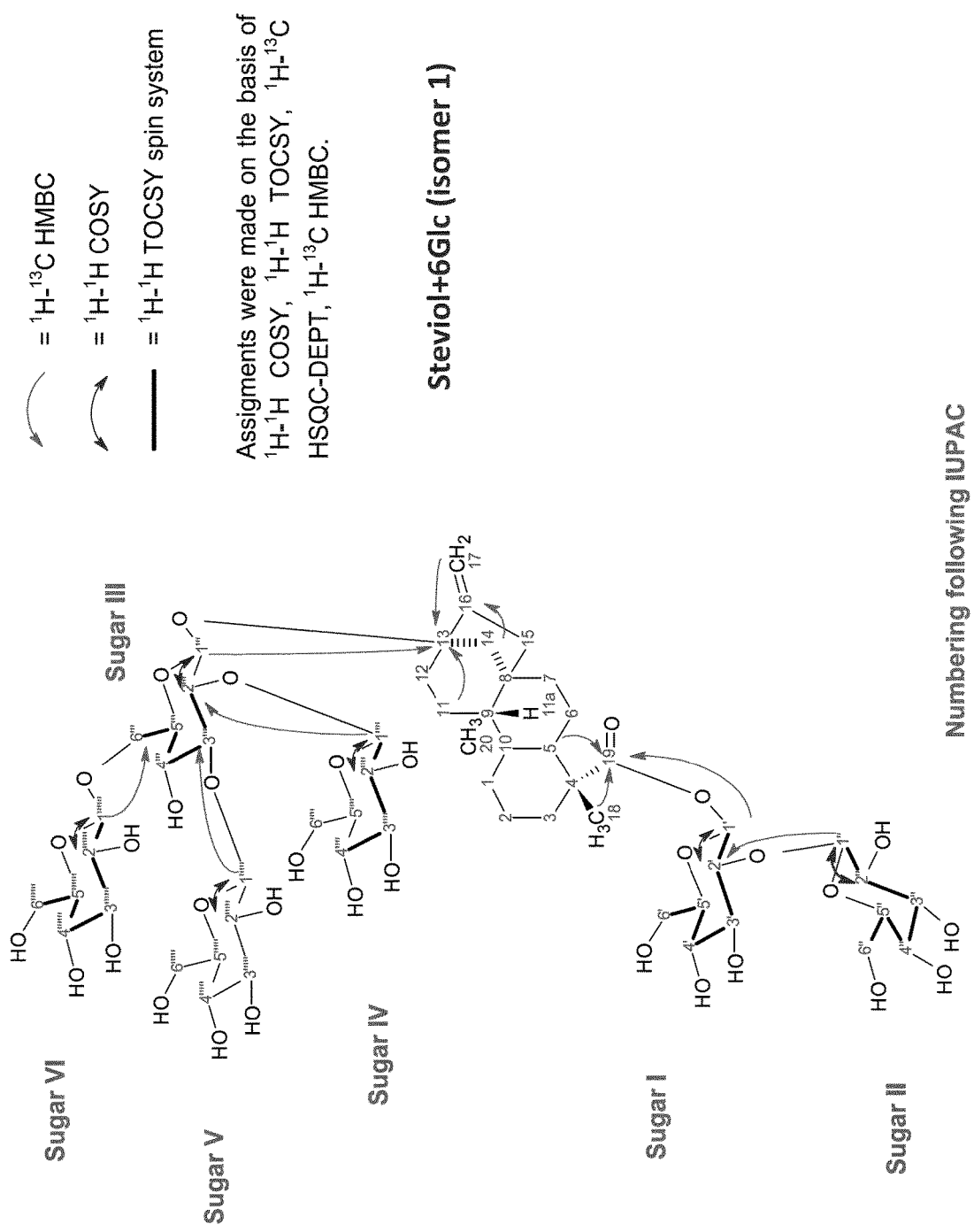
Figure 8Q:
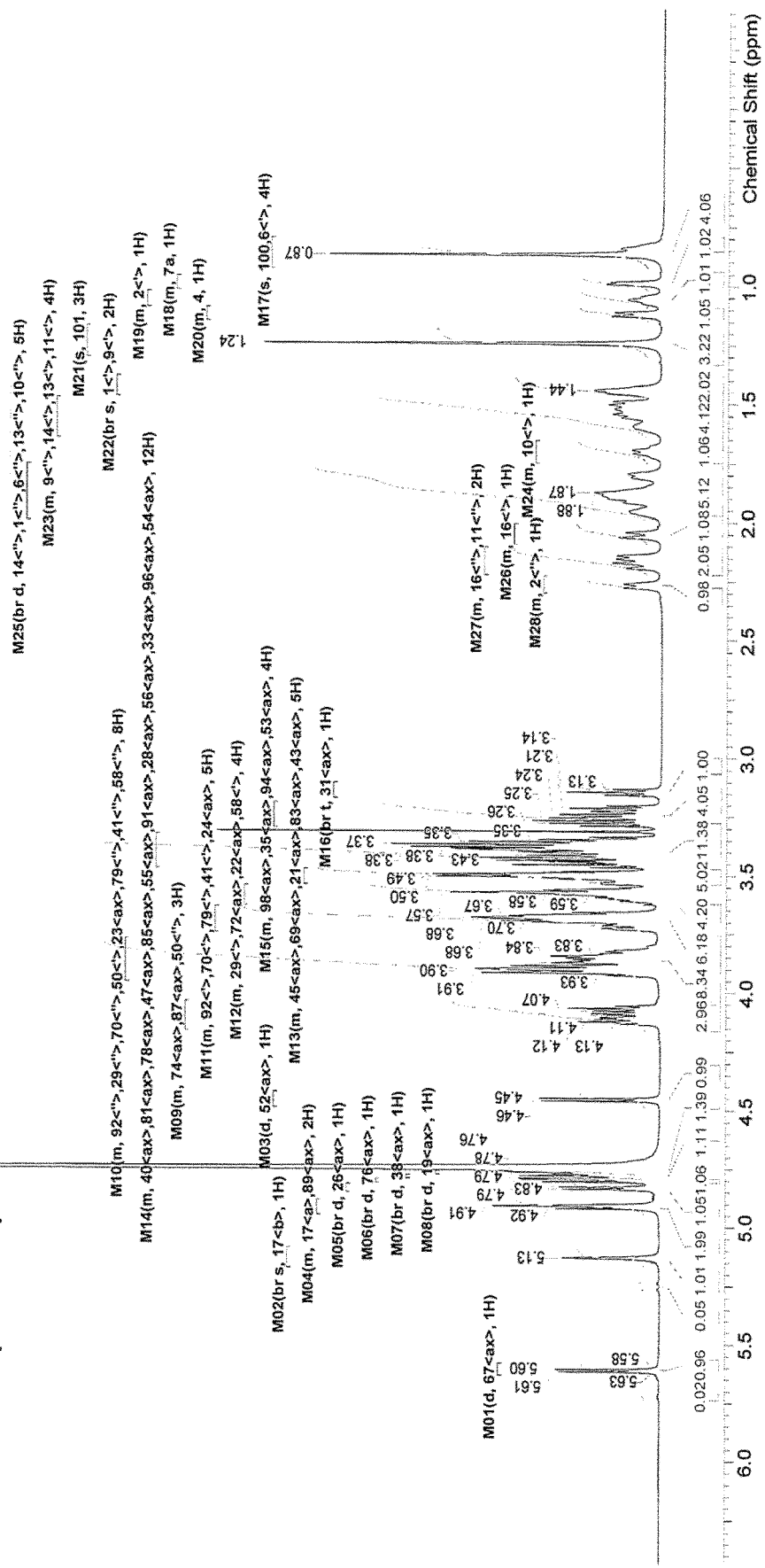
Figure 8S:
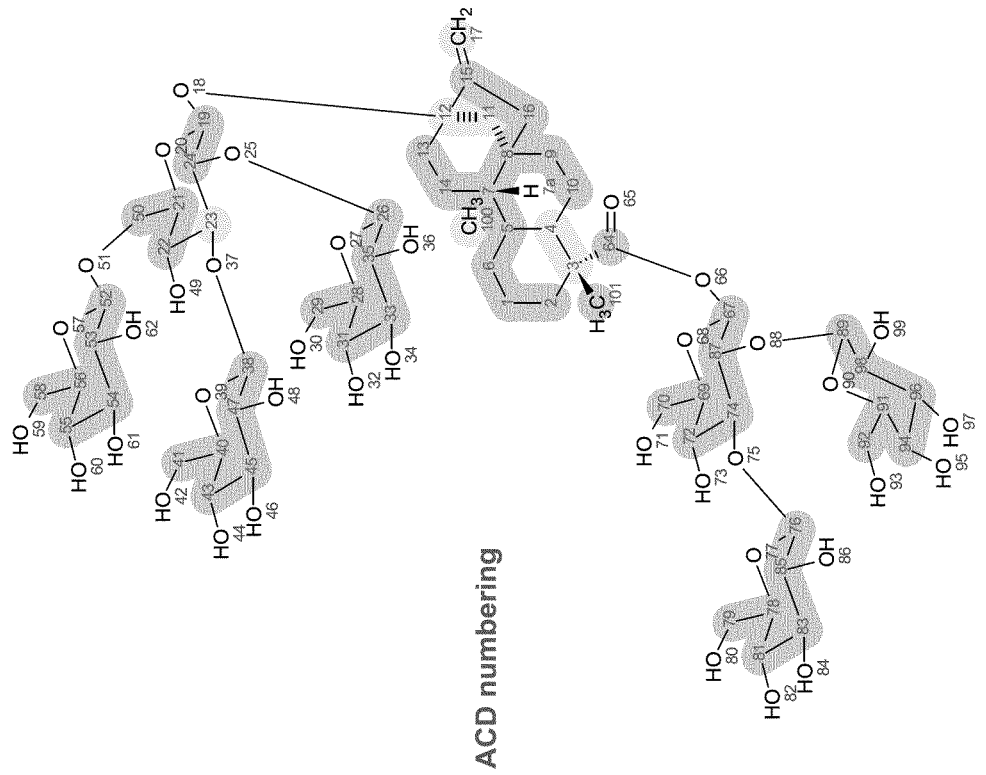
Figure 8T:
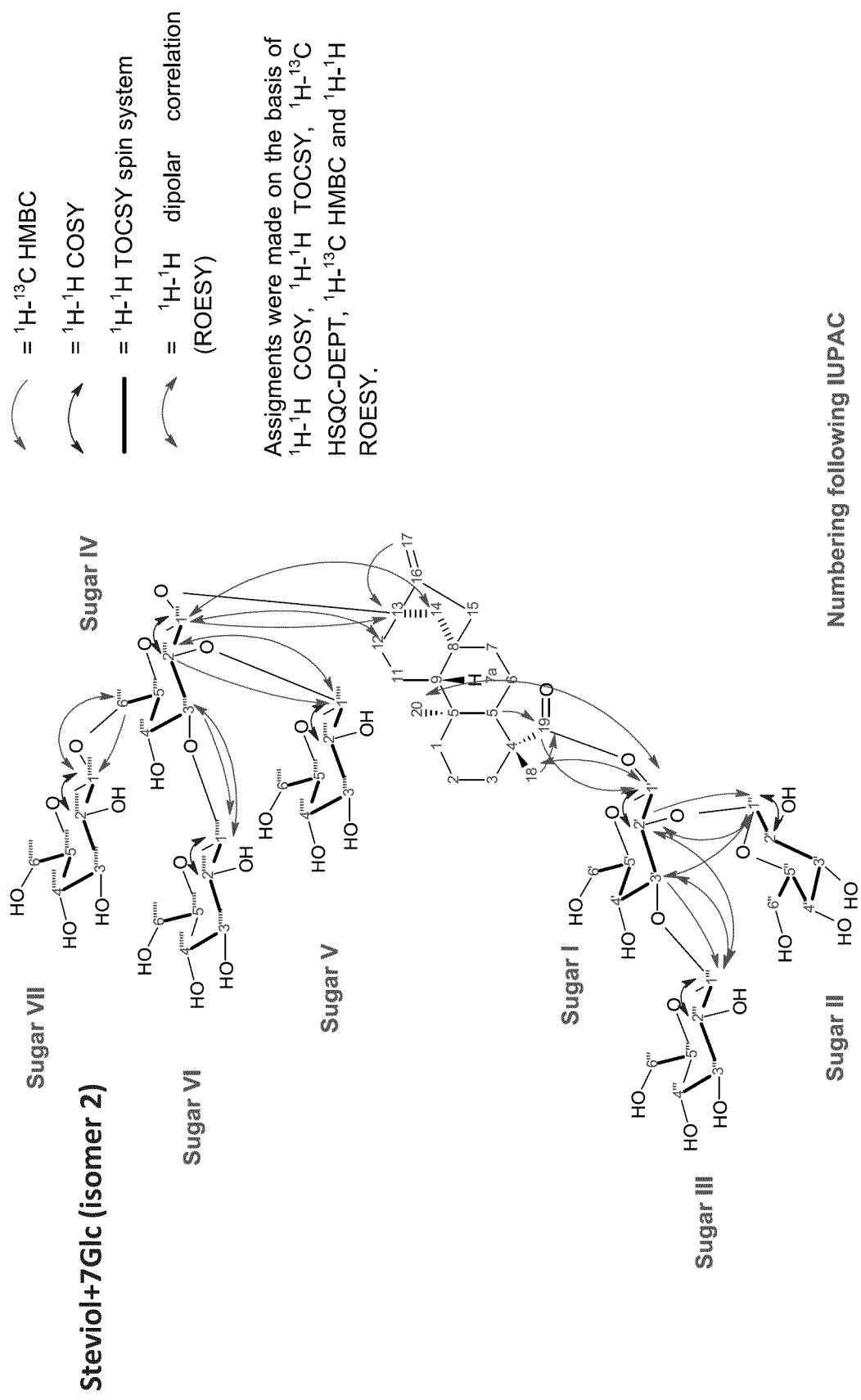
Figure 8U:
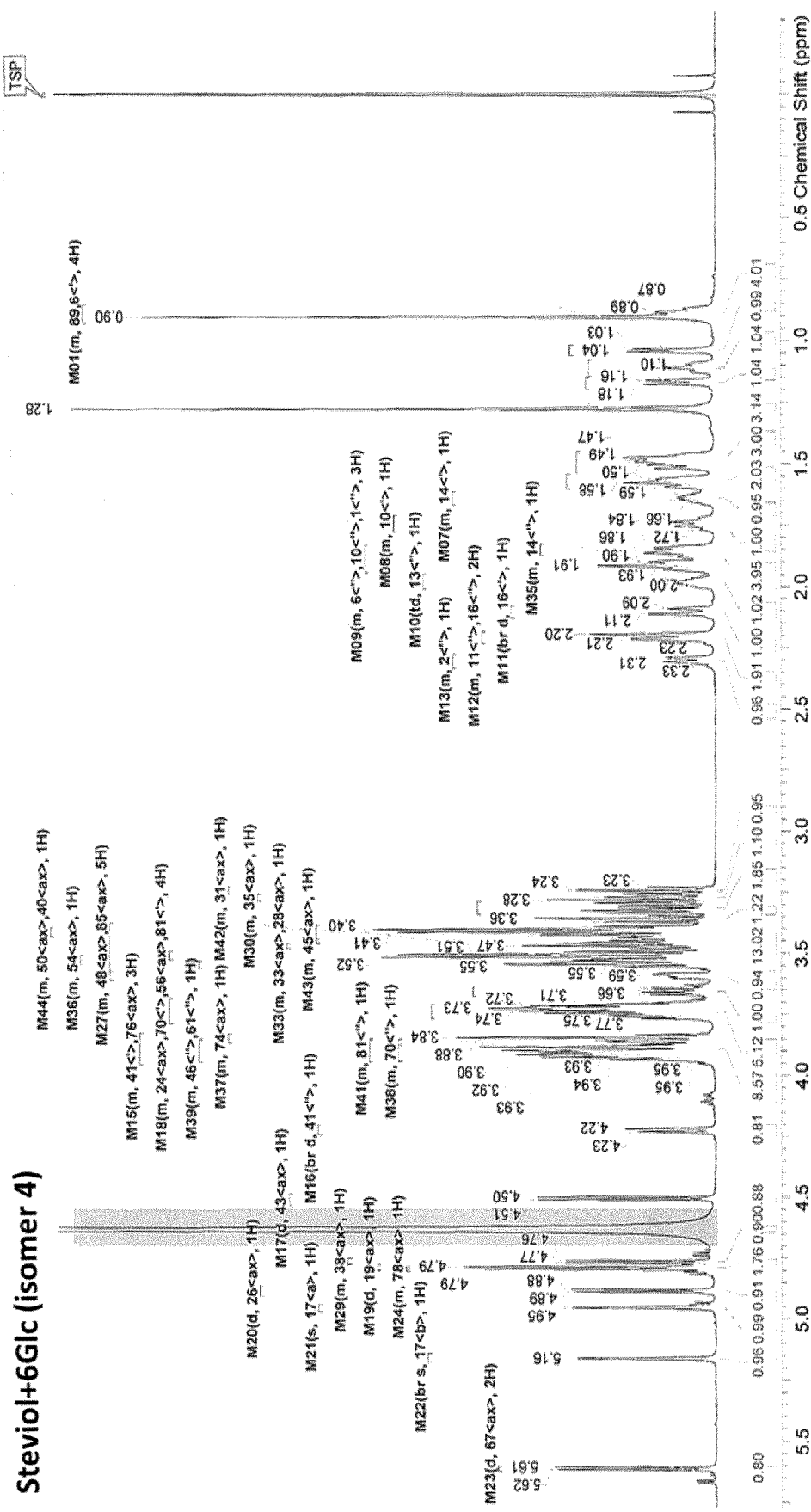
Figure 8W:
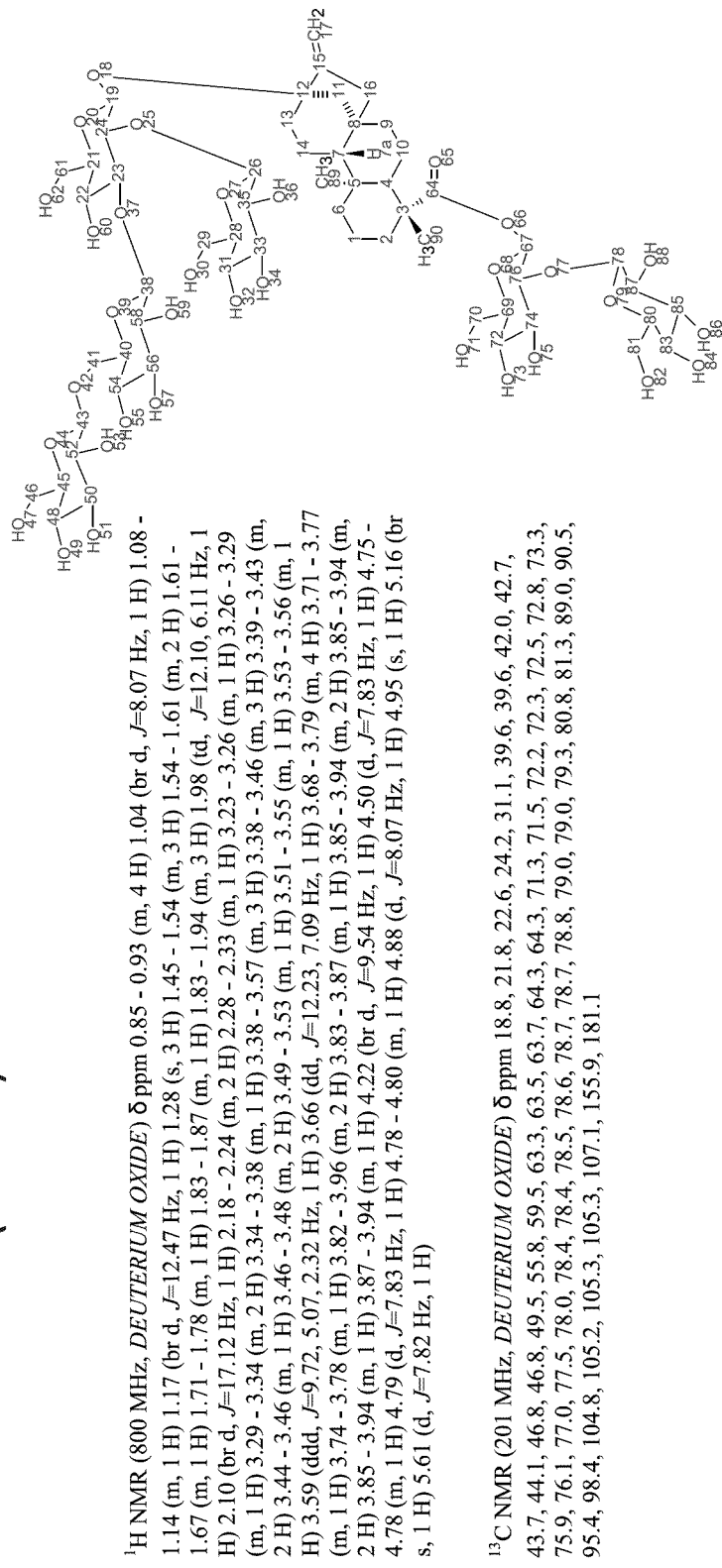
Figure 8X:
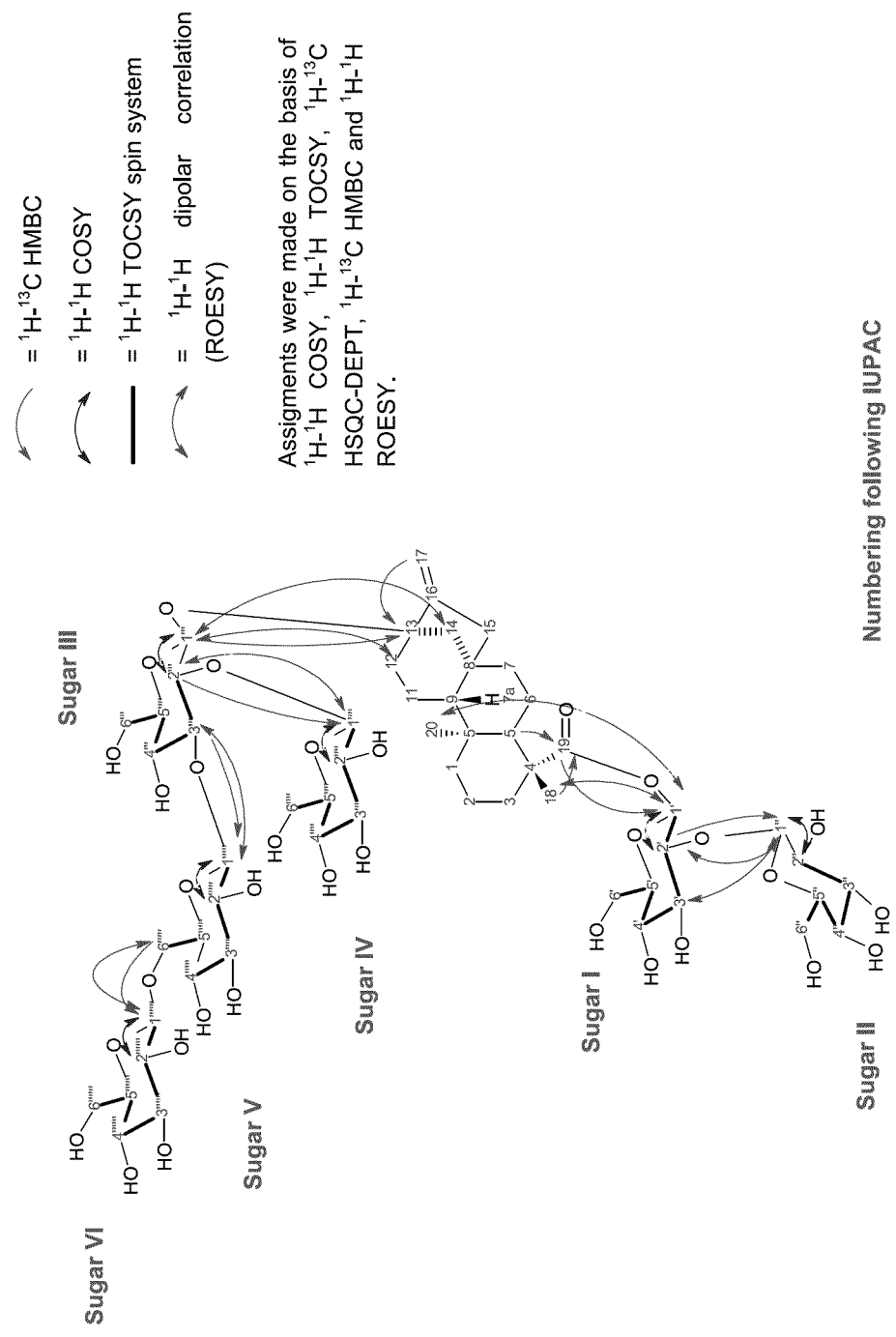
Figure 8A:
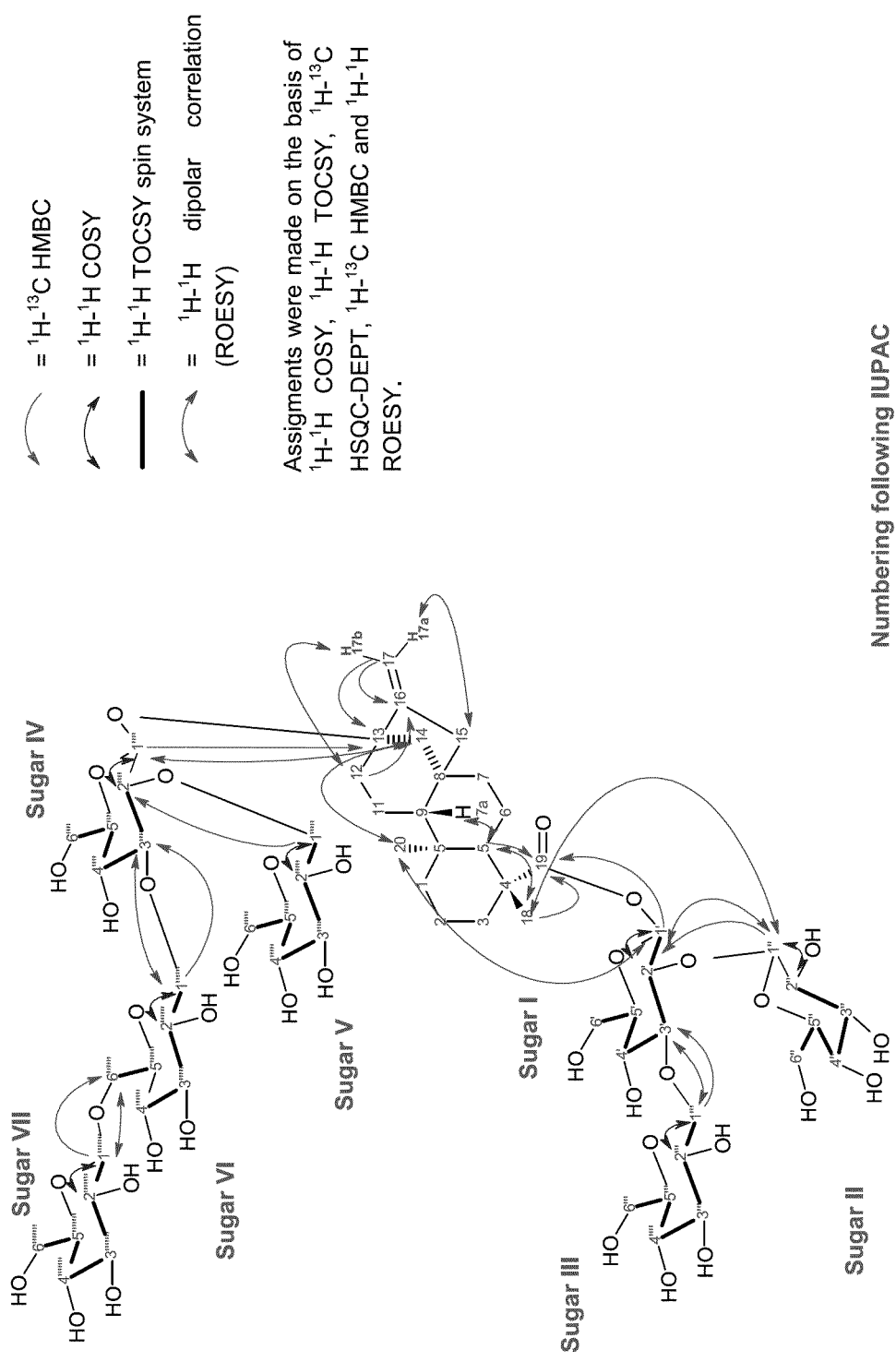
Figure 8A:
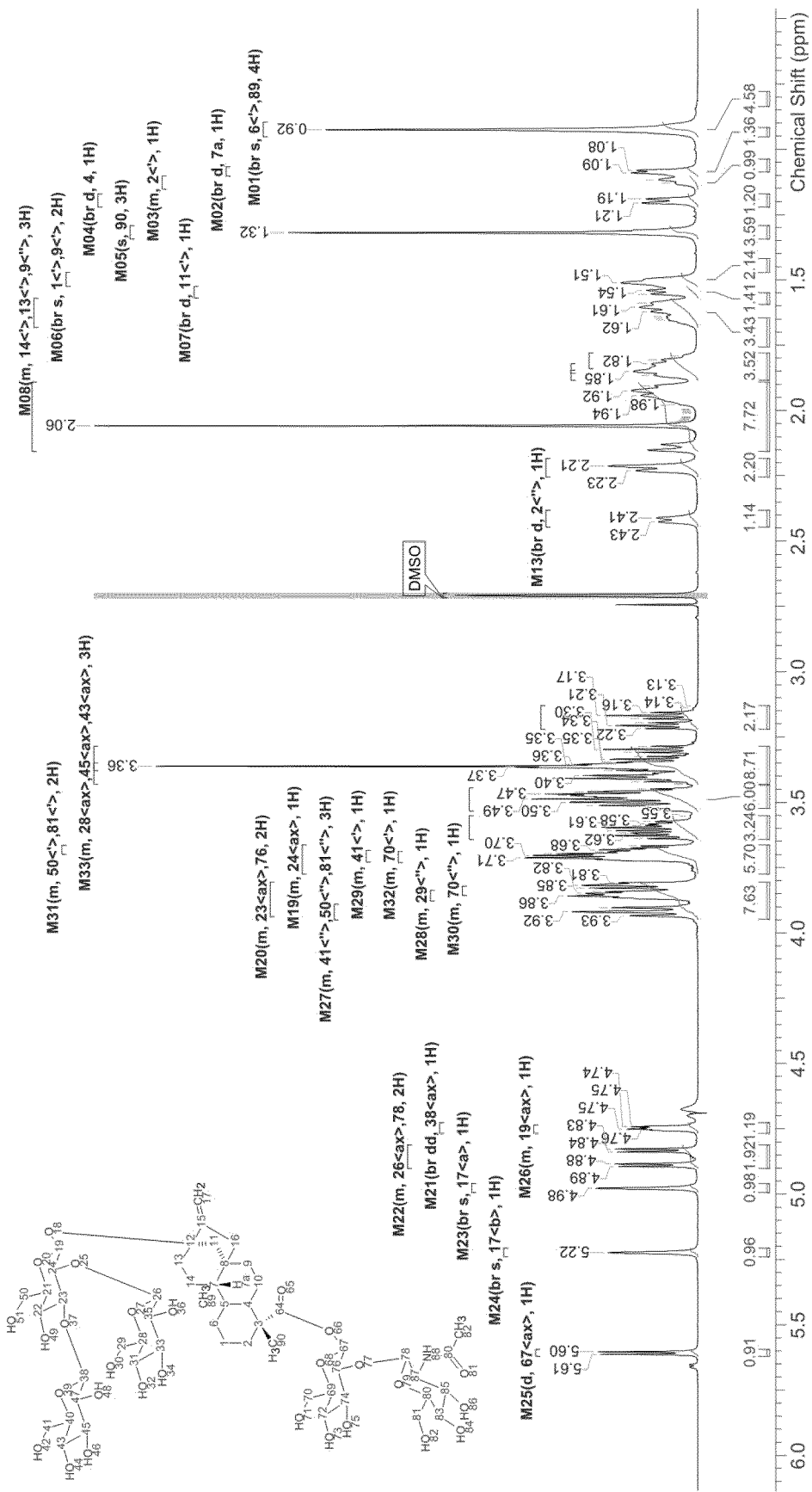
Figure 8A:
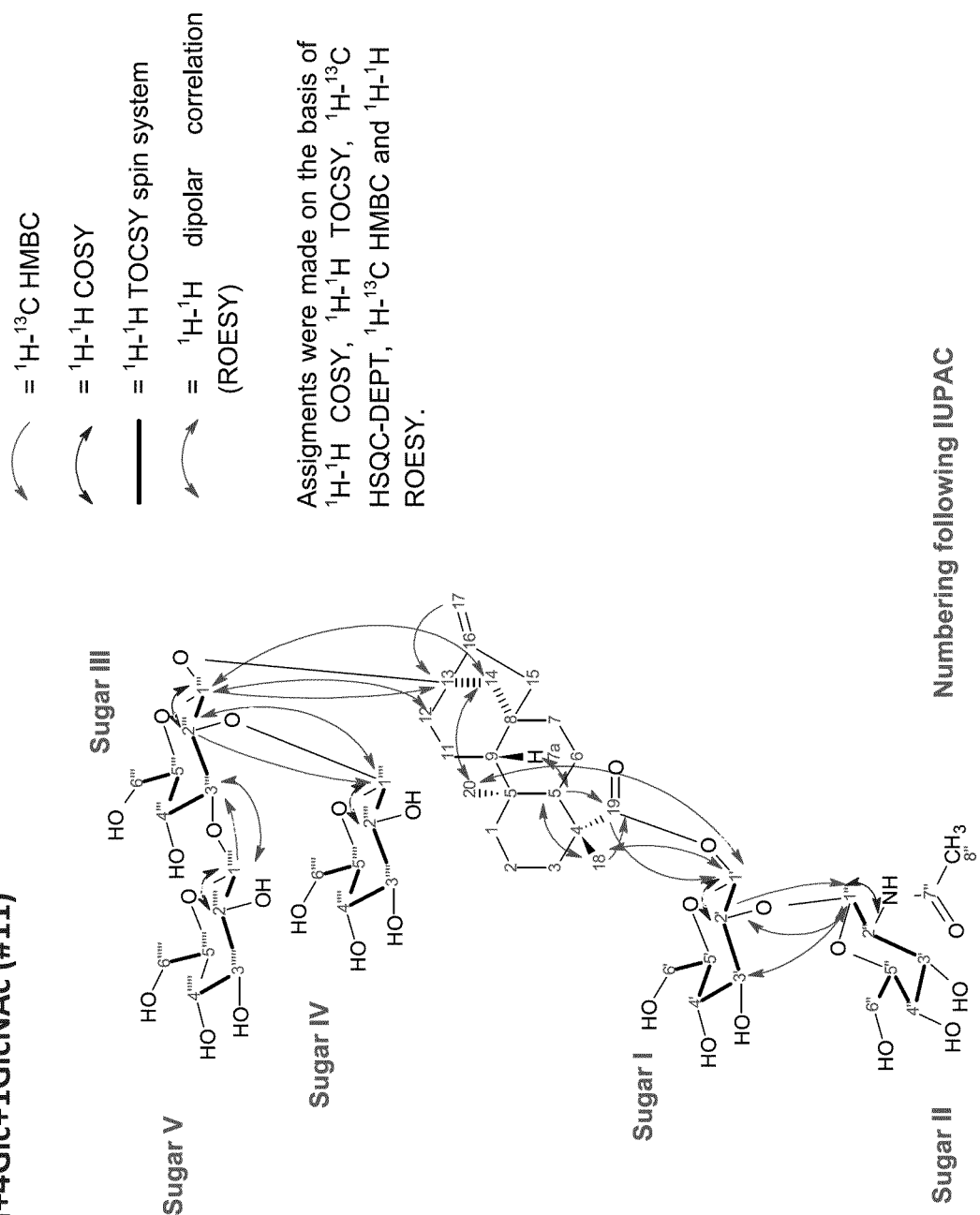
Figure 8A:
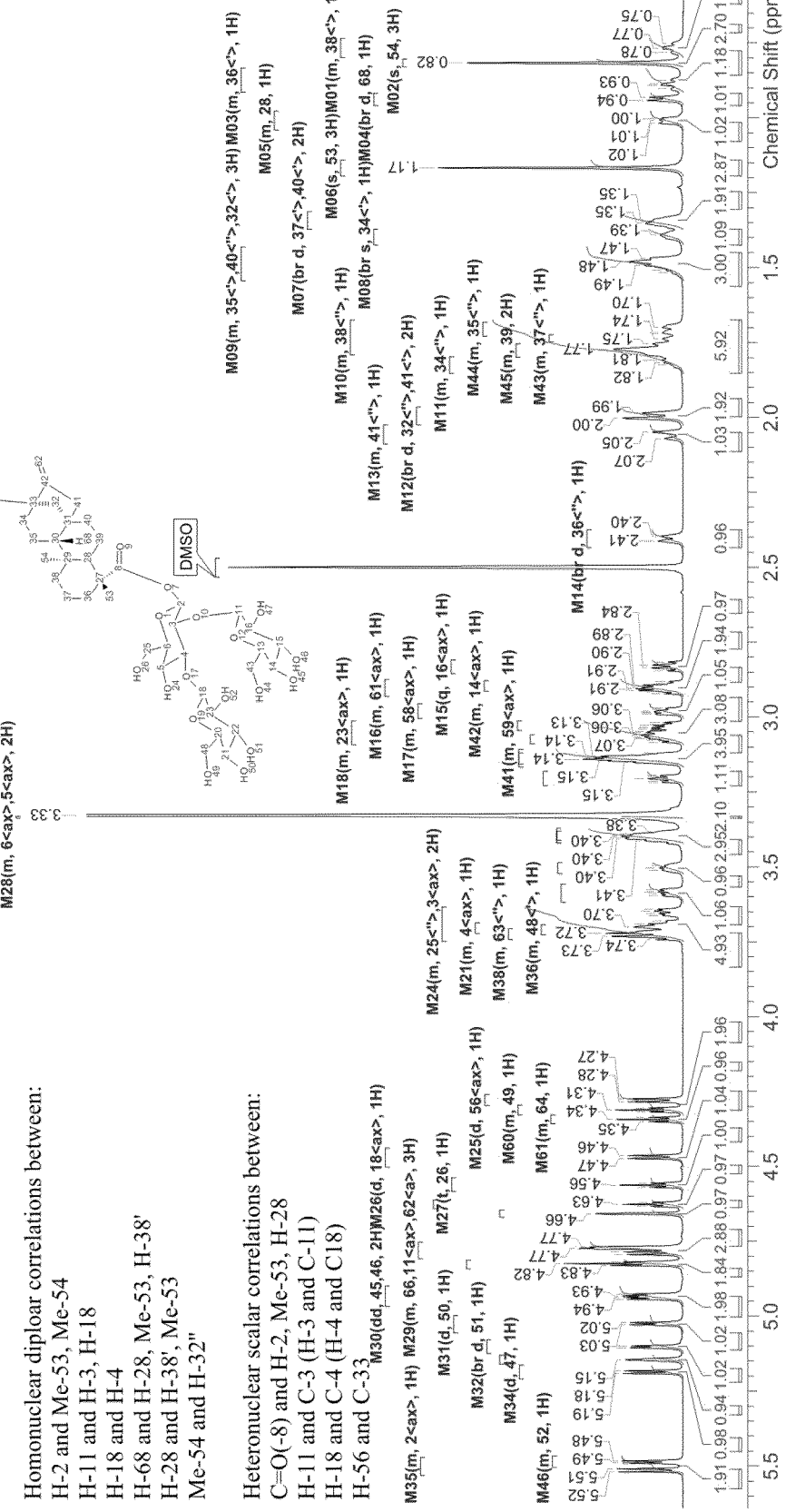
Figure 8A:
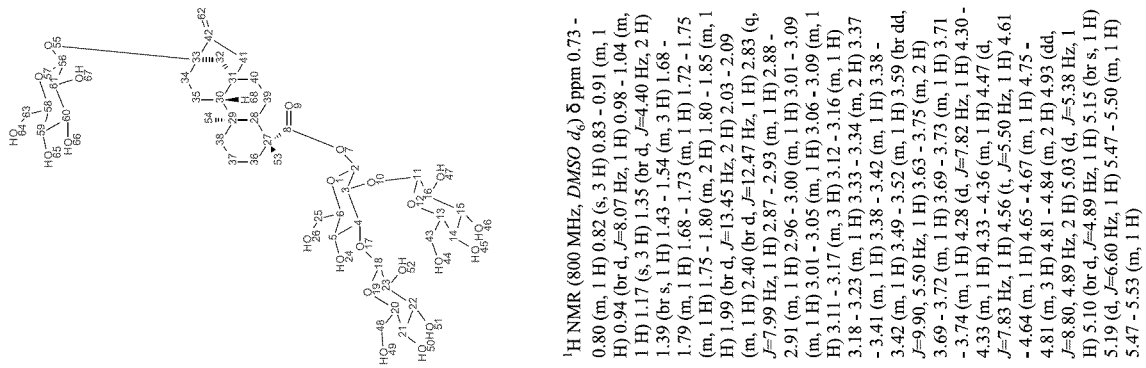
Figure 8A:
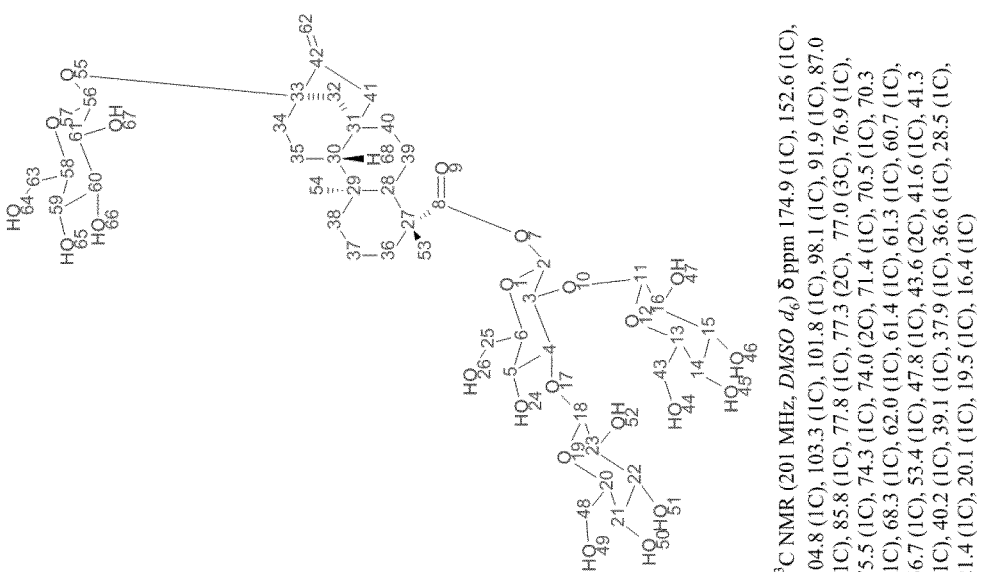
Figure 8A:
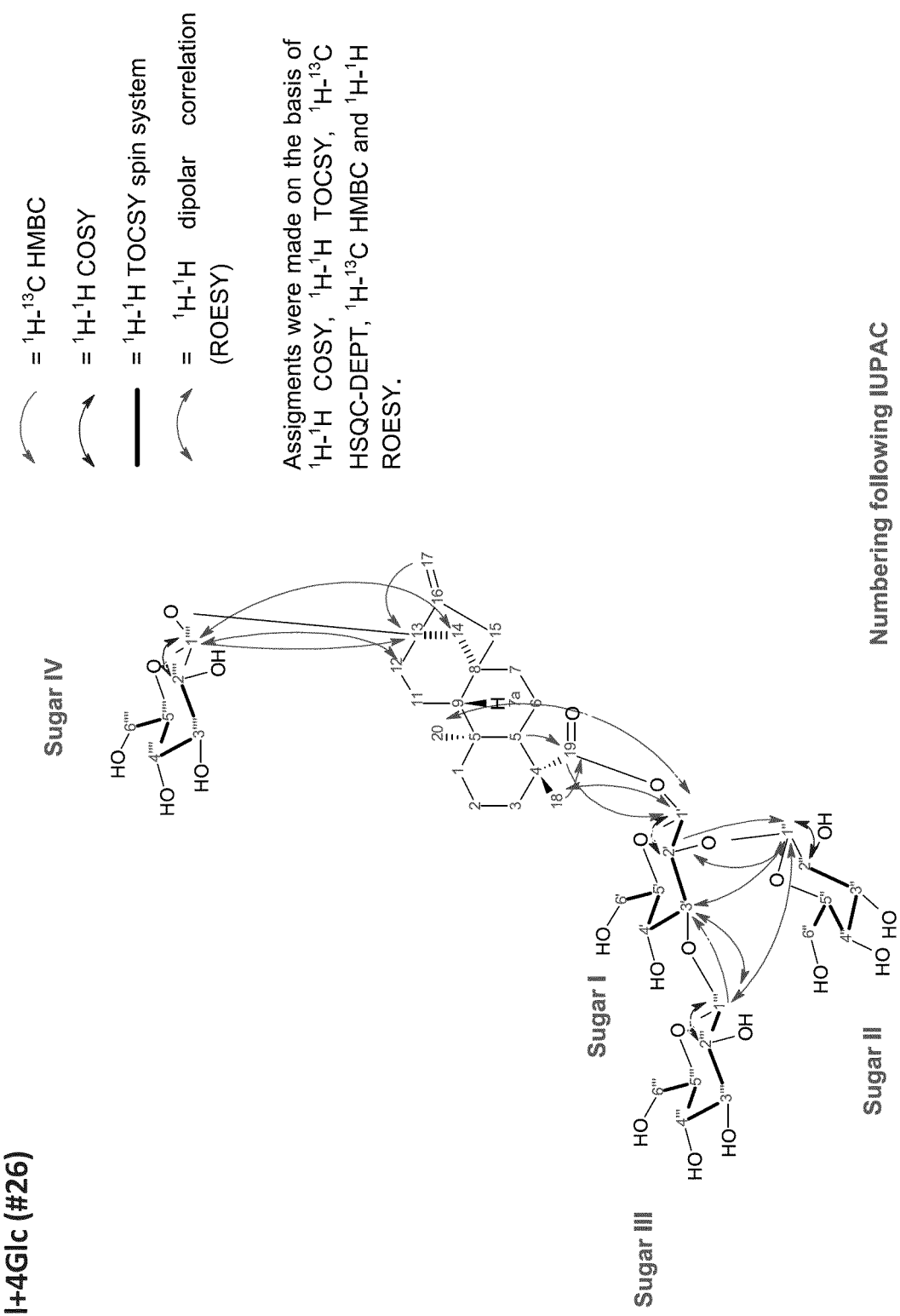
Figure 8A:
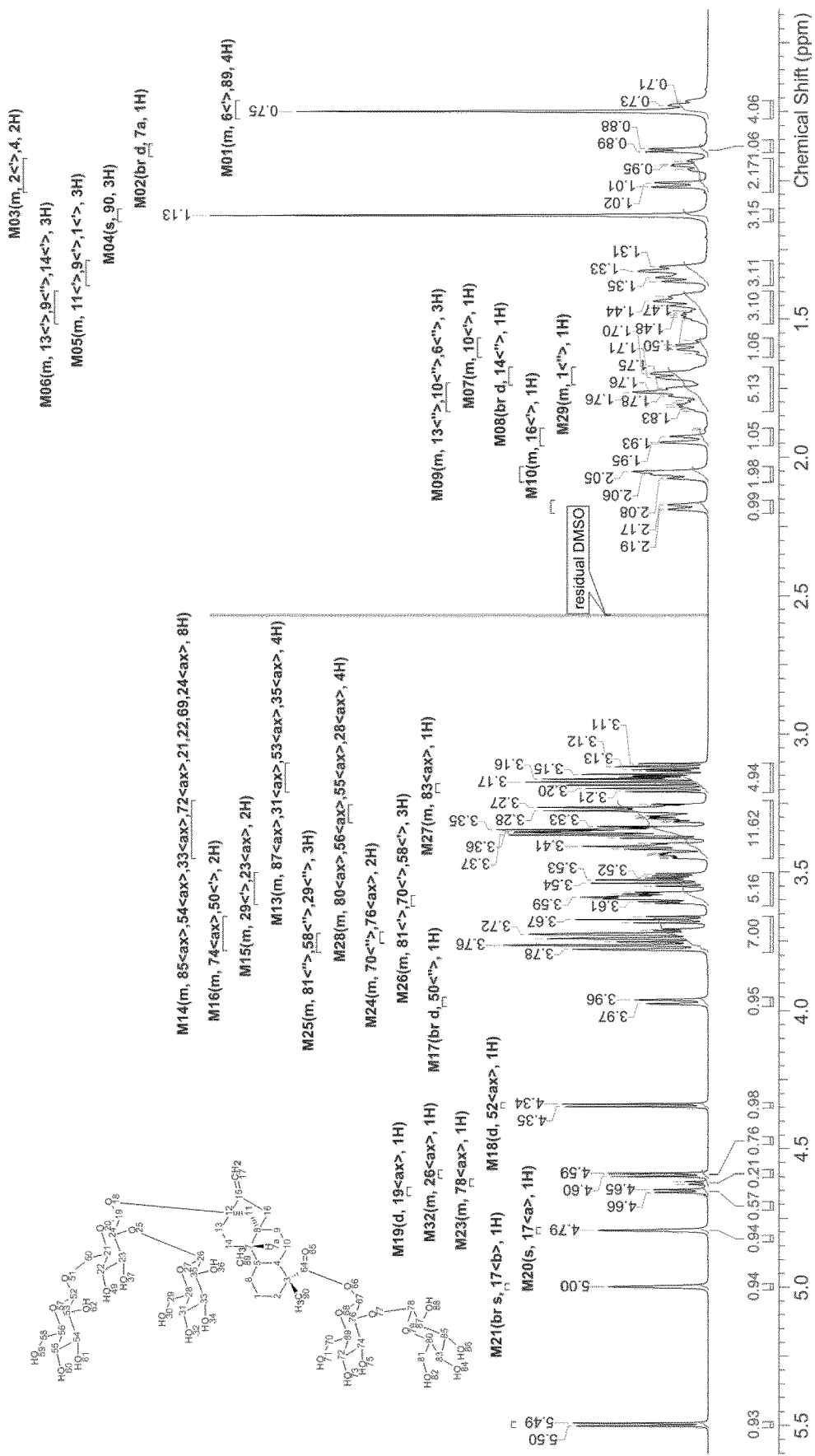
Figure 8A:
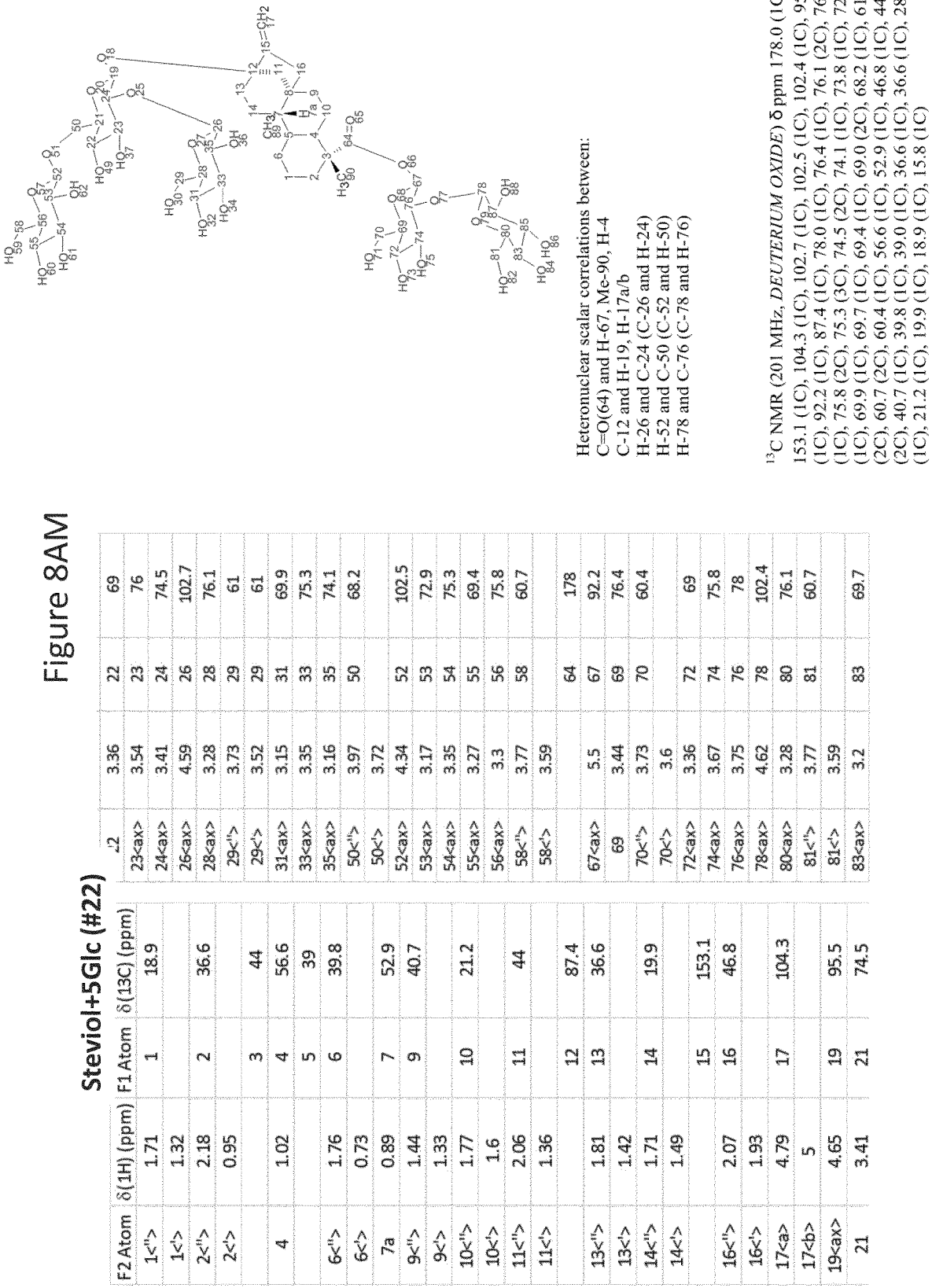
Figure 8A:
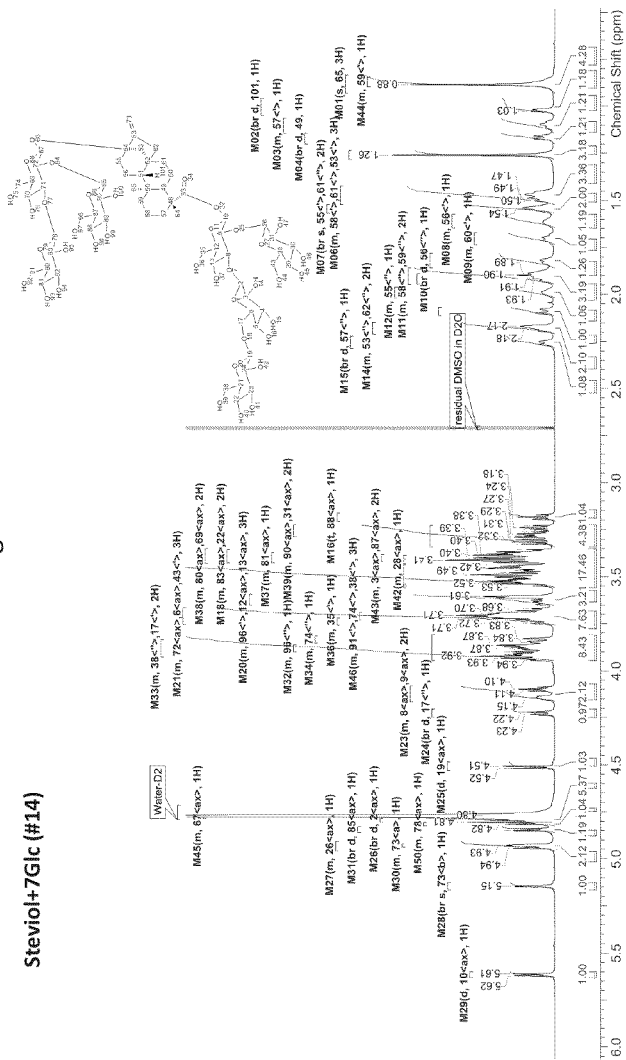
Figure 8A:
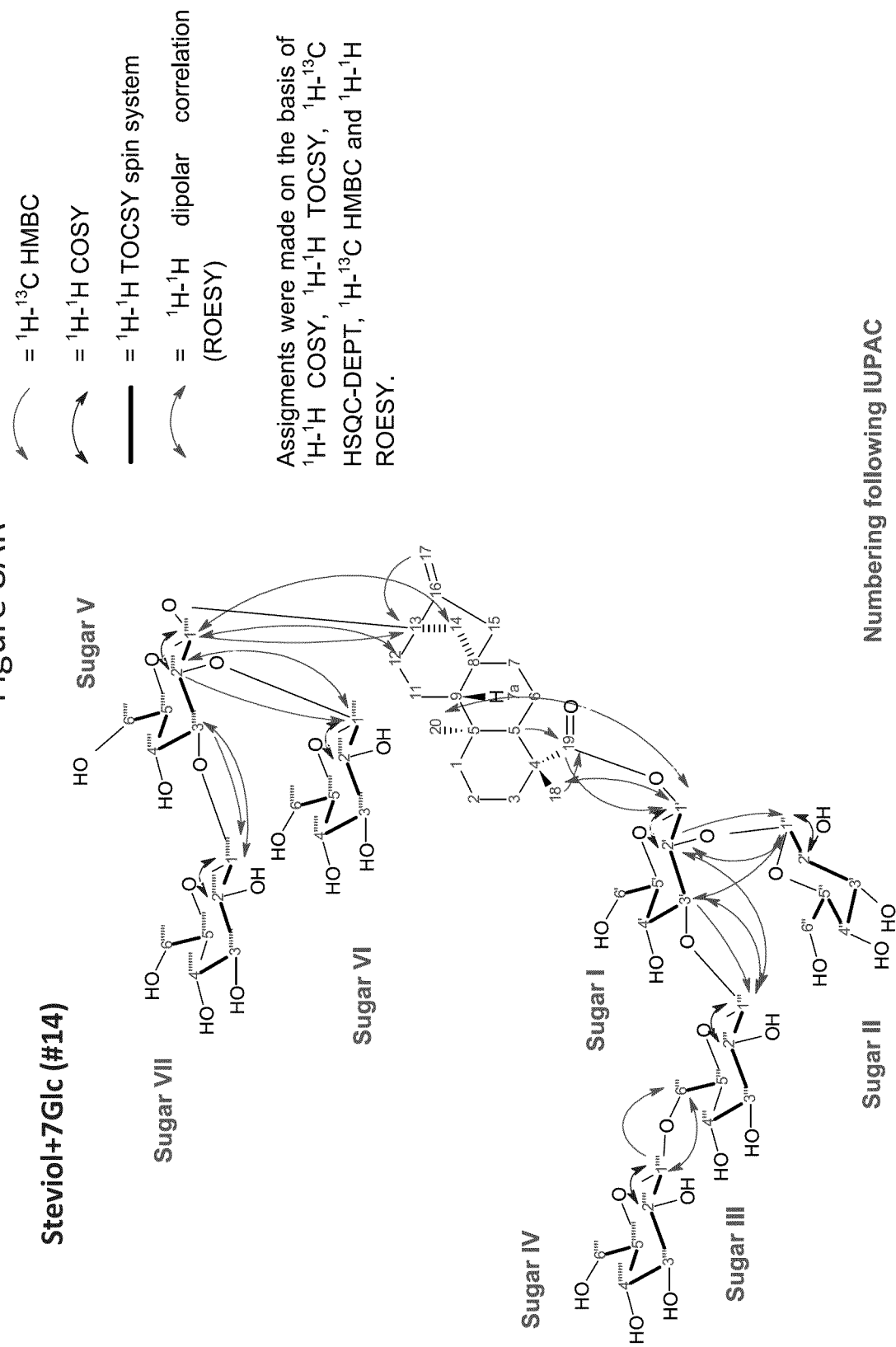

As used herein, the term "steviol glycoside" refers to rebaudioside A (RebA) (CAS #58543-16-1), rebaudioside B (RebB) (CAS #58543-17-2), rebaudioside C (RebC) (CAS #63550-99-2), rebaudioside D (RebD) (CAS #63279-13-0), rebaudioside E (RebE) (CAS #63279-14-1), rebaudioside F (RebF) (CAS #438045-89-7), rebaudioside M (RebM) (CAS #1220616-44-3), rubusoside (CAS #63849-39-4), dulcoside A (CAS #64432-06-0), rebaudioside I (RebI) (MassBank Record: FU000332), rebaudioside Q (RebQ), 1,2-stevioside (CAS #57817-89-7), 1,3-stevioside (RebG), 1,2-bioside (MassBank Record: FU000299), 1,3-bioside, steviol-13-O-glucoside (13-SMG), steviol-19-O-glucoside (19-SMG), a di-glycosylated steviol, a tri-glycosylated steviol, a tetra-glycosylated steviol, a penta-glycosylated steviol, a hexa-glycosylated steviol, a hepta-glycosylated steviol, and/or isomers thereof. See FIG. 2; see also, Steviol Glycosides Chemical and Technical Assessment 69th JECFA, 2007, prepared by Harriet Wallin, Food Agric. Org. See FIG. 2, FIG. 7, FIG. 8, and Table 1; see also, Steviol Glycosides Chemical and Technical Assessment 69th JECFA, 2007, prepared by Harriet Wallin, Food Agric. Org. Glycosylated steviol compounds can comprise one or more glucose, N-acetylglucosamine (GlcNAc), rhamnose, and/or xylose moieties. Non-limiting examples of steviol glycosides that can be produced by methods described herein are shown in Table 1, FIG. 7, and FIG. 8.

As used herein, the term "glycosylated ent-kaurenol compound" refers to di-glycosylated ent-kaurenol or tri-glycosylated ent-kaurenol. As used herein, the term "glycosylated ent-kaurenoic acid compound" refers to di-glycosylated ent-kaurenoic acid or tri-glycosylated ent-kaurenoic acid. See FIG. 7, FIG. 8, and Table 1. Glycosylated ent-kaurenol compounds and glycosylated ent-kaurenoic acid compounds can comprise one or more glucose, GlcNAc, rhamnose, and/or xylose moieties. Non-limiting examples of glycosylated ent-kaurenol compounds and glycosylated ent-kaurenoic acid compounds that can be produced by methods described herein are shown in Table 1, FIG. 7, and FIG. 8.

As used herein, the terms "steviol glycoside precursor" and "steviol glycoside precursor compound" are used to refer to intermediate compounds in the steviol glycoside biosynthetic pathway. Steviol glycoside precursors include, but are not limited to, geranylgeranyl diphosphate (GGPP), ent-copalyl-diphosphate, ent-kaurene, ent-kaurenol, ent-kaurenol, ent-kaurenoic acid, and steviol. See FIG. 1. In some embodiments, steviol glycoside precursors are themselves steviol glycoside compounds. For example, 19-SMG, rubusoside, stevioside, and RebE are steviol glycoside precursors of RebM. See FIG. 2. Steviol glycosides and/or steviol glycoside precursors can be produced in vivo (i.e., in a recombinant host), in vitro (i.e., enzymatically), or by whole cell bioconversion. As used herein, the terms "produce" and "accumulate" can be used interchangeably to describe synthesis of steviol glycosides and steviol glycoside precursors in vivo, in vitro, or by whole cell bioconversion.

As used herein, the term "cell culture broth" can be used to refer to a liquid that can support or has supported growth of a host cell, including, but not limited to, a yeast host cell. The components of a cell culture broth can include, for example, a steviol glycoside, a glycosylated ent-kaurenol compound, and/or a glycosylated ent-kaurenoic acid compound produced by the host cell, glucose, fructose, sucrose, trace metals, vitamins, salts, yeast nitrogen base (YNB), and/or amino acids.

As used herein, the term "cell lysate" can be used to refer to a fluid comprising the components of a lysed cell, i.e., a cell whose membrane has been disrupted chemically or mechanically. A cell lysate can further comprise a steviol glycoside, a glycosylated ent-kaurenol compound, and/or a glycosylated ent-kaurenoic acid compound produced by the host cell, glucose, fructose, sucrose, xylose, rhamnose, uridine diphosphate (UDP)-glucose, UDP-rhamnose, UDP-xylose, GlcNAc, trace metals, vitamins, salts, YNB, and/or amino acids. In some aspects, a cell lysate is a yeast cell lysate, such as an S. cerevisiae cell lysate, or a bacterial cell lysate, such as an E. coli cell lysate.

As used herein, the term "reaction mixture" refers to a solution for conducting an in vitro reaction. The components of a reaction mixture can include, but are not limited to, a steviol glycoside, a glycosylated ent-kaurenol compound, a glycosylated ent-kaurenoic acid compound, a polypeptide such as a UGT polypeptide, UDP-glucose, UDP-rhamnose, UDP-xylose, GlcNAC, a buffer, and/or salts.

Recombinant steviol glycoside-producing *Saccharomyces cerevisiae* (*S. cerevisiae*) strains are described in WO 2011/153378, WO 2013/022989, WO 2014/122227, and WO 2014/122328. Methods of producing steviol glycosides in recombinant hosts, by whole cell bioconversion, and in vitro are also described in WO 2011/153378, WO 2013/022989, WO 2014/122227, and WO 2014/122328.

In some embodiments, steviol glycosides and/or steviol glycoside precursors are produced in vivo through expression of one or more enzymes involved in the steviol glycoside biosynthetic pathway in a recombinant host. For example, a steviol-producing recombinant host expressing one or more of a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and a gene encoding a UGT polypeptide can produce a steviol glycoside and/or steviol glycoside precursors in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

A recombinant host described herein can comprise a gene encoding a polypeptide capable of synthesizing geranylgeranyl pyrophosphate (GGPP) from farnesyl diphosphate (FPP) and isopentenyl diphosphate (IPP), a gene encoding a polypeptide capable of synthesizing ent-copalyl dirophosphate from GGPP; a gene encoding a polypeptide capable of synthesizing ent-kaurene from ent-copalyl pyrophosphate, a gene encoding a polypeptide capable of synthesizing ent-kaurenoic acid from ent-kaurene, a gene encoding a polypeptide capable of synthesizing steviol from ent-kaurenoic acid; and/or a gene encoding a polypeptide capable of converting NADPH to NADP+. A GGPPS polypeptide can synthesize GGPP from FPP and IPP. A CDPS polypeptide can synthesize ent-copalyl dirophosphate from GGPP. A KS polypeptide can synthesize ent-kaurene from ent-copalyl pyrophosphate. A KO polypeptide can synthesize ent-kaurenoic acid from ent-kaurene. A KAH polypeptide can synthesize steviol from ent-kaurenoic acid. A CPR polypeptide can convert NADPH to NADP+.

In another example, a recombinant host expressing a gene encoding a GGPPS polypeptide, a gene encoding a CDPS polypeptide, a gene encoding a KS polypeptide, a gene encoding a KO polypeptide, a gene encoding a KAH polypeptide, and a gene encoding a CPR polypeptide can produce steviol in vivo. See, e.g., FIG. 1. The skilled worker will appreciate that one or more of these genes can be endogenous to the host provided that at least one (and in some embodiments, all) of these genes is a recombinant gene introduced into the recombinant host.

In another example, a recombinant host expressing a gene encoding a GGPPS polypeptide, a gene encoding a CDPS polypeptide, a gene encoding a KS polypeptide, a gene encoding a KO polypeptide, a gene encoding a KAH polypeptide, a gene encoding a CPR polypeptide, and one or more of a gene encoding a UGT polypeptide can produce a steviol glycoside in vivo. See, e.g., FIGS. 1 and 2. The skilled worker will appreciate that one or more of these genes can be endogenous to the host provided that at least one (and in some embodiments, all) of these genes is a recombinant gene introduced into the recombinant host.

In some aspects, the GGPPS polypeptide comprises a polypeptide having an amino acid sequence set forth in SEQ ID NO:20 (which can be encoded by the nucleotide sequence set forth in SEQ ID NO:19), SEQ ID NO:22 (which can be encoded by the nucleotide sequence set forth in SEQ ID NO:21), SEQ ID NO:24 (which can be encoded by the nucleotide sequence set forth in SEQ ID NO:23), SEQ ID NO:26 (which can be encoded by the nucleotide sequence set forth in SEQ ID NO:25), SEQ ID NO:28 (which can be encoded by the nucleotide sequence set forth in SEQ ID NO:27), SEQ ID NO:30 (which can be encoded by the nucleotide sequence set forth in SEQ ID NO:29), SEQ ID NO:32 (which can be encoded by the nucleotide sequence set forth in SEQ ID NO:31), or SEQ ID NO:116 (which can be encoded by the nucleotide sequence set forth in SEQ ID NO:115).

In some aspects, the CDPS polypeptide comprises a polypeptide having an amino acid sequence set forth in SEQ ID NO:34 (which can be encoded by the nucleotide sequence set forth in SEQ ID NO:33), SEQ ID NO:36 (which can be encoded by the nucleotide sequence set forth in SEQ ID NO:35), SEQ ID NO:38 (which can be encoded by the nucleotide sequence set forth in SEQ ID NO:37), SEQ ID NO:40 (which can be encoded by the nucleotide sequence set forth in SEQ ID NO:39), or SEQ ID NO:42

(which can be encoded by the nucleotide sequence set forth in SEQ ID NO:41). In some embodiments, the CDPS polypeptide lacks a chloroplast transit peptide.

In some aspects, the KS polypeptide comprises a polypeptide having an amino acid sequence set forth in SEQ ID NO:44 (which can be encoded by the nucleotide sequence set forth in SEQ ID NO:43), SEQ ID NO:46 (which can be encoded by the nucleotide sequence set forth in SEQ ID NO:45), SEQ ID NO:48 (which can be encoded by the nucleotide sequence set forth in SEQ ID NO:47), SEQ ID NO:50 (which can be encoded by the nucleotide sequence set forth in SEQ ID NO:49), or SEQ ID NO:52 (which can be encoded by the nucleotide sequence set forth in SEQ ID NO:51).

In some embodiments, a recombinant host comprises a gene encoding a CDPS-KS polypeptide. In some aspects, the CDPS-KS polypeptide comprises a polypeptide having an amino acid sequence set forth in SEQ ID NO:54 (which can be encoded by the nucleotide sequence set forth in SEQ ID NO:53), SEQ ID NO:56 (which can be encoded by the nucleotide sequence set forth in SEQ ID NO:55), or SEQ ID NO:58 (which can be encoded by the nucleotide sequence set forth in SEQ ID NO:57).

In some aspects, the KO polypeptide comprises a polypeptide having an amino acid sequence set forth in SEQ ID NO:60 (which can be encoded by the nucleotide sequence set forth in SEQ ID NO:59), SEQ ID NO:62 (which can be encoded by the nucleotide sequence set forth in SEQ ID NO:61), SEQ ID NO:117 (which can be encoded by the nucleotide sequence set forth in SEQ ID NO:63 or SEQ ID NO:64), SEQ ID NO:66 (which can be encoded by the nucleotide sequence set forth in SEQ ID NO:65), SEQ ID NO:68 (which can be encoded by the nucleotide sequence set forth in SEQ ID NO:67), SEQ ID NO:70 (which can be encoded by the nucleotide sequence set forth in SEQ ID NO:69), SEQ ID NO:72 (which can be encoded by the nucleotide sequence set forth in SEQ ID NO:71), SEQ ID NO:74 (which can be encoded by the nucleotide sequence set forth in SEQ ID NO:73), or SEQ ID NO:76 (which can be encoded by the nucleotide sequence set forth in SEQ ID NO:75).

In some aspects, the CPR polypeptide comprises a polypeptide having an amino acid sequence set forth in SEQ ID NO:78 (which can be encoded by the nucleotide sequence set forth in SEQ ID NO:77), SEQ ID NO:80 (which can be encoded by the nucleotide sequence set forth in SEQ ID NO:79), SEQ ID NO:82 (which can be encoded by the nucleotide sequence set forth in SEQ ID NO:81), SEQ ID NO:84 (which can be encoded by the nucleotide sequence set forth in SEQ ID NO:83), SEQ ID NO:86 (which can be encoded by the nucleotide sequence set forth in SEQ ID NO:85), SEQ ID NO:88 (which can be encoded by the nucleotide sequence set forth in SEQ ID NO:87), SEQ ID NO:90 (which can be encoded by the nucleotide sequence set forth in SEQ ID NO:89), or SEQ ID NO:92 (which can be encoded by the nucleotide sequence set forth in SEQ ID NO:91).

In some aspects, the KAH polypeptide comprises a polypeptide having an amino acid sequence set forth in SEQ ID NO:94 (which can be encoded by the nucleotide sequence set forth in SEQ ID NO:93), SEQ ID NO:97 (which can be encoded by the nucleotide sequence set forth in SEQ ID NO:95 or SEQ ID NO:96), SEQ ID NO:100 (which can be encoded by the nucleotide sequence set forth in SEQ ID NO:98 or SEQ ID NO:99), SEQ ID NO:101, SEQ ID NO:102, SEQ ID NO:103, SEQ ID NO:104, SEQ ID NO:106 (which can be encoded by the nucleotide sequence set forth in SEQ ID NO:105), SEQ ID NO:108 (which can be encoded by the nucleotide sequence set forth in SEQ ID NO:107), SEQ ID NO:110 (which can be encoded by the nucleotide sequence set forth in SEQ ID NO:109), SEQ ID NO:112 (which can be encoded by the nucleotide sequence set forth in SEQ ID NO:111), or SEQ ID NO:114 (which can be encoded by the nucleotide sequence set forth in SEQ ID NO:113).

In some embodiments, a recombinant host comprises a nucleic acid encoding a UGT85C2 polypeptide (SEQ ID NO:7), a nucleic acid encoding a UGT76G1 polypeptide (SEQ ID NO:9), a nucleic acid encoding a UGT74G1 polypeptide (SEQ ID NO:4), a nucleic acid encoding a UGT91D2 polypeptide, and/or a nucleic acid encoding a EUGT11 polypeptide (SEQ ID NO:16). In some aspects, the UGT91D2 polypeptide can be a UGT91D2e polypeptide (SEQ ID NO:11) or a UGT91D2e-b polypeptide (SEQ ID NO:13). In some aspects, the UGT85C2 polypeptide can be encoded by the nucleotide sequence set forth in SEQ ID NO:5 or SEQ ID NO:6, the UGT76G1 polypeptide can be encoded by the nucleotide sequence set forth in SEQ ID NO:8, the UGT74G1 polypeptide can be encoded by the nucleotide sequence set forth in SEQ ID NO:3, the UGT91D2e polypeptide can be encoded by the nucleotide sequence set forth in SEQ ID NO:10, the UGT91D2e-b polypeptide can be encoded by the nucleotide sequence set forth in SEQ ID NO:12, and the EUGT11 polypeptide can be encoded by the nucleotide sequence set forth in SEQ ID NO:14 or SEQ ID NO:15. The skilled worker will appreciate that expression of these genes may be necessary to produce a particular steviol glycoside but that one or more of these genes can be endogenous to the host provided that at least one (and in some embodiments, all) of these genes is a recombinant gene introduced into the recombinant host. In a particular embodiment, a steviol-producing recombinant microorganism comprises exogenous nucleic acids encoding UGT85C2, UGT76G1, or UGT91D2 polypeptides.

In another particular embodiment, a steviol-producing recombinant microorganism comprises exogenous nucleic acids encoding UGT85C2, UGT76G1, UGT74G1, and UGT91D2 polypeptides. In yet another particular embodiment, a steviol-producing recombinant microorganism comprises exogenous nucleic acids encoding UGT85C2, UGT76G1, UGT74G1, and EUGT11 polypeptides. In yet another particular embodiment, a steviol-producing recombinant microorganism comprises exogenous nucleic acids encoding UGT85C2, UGT76G1, UGT74G1, UGT91D2 (including inter alia UGT91D2e, UGT91D2m, UGT91D2e-b, and functional homologs thereof), and EUGT11 polypeptides. In yet another particular embodiment, a steviol-producing recombinant microorganism comprises exogenous nucleic acids encoding UGT85C2, UGT76G1, UGT74G1, UGT91D2, and/or EUGT11 polypeptides. In yet another particular embodiment, a steviol-producing recombinant microorganism comprises exogenous nucleic acids encoding UGT85C2, UCT76G1, UGT74G1, UGT91D2, and/or EUGT11 polypeptides.

In some embodiments, a recombinant host comprises: (a) a gene encoding a polypeptide capable of beta 1,2 glucosylation of the C2' of the 19-O glucose of a steviol glycoside; (b) a gene encoding a polypeptide capable of beta 1,2 glucosylation of the C2' of the 13-O-glucose of a steviol glycoside; (c) a gene encoding a polypeptide capable of beta 1,3 glucosylation of the C3' of the 19-O-glucose of a steviol glycoside; (d) a gene encoding a polypeptide capable of beta 1,3 glucosylation of the C3' of the 13-O-glucose of a steviol glycoside; (e) a gene encoding a polypeptide capable of beta 1,6 glucosylation of the C6' of the 13-O-glucose of a steviol glycoside; (f) a gene encoding a polypeptide capable of beta 1,6 glucosylation of the C6' of the 1,3-glucose of a 13-O diglucoside moiety of a steviol glycoside; (g) a gene encoding a polypeptide capable of glucosylation of the 13-OH of steviol or a steviol glycoside; (h) a gene encoding a polypeptide capable of glucosylation of the C-19 carboxyl of steviol or a steviol glycoside; (i) a gene encoding a polypeptide capable of beta 1,2 rhamnosylation of the C2' of the 13-O-glucose of a steviol glycoside; (j) a gene encoding a polypeptide capable of beta 1,2 xylosylation of the C2' of the 13-O-glucose of a steviol glycoside; (o) a gene encoding a polypeptide capable of beta 1,2 GlcNAc transfer to the C2' of the 19-O glucose of a steviol glycoside; (k) a gene encoding a polypeptide capable of beta 1,3 GlcNAc transfer to the C2' of the 19-O glucose of a steviol glycoside; (l) a gene encoding a polypeptide capable of beta 1,3 GlcNAc transfer to the C2' of the 13-O-glucose of a steviol glycoside; (m) a gene encoding a polypeptide capable of GlcNAc transfer to the C-19 carboxyl of steviol or a steviol glycoside; (n) a gene encoding a polypeptide capable of glucosylation of the C-19 carboxyl of kaurenoic acid or kaurenol; (o) a gene encoding a polypeptide capable of beta 1,2 glucosylation of the C2' of the 19-O glucose of a kaurenoic acid glycoside or kaurenol glycoside; (p) a gene encoding a polypeptide capable of a beta 1,2 glucosylation of a beta 1,2 diglucoside of kaurenoic acid; (q) a gene encoding a polypeptide capable of beta 1,2 GlcNAc transfer of a beta 1,2 diglucoside of kaurenoic acid; (r) a gene encoding a polypeptide capable of beta 1,3 glucosylation of the C3' of the 19-O-glucose of a kaurenoic acid glycoside or kaurenol glycoside; and/or (s) a gene encoding a polypeptide capable of beta 1,6 glucosylation of the C6' of the 1,3-glucose of a 19-O diglucoside moiety of a steviol glycoside.

Figure 3:
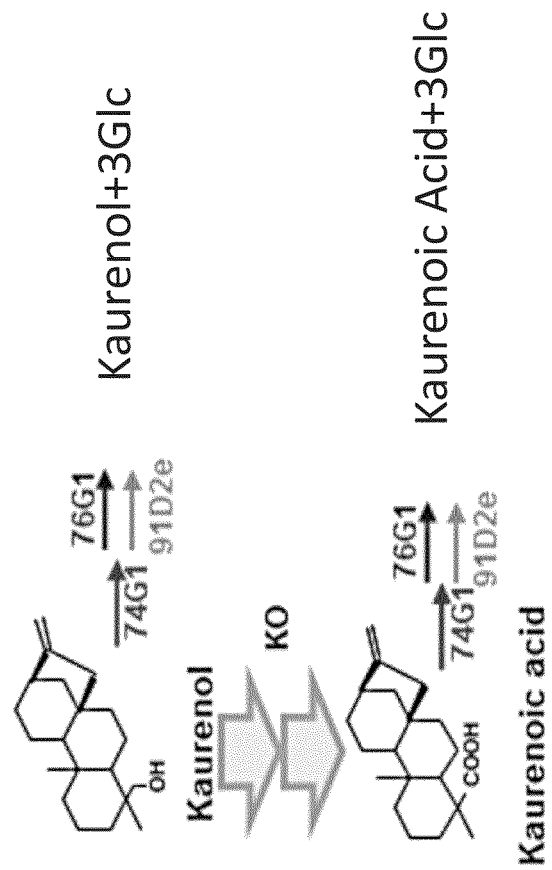
FIG. 3 shows the steviol synthetic intermediate, ent-kaurenol, and its bioconversion product, ent-kaurenoic acid, for the steviol pathway step catalyzed by a KO, along with potential glycosylation by-products (mono-, di-, and/or tri-glycosylated ent-kaurenol and mono-, di-, or tri-glycosylated ent-kaurenoic acid).

In some aspects, EUGT11 (SEQ ID NO:14/SEQ ID NO:15, SEQ ID NO:16), UGT91D2e (SEQ ID NO:10, SEQ ID NO:11), UGT91D2e-b (SEQ ID NO:12, SEQ ID NO:13), a variant thereof, or a chimeric protein thereof catalyzes beta 1,2 glucosylation of the C2' of the 19-O glucose of a steviol glycoside. Exemplary UGT91D2e variant sequences are set forth in SEQ ID NOs:1, 2, 118-121, 123, and 191-214. In some aspects, UGT91D2e (SEQ ID NO:10, SEQ ID NO:11), UGT91D2e-b (SEQ ID NO:12, SEQ ID NO:13), a variant thereof, or a chimeric protein thereof catalyzes beta 1,2 glucosylation of the C2' of the 13-O-glucose of a steviol glycoside. Exemplary UGT91D2e variant sequences are set forth in SEQ ID NOs:1, 2, 118-121, 123, and 191-214. Exemplary UGT91D2e-EUGT11 chimeric protein sequences are set forth in SEQ ID NO:17 and SEQ ID NO:18. In some aspects, UGT76G1 (SEQ ID NO:8, SEQ ID NO:9), a variant thereof, or a chimeric protein thereof catalyzes beta 1,3 glucosylation of the C3' of the 19-O-glucose of a steviol glycoside and/or beta 1,3 glucosylation of the C3' of the 13-O-glucose of a steviol glycoside. Exemplary UGT76G1 variant sequences are set forth in SEQ ID NOs:181-190 and 217-220. In some aspects, UGT85C2 (SEQ ID NO:5/SEQ ID NO:6, SEQ ID NO:7), a variant thereof, or a chimeric protein thereof catalyzes glucosylation of the 13-OH of steviol or a steviol glycoside. Exemplary UGT85C2 variant sequences are set forth in SEQ ID NOs:127 and 147-180. In some aspects, UGT74G1 (SEQ ID NO:3, SEQ ID NO:4), a variant thereof, or a chimeric protein thereof catalyzes glucosylation of the C-19 carboxyl of steviol or a steviol glycoside. In some aspects, EUGT11 (SEQ ID NO:14/SEQ ID NO:15, SEQ ID NO:16), UGT91D2e (SEQ ID NO:10, SEQ ID NO:11), UGT74G1 (SEQ ID NO:3, SEQ ID NO:4), and/or UGT76G1 (SEQ ID NO:8, SEQ ID NO:9 can accept uridine diphosphate N-acetylglucosamine (UDP-Glc-NAc) as a substrate. In some aspects, UGT74G1 glycosylates ent-kaurenol and ent-kaurenoic acid; UGT76G1 and UGT91D2e subsequently add additional glucose or GlcNAc moieties by either a 1,3- or 1,2-linkage to form tri-glycosylated compounds. See FIGS. 3, 7 and 8.

In some embodiments, steviol glycosides and/or steviol glycoside precursors are produced through contact of a steviol glycoside precursor with one or more enzymes involved in the steviol glycoside pathway in vitro. For example, contacting steviol with a UGT polypeptide can result in production of a steviol glycoside in vitro. In some embodiments, a steviol glycoside precursor is produced through contact of an upstream steviol glycoside precursor with one or more enzymes involved in the steviol glycoside pathway in vitro. For example, contacting ent-kaurenoic acid with a KAH enzyme can result in production of steviol in vitro.

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a UGT polypeptide can take up steviol and glycosylate steviol in the cell; following glycosylation in vivo, a steviol glycoside can be excreted into the culture medium. In some embodiments, the cell is permeabilized to take up a substrate to be modified or to excrete a modified product.

In some embodiments, steviol, one or more steviol glycoside precursors, and/or one or more steviol glycosides are produced by co-culturing of two or more hosts. In some embodiments, one or more hosts, each expressing one or more enzymes involved in the steviol glycoside pathway, produce steviol, one or more steviol glycoside precursors, and/or one or more steviol glycosides. For example, a host comprising a GGPPS, a CDPS, a KO, a KS, a KAH, and/or a CPR and a host comprising one or more UGTs produce one or more steviol glycosides.

In some embodiments, polypeptides suitable for producing steviol glycosides, such as 1,2-stevioside and RebD, in vitro, in a recombinant host, or by whole cell bioconversion include functional homologs of UGT91D2e (SEQ ID NO:10, SEQ ID NO:11), including UGT91D2e-b (SEQ ID NO:12, SEQ ID NO:13); UGT91D2e V286C (SEQ ID NO:1); UGT91D2e G384W (SEQ ID NO:2); UGT91D2e L211M (SEQ ID NO:118); UGT91D2e L195G (SEQ ID NO:119); UGT91D2e V196P (SEQ ID NO:120); UGT91D2e L211H (SEQ ID NO:121); UGT91D2e L213E (SEQ ID NO:191); UGT91D2e S221Y (SEQ ID NO:192); UGT91D2e E438H (SEQ ID NO:193); UGT91D2e M152T (SEQ ID NO:194); UGT91D2e L211C (SEQ ID NO:195); UGT91D2e L195S (SEQ ID NO:196); UGT91D2e L195V (SEQ ID NO:197); UGT91D2e V286S (SEQ ID NO:198); UGT91D2e S221S (SEQ ID NO:199); UGT91D2e P93V M152G (SEQ ID NO:200); UGT91D2e S99I (SEQ ID NO:201); UGT91D2e T144K P201P (SEQ ID NO:202); UGT91D2e T144L (SEQ ID NO:203); UGT91D2e T144M (SEQ ID NO:204); UGT91D2e A148K L211I (SEQ ID NO:205); UGT91D2e L195N (SEQ ID NO:206); UGT91D2e K199C (SEQ ID NO:207); UGT91D2e L211M E426G A466V (SEQ ID NO:208); UGT91D2e L211T I303I (SEQ ID NO:209); UGT91D2e V286N (SEQ ID NO:210);

UGT91D2e S114F V286S (SEQ ID NO:211); UGT91D2e G384K (SEQ ID NO:212); UGT91D2e G384Y (SEQ ID NO:213); UGT91D2e E438M (SEQ ID NO:214); and UGT91D2e L195C (SEQ ID NO:123). See Example 3.

In some embodiments, a useful UGT91D2 homolog can have one or more amino acid substitutions at residues 195, 196, 211, 286, and 384. See Table 2. Non-limiting examples of useful UGT91D2e homologs include polypeptides having substitutions (with respect to SEQ ID NO:11) at residue 93 (e.g., a valine at residue 93); 99 (e.g., an isoleucine at residue 99), 114 (e.g., a phenylalanine at residue 114); 144 (e.g., a lysine, leucine, or methionine at residue 144); 148 (e.g., a lysine at residue 148); 152 (e.g., a threonine at residue 152); 195 (e.g., a glycine, cysteine, serine, arginine, or valine at residue 195); 196 (e.g., a proline at residue 196); 199 (e.g., a cysteine at residue 199); 211 (e.g., a methionine, histidine, threonine, cysteine, or isoleucine at residue 211); 213 (e.g., a glutamic acid at 213); 221 (e.g., an isoleucine at residue 221); 286 (e.g., an alanine, cysteine, asparagine, or serine at residue 286); 384 (e.g., a tryptophan, lysine, or tyrosine at residue 384); 426 (e.g., a glycine at residue 426); 438 (e.g., a histidine or methionine at residue 438); or 466 (e.g., a valine at residue 466). See Example 3.

In some embodiments, UGT91D2e variants comprise silent mutations. For example, in some embodiments, UGT91D2e variants comprise silent mutations at residues not limited to residue 130, residue 201, or residue 221. See Example 3.

In some embodiments, UGT91D2e variants not limited to UGT91D2e V286C (SEQ ID NO:1), UGT91D2e G384W (SEQ ID NO:2), UGT91D2e L195V (SEQ ID NO:197), UGT91D2e V286S (SEQ ID NO:198), UGT91D2e T144K P201P (SEQ ID NO:202), UGT91D2e L211T I130I (SEQ ID NO:184), UGT91D2e S11F V286S (SEQ ID NO:211), and UGT91D2e E438M (SEQ ID NO:214) are selective towards rubusoside, with preferential accumulation of 1,2-stevioside. In some embodiments, UGT91D2e variants not limited to UGTD1D2e P93V M152G (SEQ ID NO:200), UGT91D2e S99I (SEQ ID NO:201), UGT91D2e T144L (SEQ ID NO:203), UGT91D2e A148K L221I (SEQ ID NO:205), and UGT91D2e G384K (SEQ ID NO:212) are selective towards RebA, with preferential accumulation of RebD. In some embodiments, UGT91D2e variants not limited to a UGT91D2e variant with a mutation at residue 211 (e.g., UGT91D2e L211M of SEQ ID NO:118) catalyze conversion of rubusoside to 1,2-stevioside and conversion of RebA to RebD, with preferential accumulation of 1,2-stevioside. See Example 3 and Tables 2 and 3.

In some embodiments, polypeptides suitable for producing steviol glycosides, such as RebA, RebD, rubusoside, and/or 1,2-stevioside in a recombinant host include UGT91D2e-b-EUGT11 chimeric enzymes, such as Chim_3 (SEQ ID NO:17) or Chim_7 (SEQ ID NO:18). See Example 4 and Table 5.

In some embodiments, Chim_7 (SEQ ID NO:18) more efficiently converts rubusoside to 1,2-stevioside, compared to EUGT11 and UGT91D2e. In some embodiments, Chim_7 (SEQ ID NO:18) fully consumes a supplied amount of rubusoside. In some embodiments, Chim_7 (SEQ ID NO:18) demonstrates 1.75-fold higher activity towards RebA than UGT91D2e-b (SEQ ID NO:12, SEQ ID NO:13). In some embodiments, Chim_3 (SEQ ID NO:17) selectively converts rubusoside to 1,2-stevioside. See Example 4 and Table 5.

In some embodiments, UGT91D2e-b-EUGT11 chimeric enzymes such as Chim_2 (SEQ ID NO:122); Chim_4 (SEQ ID NO:124); Chim_5 (SEQ ID NO:125); Chim_6 (SEQ ID NO:126); Chim_7 (SEQ ID NO:18); Chim_8 (SEQ ID NO:128); Chim_9 (SEQ ID NO:129); Chim_10 (SEQ ID NO:130); Chim_11 (SEQ ID NO:131); Chim_12 (SEQ ID NO:132); Chim_13 (SEQ ID NO:133); Chim_14 (SEQ ID NO:134) are used to produce steviol glycosides and/or steviol glycoside precursors.

In some embodiments, a useful UGT85C2 homolog can have one or more amino acid substitutions at residues 21, 48, 49, 84, 86, 87, 91, 92, 95, 122, 304, and 334. See Table 7. Non-limiting examples of useful UGT85C2 homologs include polypeptides having substitutions (with respect to SEQ ID NO:7) at residue 21 (e.g., a lysine, threonine, or valine at residue 21), 48 (e.g., a serine, histidine, tyrosine, arginine, glutamine, or tryptophan at residue 48), 49 (e.g., a valine at residue 49), 84 (e.g., a glycine, alanine, threonine, cysteine, proline, valine, or asparagine at residue 84), 86 (e.g., an arginine or glycine at residue 86); 87 (e.g., an histidine, proline, methionine or tyrosine at residue 87); 91 (e.g., an lysine, arginine, or threonine at residue 91); 92 (e.g., an phenylalanine, isoleucine, methionine, or lysine at residue 92); 122 (e.g., an serine at residue 122); 304 (e.g., a serine at residue 304); and 334 (e.g., an serine or methionine at residue 334). See SEQ ID NOs:127 and 147-180, Table 7A for UGT85C2 variants analyzed that preferentially catalyze conversion of 19-SMG over conversion of steviol, Table 7B for UGT85C2 variants that preferentially catalyze conversion of steviol over conversion of 19-SMG, and Table 7C for additional UGT85C2 variants that catalyze conversion of 19-SMG and steviol. Also see Example 5.

In some embodiments, a steviol glycoside-producing *S. cerevisiae* strain comprising a recombinant gene encoding a *Synechococcus* sp. GGPPS polypeptide (SEQ ID NO:19, SEQ ID NO:20), a recombinant gene encoding a truncated *Z. mays* CDPS polypeptide (SEQ ID NO:39, SEQ ID NO:40), a recombinant gene encoding an *A. thaliana* KS polypeptide (SEQ ID NO:51, SEQ ID NO:52), a recombinant gene encoding a recombinant *S. rebaudiana* KO polypeptide (SEQ ID NO:59, SEQ ID NO:60), a recombinant gene encoding an *A. thaliana* ATR2 polypeptide (SEQ ID NO:91, SEQ ID NO:92), a recombinant gene encoding an *O. sativa* EUGT11 polypeptide (SEQ ID NO:14/SEQ ID NO:15, SEQ ID NO:16), a recombinant gene encoding an SrKAHe1 polypeptide (SEQ ID NO:93, SEQ ID NO:94), a recombinant gene encoding an *S. rebaudiana* CPR8 polypeptide (SEQ ID NO:85, SEQ ID NO:86), a recombinant gene encoding an *S. rebaudiana* UGT74G1 polypeptide (SEQ ID NO:3, SEQ ID NO:4), a recombinant gene encoding an *S. rebaudiana* UGT76G1 polypeptide (SEQ ID NO:8, SEQ ID NO:9), a recombinant gene encoding an *S. rebaudiana* UGT91D2e polypeptide (SEQ ID NO:10, SEQ ID NO:11), a recombinant KO gene encoded by the nucleotide sequence set forth in SEQ ID NO:67 (corresponding to the amino acid sequence set forth in SEQ ID NO:117), and a recombinant CPR1 gene encoding (SEQ ID NO:77, SEQ ID NO:78) accumulates ent-kaurenoic acid+2Glc (#7), ent-kaurenoic acid+3Glc (isomer 1), ent-kaurenoic acid+3Glc (isomer 2), 19-SMG, steviol, steviol+2Glc (#23), and steviol+3Glc (#34) but does not accumulate ent-kaurenol glycosides. See Example 6 and FIGS. 4A-4C.

In some embodiments, the S84V F48S, F48H, F48Y, F48R, F48Q, F48T, F48S, I49V, P86R, P86G, and F122S variants of UGT85C2 are selective towards 19-SMG, compared to steviol (Table 7A). In some embodiments, the S84T, I87M I87P, I87Y, L91K, L91R, L91T, L92M, and I95K variants of UGT85C2 are selective towards steviol, compared to 19-SMG (Table 7B). In some embodiments, expression of UGT85C2 T304S (SEQ ID NO:127) in a steviol glycoside-producing host increases accumulation of steviol glycosides, compared to a steviol glycoside-producing host not expressing UGT85C2 T304S (SEQ ID NO:127). See Example 5.

In some embodiments, cell lysates comprising UGT85C2 or a UGT85C2 variant show a preference for either steviol or 19-SMG for a substrate. In some aspects, using steviol as a substrate, the F48H, F48Y, F48T, I49V, S84A, and L92F UGT85C2 variants exhibit high activity during incubation periods of under 40 min, and the F48H, F48Y, F48T, and I49V UGT85C2 variants exhibit high activity during incubation periods of over 40 min (Table 8A). Using 19-SMG as a substrate, the F48H, F48Y, F48T, I49V, and S84A UGT85C2 variants exhibit high activity during incubation periods of under 40 min, and the F48H, I49V, S84A, S84V, L91K, and L92F UGT85C2 variants, as well as the wild-type UGT85C2, exhibit high activity during incubation periods of over 40 min (Table 8B). In some aspects, the L91K, L91R, and L92F UGT85C2 variants exhibit a high 13-SMG/rubusoside ratio, whereas the F48Y, F48T, P86G UGT85C2 variants exhibit a low 13-SMG/rubusoside ratio. See Example 7.

In some embodiments, a useful UGT76G1 homolog can have one or more amino acid substitutions at residues 23, 26, 55, 146, 257, 283, and 337. See Example 4. Non-limiting examples of useful UGT76G1 homologs include polypeptides having substitutions (with respect to SEQ ID NO:9) at residue 21 (e.g., a lysine, threonine or valine at residue 21), residue 23 (e.g., a histidine at residue 23); residue 26 (e.g., a tryptophan at residue 26); residue 55 (e.g., a lysine at residue 55); residue 146 (e.g., a glycine at residue 146); residue 257 (e.g., a glycine at residue 257); residue 283 (e.g., a asparagine at residue 283); and residue 337 (e.g., a proline at residue 337). See SEQ ID NOs: 181-190. See Table 9 and Examples 8 and 9.

In some embodiments, expression of UGT76G1 variants that increase accumulation of RebD or RebM in steviol glycoside-producing S. cerevisiae strains (see WO 2014/122227, which has been incorporated by reference in its entirety) alter accumulation of 13-SMG, 1,2-bioside, rubusoside, RebA, RebB, RebD, RebE, RebM, RebG (1,3-stevioside), steviol+3Glc (#1), steviol+4Glc (#26), steviol+5Glc (#22), steviol+5Glc (#24), steviol+5Glc (#25), steviol+6Glc (isomer 1), and steviol+6Glc (#23), compared to expression of wild-type UGT76G1 (SEQ ID NO:9) in steviol glycoside-producing S. cerevisiae strains. See FIGS. 6, 10, 11D, and 11E and Examples 8 and 9.

In some embodiments, expression of UGT variants that increase RebD levels in S. cerevisiae also results in increased accumulation of steviol+5Glc (#22), 1,2-stevioside, steviol+6Glc (isomer 1), and steviol+3Glc (#1) but decreased accumulation of steviol+4Glc (#26), steviol+5Glc (#24), and RebG (1,3-stevioside). In some embodiments, expression of UGT76G1 H155L (SEQ ID NO:184) results in increased accumulation of steviol+5Glc (#25) but decreased accumulation of 1,2-stevioside, steviol+3Glc (#1), steviol+4Glc (#26), steviol+5Glc (#22), steviol+6Glc (isomer 1), and steviol+6Glc (#23). In some embodiments, expression of UGT76G1 S253W (SEQ ID NO:186) results in decreased accumulation of 1,2-stevioside and steviol+6Glc (isomer 1). In some embodiments, expression of UGT76G1 284G results in increased accumulation of 1,2-stevioside and steviol+6Glc (isomer 1) but decreased accumulation of RebG, steviol+4Glc (#26), steviol+5Glc (#25), and steviol+6Glc (#23). See FIG. 10 and Example 8.

In some embodiments, expression of UGT76G1 Q23H (SEQ ID NO:181), UGT76G1 I26W (SEQ ID NO:182), UGT76G1 T146G (SEQ ID NO:183), UGT76G1 H155L (SEQ ID NO:184), UGT76G1 L257G (SEQ ID NO:185), and UGT76G1 S283N (SEQ ID NO:188) decrease accumulation of steviol+4Glc (#26). In some embodiments, expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188), all of which increase production of RebD, decrease accumulation of steviol+5Glc (#25), compared to a control strain expressing wild-type UGT76G1. In some embodiments, expression of UGT76G1 H155L (SEQ ID NO:184), which increases RebM production, increases accumulation of steviol+5Glc (#25). See FIG. 11D and Example 8.

In some embodiments, expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) increases accumulation of steviol+6Glc (#23), compared to a control strain expressing wild-type UGT76G1. In some embodiments, expression of UGT76G1 H155L (SEQ ID NO:184) decreases accumulation of steviol+6Glc (#23). In some embodiments, expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) increases accumulation of steviol+7Glc (isomer 2), compared to a control strain expressing wild-type UGT76G1. In some embodiments, expression of UGT76G1 H155L (SEQ ID NO:184) decreases accumulation of steviol+7Glc (isomer 2). In some embodiments, expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) increases accumulation of steviol+7Glc (isomer 5). See FIG. 11D and Example 8.

In some embodiments, a host expressing a gene encoding a UGT variant or UGT chimeric polypeptide produces an increased level of glycosylated ent-kaurenoic acid and/or ent-kaurenol relative to a host not expressing a gene encoding a UGT variant or UGT chimeric polypeptide. In some embodiments, the UGT variant or UGT chimeric polypeptide comprises a UGT91D2e variant, a gene encoding a UGT91D2e-b-EUGT11 chimeric polypeptide, a gene encoding a UGT85C2 variant, and/or a gene encoding a UGT76G1 variant.

In some embodiments, a host expressing a gene encoding a UGT variant or UGT chimeric polypeptide produces a decreased level of glycosylated ent-kaurenoic acid and/or ent-kaurenol relative to a host not expressing a gene encoding a UGT variant or UGT chimeric polypeptide. In some embodiments, the UGT variant or UGT chimeric polypeptide comprises a UGT91D2e variant, a gene encoding a UGT91D2e-b-EUGT11 chimeric polypeptide, a gene encoding a UGT85C2 variant, and/or a gene encoding a UGT76G1 variant.

In some embodiments, levels of ent-kaurenoic acid+2Glc (#7), ent-kaurenoic acid+3Glc (isomer 1), ent-kaurenoic acid+3Glc (isomer 2), ent-kaurenol+2Glc (#8), and ent-kaurenol+3Glc (isomer 1) co-eluted with ent-kaurenol+3Glc (#6) are altered in steviol glycoside-producing S. cerevisiae strains expressing wild-type UGT76G1 (SEQ ID NO:9), compared to S. cerevisiae strains expressing UGT76G1 Q23H (SEQ ID NO:181), UGT76G1 I26W (SEQ ID NO:182), UGT76G1 T146G (SEQ ID NO:183), UGT76G1 H155L (SEQ ID NO:184), UGT76G1 L257G (SEQ ID NO:185), UGT76G1 S253W (SEQ ID NO:186), UGT76G1

T284G (SEQ ID NO:187), UGT76G1 S283N (SEQ ID NO:188), UGT76G1 K337P (SEQ ID NO:189), or UGT76G1 T55K (SEQ ID NO:190). See FIG. 9, FIGS. 11A-11C, and Example 8.

In some embodiments, *S. cerevisiae* strains expressing UGT76G1 variants that increase RebD levels also increase accumulation of ent-kaurenoic acid+2Glc (#7) and ent-kaurenoic acid+2Glc (isomer 1) but decrease accumulation of ent-kaurenoic acid+3Glc (isomer 2), compared to an *S. cerevisiae* strain expressing wild-type UGT76G1. In some embodiments, UGT76G1 variants that increase RebD levels also increase accumulation of ent-kaurenol+2Glc (#8) but decrease accumulation of ent-kaurenol+3Glc (isomer 1) co-eluted with ent-kaurenol+3Glc (#6). In some embodiments, expression of UGT76G1 H155L (SEQ ID NO:184), a variant that increases levels of RebM, decreases accumulation of ent-kaurenoic acid+2Glc (#7) and ent-kaurenoic acid+3Glc (isomer 1). See FIG. 9 and Example 8.

In some embodiments, total levels of glycosylated ent-kaurenoic acid (ent-kaurenoic acid+2Glc (#7)+ent-kaurenoic acid+3Glc (isomer 1)+ent-kaurenoic acid+3Glc (isomer 2)) are increased in steviol glycoside-producing *S. cerevisiae* strains expressing UGT76G1 Q23H (SEQ ID NO:181), UGT76G1 I26W (SEQ ID NO:182), and UGT L257G (SEQ ID NO:185). In some embodiments, total levels of glycosylated ent-kaurenol (ent-kaurenol+3Glc (isomer 1) co-eluted with ent-kaurenol+3Glc (#6) and ent-kaurenol+2Glc (#8) are altered for in steviol glycoside-producing *S. cerevisiae* strains expressing UGT76G1 Q23H (SEQ ID NO:181), UGT76G1 I26W (SEQ ID NO:182), and UGT76G1 T146G (SEQ ID NO:183). See FIGS. 11B and 11C and Example 8.

In some embodiments, UGT variants not limited to variants of UGT76G1, UGT85C2, and/or UGT91D2e alter ratios of steviol glycosides produced to GlcNAc compounds and isomers thereof produced in vitro, in vivo in a host, and/or by whole cell bioconversion. Exemplary GlcNAc structures include ent-kaurenoic acid+2Glc+1GlcNAc and steviol+4Glc+1GlcNAc (#11). See, e.g., FIGS. 7A, 7D, 8G-8I, and 8AC-8AF and Examples 6, 8, and 9.

In some embodiments, a steviol glycoside or steviol glycoside precursor composition produced in vivo, in vitro, or by whole cell bioconversion comprises fewer contaminants or less of any particular contaminant than a stevia extract from, inter alia, a stevia plant. Contaminants can include plant-derived compounds that contribute to off-flavors. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α-amyrin, β-amyrin, lupeol, β-amryin acetate, pentacyclic triterpenes, centauredin, quercitin, epi-alpha-cadinol, carophyllenes and derivatives, beta-pinene, beta-sitosterol, and gibberellins.

As used herein, the terms "detectable amount," "detectable concentration," "measurable amount," and "measurable concentration" refer to a level of steviol glycosides measured in area-under-curve (AUC), μM/OD$_{600}$, mg/L, μM, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vis), mass spectrometry (MS), and nuclear magnetic resonance spectroscopy (NMR).

As used herein, the term "undetectable concentration" refers to a level of a compound that is too low to be measured and/or analyzed by techniques such as TLC, HPLC, UV-Vis, MS, or NMR. In some embodiments, a compound of an "undetectable concentration" is not present in a steviol glycoside or steviol glycoside precursor composition.

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

Functional Homologs

Functional homologs of the polypeptides described above are also suitable for use in producing steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol glycoside biosynthesis polypeptides. Sequence analysis can involve BLAST, Reciprocal BLAST, or PSI-BLAST analysis of non-redundant databases using a UGT amino acid sequence as the reference sequence. Amino acid sequence is, in some instances, deduced from the nucleotide sequence.

Those polypeptides in the database that have greater than 40% sequence identity are candidates for further evaluation for suitability as a steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol glycoside biosynthesis polypeptides, e.g., conserved functional domains. In some embodiments, nucleic acids and polypeptides are identified from transcriptome data based on expression levels rather than by using BLAST analysis.

Conserved regions can be identified by locating a region within the primary amino acid sequence of a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol in a recombinant host include functional homologs of UGTs.

Methods to modify the substrate specificity of, for example, a UGT, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, Phytochemistry 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program Clustal Omega (version 1.2.1, default parameters), which allows alignments of nucleic acid or polypeptide sequences to be carried out across their entire length (global alignment). Chenna et al., 2003, Nucleic Acids Res. 31(13):3497-500.

Clustal Omega calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method:% age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The Clustal Omega output is a sequence alignment that reflects the relationship between sequences. Clustal Omega can be run, for example, at the Baylor College of Medicine Search Launcher site on the World Wide Web (searchlauncher.bcm.tmc.edu/multi-align/multi-align.html) and at the European Bioinformatics Institute site at http://www.ebi.ac.uk/Tools/msa/clustalo/.

To determine a % identity of a candidate nucleic acid or amino acid sequence to a reference sequence, the sequences are aligned using Clustal Omega, the number of identical matches in the alignment is divided by the length of the reference sequence, and the result is multiplied by 100. It is noted that the % identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional UGT proteins can include additional amino acids that are not involved in the enzymatic activities carried out by the enzymes. In some embodiments, UGT proteins are fusion proteins. The terms "chimera," "fusion polypeptide," "fusion protein," "fusion enzyme," "fusion construct," "chimeric protein," "chimeric polypeptide," "chimeric construct," and "chimeric enzyme" can be used interchangeably herein to refer to proteins engineered through the joining of two or more genes that code for different proteins. In some embodiments, a nucleic acid sequence encoding a UGT polypeptide can include a tag sequence that encodes a "tag" designed to facilitate subsequent manipulation (e.g., to facilitate purification or detection), secretion, or localization of the encoded polypeptide. Tag sequences can be inserted in the nucleic acid sequence encoding the polypeptide such that the encoded tag is located at either the carboxyl or amino terminus of the polypeptide. Non-limiting examples of encoded tags include green fluorescent protein (GFP), human influenza hemagglutinin (HA), glutathione S transferase (GST), polyhistidine-tag (HIS tag), and Flag™ tag (Kodak, New Haven, CT). Other examples of tags include a chloroplast transit peptide, a mitochondrial transit peptide, an amyloplast peptide, signal peptide, or a secretion tag.

In some embodiments, a fusion protein is a protein altered by domain swapping. As used herein, the term "domain swapping" is used to describe the process of replacing a domain of a first protein with a domain of a second protein. In some embodiments, the domain of the first protein and the domain of the second protein are functionally identical or functionally similar. In some embodiments, the structure and/or sequence of the domain of the second protein differs from the structure and/or sequence of the domain of the first protein. In some embodiments, a UGT polypeptide is altered by domain swapping.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. In such cases, a nucleic acid that overexpresses the polypeptide or gene product may be included in a recombinant construct that is transformed into the strain. Alternatively, mutagenesis can be used to generate mutants in genes for which it is desired to increase or enhance function.

Host Microorganisms

Recombinant hosts can be used to express polypeptides for the producing steviol glycosides. A number of prokaryotes and eukaryotes are suitable for use in constructing the recombinant microorganisms described herein, e.g., gram-negative bacteria, fungi (i.e., yeast), mammalian, insect, plant, and algae cells. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a temperature(s) for a period of time, wherein the temperature and period of time facilitate the production of a steviol glycoside. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, ent-kaurene and ent-kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the period of time, wherein the temperature and period of time facilitate the production of a steviol glycoside, steviol and/or one or more steviol glycosides can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC. See also, WO 2009/140394.

It will be appreciated that the various genes and modules discussed herein can be present in two or more recombinant hosts rather than a single host. When a plurality of recombinant hosts is used, they can be grown in a mixed culture to accumulate steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans*, and *Yarrowia lipolytica*.

In some embodiments, a microorganism can be a prokaryote such as *Escherichia* bacteria cells, for example, *Escherichia coli* cells; *Lactobacillus* bacteria cells; *Lactococcus* bacteria cells; *Cornebacterium* bacteria cells; *Acetobacter* bacteria cells; *Acinetobacter* bacteria cells; or *Pseudomonas* bacterial cells.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *S. cerevisiae*.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella salina, Haematococcus pluvialis, Chlorella* sp., *Undaria pinnatifida, Sargassum, Laminaria japonica, Scenedesmus almeriensis*.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella,* and *Phanerochaete* spp.

*Agaricus, Gibberella,* and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans (Blastobotrys adeninivorans)*

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorganism. *Yarrowia lipolytica* can accumulate lipid content to approximately 40% of its dry cell weight and is a model organism for lipid accumulation and remobilization. See e.g., Nicaud, 2012, Yeast 29(10):409-18; Beopoulos et al., 2009, *Biochimie* 91(6):692-6; Bankar et al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha (Pichia angusta)*

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella* mosses, when grown in suspension culture, have characteristics similar to yeast or other fungal cultures. This genera can be used for producing plant secondary metabolites, which can be difficult to produce in other types of cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD or RebM) and have a consistent taste profile. As used herein, the term "enriched" is used to describe a steviol glycoside composition with an increased proportion of a particular steviol glycoside, compared to a steviol glycoside composition (extract) from a stevia plant. Thus, the recombinant hosts described herein can facilitate the production of compositions that are tailored to meet the sweetening profile desired for a given food product and that have a proportion of each steviol glycoside that is consistent from batch to batch. In some embodiments, hosts described herein do not produce or produce a reduced amount of undesired plant by-products found in *Stevia* extracts. Thus, steviol glycoside compositions produced by the recombinant hosts described herein are distinguishable from compositions derived from *Stevia* plants.

It will be appreciated that the amount of an individual steviol glycoside (e.g., RebA, RebB, RebD, or RebM) produced by the recombinant host cell disclosed herein can accumulate in the cell culture broth from about 1 to about 7,000 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, at least about 2,800 mg/L, or at least about 7,000 mg/L. In some aspects, the amount of an individual steviol glycoside produced by the recombinant host cell disclosed herein can exceed 7,000 mg/L in the cell culture broth.

It will be appreciated that the amount of a combination of steviol glycosides (e.g., RebA, RebB, RebD, or RebM) produced by the recombinant host cell disclosed herein can accumulate in the cell culture broth from about 1 mg/L to about 7,000 mg/L, e.g., about 200 to about 1,500, at least about 2,000 mg/L, at least about 3,000 mg/L, at least about 4,000 mg/L, at least about 5,000 mg/L, at least about 6,000 mg/L, or at least about 7,000 mg/L. In some aspects, the amount of a combination of steviol glycosides produced by the recombinant host cell disclosed herein can exceed 7,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing a steviol glycoside precursor, while a second microorganism comprises steviol glycoside biosynthesis genes. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. It will also be appreciated that in some embodiments, a recombinant microorganism is grown using nutrient sources other than a culture medium and utilizing a system other than a fermenter.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328.

For example, substantially pure steviol or steviol glycoside such as RebM or RebD can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current Stevia products.

In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis. In some embodiments, a steviol glycoside composition produced herein is a component of a pharmaceutical composition. See, e.g., Steviol Glycosides Chemical and Technical Assessment 69th JECFA, 2007, prepared by Harriet Wallin, Food Agric. Org.; EFSA Panel on Food Additives and Nutrient Sources added to Food (ANS), "Scientific Opinion on the safety of steviol glycosides for the proposed uses as a food additive," 2010, *EFSA Journal* 8(4):1537; U.S. Food and Drug Administration GRAS Notice 323; U.S Food and Drug Administration GRAS Notice Notice 329; WO 2011/037959; WO 2010/146463; WO 2011/046423; and WO 2011/056834.

For example, such a steviol glycoside composition can have from 90-99 weight % RebA and an undetectable amount of stevia plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3 weight % RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of stevia plant-derived contaminants.

Such a steviol glycoside composition can be a RebD-enriched composition having greater than 3 weight % RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of stevia plant-derived contaminants.

Such a steviol glycoside composition can be a RebE-enriched composition having greater than 3 weight % RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of stevia plant-derived contaminants.

Such a steviol glycoside composition can be a RebM-enriched composition having greater than 3 weight % RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of stevia plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycosides compositions enriched for RebA, RebB, RebD, RebE, or RebM, can be package in a sachet, for example, at from 10,000 to 30,000 mg steviol glycoside/kg product on a dry weight basis, for tabletop use. In some embodiments, a steviol glycoside produced in vitro, in vivo, or by whole cell bioconversion The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1: LC-MS Analytical Procedures

LC-MS analyses for Examples 3 and 4 were performed using an Agilent 1200 Series HPLC system (Agilent Technologies) fitted with a Phenomenex® Kinetex C18 column (150×2.1 mm, 2.6 μm particles, 100 Å pore size) connected to a TSQ Quantum Access (ThermoFisher Scientific) triple quadropole mass spectrometer with a heated electrospray ion (HESI) source. Elution was carried out using a mobile phase of eluent B (MeCN with 0.1% Formic acid) and eluent A (water with 0.1% Formic acid) by increasing the gradient from 10-40% B from min 0.0 to 1.0, increasing 40-50% B in min 1.0 to 6.5, and increasing 50-100% B from min 6.5 to 7.0. The flow rate was 0.4 mL/min, and the column temperature was 30° C. 1,2-stevioside and RebD were detected using SIM (Single Ion Monitoring) in positive mode.

LC-MS analyses for Examples 8 and 9 were performed on Waters ACQUITY UPLC® (Waters Corporation) with a Waters ACQUITY UPLC® BEH C18 column (2.1×50 mm, 1.7 μm particles, 130 Å pore size) equipped with a pre-column (2.1×5 mm, 1.7 μm particles, 130 Å pore size) coupled to a Waters ACQUITY TQD triple quadropole mass spectrometer with electrospray ionization (ESI) operated in negative ionization mode. Compound separation was achieved using a gradient of the two mobile phases: A (water with 0.1% formic acid) and B (MeCN with 0.1% formic acid) by increasing from 20% to 50% B between 0.3 to 2.0 min, increasing to 100% B at 2.01 min, holding 100% B for 0.6 min, and re-equilibrating for 0.6 min. The flow rate was 0.6 mL/min, and the column temperature was set at 55° C. Steviol glycosides were monitored using SIM (Single Ion Monitoring) and quantified by comparing against authentic standards. See Table 1 for m/z trace and retention time values of steviol glycosides detected.

TABLE 1

LC-MS Analytical Data for Steviol and Steviol Glycosides

| Compound | MS Trace | RT (min) | FIG.(s) | Table(s) |
|---|---|---|---|---|
| steviol + 5Glc (#22) [also referred to as compound 5.22] | 1127.48 | 0.85 | 6D, 7E, 8AK-8AN, 10A, 10B, 11D | 9C, 9F, 9I |
| steviol + 6Glc (isomer 1) [also referred to as compound 6.1] | 1289.53 | 0.87 | 6D, 7B, 8M-8P, 10A, 10B, 11D | 9C, 9F, 9I |
| steviol + 7Glc (isomer 2) [also referred to as compound 7.2] | 1451.581 | 0.94 | 6D, 7B, 8Q-8T, 11D | 9C, 9F, 9I |
| steviol + 6Glc (#23) [also referred to as compound 6.23] | 1289.53 | 0.97 | 6D, 10A, 10B, 11D | 9F, 9I |
| RebE | 965.42 | 1.06 | 6B, 6C, 10C, 11E | 9A, 9D, 9G |
| RebD | 1127.48 | 1.08 | 6A, 6C, 10C, 11E | 2, 3, 5, 9A, 9D, 9G |
| RebM | 1289.53 | 1.15 | 6A, 6C, 10C, 11E | 9A, 9D, 9G |
| steviol + 7Glc (isomer 5) [also referred to as compound 7.5] | 1451.581 | 1.09 | 7C, 8Y-8AB, 11D | 9F, 9I |
| steviol + 7Glc (#13) [also referred to as compound 7.13] | 1451.581 | 0.94 | 6D | |
| steviol + 4Glc (#26) [also referred to as compound 4.26] | 965.42 | 1.21 | 6D, 7D, 8AG-8AJ, 10A, 10B, 11D | 9C, 9F, 9H |
| steviol + 4Glc (#33) [also referred to as compound 4.33] | 965.42 | 1.49 | | 9C, 9I |
| steviol + 5Glc (#24) [also referred to as compound 5.24] | 1127.48 | 1.18 | 6D, 10A, 10B, 11D | 9F, 9I |
| steviol + 4Glc (#25) [also referred to as compound 5.25] | 1127.48 | 1.40 | 6D, 10A, 10B, 11D | 5, 9C, 9F, 9I |
| RebA | 965.42 | 1.43 | 6A, 6C, 10C, 11E | 9A, 9D, 9G |
| RebI | 1127.48 | 1.4 | | 9H |
| 1,2-stevioside | 803.37 | 1.43 | 10B, 11D | 2, 3, 5, 9B, 9E, 9H |
| steviol + 3Glc (#1) [also referred to as compound 3.1] | 803.37 | 1.52 | 6D, 10A, 10B, 11D | 9B, 9E |
| steviol + 2Glc (#23) [also referred to as compound 2.23] | 641.32 | 1.57 | 4C | |
| steviol + 3Glc (#34) [also referred to as compound 3.34] | 803.37 | | 4C | 9C, 9E |
| RebQ | 965.42 | 1.59 | | |
| 1,3-stevioside (RebG) | 803.37 | 1.60 | 6B-6D, 10B, 11E | 9D, 9G |
| rubusoside | 641.32 | 1.67 | 5, 6B, 6C, 10C, 11E | 5, 8B, 8C, 9D, 9G |

TABLE 1-continued

LC-MS Analytical Data for Steviol and Steviol Glycosides

| Compound | MS Trace | RT (min) | FIG.(s) | Table(s) |
|---|---|---|---|---|
| RebB | 803.37 | 1.76 | 6A, 6C, 10C, 11E | 9A, 9D, 9G |
| 1,2-bioside | 641.32 | 1.80 | 6B-D, 10C, 11D, 11E | 9A, 9D, 9G |
| 1,3-bioside | 641.32 | 1.95 | | 9E |
| 13-SMG | 479.26 | 2.04 | 4B, 6A, 6C, 10C, 11E | 8A, 8B, 8C, 9A, 9D, 9G |
| 19-SMG | 525.27 | 1.98 | 4B | 7A, 7B, 7C, 8B, 8C, 9E, 9H |
| ent-kaurenoic acid + 3Glc (isomer 1) [also referred to as compound KA3.1] | 787.37 | 2.16 | 4A, 7A, 8A-8C, 9A, 11A, 11B | 9B, 9E, 9H |
| ent-kaurenoic acid + 3Glc (isomer 2) [also referred to as compound KA3.2] | 787.37 | 2.28 | 4A, 7A, 8D-8F, 9A, 11A, 11B | 9B, 9E, 9H |
| ent-kaurenol + 3Glc (isomer 1) co-eluted with ent-kaurenol + 3Glc (#6) [also referred to as compounds KL3.1 and KL3.6] | 773.4 | 2.36 | 4A, 7A, 8J-8L, 9B, 11A, 11C | |
| ent-kaurenoic acid + 2Glc (#7) [also referred to as compound KA2.7] | 625.32 | 2.35 | 4A, 9A, 11A, 11B | 9B, 9D, 9H |
| ent-kaurenol + 2Glc (#8) [also referred to as compound KL2.8] | 611.34 | 2.38 | 9B, 7B, 11A, 11C | 9B, 9E |
| Steviol | 317.21 | 2.39 | 4C | 7A, 7B, 7C, 8A, 8B, 8C, 9F |

Steviol glycosides, including GlcNAc-derivatives, glycosylated ent-kaurenol, and/or glycosylated ent-kaurenoic acid can be isolated using a method described herein. For example, following fermentation, a culture broth can be centrifuged for 30 min at 7000 rpm at 4° C. to remove cells, or cells can be removed by filtration. The cell-free lysate can be obtained, for example, by mechanical disruption or enzymatic disruption of the host cells and additional centrifugation to remove cell debris. Mechanical disruption of the dried broth materials can also be performed, such as by sonication. The dissolved or suspended broth materials can be filtered using a micron or sub-micron prior to further purification, such as by preparative chromatography. The fermentation media or cell-free lysate can optionally be treated to remove low molecular weight compounds such as salt; and can optionally be dried prior to purification and re-dissolved in a mixture of water and solvent. The supernatant or cell-free lysate can be purified as follows: a column can be filled with, for example, HP20 Diaion® resin (Supelco) or other suitable non-polar adsorbent or reverse phase chromatography resin, and an aliquot of supernatant or cell-free lysate can be loaded on to the column and washed with water to remove the hydrophilic components. The steviol glycoside product can be eluted by stepwise incremental increases in the solvent concentration in water or a gradient from, e. g., 0%→100% methanol). The levels of steviol glycosides, glycosylated ent-kaurenol, and/or glycosylated ent-kaurenoic acid in each fraction, including the flow-through, can then be analyzed by LC-MS. Fractions can then be combined and reduced in volume using a vacuum evaporator. Additional purification steps can be utilized, if desired, such as additional chromatography steps and crystallization.

Example 2: Strain Engineering and Fermentation

Steviol glycoside-producing S. cerevisiae strains were constructed as described in WO 2011/153378, WO 2013/022989, WO 2014/122227, and WO 2014/122328, each of which is incorporated by reference in their entirety. For example, a yeast strain comprising one or more copies of a recombinant gene encoding a Synechococcus sp. GGPPS polypeptide (SEQ ID NO:19, SEQ ID NO:20), a recombinant gene encoding a truncated Z. mays CDPS polypeptide (SEQ ID NO:39, SEQ ID NO:40), a recombinant gene encoding an A. thaliana KS polypeptide (SEQ ID NO:51, SEQ ID NO:52), a recombinant gene encoding a recombinant S. rebaudiana KO polypeptide (SEQ ID NO:59, SEQ ID NO:60), a recombinant gene encoding an A. thaliana ATR2 polypeptide (SEQ ID NO:91, SEQ ID NO:92), a recombinant gene encoding an O. sativa EUGT11 polypeptide (SEQ ID NO:14/SEQ ID NO:15, SEQ ID NO:16), a recombinant gene encoding an SrKAHe1 polypeptide (SEQ ID NO:93, SEQ ID NO:94), a recombinant gene encoding an S. rebaudiana CPR8 polypeptide (SEQ ID NO:85, SEQ ID NO:86), a recombinant gene encoding an S. rebaudiana UGT85C2 polypeptide (SEQ ID NO:5/SEQ ID NO:6, SEQ ID NO:7) or a UGT85C2 variant (or functional homolog) of SEQ ID NO:7, a recombinant gene encoding an S. rebaudiana UGT74G1 polypeptide (SEQ ID NO:3, SEQ ID NO:4) or a UGT74G1 variant (or functional homolog) of SEQ ID NO:4, a recombinant gene encoding an S. rebaudiana UGT76G1 polypeptide (SEQ ID NO:8, SEQ ID NO:9) or a UGT76G1 variant (or functional homolog) of SEQ ID NO:9, and a recombinant gene encoding an S. rebaudiana UGT91D2e polypeptide (SEQ ID NO:10, SEQ ID NO:11) or a UGT91D2e variant (or functional homolog) of SEQ ID NO:11 such as a UGT91D2e-b (SEQ ID NO:12, SEQ ID NO:13) polypeptide produced steviol glycosides.

Example 3: Modulation of Substrate-Specificity of UGT91D2e

UGT91D1 (GenBank Accession No. AY345980) is highly expressed in the Stevia plant and thought to be a functional UGT. However, its substrate is not a steviol glycoside. This suggests that UGT91D1 has a different substrate than UGT91D2e, which may be defined by the 22 amino acids with which it differs from UGT91D2e. A UGT91D2e site saturation library (SSL) screen of the 22 amino acids differing from UGT91D1 was prepared using Geneart® (Life Technologies) and degenerate NNK-primers.

UGT91D2 SSL clones were expressed in E. coli XJb (DE3) Autolysis™ cells (Zymo Research). Colonies were grown overnight in 96 deep-well plates at 37° C. with 1 mL NZCYM (pH 7.0) comprising 15 g Tryptone, 7.5 g NaCl, 7.5 g yeast extract, 1.5 g casamino acids, 3 g $MgSO_4$ and fortified with 100 mg/L ampicillin and 33 mg/L chloramphenicol. 150 μL overnight cultures were transferred to 24 deep-well plates comprising 3 mL NZCYM with ampicillin, 0.1 mM isopropyl-β-D-1-thiogalactopyranoside (IPTG), 3 mM L-arabinose, and 2% (v/v) ethanol and incubated 20 h at 20° C. Cells were pelleted and lysed in 100 μL lysis buffer (10 mM Tris-HCl pH 8.0, 5 mM $MgCl_2$, 1 mM $CaCl_2$, 3 tablets/100 mL Complete mini protease inhibitor cocktail (Roche)) by a single freeze-thaw cycle and 50 μL DNase mix (1 μL 1.4 mg/mL deoxyribonuclease (Calbiochem), 1.2 μL 500 mM MgCl$_2$, and 47.8 μL of 4×PBS buffer). Plates were shaken at 500 rpm for 5 min at 25° C. to allow degradation of genomic DNA. Plates were then spun down at 4000 rpm for 30 min at 4° C. See WO 2013/022989, which is incorporated by reference in its entirety.

Activity of UGT91D2e variants was tested in vitro to assess the specificity of the UGT91D2e variants towards the substrates, rubusoside and RebA. 6 μL of the lysates were diluted with 24 μL of reaction mixture (final concentration: 100 mM Tris-HCl (pH 8.0), 5 mM MgCl$_2$, 1 mM KCl, 300 μM uridine diphosphate glucose (UDPG), and 100 μM rubusoside or RebA). The reaction mixture was incubated at 30° C. for 24 h, and 1,2-stevioside and RebD production was measured by LC-MS. Results are shown in Table 2.

TABLE 2

Activity of UGT91D2e-b and UGT91D2e variants on rubusoside and RebA, producing 1,2-stevioside and RebD, respectively.

| | 1,2-stevioside (μM) | RebD (μM) | 1,2-stevioside/RebD |
|---|---|---|---|
| UGT91D2e-b (SEQ ID NO: 13) | 264.9 | 2.7 | 98.1 |
| UGT91D2e V286C (SEQ ID NO: 1) | 59.3 | 0.0 | N/A (No activity on RebA) |
| UGT91D2e G384W (SEQ ID NO: 2) | 205.6 | 0.0 | N/A (No activity on RebA) |
| UGT91D2e L211M (SEQ ID NO: 118) | 129.7 | 3.7 | 35.1 |
| UGT91D2e L195G (SEQ ID NO: 119) | 178.4 | 0.9 | 198.2 |
| UGT91D2e V196P (SEQ ID NO: 120) | 162.1 | 2.4 | 67.5 |
| UGT91D2e L211H (SEQ ID NO: 121) | 123.5 | 5.1 | 24.2 |

As shown in Table 2, rubusoside and RebA were substrates of UGT91D2e-b (SEQ ID NO:13), UGT91D2e L211M (SEQ ID NO:118), UGT91D2e L195G (SEQ ID NO:119), UGT91D2e V196P (SEQ ID NO:120), and UGT91D2e L211H (SEQ ID NO:121), as 1,2-stevioside and RebD were produced upon contact of the enzymes with either rubusoside or RebA. However, the ratio of 1,2-stevioside/RebD produced by UGT91D2e-b (SEQ ID NO:13), UGT91D2e L211M (SEQ ID NO:118), UGT91D2e L195G (SEQ ID NO:119), UGT91D2e V196P (SEQ ID NO:120), and UGT91D2e L211H (SEQ ID NO:121) fluctuated from 24.2 to 198.2, indicating that the enzymes were not equally selective towards either substrate. The UGT91D2e V286C and UGT91D2e G384W variants were selective towards rubusoside; no RebD was produced upon contact of either variant with RebA.

Additional variants of UGT91D2e were found to demonstrate substrate specificity towards rubusoside or RebA using the above-described assay. See Table 3. The variants of SEQ ID NO:200 (P93V M152G), SEQ ID NO:201 (S99I), SEQ ID NO:203 (T144L), SEQ ID NO:205 (A148K L221I), SEQ ID NO:212 (G384K) were selective towards RebA. The UGT91D2e variants of SEQ ID NO:197 (L195V), SEQ ID NO:198 (V286S), SEQ ID NO:202 (T144K P201P (silent)), SEQ ID NO:209 (L211T I130I (silent)), SEQ ID NO:211 (S114F V286S), SEQ ID NO:214 (E438M) were selective towards rubusoside.

TABLE 3

Activity of UGT91D2e variants on rubusoside and RebA, producing 1,2-stevioside and RebD, respectively.

| Variant | 1,2-stevioside (μM) | RebD (μM) | 1,2-stevioside/RebD |
|---|---|---|---|
| UGT91D2e L213E (SEQ ID NO: 191) | 13.6 | 1.1 | 12.4 |
| UGT91D2e S221Y (SEQ ID NO: 192) | 13.1 | 27.1 | 0.5 |
| UGT91D2e E438H (SEQ ID NO: 193) | 5.1 | 1.4 | 3.6 |
| UGT91D2e M152T (SEQ ID NO: 194) | 16.8 | 1.5 | 11.2 |
| UGT91D2e L211C (SEQ ID NO: 195) | 7.3 | 1.6 | 15.8 |
| UGT91D2e L195S (SEQ ID NO: 196) | 16.4 | 1.4 | 11.7 |
| UGT91D2e L195V (SEQ ID NO: 197) | 35.9 | 0.0 | N/A (No activity on RebA) |
| UGT91D2e V286S (SEQ ID NO: 198) | 14.2 | 0.0 | N/A (No activity on RebA) |
| UGT91D2e S221S (silent) (SEQ ID NO: 199) | 16.2 | 1.7 | 9.5 |
| UGT91D2e P93V M152G (SEQ ID NO: 200) | 0.2 | 2.5 | 0.1 |
| UGT91D2e S99I (SEQ ID NO: 201) | 0.2 | 2.6 | 0.1 |
| UGT91D2e T144K P201P (silent) (SEQ ID NO: 202) | 1.6 | 0.0 | N/A (No activity on RebA) |
| UGT91D2e T144L (SEQ ID NO: 203) | 0.0 | 2.6 | 0.0 (No activity on rubusoside) |
| UGT91D2e T144M (SEQ ID NO: 204) | 1.3 | 1.6 | 0.8 |
| UGT91D2e A148K L211I (SEQ ID NO: 205) | 0.2 | 2.7 | 0.1 |
| UGT91D2e L195N (SEQ ID NO: 206) | 5.1 | 1.0 | 5.1 |
| UGT91D2e K199C (SEQ ID NO: 207) | 2.6 | 1.3 | 2.0 |
| UGT91D2e L211M E426G A466V (SEQ ID NO: 208) | 79.1 | 1.1 | 71.9 |
| UGT91D2e L211T I303I (silent) (SEQ ID NO: 209) | 2.7 | 0.0 | N/A (No activity on RebA) |
| UGT91D2e V286N (SEQ ID NO: 210) | 3.0 | 0.0 | N/A (No activity on RebA) |
| UGT91D2e S114F V286S (SEQ ID NO: 211) | 5.9 | 0.0 | N/A (No activity on RebA) |
| UGT91D2e G384K (SEQ ID NO: 212) | 0.0 | 2.2 | 0.0 (No activity on rubusoside) |
| UGT91D2e G384Y (SEQ ID NO: 213) | 2.9 | 1.9 | 1.5 |
| UGT91D2e E438M (SEQ ID NO: 214) | 4.7 | 0.0 | N/A (No activity on RebA) |
| UGT91D2e L195C (SEQ ID NO: 123) | 3.2 | 1.3 | 2.5 |

Example 4: Evaluation of UGT91D2e-b-EUGT11 Chimeric Enzymes

UGT91D2e-b-EUGT11 chimeric enzymes were tested in vitro to access activity on the substrates, rubusoside and RebA. UGT91D2e-b-EUGT11 chimeras were created by polymerase chain reaction (PCR)-amplification and overlap extension PCR using the primers in Table 4.

TABLE 4

Primers Used to Create UGT91D2e-b-EUGT11 Chimeric Enzymes.

| Description | Sequence | SEQ ID |
|---|---|---|
| Vector (forward) | GGCAAGCCACGTTTGGTG | SEQ ID NO: 135 |
| Vector (reverse) | GGAGCTGCATGTGTCAGAGG | SEQ ID NO: 136 |
| EUGT11 fragment 1/ UGT91D2e-b fragment 2 (forward) | CGATGTATTTCATCACTGGTTGCC ATCCATCGCGGCT | SEQ ID NO: 137 |
| EUGT11/UGT91D2e-b fragment 2 (reverse) | AGCCGCGATGGATGGCAACCAGT GATGAAATACATCG | SEQ ID NO: 138 |
| UGT91D2e-b fragment 1/ EUGT11 fragment 2 (forward) | TTATGATTATACTCACTACTGGGC TGCTGCAGCCGCATTG | SEQ ID NO: 139 |
| UGT91D2e-b fragment 1/ EUGT11 fragment 2 (reverse) | AGCCGCGATGGATGGCAACCAGT GATGAAATACATCG | SEQ ID NO: 140 |
| EUGT11 fragment 2/ UGT91D2e-b fragment 3 (forward) | CAAACCTATTACTTTCCTTGGTTT ACTGCCACCGGAAATAC | SEQ ID NO: 141 |
| EUGT11 fragment 2/ UGT91D2e-b fragment 3 (reverse) | GTATTTCCGGTGGCAGTAAACCA AGGAAAGTAATAGGTTTG | SEQ ID NO: 142 |
| UGT91D2e-b fragment 2/ EUGT11 fragment 3 (forward) | CCGGTGGTTCCGGTGGGACTAAT GCCTCCATTACATGA | SEQ ID NO: 143 |
| UGT91D2e-b fragment 2/ EUGT11 fragment 3 (reverse) | TCATGTAATGGAGGCATTAGTCCC ACCGGAACCACCGG | SEQ ID NO: 144 |
| EUGT11 fragment 3/ UGT91D2e-b fragment 4 (forward) | GAACGCAGGTCTGCAGGTTCCAA GAAATGAGGAAGATGG | SEQ ID NO: 145 |
| EUGT11 fragment 3/ UGT91D2e-b fragment 4 (reverse) | CCATCTTCCTCATTTCTTGGAACC TGCAGACCTGCGTTC | SEQ ID NO: 146 |

UGT91D2e-b-EUGT11 chimeric enzymes were expressed in *E. coli* XJb(DE3) Autolysis™ cells (Zymo Research). Colonies were grown in 50 mL NZCYM (pH 7.0) with ampicillin and chloramphenicol and re-inoculated into 500 mL NZCYM with IPTG, L-arabinose, and ethanol. Cell lysate preparations were done in 15 mL lysis buffer followed by 150 µL DNase and 200 µL 500 mM $MgCl_2$. GST-tag affinity purification of the chimeras was performed by adding ⅓ volume of 4×PBS buffer (560 mM NaCl, 10.8 mM KCl, 40 mM $Na_2HPO_4$, 7.2 mM $KH_2PO_4$ (pH 7.3)) to the lysate supernatant, followed by incubation (2 h, 4° C.) with Glutathione Sepharose 4B (GE Healthcare) and loading onto Poly-Prep® Chromatography Columns (Bio-Rad). The beads were washed twice with 1×PBS buffer and eluted with 50 mM Tris-HCl (pH 8.0) and 10 mM reduced glutathione. Eluted protein was stabilized by addition of glycerol to a final concentration of 50%. SDS-PAGE was performed using NuPAGE® 4-12% Bis-Tris 1.0 mm precast gels (Invitrogen), NuPAGE MOPS (Invitrogen) running buffer and SimplyBlue SafeStain (Invitrogen). The amounts of chimeras produced were determined from the relative staining intensity of the gel images using ImageJ software.

Chimeras were screened by adding 20 µL purified UGT91D2e-b, EUGT11, or UGT91D2e-b-EUGT11 chimeric enzymes (0.02 mg/mL) to a total volume of 80 µL reaction mixture comprising 100 mM Tris-HCl (pH 8.0), 5 mM $MgCl_2$, 1 mM KCl, 300 µM uridine diphosphate glucose (UDPG), and 100 µM rubusoside or RebA. The reactions were incubated at 30° C. for 24 h, and levels of RebA, RebD, rubusoside, and 1,2-stevioside were measured by LC-MS. Not all of the chimeras purified were active in the above described assay (see Table 5 for enzymes having activity on rubusoside and/or RebA).

TABLE 5

EUGT11, UGT91D2e-b, and EUGT11-UGT91D2e-b chimeric enzyme activity on RebA and rubusoside.

| | RebA (µM) | RebD (µM) | rubusoside (µM) | 1,2-stevioside (AUC) |
|---|---|---|---|---|
| EUGT11 (SEQ ID NO: 16) | 32.230 | 101.300 | 34.899 | 1188497 |
| UGT91D2e-b (SEQ ID NO: 13) | 97.314 | 6.580 | 41.157 | 2660570 |
| Chim_3 (SEQ ID NO: 17) | 109.764 | NF | 138.911 | 11435 |
| Chim_7 (SEQ ID NO: 18) | 88.502 | 11.510 | NF | 3693895 |

*NF = Not Found

As shown in Table 5, Chim_7 (SEQ ID NO:18) more efficiently converted rubusoside to 1,2-stevioside, compared to EUGT11 and UGT91D2e. Chim_7 (SEQ ID NO:18) fully consumed the supplied amount of rubusoside, unlike EUGT11 or UGT91D2e. When incubating EUGT11 with rubusoside, the C19-position of rubusoside was 1,2-glycosylated, and RebE and 1,2-stevioside were also produced (Table 5). Additionally, Chim_7 (SEQ ID NO:18) demonstrated 1.75-fold higher activity towards RebA than UGT91D2e-b. Chim_3 (SEQ ID NO:17) selectively converted rubusoside to 1,2-stevioside; no RebA was converted to RebD by Chim_3 (SEQ ID NO:17) (Table 5).

Example 5: Evaluation of UGT85C2 Variants

Three homology models of UGT85C2 were generated with the ORCHESTRA module in Sybyl-X 2.0 (Certara) using a combination of the three PDB templates (Model 1: 2PQ6, 2VCE, 2CIX; Model 2: 2PQ6; Model 3: 2PQ6, 2CIX) and using standard settings and sequences for UGT85H2, UGT72B1, and VvGT1 (see PDB2PQ6, PDB2VCE, and PCB2CIX). Model geometry and quality were checked with the molprobity and ProQ webservers (see Chen et al., Acta Crystallographica. Section D, Biological Crystallography 66(Pt 1):12-21 (2010), Davis et al., Nucleic Acids Research 35:W375-83 (2007), Wallner & Elofsson, Protein Science: A Publication of the Protein Society 12(5):1073-86 (2003). The fluorinated UDPG sugar donor analog, UDP-2FGlc, from PDB:2VCE was imported into the UDPG binding site of UGT85C2 prior to the acceptors steviol, 13-SMG, 19-SMG, or rubusoside. Steviol and steviol glycosides were prepared using the Sybyl-X small molecule builder and docked into the active site of the enzyme with the Surflex Dock suite using standard GeomX settings. The sites for the site saturation library (SSL) were determined by selecting all the residues within 3 Å of the ligands in the docking analysis that were not 100% conserved in the PDB-templates. See Table 6.

TABLE 6

SSL residues for UGT85C2 Docking Analysis.

| | UGT85C2 Model #1 | UGT85C2 Model #2 | UGT85C2 Model #3 | Conserved |
|---|---|---|---|---|
| Phe18 | x | x | x | |
| Pro19 | x | x | x | C |
| Ala20 | x | x | x | |
| Gln21 | x | x | x | |
| Ser22 | x | x | x | |
| His23 | x | x | x | C |
| Lys25 | | x | x | |
| Phe48 | | x | x | |
| Ile49 | | | x | |
| Gln52 | | | x | |
| Glu82 | | x | | |
| Ala83 | | x | | |
| Ser84 | | x | | |
| Pro86 | | | x | |
| Ile87 | | | x | |
| Arg88 | x | | x | |
| Leu91 | x | | x | |
| Leu92 | x | | | |
| Ile95 | x | | | |
| Phe122 | x | | | |
| Thr143 | x | x | | |
| Leu144 | x | x | x | |
| Asp198 | | x | | |
| Val207 | | x | | |
| Phe210 | x | | | |
| Thr211 | x | | | |
| Asn300 | x | | | |
| Phe301 | x | | | C |
| Gly302 | x | | x | C |
| Ser303 | x | | x | |
| Thr304 | x | x | x | |
| Thr305 | x | x | x | |
| Val306 | | | x | |
| Leu334 | | | x | |
| Trp359 | | | x | C |
| Gln362 | | x | | C |
| His377 | x | x | | C |

TABLE 6-continued

SSL residues for UGT85C2 Docking Analysis.

| | UGT85C2 Model #1 | UGT85C2 Model #2 | UGT85C2 Model #3 | Conserved |
|---|---|---|---|---|
| Gly379 | | x | x | C |
| Trp380 | x | x | x | C |
| Gly381 | | x | x | |
| Ser382 | x | x | x | C |
| Tyr398 | | x | x | |
| Trp400 | x | x | x | |
| Asp401 | x | x | x | |
| Gln402 | x | x | | C | x: Residue within 3 Å of steviol, 19-SMG, and UDPG in the docking analysis
C: Conserved residue SSL clones were generated for the 34 non-conserved amino acids in Table 6 predicted to be within 3 Å of the ligands residues. A modified version of the whole plasmid amplification method (Zheng et al. Nucleic Acids Research 32(14):e115 (2004)) was used with overlapping NNK-primers and Phusion polymerase. 10 µL PCR reaction was treated with 10 U DpnI (New England Biolabs) at 37° C. for 1 h, heat inactivated at 65° C. for 20 min, and transformed into E. coli DH5α cells. Colonies were selected on Luria Broth (LB)+kanamycin agar plates and grown in 4 mL LB fortified with kanamycin. Plasmids were purified using the GeneJET™ miniprep kit (Thermo Fisher Scientific) and sequenced.

The sequence-verified site saturation library (SSL) clones were transformed into E. coli XJb(DE3) Autolysis™ cells (Zymo Research) and selected on LB+kanamycin agar plates. Single colonies were inoculated into 1 mL NZCYM fortified with 30 mg/L kanamycin and incubated overnight at 37° C. and 200 rpm orbital shaking. 50 µL of the overnight culture were transferred into 1 mL of fresh NZCYM fortified with 30 mg/L kanamycin, 3 mM arabinose, and 0.1 mM IPTG and incubated overnight at 20° C. and 200 rpm orbital shaking. The cells were spun down at 3220 g/10 min at 4° C. and resuspended in 50 µL GT-buffer (10 mM Tris-HCl (pH 7.5), 5 mM $MgCl_2$, 1 mM $CaCl_2$) comprising complete Mini EDTA free protease inhibitor cocktail (1 tablet/25 mL GT-buffer; Roche Diagnostics). Pellets were resuspended by orbital shaking at 200 rpm/5 min at 4° C. Cells were incubated at −80° C. for minimum 15 min before initiation of lysing step.

The cells were lysed by heating the samples to 25° C. and adding 25 µL DNAse I mix comprising of 2.39 mL 4×His binding buffer (80 mM Tris-HCl (pH 7.5), 500 mM NaCl, 10 mM Imidazole) with 50 µL 1.4 mg/mL DNAse I bovine pancreas (Calbiochem) and 60 µL $MgCl_2$ (500 mM). The lysates were filtered through a 1.2 µm 96-well filterplate (EMD Millipore) and transferred to another 1.2 µm filterplate comprising 50 µL His-select beads (Sigma-Aldrich) prewashed twice with 1× binding buffer. The lysates and beads were then incubated for 2 h at 4° C. with 500 rpm orbital shaking. The plates were spun down at 450 g/2 min. Total protein concentration in the flow-through was measured using the Bradford assay reagent (Sigma-Aldrich), the samples were washed twice by centrifuging the samples, removing supernatants and adding 50 µL 1×His binding buffer. Elution buffer (20 mM Tris-HCl (pH 7.5), 500 mM NaCl, 250 mM imidazole) was added to the beads and incubated for 5 min at 4° C. at 500 rpm orbital shaking and the proteins eluted into a 96 well PCR plate (FrameStar 96, 4titude). The purifications were evaluated by running samples of the flow-through, washing steps and eluate on NuPAGE® SDS-PAGE gel system with 4-12% Bis-Tris precast gels (Invitrogen).

Activity of the purified UGT85C2 variants was measured. 2.0 μg/mL UGT85C2 variant was incubated for 20 min at 37° C. with reaction buffer (100 mM Tris-HCl (pH 8.0), 1 mM KCl, Calf Intestinal Alkaline Phosphatase (New England Biolabs), 120 μM UDPG, and either 40 μM steviol or 40 μM 19-SMG). In this assay, the glucose on UDPG was transferred to steviol or 19-SMG; the products were UDP and either 13-SMG or rubusoside. The phosphates on UDP were then released by a phosphatase, and the amount of phosphate released was measured at $Abs_{600}$ using the Malachite green protocol (Baykov et al., Analytical Biochemistry 171(2):266-70). Values were normalized by total protein released measured by using Bradford reagent (Sigma-Aldrich).

Candidates were selected as having activity of one standard deviation or higher than wild-type activity or having less than 50% activity on one substrate while maintaining wild-type activity on the other (e.g., exhibiting substrate-specificity). The $Abs_{600}$ ratios of a steviol sample to a 19-SMG sample for wild-type UGT85C2 (SEQ ID NO:7) averaged 0.94, indicating that the wild-type UGT85C2 catalyzes conversion of steviol and 19-SMG with little or no preference of substrate. Table 7A shows the UGT85C2 variants analyzed that preferentially catalyzed conversion of 19-SMG over conversion of steviol, Table 7B shows the UGT85C2 variants analyzed that preferentially catalyzed conversion of steviol over conversion of 19-SMG, and Table 7C shows the UGT85C2 variants analyzed that catalyzed conversion of 19-SMG and steviol with little preference for either substrate. Particular clones generated by the site saturation library (SSL) screen were selected more than once, corresponding to more than one entry in Tables 7A-C.

TABLE 7A

UGT85C2 SSL screen candidates that were selective towards 19-SMG as a substrate.

| Steviol ($Abs_{600}$) | 19-SMG ($Abs_{600}$) | Steviol/19-SMG $Abs_{600}$ Ratio | Sum ($Abs_{600}$) | Mutation | UGT85C2 Variant SEQ ID |
|---|---|---|---|---|---|
| 0.105 | 0.165 | 0.636 | 0.27 | F48S | SEQ ID NO: 150 |
| 0.099 | 0.136 | 0.728 | 0.235 | F48H | SEQ ID NO: 151 |
| 0.089 | 0.142 | 0.627 | 0.231 | F48Y | SEQ ID NO: 152 |
| 0.080 | 0.117 | 0.684 | 0.197 | F48R | SEQ ID NO: 153 |
| 0.068 | 0.126 | 0.540 | 0.194 | F48Q | SEQ ID NO: 154 |
| 0.068 | 0.112 | 0.607 | 0.18 | F48T | SEQ ID NO: 156 |
| 0.065 | 0.114 | 0.570 | 0.179 | F48S | SEQ ID NO: 150 |
| 0.094 | 0.141 | 0.667 | 0.235 | I49V | SEQ ID NO: 157 |
| 0.078 | 0.111 | 0.703 | 0.189 | I49V | SEQ ID NO: 157 |
| 0.116 | 0.238 | 0.487 | 0.354 | S84V | SEQ ID NO: 164 |
| −0.020 | 0.153 | 19-SMG | 0.133 | S84V | SEQ ID NO: 164 |
| 0.096 | 0.230 | 0.417 | 0.326 | P86R | SEQ ID NO: 165 |
| 0.083 | 0.196 | 0.423 | 0.279 | P86R | SEQ ID NO: 165 |
| 0.065 | 0.17 | 0.382 | 0.235 | P86R | SEQ ID NO: 165 |
| 0.042 | 0.18 | 0.233 | 0.222 | P86G | SEQ ID NO: 166 |
| −0.003 | 0.169 | 19-SMG | 0.166 | P86R | SEQ ID NO: 165 |

TABLE 7B

UGT85C2 SSL screen candidates that were selective towards steviol as a substrate.

| Steviol ($Abs_{600}$) | 19-SMG ($Abs_{600}$) | Steviol/19-SMG Ratio | Sum ($Abs_{600}$) | Mutation | UGT85C2 Variant SEQ ID |
|---|---|---|---|---|---|
| 0.382 | −0.081 | Steviol | 0.301 | S84T | SEQ ID NO: 160 |
| 0.242 | −0.083 | Steviol | 0.159 | S84T | SEQ ID NO: 160 |
| 0.521 | −0.033 | Steviol | 0.488 | I87M | SEQ ID NO: 169 |
| 0.261 | 0.190 | 1.374 | 0.451 | I87Y | SEQ ID NO: 170 |
| 0.372 | 0.159 | 2.340 | 0.531 | L91K | SEQ ID NO: 171 |
| 0.369 | 0.134 | 2.754 | 0.503 | L91K | SEQ ID NO: 171 |
| 0.228 | 0.104 | 2.192 | 0.332 | L91R | SEQ ID NO: 172 |
| 0.202 | 0.079 | 2.557 | 0.281 | L91R | SEQ ID NO: 172 |
| 0.147 | 0.041 | 3.585 | 0.188 | L91T | SEQ ID NO: 173 |
| 0.606 | 0.266 | 2.278 | 0.872 | I95K | SEQ ID NO: 177 |

TABLE 7C

UGT85C2 SSL screen candidates that were not substrate selective towards steviol or 19-SMG.

| Steviol ($Abs_{600}$) | 19-SMG ($Abs_{600}$) | Steviol/19-SMG Ratio | Sum ($Abs_{600}$) | Mutation | UGT85C2 Variant SEQ ID |
|---|---|---|---|---|---|
| 0.229 | 0.268 | 0.854 | 0.497 | Q21L | SEQ ID NO: 147 |
| 0.231 | 0.261 | 0.885 | 0.492 | Q21T | SEQ ID NO: 148 |
| 0.214 | 0.252 | 0.849 | 0.466 | Q21V | SEQ ID NO: 149 |
| 0.083 | 0.098 | 0.847 | 0.181 | F48W | SEQ ID NO: 155 |
| 0.359 | 0.332 | 1.081 | 0.691 | S84G | SEQ ID NO: 158 |
| 0.306 | 0.331 | 0.924 | 0.637 | S84A | SEQ ID NO: 159 |
| 0.296 | 0.292 | 1.014 | 0.588 | S84C | SEQ ID NO: 161 |
| 0.250 | 0.299 | 0.836 | 0.549 | S84P | SEQ ID NO: 162 |
| 0.250 | 0.256 | 0.977 | 0.506 | S84A | SEQ ID NO: 159 |
| 0.219 | 0.262 | 0.836 | 0.481 | S84N | SEQ ID NO: 163 |
| 0.355 | 0.306 | 1.160 | 0.661 | I87H | SEQ ID NO: 167 |
| 0.326 | 0.274 | 1.190 | 0.600 | I87P | SEQ ID NO: 168 |
| 0.308 | 0.282 | 1.092 | 0.590 | I87M | SEQ ID NO: 169 |
| 0.279 | 0.216 | 1.292 | 0.495 | I87Y | SEQ ID NO: 170 |
| 0.474 | 0.426 | 1.113 | 0.900 | L92F | SEQ ID NO: 174 |
| 0.387 | 0.331 | 1.169 | 0.718 | L92I | SEQ ID NO: 175 |
| 0.342 | 0.260 | 1.315 | 0.602 | L92M | SEQ ID NO: 176 |
| 0.39 | 0.598 | 0.652 | 0.988 | F122S | SEQ ID NO: 178 |
| 0.297 | 0.248 | 1.198 | 0.545 | L334S | SEQ ID NO: 179 |
| 0.27 | 0.233 | 1.159 | 0.503 | L334M | SEQ ID NO: 180 |

The purified S84V and P86R variants of UGT85C2 were selective towards 19-SMG; UGT85C2 S84V and UGT85C2 P86R did not demonstrate activity on steviol (Table 7A). The purified F48S, F48H, F48Y, F48R, F48Q, F48T, F48S, I49V, P86R, P86G, and F122S UGT85C2 variants also showed selectivity towards 19-SMG (Table 7A). However, the purified S84T and I87M variants of UGT85C2 were selective towards steviol; UGT85C2 S84T and UGT85C2 I87M did not demonstrate activity on 19-SMG (Table 7B). The purified I87P, I87Y, L91K, L91R, L91T, L92M, and I95K UGT85C2 variants also showed selectivity towards steviol (Table 7B).

Example 6: Characterization of Steviol Glycoside-Producing Yeast Strain Deleted of UGT85C2

A modified version of the steviol glycoside-producing *S. cerevisiae* strain described in Example 2, a recombinant KO gene encoded by the nucleotide sequence set forth in SEQ ID NO:67 (corresponding to the amino acid sequence set forth in SEQ ID NO:117) and a recombinant CPR1 gene encoding (SEQ ID NO:77, SEQ ID NO:78) was deleted for *S. rebaudiana* UGT85C2 polypeptide (SEQ ID NO:5/SEQ ID NO:6, SEQ ID NO:7). Sixteen independent clones were grown in Synthetic Complete (SC) medium at 30° C. for 5 days with shaking (400 rpm for deep wells) prior to harvest. Culture samples (without cell removal) were heated in the presence of DMSO for detection of total glycoside levels with LC-MS.

Figure 4B:
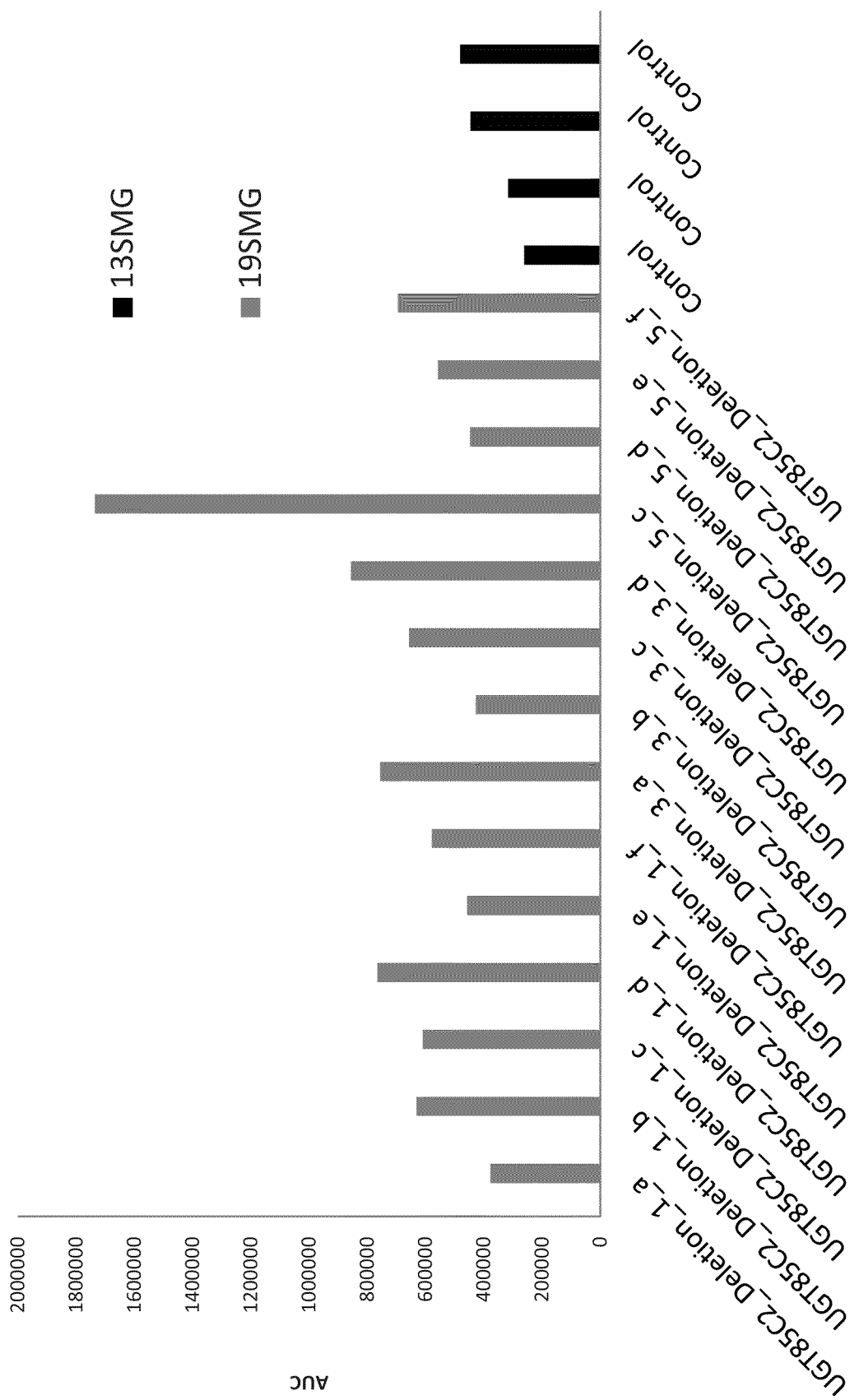
FIG. 4B shows accumulation of 19-SMG by a steviol glycoside-producing S. cerevisiae strain deleted of UGT85C2 (SEQ ID NO:7).
Figure 4C:
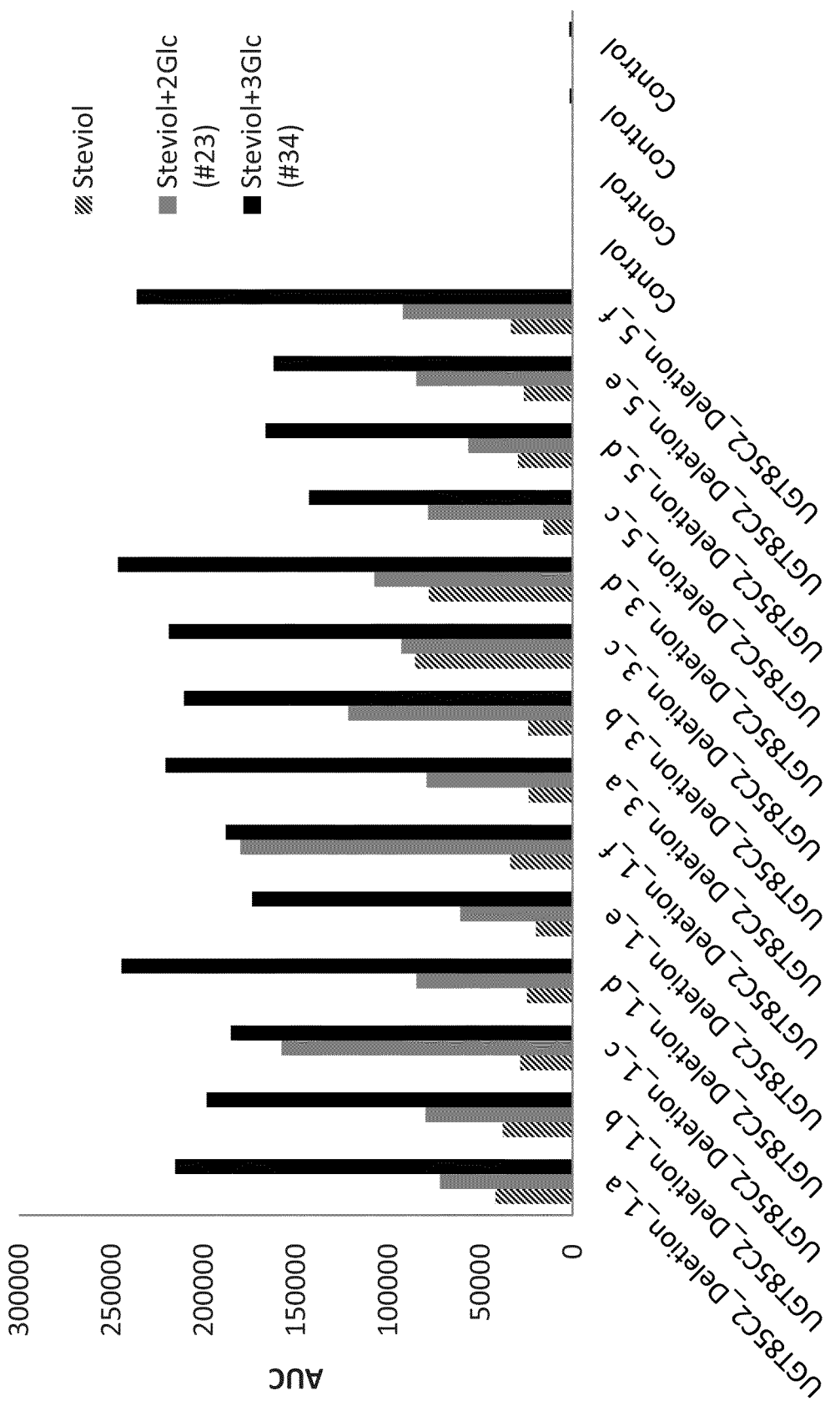
FIG. 4C shows accumulation of steviol, steviol+2Glc (#23), and steviol+3Glc (#34) by a steviol glycoside-producing S. cerevisiae strain deleted of UGT85C2 (SEQ ID NO:7). See Example 6.

As shown in FIG. 4A, culture samples of cells deleted of UGT85C2 did not accumulate ent-kaurenol glycosides (ent-kaurenol+3Glc (isomer 1), ent-kaurenol+3Glc (#6), or ent-kaurenol_2Glc (#8), as compared to the control strain (not deleted for UGT85C2). This result suggests that UGT85C2 is responsible for the 19-O-glucosylation of ent-kaurenol. Also as shown in FIG. 4A, culture samples of cells deleted of UGT85C2 did accumulate ent-kaurenoic acid glycosides (ent-kaurenoic acid+2Glc (#7), ent-kaurenoic acid+3Glc (isomer 1), and ent-kaurenoic acid+3Glc (isomer 2)). Whereas control samples accumulated 13-SMG, culture samples of cells deleted of UGT85C2 accumulated 19-SMG, steviol, steviol+2Glc (#23), and steviol+3Glc (#34). See FIGS. 4B and 4C. Steviol+2Glc (#23) and steviol+3Glc (#34) likely have two or three glucose moieties, respectively, attached on the 19 position of the steviol backbone.

Structures of isolated tri-glycosylated ent-kaurenoic acid, elucidated by NMR, are shown in FIG. 7A, along with a structure of tri-glycosylated ent-kaurenol. These structures were solved by means of standard homo- and heteronuclear multipulse NMR experiments, $^1$H, $^1$H-COSY, $^1$H, $^1$H-ROESY, $^1$H, $^{13}$C-HSQC, and $^1$H, $^{13}$C-HMBC. Compounds were dissolved in 60 μL DMSO-d6 and measured at 25° C. Spectra of these compounds were acquired on an 800 MHz Bruker Avance instrument (800 MHz for $^1$H, 201 MHz for $^{13}$C) equipped with a cryogenic probe (5 mm CPTCI 1H-13C/15N/D Z-GRD Z44909/0010). In addition, $^1$H-NMR spectra were obtained for 3 molecules detected by LC-MS that were concordant with a general ent-kaurenoic acid+2Glc, ent-kaurenol+3Glc (isomer 2), and ent-kaurenol+Glc+GlcNAc structures. See FIGS. 8A-8L for $^1$H NMR spectra and $^1$H and $^{13}$C NMR chemical shifts for these compounds.

UGT85C2 variants were subsequently cloned into USER vectors (for integration at ChrXII-1) using a forward primer (SEQ ID NO:215) and a reverse primer (SEQ ID NO:216) and the PGK1 promoter. The UGT85C2 variants were then integrated into the steviol glycoside-producing strain deleted of UGT85C2. Transformants were re-streaked from transformation plates. Pre-cultures were set up from re-streaked plates in 500 μL synthetic complete-URA (SC-URA) media in a 96 deep well plate (DWP) and grown at 30° C. and 300 rpm overnight. Cultures were set up by transferring 50 μL of the pre-cultures to a 96 well DWP comprising 500 μL SC-URA media.

After 1 day of incubation, cultures were set up from pre-cultures (50 μL in 500 μL SC-URA) and grown in Duetz system for 5 days (same conditions as for pre-cultures). The $OD_{600}$ was measured on plate reader in a 1:10 dilution, and samples were harvested by transferring 50 μL sample to 50 μL 100% DMSO. The mixtures were heated to 80° C. for 10 min and subsequently spun down (4000 rcf, 4° C., 10 min). 15 μL of each supernatant were mixed with 105 μL 50% DMSO (total dilution of 1:16), and the samples were analyzed by LC-MS.

Example 7: Assessment of UGT85C2 Variant Activity in Cell Lysates

Purified variant UGT85C2 DNA from Example 6 was individually transformed into XJB autolysis z-competent cells. Pre-cultures of three colonies from each transformation plate were inoculated into 600 μL LB comprising kanamycin (600 mg/L) and incubated overnight at 200 rpm and 37° C. in a 96 well DWP. Protein production and cell wall degradation were induced by transferring 50 μL of the pre-cultures to a new 96 well DWP comprising 1 mL/well of NZCYM broth comprising kanamycin (600 mg/L)+3 mL/L 1M Arabinose and 100 μL/L 1M IPTG. Cultures were incubated at 20° C., 200 rpm for approximately 20 h before pelleting the cells (4000 rcf, 5 min, 4° C.) and removing the supernatant. To each well, 50 μL GT buffer with protease inhibitor (cOmplete™, Mini, EDTA-free Protease Inhibitor Cocktail Tablets, 11836170001 Roche) was added. Pellets were resuspended by shaking at 200 rpm for 5 min at 4° C. A 75 μL aliquot of each sample was transferred to a PCR plate and frozen at −80° C. Pellets were thawed at room temperature, and 25 μL/well DNAse mix (2.39 mL 4× binding buffer+50 μL DNAse I (1.4 mg/mL)+60 μL $MgCl_2$ (1 M) per plate) were added when samples were nearly thawed. The plate was incubated at room temperature for 5 min with gentle shaking and subsequently centrifuged at 4000 rcf for 5 min. Each supernatant was transferred to a fresh PCR plate for activity measurements.

Each supernatant was incubated in an assay reaction mix comprising a final concentration of 100 mM Tris (pH 8.0), 4 mM $MgCl_2$, 1 mM KCl, 300 μM UDP-Glucose, and 100 μM substrate. The substrates were either steviol or 19-SMG. A purified wild-type UGT85C2 enzyme and a UGT85C2 bacterial lysate were used as positive controls. Reactions were incubated at 30° C. (on a plate shaker), and the reactions were stopped after 20 min, 40 min, and 19 h by mixing 20 μL sample with 20 μL 100% DMSO. The samples were further diluted by adding 60 μL 50% DMSO and subsequently analyzed by LC-MS. AUC values corresponding to measured 13-SMG, 19-SMG, rubusoside, and steviol levels are shown in Tables 8A-C.

TABLE 8A

Measured 13-SMG and steviol AUC values in UGT85C2 variant activity assay using steviol as a substrate.

| | 13-SMG | | | Steviol | | |
|---|---|---|---|---|---|---|
| UGT85C2 Variant | 20 min | 40 min | 19 h | 20 min | 40 min | 19 h |
| F48S (SEQ ID NO: 150) | 38195 | 55395 | 76045 | 21355 | 9955 | |
| F48H (SEQ ID NO: 151) | 49840 | 64105 | 79000 | 17670 | 4035 | |
| F48Y (SEQ ID NO: 152) | 36980 | 53005 | 83100 | 26675 | 16135 | |
| F48R (SEQ ID NO: 153) | 37990 | 55510 | 71810 | 25540 | 11075 | |
| F48Q (SEQ ID NO: 154) | 33660 | 46010 | 72550 | 30565 | 16135 | |
| F48W (SEQ ID NO: 155) | 37580 | 56220 | 76490 | 25280 | 8615 | |
| F48T (SEQ ID NO: 156) | 40505 | 57280 | 78080 | 20405 | 10340 | |

TABLE 8A-continued

Measured 13-SMG and steviol AUC values in UGT85C2 variant activity assay using steviol as a substrate.

| UGT85C2 Variant | 13-SMG | | | Steviol | | |
|---|---|---|---|---|---|---|
| | 20 min | 40 min | 19 h | 20 min | 40 min | 19 h |
| I49V (SEQ ID NO: 157) | 48345 | 60720 | 75420 | 17545 | 4305 | |
| S84G (SEQ ID NO: 158) | 33960 | 50770 | 76070 | 29500 | 15870 | |
| S84A (SEQ ID NO: 159) | 43135 | 62000 | 75715 | 21445 | 5190 | |
| S84C (SEQ ID NO: 161) | 25780 | 39330 | 71060 | 34285 | 22700 | |
| S84V (SEQ ID NO: 164) | 27045 | 43200 | 74505 | 32100 | 17715 | |
| P86R (SEQ ID NO: 165) | 23240 | 34440 | 71955 | 33670 | 25395 | |
| P86G (SEQ ID NO: 166) | 28000 | 43525 | 74300 | 27640 | 14380 | |
| I87H (SEQ ID NO: 167) | 7290 | 10465 | 43495 | 51340 | 41690 | 21865 |
| I87P (SEQ ID NO: 168) | 32165 | 48565 | 76700 | 29475 | 13945 | |
| I87Y (SEQ ID NO: 170) | 36905 | 47250 | 71390 | 31220 | 14065 | |
| L91K (SEQ ID NO: 171) | 25810 | 37830 | 72435 | 29455 | 19015 | 2770 |
| L91R (SEQ ID NO: 172) | 27560 | 40235 | 75830 | 34275 | 22140 | 2470 |
| L92F (SEQ ID NO: 174) | 49205 | 62540 | 72385 | 15635 | 3570 | |

TABLE 8B

Measured 13-SMG, 19-SMG, and rubusoside AUC values in UGT85C2 variant activity assay using 19-SMG as a substrate.

| UGT85C2 Variant | 19-SMG | | | rubusoside | | |
|---|---|---|---|---|---|---|
| | 20 min | 40 min | 19 h | 20 min | 40 min | 19 h |
| F48S (SEQ ID NO: 150) | 171625 | 147690 | 3720 | 18935 | 30650 | 92800 |
| F48H (SEQ ID NO: 151) | 165365 | 129495 | 1830 | 24415 | 40520 | 99660 |
| F48Y (SEQ ID NO: 152) | 161680 | 128705 | 2815 | 23130 | 39385 | 97180 |
| F48R (SEQ ID NO: 153) | 166035 | 142095 | 6120 | 17335 | 30075 | 93750 |
| F48Q (SEQ ID NO: 154) | 169560 | 145130 | 3235 | 16570 | 28495 | 81190 |
| F48W (SEQ ID NO: 155) | 168175 | 147640 | 3920 | 16040 | 28030 | 95530 |
| F48T (SEQ ID NO: 156) | 166190 | 134425 | 2960 | 22445 | 37520 | 96620 |
| I49V (SEQ ID NO: 157) | 170460 | 133705 | 1935 | 20340 | 35300 | 97440 |
| S84G (SEQ ID NO: 158) | 175515 | 147045 | 3165 | 14645 | 24745 | 91945 |
| S84A (SEQ ID NO: 159) | 163565 | 131735 | 1790 | 19805 | 31845 | 90090 |
| S84C (SEQ ID NO: 161) | 183175 | 159805 | 44230 | 11040 | 17040 | 77130 |
| S84V (SEQ ID NO: 164) | 183415 | 168240 | 6600 | 11975 | 20075 | 98555 |
| P86R (SEQ ID NO: 165) | 186925 | 154290 | 12670 | 12075 | 20350 | 85755 |
| P86G (SEQ ID NO: 166) | 175265 | 146080 | 5720 | 17660 | 29815 | 93195 |
| I87H (SEQ ID NO: 167) | 197170 | 191250 | 149025 | 3045 | 5300 | 27610 |
| I87P (SEQ ID NO: 168) | 167935 | 143945 | 8795 | 16675 | 28290 | 96865 |
| I87Y (SEQ ID NO: 170) | 176815 | 142820 | 4750 | 16635 | 26615 | 93205 |
| L91K (SEQ ID NO: 171) | 188110 | 182210 | 177120 | 5350 | 8545 | 20345 |
| L91R (SEQ ID NO: 172) | 188750 | 180040 | 149165 | 7535 | 12140 | 29160 |
| L92F (SEQ ID NO: 174) | 187295 | 155170 | 2695 | 11335 | 22340 | 98920 |

TABLE 8C

Measured 13-SMG, 19-SMG, rubusoside, and steviol AUC values in control UGT85C2 assays.

| | 13-SMG | | | 19-SMG | | | rubusoside | | | Steviol | | |
|---|---|---|---|---|---|---|---|---|---|---|---|---|
| | 20 min | 40 min | 19 h | 20 min | 40 min | 19 h | 20 min | 40 min | 19 h | 20 min | 40 min | 19 h |
| Substrate: Steviol WT UGT85C2 (SEQ ID NO: 7) | 60635 | 67575 | 73750 | | | | | | 490 | | | |
| Substrate: 19-SMG WT UGT85C2 (SEQ ID NO: 7) | | | | 53380 | 4635 | 1775 | 85560 | 108620 | 100300 | | | |
| Substrate: Steviol No UGT85C2 | | | | | | | | | | 53745 | 46585 | 54250 |
| Substrate: 19-SMG No UGT85C2 | | | | 224605 | 206230 | 199490 | | | | | | |

Accumulation of 19-SMG and rubusoside was not observed in UGT85C2 variant activity assays using steviol as a substrate. Using steviol as the substrate, the F48H, F48Y, F48T, I49V, S84A, and L92F UGT85C2 variants demonstrated high activity during incubation periods of under 40 min, and the F48H, F48Y, F48T, and I49V UGT85C2 variants demonstrated high activity during incubation periods of over 40 min (Table 8A). Using 19-SMG as the substrate, the F48H, F48Y, F48T, I49V, and S84A UGT85C2 variants demonstrated high activity during incubation periods of under 40 min, and the F48H, I49V, S84A, S84V, L91K, and L92F UGT85C2 variants, as well as the wild-type UGT85C2, demonstrated high activity during incubation periods of over 40 min (Table 8B). Slow conversion of steviol and 19-SMG was observed for UGT85C2 I87H (Tables 8A and 8B).

13-SMG/rubusoside ratios were calculated for the UGT85C2 variants. A high 13-SMG/rubusoside ratio indicates preference of a UGT85C2 variant for steviol, whereas a low 13-SMG/rubusoside ratio indicates preference of a UGT85C2 variant for 19-SMG. The L91K, L91R, and L92F UGT85C2 variants demonstrated a high 13-SMG/rubusoside ratio, whereas the F48Y, F48T, P86G UGT85C2 variants demonstrated a low 13-SMG/rubusoside ratio.

Figure 5:
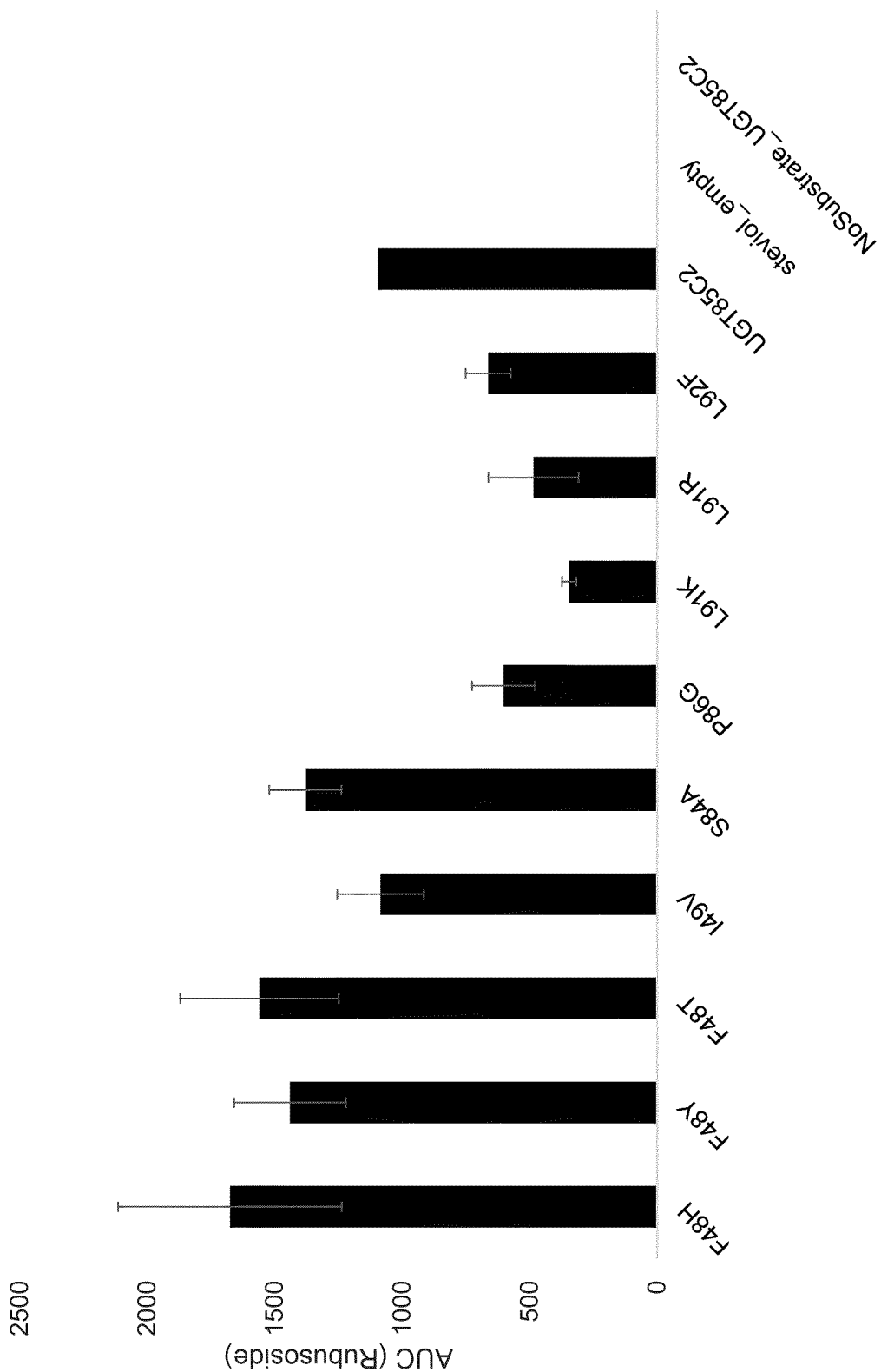
FIG. 5 shows conversion of steviol to rubusoside by bacterial lysates comprising UGT85C2 variants. Bacterial lysates were incubated with steviol for 24 h. See Example 7.

The UGT85C2 variants were found to convert steviol to rubusoside after 24 h. Rubusoside levels (in AUC) are shown in FIG. 5. Mutations in the amino acid 48 and 49 positions produced increased levels of rubusoside, as compared to the control. The variants with mutations in amino acids at position 86, 91 and 92 seem to produce lower levels of rubusoside.

Example 8: Evaluation of UGT76G1 Variants

UGT76G1 variants were tested in a modified version of a steviol glycoside-producing *S. cerevisiae* strain as described in Example 2 to determine the effects on steviol glycosides, tri-glycosylated ent-kaurenol, and tri-glycosylated ent-kaurenoic acid levels. The background strain was described in Example 9 of WO 2014/122227, wherein both copies of UGT76G1 were deleted by homologous recombination using selective markers. The strain comprised a reintegrated wild-type UGT76G1 (WT control) or variants of UGT76G1 at the chromosome level.

Expression of UGT76G1 H155L (SEQ ID NO:184) increased the ratio of RebM/RebD produced, as compared to wild-type UGT76G1. Expression of UGT76G1 Q23H (SEQ ID NO:181), UGT76G1 T146G (SEQ ID NO:183), UGT76G1 L257G (SEQ ID NO:185), or UGT76G1 S283N (SEQ ID NO:188) in the strain all resulted in increased accumulation of ent-kaurenoic acid+2Glc (#7), 1,2-bioside, 1,2-stevioside, RebE, RebD, steviol+5Glc (#22), and steviol+6Glc (isomer 1), increased the ratio of RebD/RebM produced, and decreased accumulation of RebB and RebA, as compared to wild-type UGT76G1. See Tables 9A-9C. Specifically, expression of UGT76G1 T146G (SEQ ID NO:183), resulted in increased accumulation of ent-kaurenoic acid+3Glc (isomer 1), steviol+3Glc (#1), and Stev3Glc (#34), as compared to wild-type UGT76G1. Expression of UGT76G1 L257G (SEQ ID NO:185) increased the amount of steviol+7Glc (isomer 2), as compared to wild-type UGT76G1. Expression of UGT76G1 S283N (SEQ ID NO:188) increased the amount of steviol+3Glc (#1) and Stev3Glc (#34), as compared to wild-type UGT76G1. See Tables 9A-9C.

TABLE 9A

Accumulation of steviol glycosides (in μM) in a host comprising wild-type UGT76G1 or a UGT76G1 variant.

| | 13-SMG | 1,2-bioside | RebB | RebA | RebE | RebD | RebM |
|---|---|---|---|---|---|---|---|
| Wild-type (SEQ ID NO: 9) | 13.5 ± 3.8 | N/A | 1.5 ± 0.4 | 4.7 ± 1.9 | N/A | 5.2 ± 2.5 | 29.3 ± 15.5 |
| H155L (SEQ ID NO: 184) | 13.9 ± 2.4 | N/A | 1.8 ± 0.2 | 6.5 ± 1.5 | N/A | 2.1 ± 0.3 | 38.8 ± 12.6 |
| Q23H (SEQ ID NO: 181) | 13.4 ± 2.2 | 1.8 ± 0.4 | 0.9 ± 0.1 | 1.3 ± 0.2 | 4.6 ± 0.6 | 17.7 ± 6.4 | 1.9 ± 0.7 |
| T146G (SEQ ID NO: 183) | 13.9 ± 2.7 | 2.0 ± 0.4 | 0.6 ± 0.3 | 0.7 ± 0.5 | 7.4 ± 1.9 | 14.1 ± 3.5 | 1.1 ± 0.2 |
| L257G (SEQ ID NO: 185) | 13.6 ± 0.9 | 1.2 ± 0.1 | 0.9 ± 0.2 | 2.3 ± 0.3 | 2.8 ± 0.4 | 32.0 ± 6.1 | 7.0 ± 1.5 |
| S283N (SEQ ID NO: 188) | 13.5 ± 1.4 | 2.1 ± 0.4 | 0.5 ± 0.1 | 0.3 ± 0.5 | 7.9 ± 1.0 | 14.4 ± 3.9 | 0.9 ± 0.4 |
| Q23H + H155L (SEQ ID NO: 217) | 12.4 ± 1.1 | 1.4 ± 0.3 | 0.8 ± 0.1 | 1.9 ± 0.5 | 4.0 ± 0.4 | 22.4 ± 5.9 | 8.4 ± 3.4 |
| T146G + H155L (SEQ ID NO: 218) | 13.8 ± 1.3 | 1.4 ± 0.2 | 0.8 ± 0.1 | 2.2 ± 0.1 | 3.4 ± 0.4 | 26.5 ± 2.5 | 9.5 ± 1.9 |
| L257G + H155L (SEQ ID NO: 219) | 14.1 ± 1.3 | 0.9 ± 0.4 | 1.0 ± 0.1 | 3.1 ± 0.5 | 1.8 ± 0.5 | 23.8 ± 5.2 | 15.9 ± 1.5 |
| S283N + H155L (SEQ ID NO: 220) | 13.4 ± 2.6 | 2.3 ± 0.5 | 0.5 ± 0.3 | 0.3 ± 0.5 | 7.2 ± 1.8 | 10.1 ± 4.3 | 1.2 ± 0.6 |

TABLE 9B

Accumulation of steviol glycosides, glycosylated ent-kaurenoic acid, or glycosylated kaurenol (in AUC) in a host comprising wild-type UGT76G1 or a UGT76G1 variant.

| | KA + 2Glc (#7) | KA + 3Glc (isomer 1) | KA + 3Glc (isomer 2) | KL + 2Glc (#8) | KL + 3Glc (isomer 1 and isomer 2) | 1,2-stevioside | steviol + 3Glc (#1) |
|---|---|---|---|---|---|---|---|
| Wild-type (SEQ ID NO: 9) | N/A | N/A | 859 ± 1089 | N/A | N/A | 887 ± 668 | N/A |
| H155L (SEQ ID NO: 184) | N/A | N/A | 1862 ± 1825 | N/A | 550 ± 1035 | 874 ± 754 | N/A |
| Q23H (SEQ ID NO: 181) | 3118 ± 1068 | 592 ± 1165 | N/A | N/A | N/A | 6716 ± 966 | 466 ± 500 |
| T146G (SEQ ID NO: 183) | 3109 ± 1441 | 1355 ± 951 | N/A | N/A | N/A | 8313 ± 1498 | 1243 ± 601 |
| L257G (SEQ ID NO: 185) | 2562 ± 1267 | 1062 ± 1199 | N/A | N/A | N/A | 5716 ± 837 | N/A |
| S283N (SEQ ID NO: 188) | 3872 ± 1086 | 1200 ± 1929 | N/A | N/A | N/A | 8572 ± 1325 | 1162 ± 644 |
| Q23H + H155L (SEQ ID NO: 217) | 2690 ± 423 | N/A | 236 ± 668 | N/A | N/A | 6690 ± 734 | 110 ± 311 |
| T146G + H155L (SEQ ID NO: 218) | 2416 ± 555 | N/A | N/A | N/A | N/A | 6172 ± 524 | 208 ± 385 |
| L257G + H155L (SEQ ID NO: 219) | 1634 ± 1227 | 212 ± 600 | 1524 ± 1318 | N/A | 222 ± 628 | 5458 ± 1068 | N/A |
| S283N + H155L (SEQ ID NQ: 220) | 3886 ± 750 | 496 ± 929 | N/A | 408 ± 1154 | N/A | 8036 ± 1601 | 1118 ± 614 |

KA: ent-kaurenoic acid
KL: ent-kaurenol

TABLE 9C

Accumulation of steviol glycosides (in AUC) in a host comprising wild-type UGT76G1 or a UGT76G1 variant.

| | steviol + 3 Glc (#34) | steviol + 4 Glc (#26) | steviol + 4 Glc (#33) | steviol + 5 Glc (#22) | steviol + 5 Glc (#25) | steviol + 6 Glc (isomer 1) | steviol + 7 Glc (isomer 2) |
|---|---|---|---|---|---|---|---|
| Wild-type (SEQ ID NO: 9) | N/A | 2443 ± 1164 | N/A | N/A | N/A | N/A | N/A |
| H155L (SEQ ID NO: 184) | N/A | 1020 ± 731 | N/A | N/A | 938 ± 1039 | N/A | N/A |
| Q23H (SEQ ID NO: 181) | 472 ± 507 | 818 ± 726 | N/A | 19804 ± 4600 | N/A | 7350 ± 4013 | N/A |
| T146G (SEQ ID NO: 183) | 1262 ± 605 | 1509 ± 376 | 114 ± 302 | 38469 ± 8953 | N/A | 7365 ± 3483 | N/A |
| L257G (SEQ ID NO: 185) | 104 ± 294 | 1038 ± 459 | N/A | 11638 ± 2268 | N/A | 10722 ± 1871 | 3870 ± 2463 |
| S283N (SEQ ID NO: 188) | 1168 ± 655 | 1572 ± 625 | 104 ± 294 | 44460 ± 11455 | N/A | 12174 ± 5214 | N/A |
| Q23H + H155L (SEQ ID NO: 217) | 122 ± 345 | 964 ± 459 | N/A | 16600 ± 3617 | N/A | 4404 ± 2744 | 5230 ± 3262 |
| T146G + H155L (SEQ ID NO: 218) | 212 ± 383 | 1114 ± 192 | N/A | 14362 ± 1802 | N/A | 2498 ± 2743 | 4840 ± 2053 |
| L257G + H155L (SEQ ID NO: 219) | N/A | 782 ± 725 | N/A | 6354 ± 4578 | N/A | 2408 ± 2584 | 5780 ± 977 |
| S283N + H155L (SEQ ID NO: 220) | 1186 ± 673 | 1020 ± 739 | N/A | 38410 ± 17463 | N/A | 3864 ± 3520 | N/A |

The double UGT76G1 variants were also tested. The double variants were: UGT76G1 Q23H H155L (SEQ ID NO:217), UGT76G1 T146G H155L (SEQ ID NO:218), UGT76G1 L257G H155L (SEQ ID NO:219), and UGT76G1 S283N H155L (SEQ ID NO:220). Double variants UGT76G1 Q23H H155L (SEQ ID NO:217), UGT76G1 T146G H155L (SEQ ID NO:218), and UGT76G1 L257G H155L (SEQ ID NO:219) resulted in increased RebM accumulation, as compared to the three single variants UGT76G1 Q23H (SEQ ID NO:181), UGT76G1 T146G (SEQ ID NO:183), and UGT76G1 L257G (SEQ ID NO:185). See Tables 9A-90. Specifically, expression of UGT76G1 Q23H H155L (SEQ ID NO:217) increased the amount of RebM and steviol+7Glc (isomer 2), compared to the UGT76G1 Q23H (SEQ ID NO:181) variant. Expression of UGT76G1 T146G H155L (SEQ ID NO:218) increased accumulation of RebA, RebD, RebM, and steviol+7Glc (isomer 2) and decreased accumulation of ent-kaurenoic acid+3Glc (isomer1), 1,2-bioside, 1,2-stevioside, steviol+3Glc (#1), Stev3Glc (#34), RebE, and steviol+5Glc (#22), as compared to the UGT76G1 T146G (SEQ ID NO:183) variant. Expression of UGT76G1 L257G H155L (SEQ ID NO:219) increased accumulation of ent-kaurenoic acid+3Glc (isomer 2), RebA, and RebM and decreased accumulation of RebE and steviol+6Glc (isomer 1), as compared to the UGT76G1 L257G (SEQ ID NO:185) variant. See Tables 9A-9C. Thus, synergistic effects were observed for UGT76G1 double variants.

UGT76G1 variants were also analyzed in a modified version of the strain described above, which comprised a higher copy number of UGT91D2e (SEQ ID NO:10, SEQ ID NO:11), UGT74G1 (SEQ ID NO:3, SEQ ID NO:4), and ATR2 (SEQ ID NO:91, SEQ ID NO:92). Steviol glycoside-producing *S. cerevisiae* strains expressing UGT76G1 variants that resulted in increased RebD levels, including UGT76G1 Q23H, UGT76G T146G, and S283N, also increased accumulation of ent-kaurenoic acid+2Glc (#7) and ent-kaurenoic acid+2Glc (isomer 1) but decreased accumulation of ent-kaurenoic acid+3Glc (isomer 2), compared to steviol glycoside-producing *S. cerevisiae* strains expressing wild-type UGT76G1. See FIG. 9A. UGT76G1 variants that increased RebD levels also increased accumulation of ent-kaurenol+2Glc (#8) but decreased accumulation of ent-kaurenol+3Glc (isomer 1) co-eluted with ent-kaurenol+3Glc (#6) (FIG. 9B).

Expression of the UGT76G1 H155L variant (SEQ ID NO:184), a variant that increased levels of RebM, resulted in decreased accumulation of ent-kaurenoic acid+2Glc (#7) and ent-kaurenoic acid+3Glc (isomer 1) (FIG. 9A). Levels of ent-kaurenol glycosides were not significantly altered upon expression of UGT76G1 variants that increased levels of RebM, compared to strains expressing wild-type UGT76G1 (FIG. 9B).

Figure 10A:
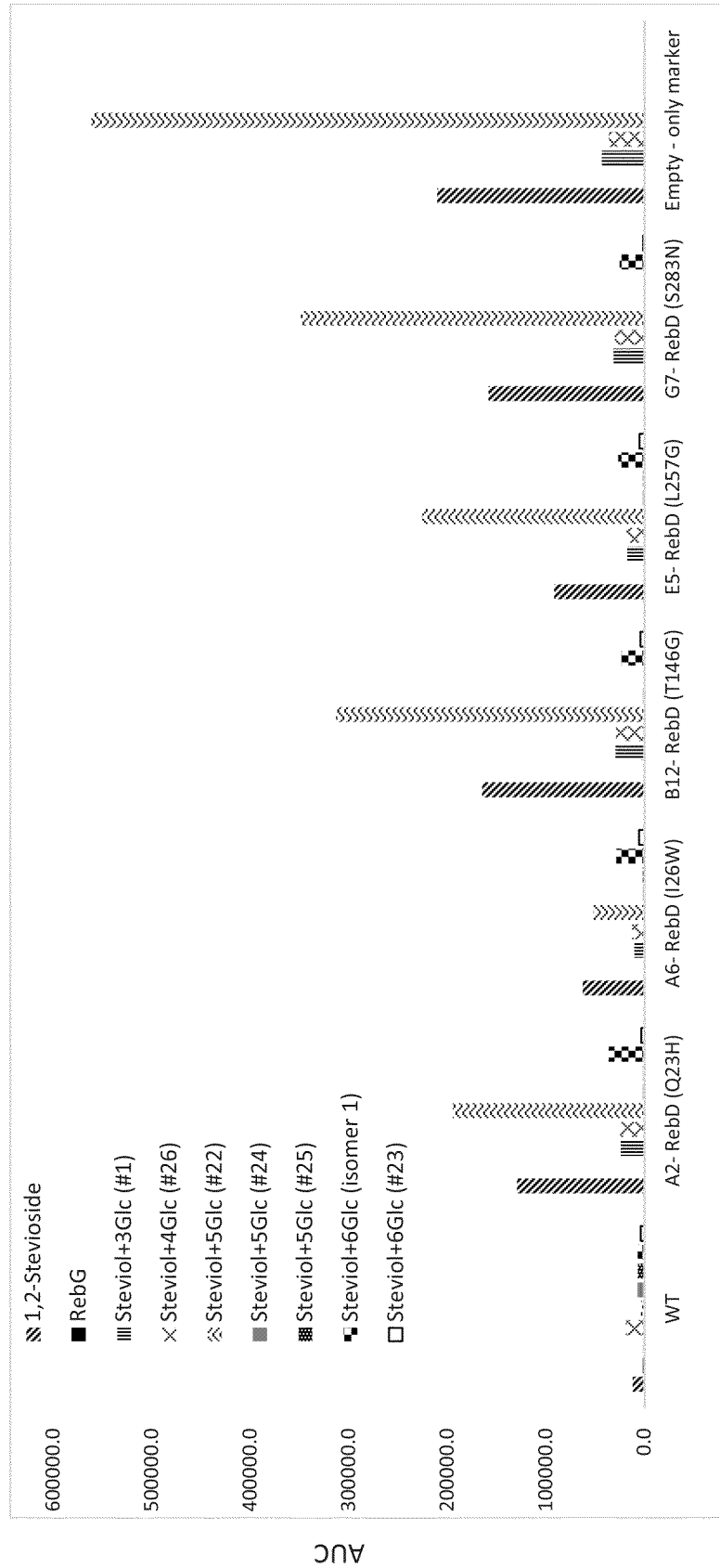
FIG. 10A shows accumulation of 1,2-stevioside, RebG, steviol+3Glc (#1), steviol+4Glc (#26), steviol+5Glc (#22), steviol+5Glc (#24), steviol+5Glc (#25), steviol+6Glc (isomer 1), and steviol+6Glc (#23) in *S. cerevisiae* expressing RebD-producing UGT76G1 variants.
Figure 10B:
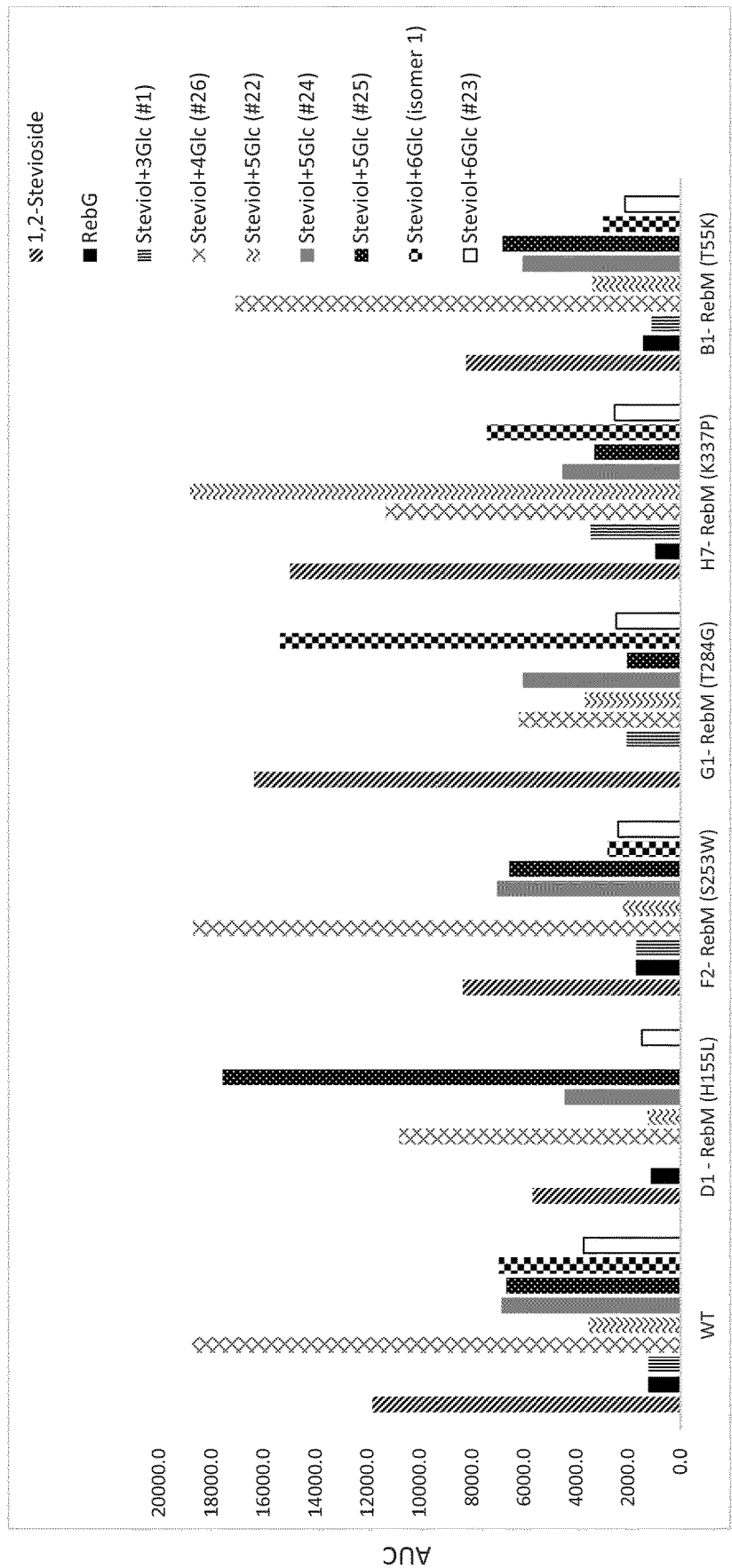
FIG. 10B shows accumulation of 1,2-stevioside, RebG, steviol+3Glc (#1), steviol+4Glc (#26), steviol+5Glc (#22), steviol+5Glc (#24), steviol+5Glc (#25), steviol+6Glc (isomer 1), and steviol+6Glc (#23) in *S. cerevisiae* expressing RebM-producing UGT76G1 variants.
Figure 10C:
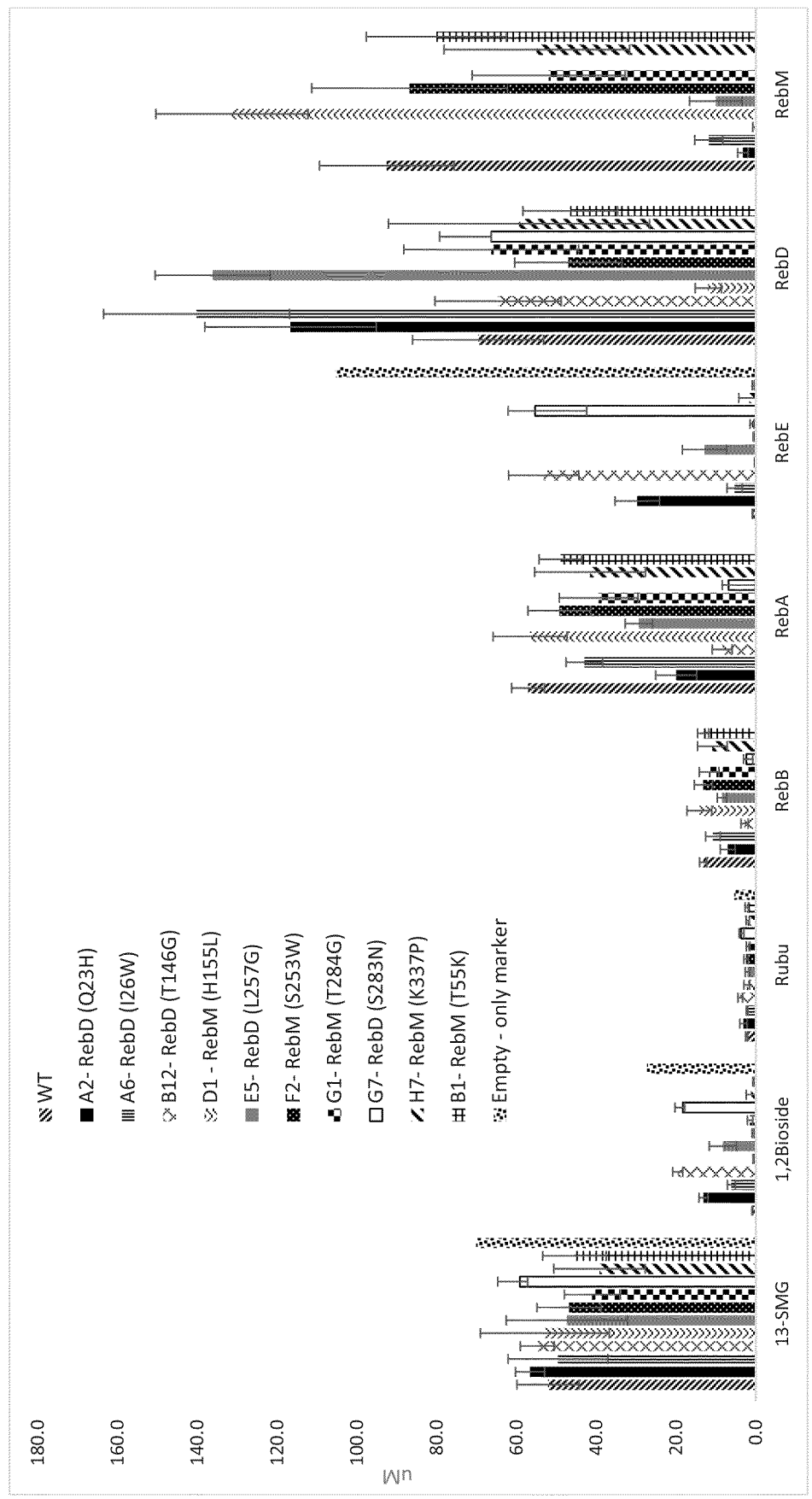
FIG. 10C shows accumulation of 13-SMG, 1,2-bioside, rubusoside, RebA, RebB, RebD, RebE, and RebM in *S. cerevisiae* expressing UGT76G1 variants. See Example 8.

Levels of 13-SMG, 1,2-bioside, rubusoside, RebA, RebB, RebD, RebE, RebM, RebG (1,3-stevioside), steviol+3Glc (#1), steviol+4Glc (#26), steviol+5Glc (#22), steviol+5Glc (#24), steviol+5Glc (#25), steviol+6Glc (isomer 1), and steviol+6Glc (#23) produced in the steviol glycoside-producing strain are shown in FIGS. 10A-10C. Expression of UGT variants that resulted in increased RebD levels also increased accumulation of steviol+5Glc (#22), 1,2-stevioside, steviol+6Glc (isomer 1), and Steviol+3Glc (#1) but decreased accumulation of steviol+4Glc (#26), steviol+5Glc (#24), and RebG (1,3-stevioside) (FIG. 10A). Expression of UGT76G1 H155L (SEQ ID NO:184) resulted in increased accumulation of steviol+5Glc (#25) but decreased accumulation of 1,2-stevioside, steviol+3Glc (#1), steviol+4Glc (#26), steviol+5Glc (#22), steviol+6Glc (isomer 1), and steviol+6Glc (#23) (FIG. 10B). Expression of UGT76G1 S253W (SEQ ID NO:186) resulted in decreased accumulation of 1,2-stevioside and steviol+6Glc (isomer 1) (FIG. 10B). Expression of UGT76G1 284G resulted in increased accumulation of 1,2-stevioside and steviol+6Glc (isomer 1) but decreased accumulation of RebG, steviol+4Glc (#26), steviol+5Glc (#25), and steviol+6Glc (#23) (FIG. 10B). FIG. 10C shows accumulation of 13-SMG, 1,2-bioside, rubusoside, RebA, RebB, RebD, RebE, and RebM in *S. cerevisiae* expressing wild-type UGT76G1 (SEQ ID NO:9) or a UGT76G1 variant that increases accumulation of RebD or RebM.

The steviol glycoside-producing strain comprising a higher copy number of UGT91D2e (SEQ ID NO:10, SEQ ID NO:11), UGT74G1 (SEQ ID NO:3, SEQ ID NO:4), and ATR2 (SEQ ID NO:91, SEQ ID NO:92) was further tested in a separate experiment. As shown in Tables 9D-9F, expression of UGT76G1 H155L (SEQ ID NO:184) resulted in increased accumulation of steviol+5Glc (#25), increased the ratio of RebM/RebD produced, and decreased accumulation of 1,2-bioside, steviol+3Glc (#1), RebE, steviol+6Glc (isomer 1), and steviol+6Glc (#23), as compared to wild-type UGT76G1. Expression of UGT76G1 Q23H (SEQ ID NO:181), UGT76G1 T146G (SEQ ID NO:183), UGT76G1 L257G (SEQ ID NO:185), or UGT76G1 S283N (SEQ ID NO:188) increased accumulation of 1,2-bioside, 1,2-stevioside, steviol+3Glc (#1), Stev+3Glc (#34), RebE, and steviol+5Glc (#22), increased the ratio of RebD/RebM produced, and decreased accumulation of RebG, RebA, steviol+5Glc (#25), steviol+7Glc (isomer 2), and steviol+7Glc (isomer 5). Specifically, expression of UGT76G1 Q23H (SEQ ID NO:181) resulted in increased accumulation of rubusoside, steviol+6Glc (isomer 1) and decreased accumulation of RebB and steviol+5Glc (#24). Expression of UGT76G1 T146G (SEQ ID NO:183) resulted in increased accumulation of rubusoside and decreased accumulation of RebB, steviol+5Glc (#24) and steviol+6Glc (#23). Expression of UGT76G1 L257G (SEQ ID NO:185) resulted in increased accumulation of steviol+6Glc (isomer 1). Expression of UGT76G1 S283N (SEQ ID NO:188) resulted in increased accumulation of rubusoside and decreased accumulation of RebB, steviol+5Glc (#24) and steviol+6Glc (#23). See Tables 9D-F.

TABLE 9D

Accumulation of steviol glycosides (in µM) in a host comprising wild-type UGT76G1 or a UGT76G1 variant.

|  | 13-SMG | 1,2-bioside | Rubu | RebG | RebB | RebA | RebE | RebD | RebM |
|---|---|---|---|---|---|---|---|---|---|
| Wild-type (SEQ ID NO: 9) | 37.6 ± 8.8 | 1.3 ± 0.5 | 1.2 ± 0.2 | 0.2 ± 0.2 | 8.4 ± 2.3 | 32.5 ± 7.5 | 0.4 ± 0.1 | 30.4 ± 12.5 | 43.0 ± 9.6 |
| H155L (SEQ ID NO: 184) | 35.3 ± 7.0 | 0.4 ± 0.1 | 1.3 ± 0.1 | 0.2 ± 0.2 | 8.9 ± 2.1 | 35.2 ± 9.3 | 0.1 ± 0.1 | 5.7 ± 1.8 | 64.5 ± 7.1 |
| Q23H (SEQ ID NO: 181) | 40.8 ± 6.9 | 11.1 ± 1.5 | 2.4 ± 0.4 | N/A | 4.3 ± 1.3 | 7.2 ± 2.0 | 11.8 ± 4.5 | 35.1 ± 6.5 | 1.0 ± 0.4 |
| T146G (SEQ ID NO: 183) | 41.4 ± 6.9 | 16.1 ± 1.4 | 3.1 ± 0.4 | N/A | 1.5 ± 0.5 | 2.4 ± 1.1 | 19.2 ± 3.2 | 15.0 ± 5.3 | 0.2 ± 0.2 |
| L257G (SEQ ID NO: 185) | 32.4 ± 6.2 | 6.9 ± 1.0 | 1.8 ± 0.5 | N/A | 5.2 ± 1.8 | 12.1 ± 4.8 | 4.7 ± 1.6 | 41.7 ± 10.4 | 2.3 ± 0.9 |
| S283N (SEQ ID NO: 188) | 39.8 ± 7.2 | 15.1 ± 2.8 | 2.6 ± 0.4 | N/A | 1.5 ± 0.5 | 2.9 ± 1.2 | 16.2 ± 4.8 | 19.2 ± 6.9 | 0.3 ± 0.1 |
| Q23H + H155L (SEQ ID NO: 217) | 39.4 ± 4.5 | 9.0 ± 1.3 | 2.1 ± 0.2 | N/A | 4.7 ± 0.9 | 8.3 ± 2.6 | 8.8 ± 1.6 | 34.1 ± 4.5 | 3.0 ± 1.2 |
| T146G + H155L (SEQ ID NO: 218) | 33.0 ± 8.0 | 8.5 ± 2.0 | 1.9 ± 0.7 | N/A | 3.8 ± 1.0 | 9.2 ± 2.9 | 6.6 ± 1.7 | 36.5 ± 4.7 | 3.1 ± 0.9 |
| L257G + H155L (SEQ ID NO: 219) | 44.4 ± 6.6 | 4.9 ± 0.9 | 1.5 ± 0.3 | N/A | 8.2 ± 1.2 | 19.2 ± 4.0 | 3.4 ± 1.0 | 47.8 ± 4.5 | 12.3 ± 3.3 |
| S283N + H155L (SEQ ID NQ: 220) | 42.9 ± 6.6 | 14.5 ± 1.1 | 2.8 ± 0.2 | N/A | 2.1 ± 0.7 | 2.7 ± 0.9 | 16.7 ± 1.9 | 17.2 ± 3.7 | 0.7 ± 0.3 |

TABLE 9E

Accumulation of steviol glycosides, glycosylated ent-kaurenoic acid, or glycosylated kaurenol (in AUC) in a host comprising wild-type UGT76G1 or a UGT76G1 variant.

| | KA + 2Glc (#7) | KA + 3Glc (isomer 1) | KA + 3Glc (isomer 2) | KL + 2Glc (#8) | KL + 3Glc (isomer 1 and isomer 2) | 19-SMG |
|---|---|---|---|---|---|---|
| Wild-type (SEQ ID NO: 9) | 14444 ± 5537 | 2472 ± 1360 | 47650 ± 20783 | 8102 ± 4937 | 123288 ± 20872 | 2174 ± 1054 |
| H155L (SEQ ID NO: 184) | 1096 ± 1570 | N/A | 48264 ± 17847 | 1770 ± 1118 | 105904 ± 33369 | 2072 ± 940 |
| Q23H (SEQ ID NO: 181) | 140332 ± 26599 | 10386 ± 2233 | 2914 ± 2162 | 183464 ± 22523 | 53058 ± 11295 | 2364 ± 520 |
| T146G (SEQ ID NO: 183) | 158245 ± 18966 | 7339 ± 2016 | N/A | 266539 ± 21693 | 21515 ± 3812 | 1961 ± 1049 |
| L257G (SEQ ID NO: 185) | 111152 ± 39204 | 9732 ± 3604 | 7486 ± 3428 | 100144 ± 34855 | 67696 ± 22294 | 2010 ± 480 |
| S283N (SEQ ID NO: 188) | 149050 ± 55275 | 8722 ± 3756 | N/A | 222832 ± 63472 | 19864 ± 6586 | 1980 ± 875 |
| Q23H + H155L (SEQ ID NO: 217) | 107934 ± 18511 | 9230 ± 944 | 15348 ± 3586 | 86190 ± 13792 | 84080 ± 7629 | 2712 ± 674 |
| T146G + H155L (SEQ ID NO: 218) | 104146 ± 17815 | 9346 ± 1964 | 13674 ± 4859 | 98980 ± 30306 | 81762 ± 19834 | 2034 ± 768 |
| L257G + H155L (SEQ ID NO: 219) | 68986 ± 17561 | 7974 ± 1665 | 34450 ± 6021 | 34730 ± 9050 | 99436 ± 7792 | 2800 ± 1291 |
| S283N + H155L (SEQ ID NO: 220) | 146704 ± 15045 | 8168 ± 1243 | 1706 ± 1880 | 191804 ± 25165 | 31296 ± 6636 | 2694 ± 574 |

| | 1,3-bioside | 1,2-stevioside | steviol + 3Glc (#1) | steviol + 3Glc (#34) |
|---|---|---|---|---|
| Wild-type (SEQ ID NO: 9) | 274 ± 775 | 23410 ± 10331 | 2226 ± 1961 | 1512 ± 2135 |
| H155L (SEQ ID NO: 184) | N/A | 13466 ± 2764 | N/A | N/A |
| Q23H (SEQ ID NO: 181) | N/A | 199500 ± 50824 | 21436 ± 6924 | 21436 ± 6924 |
| T146G (SEQ ID NO: 183) | N/A | 237205 ± 38885 | 27438 ± 6704 | 27438 ± 6704 |
| L257G (SEQ ID NO: 185) | N/A | 123746 ± 31888 | 13040 ± 2074 | 13070 ± 2086 |
| S283N (SEQ ID NO: 188) | N/A | 205128 ± 58796 | 28660 ± 10712 | 28660 ± 10712 |
| Q23H + H155L (SEQ ID NO: 217) | N/A | 162262 ± 12368 | 19104 ± 3180 | 19148 ± 3184 |
| T146G + H155L (SEQ ID NO: 218) | N/A | 138510 ± 32208 | 18846 ± 4723 | 18900 ± 4624 |
| L257G + H155L (SEQ ID NO: 219) | N/A | 118750 ± 15972 | 10356 ± 1814 | 10376 ± 1838 |
| S283N + H155L (SEQ ID NO: 220) | N/A | 200156 ± 11694 | 25406 ± 6048 | 25406 ± 6048 |

KA: ent-kaurenoic acid
KL: ent-kaurenol

TABLE 9F

Accumulation of steviol glycosides (in AUC) in a host comprising wild-type UGT76G1 or a UGT76G1 variant.

| | steviol + 4Glc (#26) | steviol + 5Glc (#22) | steviol + 5Glc (#24) | steviol + 5Glc (#25) | steviol + 6Glc (isomer 1) |
|---|---|---|---|---|---|
| Wild-type (SEQ ID NO: 9) | 38936 ± 21188 | 3288 ± 3892 | 2194 ± 2020 | 9068 ± 3994 | 12294 ± 10105 |
| H155L (SEQ ID NO: 184) | 20000 ± 4629 | 178 ± 503 | 1530 ± 2310 | 29526 ± 15999 | 122 ± 345 |
| Q23H (SEQ ID NO: 181) | 26366 ± 7357 | 161044 ± 57250 | N/A | N/A | 26590 ± 3671 |
| T146G (SEQ ID NO: 183) | 25070 ± 6192 | 224315 ± 53331 | N/A | N/A | 10320 ± 3647 |
| L257G (SEQ ID NO: 185) | 17638 ± 5814 | 81252 ± 31941 | 258 ± 730 | N/A | 31616 ± 5164 |
| S283N (SEQ ID NO: 188) | 24980 ± 8098 | 219964 ± 61935 | N/A | N/A | 19666 ± 5418 |
| Q23H + H155L (SEQ ID NO: 217) | 23100 ± 2234 | 142460 ± 24407 | N/A | N/A | 15108 ± 1958 |

TABLE 9F-continued

Accumulation of steviol glycosides (in AUC) in a host comprising wild-type UGT76G1 or a UGT76G1 variant.

| | | | | | |
|---|---|---|---|---|---|
| T146G + H155L (SEQ ID NO: 218) | 19064 ± 3666 | 120990 ± 34224 | N/A | N/A | 13048 ± 2270 |
| L257G + H155L (SEQ ID NO: 219) | 17126 ± 2237 | 56416 ± 15937 | 928 ± 1293 | N/A | 17756 ± 2361 |
| S283N + H155L (SEQ ID NQ: 220) | 23536 ± 2818 | 213846 ± 31505 | N/A | N/A | 11222 ± 2649 |

| | steviol + 6Glc (#23) | steviol + 7Glc (isomer 2) | steviol + 7Glc (isomer 5) | Steviol |
|---|---|---|---|---|
| Wild-type (SEQ ID NO: 9) | 5838 ± 2979 | 13784 ± 4806 | 7630 ± 3054 | N/A |
| H155L (SEQ ID NO: 184) | 2000 ± 830 | 6494 ± 2530 | 10782 ± 2519 | N/A |
| Q23H (SEQ ID NO: 181) | 3108 ± 1514 | 2964 ± 1547 | 918 ± 1268 | N/A |
| T146G (SEQ ID NO: 183) | 304 ± 804 | 322 ± 853 | 286 ± 756 | N/A |
| L257G (SEQ ID NO: 185) | 5088 ± 1171 | 5154 ± 1398 | 1590 ± 1335 | 1246 ± 3524 |
| S283N (SEQ ID NO: 188) | 846 ± 1170 | 264 ± 747 | 296 ± 837 | N/A |
| Q23H + H155L (SEQ ID NO: 217) | 3582 ± 819 | 5996 ± 1705 | 596 ± 1121 | N/A |
| T146G + H155L (SEQ ID NO: 218) | 4288 ± 889 | 4640 ± 1866 | 1306 ± 1449 | N/A |
| L257G + H155L (SEQ ID NO: 219) | 5856 ± 960 | 15114 ± 1900 | 2230 ± 985 | N/A |
| S283N + H155L (SEQ ID NQ: 220) | 1162 ± 1288 | 1042 ± 1117 | N/A | N/A |

Expression of UGT76G1 Q23H H155L (SEQ ID NO:217) increased accumulation of ent-kaurenoic acid+3Glc (isomer 2) and ent-kaurenol+3Glc (isomer 1) and decreased accumulation of ent-kaurenol+2Glc (#8) and steviol+6Glc (isomer 1), as compared to UGT76G1 Q23H (SEQ ID NO:181). UGT76G1 T146G H155L (SEQ ID NO:218) increased accumulation of ent-kaurenoic acid+3Glc (isomer 2), ent-kaurenol+3Glc (isomer 1), RebB, RebA, RebD, steviol+6Glc (#23), and steviol+7Glc (isomer 2) and decreased accumulation of ent-kaurenoic acid+2Glc (#7), ent-kaurenol+2Glc (#8), 1,2-bioside, rubusoside, 1,2-stevioside, RebE, steviol+5Glc (#22), as compared to UGT76G1 T146G (SEQ ID NO:183). Expression of UGT76G1 L257G H155L (SEQ ID NO:219) increased accumulation of ent-kaurenoic acid+3Glc (isomer 2), ent-kaurenol+3Glc (isomer 1), and steviol+7Glc (isomer 2) and decreased accumulation of ent-kaurenol+2Glc (#8), 1,2-bioside, and steviol+6Glc (isomer 1), as compared to UGT76G1 L257G (SEQ ID NO:185). As well, UGT76G1 L257G H155L (SEQ ID NO:219) increased accumulation of RebD, as compared to wild-type UGT76G1. Expression of UGT76G1 S283N H155L (SEQ ID NO:220) decreased accumulation of steviol+6Glc (isomer 1), as compared to UGT76G1 S283N (SEQ ID NO:188). See Tables 9D-F.

UGT76G1 variants were also expressed in a steviol glycoside-producing strain comprising an extra copy of CPR1 (SEQ ID NO:77, SEQ ID NO:78), an extra copy of SrKAHe1 (SEQ ID NO:93, SEQ ID NO:94), and an extra copy of a UGT76G1 (SEQ ID NO:8, SEQ ID NO:9) or a UGT76G1 variant. Accumulation of steviol glycosides, tri-glycosylated ent-kaurenol, and tri-glycosylated ent-kaurenoic acid levels were measured. See FIG. 11.

Figure 11A:
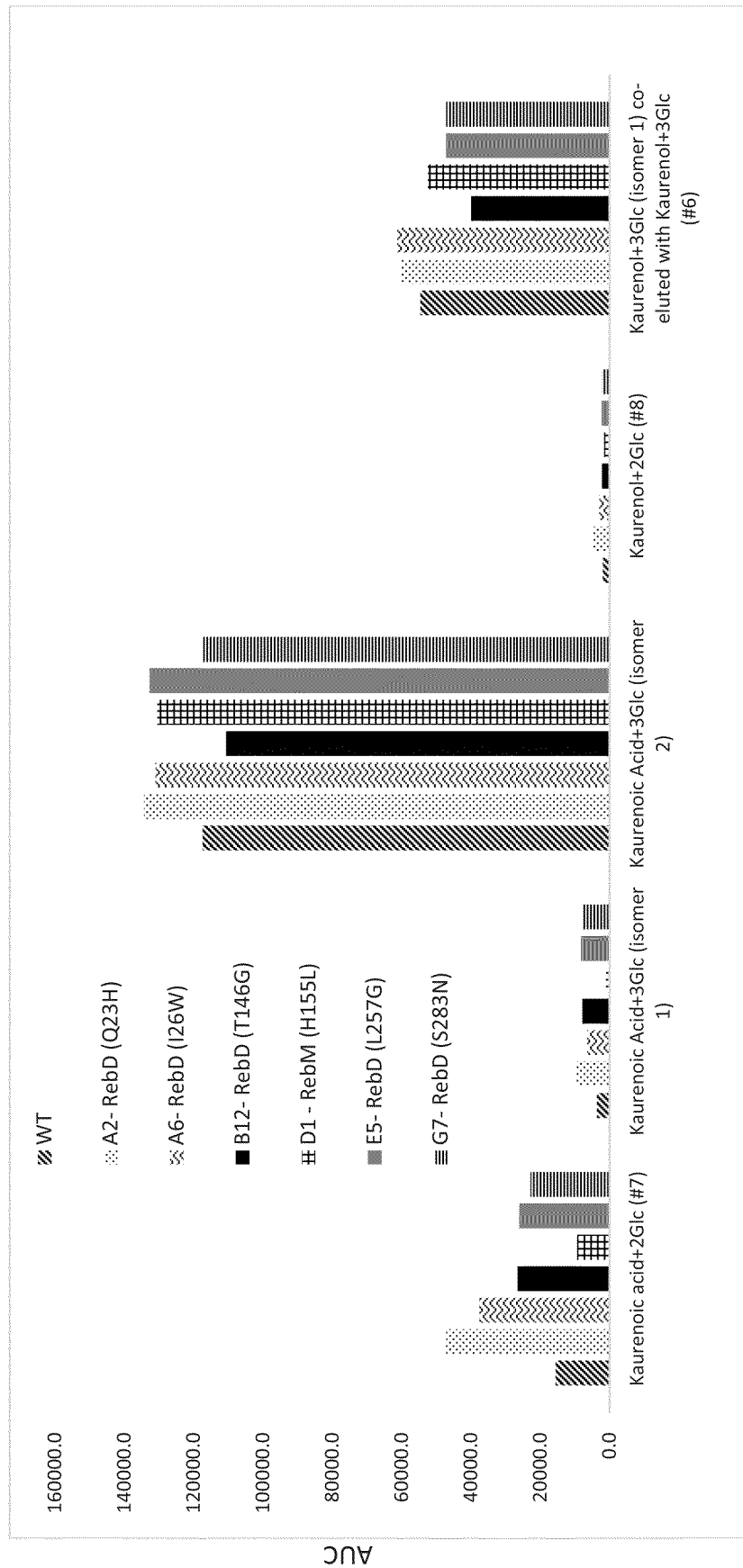
FIG. 11A shows accumulation of ent-kaurenoic acid+2Glc (#7), ent-kaurenoic acid+3Glc (isomer 1), ent-kaurenoic acid+3Glc (isomer 2), ent-kaurenol+2Glc (#8), and ent-kaurenol+3Glc (isomer 1) co-eluted with ent-kaurenol+3Glc (#6) in an *S. cerevisiae* steviol glycoside production strain (control strain comprised three copies of wild-type UGT76G1 (SEQ ID NO:9); variant strains comprised two copies of wild-type UGT76G1 and one copy of a UGT76G1 variant).
Figure 11C:
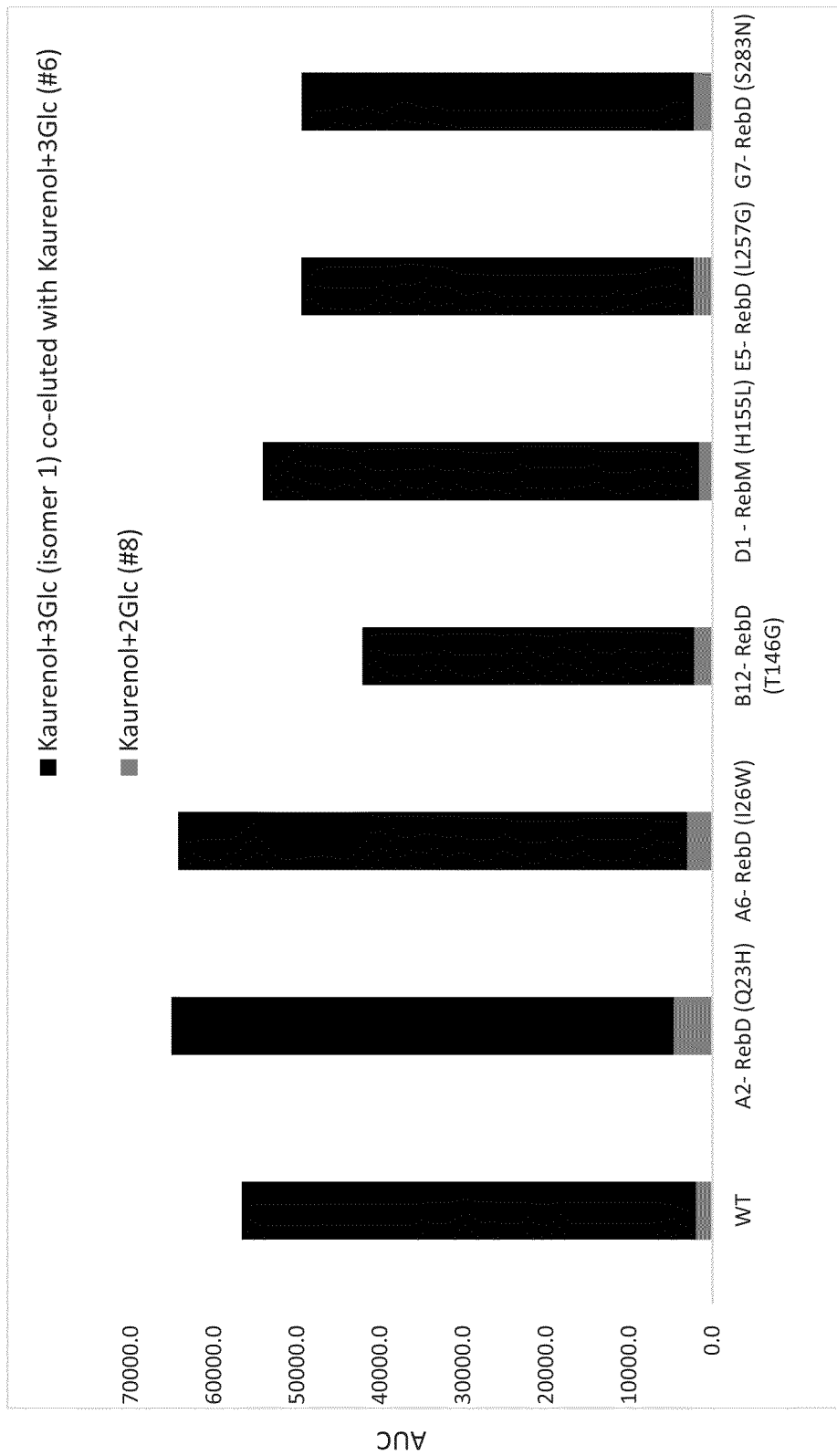
FIG. 11C shows total levels of glycosylated ent-kaurenol (ent-kaurenol+3Glc (isomer 1) co-eluted with ent-kaurenol+3Glc (#6) and ent-kaurenol+2Glc (#8) in an *S. cerevisiae* steviol glycoside production strain expressing UGT76G1 variants.

UGT76G1 variants that increased accumulation of RebD or RebM were also expressed in a steviol glycoside production S. cerevisiae strain comprising an extra copy of CPR1 (SEQ ID NO:77, SEQ ID NO:78) and an extra copy of SrKAHe1 (SEQ ID NO:93, SEQ ID NO:94). The control steviol glycoside production strain comprised three copies of wild-type UGT76G1 (SEQ ID NO:9), and the variant-comprising strains comprised two copies of wild-type UGT76G1 (SEQ ID NO:9) and one copy of a UGT76G1 variant. FIG. 11A shows levels of ent-kaurenoic acid+2Glc (#7), ent-kaurenoic acid+3Glc (isomer 1), ent-kaurenoic acid+3Glc (isomer 2), ent-kaurenol+2Glc (#8), and ent-kaurenol+3Glc (isomer 1) co-eluted with ent-kaurenol+3Glc (#6) in production strains expressing wild-type UGT76G1 (SEQ ID NO:9), UGT76G1 Q23H (SEQ ID NO:181), UGT76G1 I26W (SEQ ID NO:182), UGT76G1 T146G (SEQ ID NO:183), UGT76G1 H155L (SEQ ID NO:184), UGT76G1 L257G (SEQ ID NO:185), or UGT76G1 S283N (SEQ ID NO:188). Total levels of glycosylated ent-kaurenoic acid (ent-kaurenoic acid+2Glc (#7)+ent-kaurenoic acid+3Glc (isomer 1)+ent-kaurenoic acid+3Glc (isomer 2)) were most significantly increased in production strains expressing UGT76G1 Q23H (SEQ ID NO:181), UGT76G1 I26W (SEQ ID NO:182), and UGT76G1 L257G (SEQ ID NO:185) (FIG. 11B), and total levels of glycosylated ent-kaurenol (ent-kaurenol+3Glc (isomer 1) co-eluted with ent-kaurenol+3Glc (#6) and ent-kaurenol+2Glc (#8) were most significantly affected for production strains expressing UGT76G1 Q23H (SEQ ID NO:181), UGT76G1 I26W (SEQ ID NO:182), and UGT76G1 T146G (SEQ ID NO:183) (FIG. 11C).

Figure 11D:
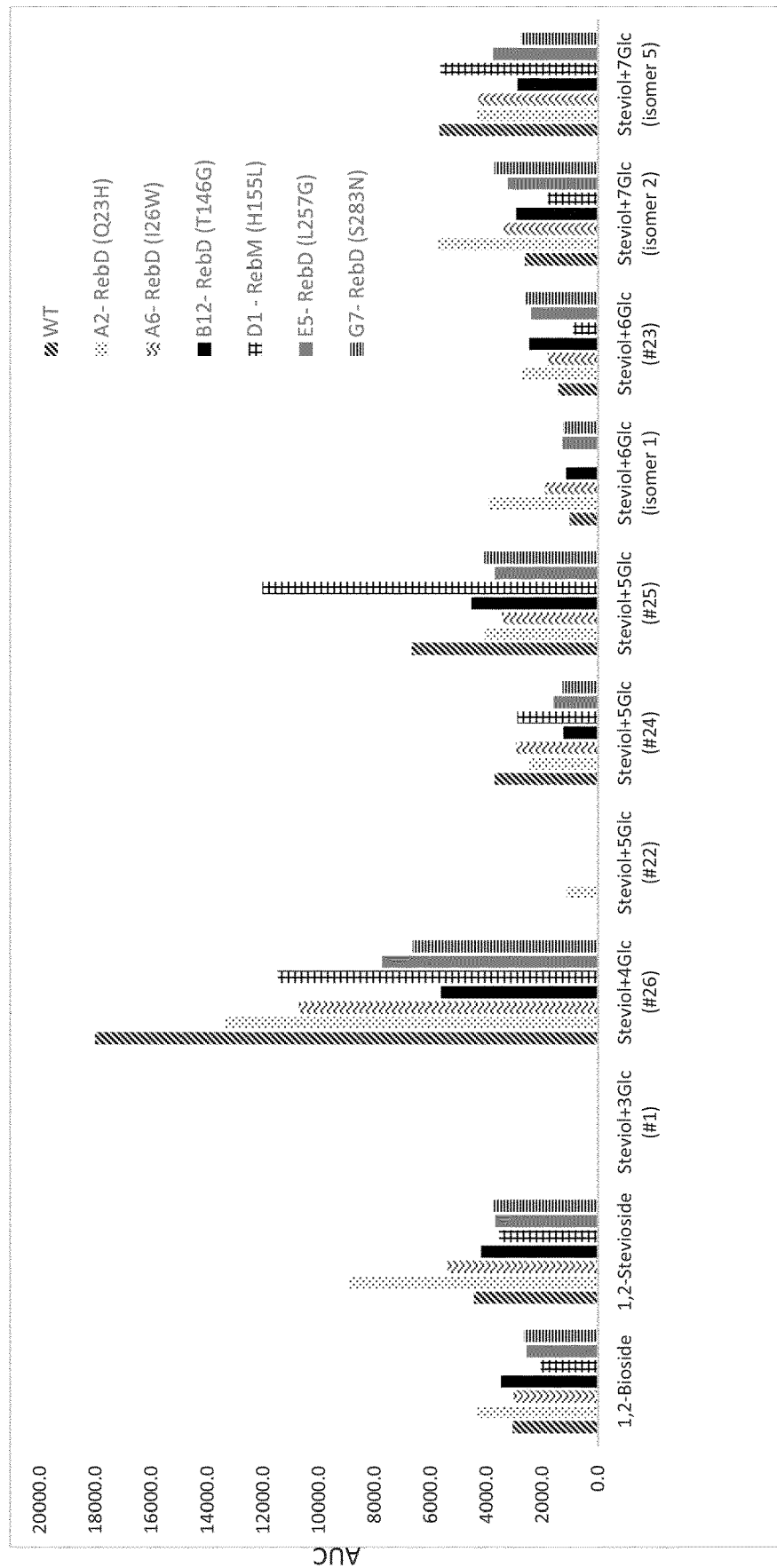
FIG. 11D shows accumulation of 1,2-bioside, 1,2-stevioside, steviol+3Glc (#1), steviol+4Glc (#26), steviol+5Glc (#22), steviol+5Glc (#24), steviol+5Glc (#25), steviol+6Glc (isomer 1), steviol+6Glc (#23), steviol+7Glc (isomer 2), and steviol+7Glc (isomer 5) in an *S. cerevisiae* steviol glycoside production strain expressing UGT76G1 variants.

FIGS. 11D and 11E show accumulation of 1,2-bioside, 1,2-stevioside, steviol+3Glc (#1), steviol+4Glc (#26), steviol+5Glc (#22), steviol+5Glc (#24), steviol+5Glc (#25), steviol+6Glc (isomer 1), steviol+6Glc (#23), steviol+7Glc (isomer 2), steviol+7Glc (isomer 5), 13-SMG, rubusoside, RebG (1,3-stevioside), RebA, RebB, RebD, RebE, and RebM in production strains expressing wild-type UGT76G1 (SEQ ID NO:9), UGT76G1 Q23H (SEQ ID NO:181), UGT76G1 I26W (SEQ ID NO:182), UGT76G1 T146G (SEQ ID NO:183), UGT76G1 H155L (SEQ ID NO:184), UGT76G1 L257G (SEQ ID NO:185), or UGT76G1 S283N (SEQ ID NO:188).

All UGT76G1 variants tested in FIG. 11D showed decreased accumulation of steviol+4Glc (#26). Expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188), all of which increased production of RebD, resulted in decreased accumulation of steviol+5Glc (#25), compared to a control strain expressing wild-type UGT76G1 (FIG. 11D). However, expression of the UGT76G1 H155L (SEQ ID NO:184) variant, which increased RebM production, resulted in increased accumulation of steviol+5Glc (#25) (FIG. 11D).

Expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) resulted in increased accumulation of steviol+6Glc (#23), compared to a control strain expressing wild-type UGT76G1, whereas expression of the UGT76G1 H155L (SEQ ID NO:184) variant resulted in decreased accumulation of steviol+6Glc (#23) (FIG. 11D). Expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) resulted in increased accumulation of steviol+7Glc (isomer 2), compared to a control strain expressing wild-type UGT76G1, whereas expression of the UGT76G1 H155L (SEQ ID NO:184) variant resulted in decreased accumulation of steviol+7Glc (isomer 2) (FIG. 11D). Expression of UGT76G1 Q23H (SEQ ID NO:181), UGT76G1 I26W (SEQ ID NO:182), UGT76G1 T146G (SEQ ID NO:183), UGT76G1 L257G (SEQ ID NO:185), or UGT76G1 S283N (SEQ ID NO:188) resulted in increased accumulation of steviol+7Glc (isomer 5) (FIG. 11D).

The steviol glycoside-producing strain comprising a higher copy number of CPR1 (SEQ ID NO:77, SEQ ID NO:78) and SrKAHe1 (SEQ ID NO:93, SEQ ID NO:94) was further tested in a separate experiment. As shown in Tables 9G-9I, expression of UGT76G1 H155L (SEQ ID NO:184) reduced the levels of ent-kaurenoic acid+3Glc (isomer 1), RebD, steviol+6Glc (#23), steviol+7Glc (isomer 2), as compared to wild-type UGT76G1. Expression of UGT76G1 Q23H (SEQ ID NO:181), UGT76G1 T146G (SEQ ID NO:183), UGT76G1 L257G (SEQ ID NO:185), or UGT76G1 S283N (SEQ ID NO:188) each reduced accumulation of steviol+4Glc (#26) and steviol+5Glc (#24), as compared to wild-type UGT76G1. Specifically, expression UGT76G1 T146G (SEQ ID NO:183) increased the amount of ent-kaurenoic acid+2Glc (#7), ent-kaurenoic acid+3Glc (isomer 1), RebD, steviol+6Glc (#23), and steviol+7Glc (isomer 2) and reduced the amount of RebG, steviol+5Glc #25, as compared to wild-type UGT76G1. Expression of UGT76G1 L257G (SEQ ID NO:185) increased accumulation of ent-kaurenoic acid+3Glc (isomer 1) and reduced accumulation of ent-kaurenoic acid+3Glc (isomer 2) and steviol+5Glc (#25), as compared to wild-type UGT76G1. Expression of UGT76G1 S283N (SEQ ID NO:188) increased accumulation of ent-kaurenoic acid+3Glc (isomer 1), RebD, steviol+6Glc (isomer 1), and steviol+7Glc (isomer 2) and reduced accumulation of RebG and steviol+5G1 (#25), as compared to wild-type UGT76G1. Expression of UGT76G1 L257G H155L reduced accumulation of ent-kaurenoic acid+3Glc (isomer 1), as compared to the single variant UGT76G1 L257G. Expression of the double variant UGT76G1 Q23H H155L reduced accumulation of steviol+5Glc (#25), as compared to wild-type UGT76G1. Expression of the double variant UGT76G1 S283N H155L reduced accumulation of ent-kaurenoic acid+3Glc (isomer 2), as compared to wild-type UGT76G1. See Tables 9G-9I.

TABLE 9G

Accumulation of steviol glycosides (in µM) in a host comprising wild-type UGT76G1 or a UGT76G1 variant.

| | 13-SMG | 1,2-bioside | Rubu | RebG | RebB | RebA | RebE | RebD | RebM |
|---|---|---|---|---|---|---|---|---|---|
| Wild-type (SEQ ID NO: 9) | 66.9 ± 4.7 | 0.4 ± 0.1 | 1.2 ± 0.2 | 0.7 ± 0.3 | 5.6 ± 0.4 | 30.3 ± 2.4 | 0.5 ± 0.4 | 31.0 ± 6.7 | 199.3 ± 14.2 |
| H155L (SEQ ID NO: 184) | 63.1 ± 4.6 | 0.3 ± 0.1 | 1.3 ± 0.3 | 0.9 ± 0.3 | 5.5 ± 0.5 | 29.6 ± 1.9 | 0.1 ± 0.2 | 12.0 ± 10.8 | 210.0 ± 19.3 |
| Q23H (SEQ ID NO: 181) | 62.2 ± 13.9 | 0.4 ± 0.1 | 0.8 ± 0.3 | 0.2 ± 0.3 | 5.2 ± 0.9 | 27.7 ± 3.3 | 0.6 ± 0.2 | 42.0 ± 9.8 | 179.2 ± 19.6 |
| T146G (SEQ ID NO: 183) | 64.8 ± 5.2 | 0.5 ± 0.2 | 1.0 ± 0.1 | 0.1 ± 0.2 | 5.3 ± 0.8 | 27.9 ± 3.1 | 0.8 ± 0.1 | 46.2 ± 6.7 | 180.4 ± 24.2 |
| L257G (SEQ ID NO: 185) | 68.7 ± 9.2 | 0.4 ± 0.1 | 0.6 ± 0.4 | 0.2 ± 0.3 | 5.5 ± 0.6 | 29.6 ± 3.4 | 0.6 ± 0.4 | 45.6 ± 9.3 | 187.3 ± 14.7 |
| S283N (SEQ ID NO: 188) | 67.4 ± 13.3 | 0.4 ± 0.1 | 0.7 ± 0.5 | 0.1 ± 0.2 | 5.7 ± 0.7 | 32.0 ± 4.2 | 0.8 ± 0.4 | 52.7 ± 7.4 | 189.2 ± 14.1 |
| Q23H + H155L (SEQ ID NO: 217) | 65.2 ± 4.3 | 0.3 ± 0.0 | 0.8 ± 0.4 | 0.3 ± 0.3 | 5.3 ± 0.3 | 27.1 ± 2.8 | 0.7 ± 0.3 | 37.5 ± 5.4 | 187.5 ± 10.8 |
| T146G + H155L (SEQ ID NO: 218) | 64.3 ± 9.8 | 0.5 ± 0.1 | 0.8 ± 0.3 | 0.1 ± 0.2 | 5.4 ± 0.6 | 27.3 ± 4.3 | 0.7 ± 0.4 | 40.0 ± 8.7 | 171.2 ± 29.8 |
| L257G + H155L (SEQ ID NO: 219) | 58.5 ± 15.9 | 0.3 ± 0.1 | 0.5 ± 0.5 | 0.3 ± 0.3 | 5.2 ± 1.5 | 25.1 ± 7.9 | 0.7 ± 0.3 | 30.4 ± 13.3 | 167.6 ± 33.6 |
| S283N + H155L (SEQ ID NO: 220) | 61.2 ± 11.8 | 0.4 ± 0.1 | 0.6 ± 0.5 | 0.0 ± 0.0 | 5.2 ± 1.0 | 25.0 ± 5.5 | 0.6 ± 0.5 | 37.5 ± 12.0 | 152.5 ± 35.2 |

TABLE 9H

Accumulation of steviol glycosides, glycosylated ent-kaurenoic acid, or glycosylated kaurenol (in AUC) in a host comprising wild-type UGT76G1 or a UGT76G1 variant.

| | KA + 2Glc (#7) | KA + 3Glc (isomer 1) | KA + 3Glc (isomer 2) | KL + 3Glc (isomer 1 and isomer 2) | 19-SMG | 1,2-stevioside | RebI | steviol + 4Glc (#26) |
|---|---|---|---|---|---|---|---|---|
| Wild-type (SEQ ID NO: 9) | 2422 ± 419 | 1962 ± 383 | 40290 ± 3139 | 11500 ± 1169 | 422 ± 270 | 4712 ± 656 | N/A | 11194 ± 2466 |
| H155L (SEQ ID NO: 184) | 2894 ± 401 | 418 ± 841 | 40350 ± 2392 | 10326 ± 759 | 376 ± 316 | 4466 ± 359 | 512 ± 992 | 9086 ± 1374 |
| Q23H (SEQ ID NO: 181) | 3340 ± 1018 | 3044 ± 747 | 41140 ± 5158 | 11404 ± 1306 | 476 ± 317 | 4452 ± 595 | N/A | 6550 ± 771 |
| T146G (SEQ ID NO: 183) | 3362 ± 509 | 2934 ± 399 | 40636 ± 5193 | 10880 ± 872 | 400 ± 350 | 4600 ± 511 | N/A | 6996 ± 695 |
| L257G (SEQ ID NO: 185) | 2816 ± 240 | 2712 ± 264 | 34402 ± 2377 | 10820 ± 708 | 254 ± 272 | 4770 ± 642 | N/A | 5884 ± 674 |
| S283N (SEQ ID NO: 188) | 3114 ± 585 | 2914 ± 346 | 35830 ± 2929 | 11430 ± 641 | 188 ± 348 | 4986 ± 562 | N/A | 5734 ± 442 |
| Q23H + H155L (SEQ ID NO: 217) | 2622 ± 286 | 2250 ± 408 | 37176 ± 3860 | 10376 ± 1049 | 264 ± 283 | 4404 ± 416 | N/A | 6036 ± 906 |
| T146G + H155L (SEQ ID NO: 218) | 2884 ± 354 | 2424 ± 324 | 34100 ± 5312 | 10026 ± 1326 | 248 ± 347 | 4438 ± 1060 | N/A | 5836 ± 10777 |
| L257G + H155L (SEQ ID NO: 219) | 2364 ± 691 | 1798 ± 368 | 32044 ± 5509 | 9472 ± 1812 | 256 ± 363 | 3690 ± 1217 | N/A | 5254 ± 1189 |
| S283N + H155L (SEQ ID NO: 220) | 3162 ± 1250 | 2656 ± 980 | 31504 ± 4414 | 9386 ± 1425 | 384 ± 331 | 4014 ± 925 | N/A | 5638 ± 1696 |

KA: ent-kaurenoic acid
KL: ent-kaurenol

TABLE 9I

Accumulation of steviol glycosides (in AUC) in a host comprising wild-type UGT76G1 or a UGT76G1 variant.

| | steviol + 4Glc (#33) | steviol + 5Glc (#22) | steviol + 5Glc (#24) | steviol + 5Glc (#25) | steviol + 6Glc (isomer 1) | steviol + 6Glc (#23) | steviol + 7Glc (isomer 2) | steviol + 7Glc (isomer 5) |
|---|---|---|---|---|---|---|---|---|
| Wild-type (SEQ ID NO: 9) | N/A | N/A | 7416 ± 1103 | 5230 ± 789 | 1572 ± 1044 | 3622 ± 590 | 7078 ± 912 | 4474 ± 2521 |
| H155L (SEQ ID NO: 184) | 122 ± 345 | N/A | 7452 ± 2166 | 9450 ± 4068 | 320 ± 905 | 1868 ± 825 | 3894 ± 1243 | 4760 ± 1318 |
| Q23H (SEQ ID NO: 181) | N/A | 108 ± 305 | 4382 ± 1490 | 3412 ± 1176 | 2792 ± 1053 | 4520 ± 985 | 9388 ± 1677 | 4158 ± 1528 |
| T146G (SEQ ID NO: 183) | N/A | 114 ± 322 | 3598 ± 1630 | 2996 ± 745 | 3356 ± 1047 | 5438 ± 636 | 10406 ± 910 | 3700 ± 1726 |
| L257G (SEQ ID NO: 185) | N/A | N/A | 4336 ± 1158 | 3484 ± 754 | 2860 ± 842 | 4158 ± 1149 | 9348 ± 1429 | 4420 ± 1036 |
| S283N (SEQ ID NO: 188) | N/A | N/A | 4834 ± 1338 | 3358 ± 546 | 3566 ± 784 | 4350 ± 909 | 9796 ± 1619 | 3924 ± 1203 |
| Q23H + H155L (SEQ ID NO: 217) | N/A | N/A | 4468 ± 1172 | 3668 ± 679 | 1932 ± 380 | 3798 ± 619 | 8764 ± 1384 | 3528 ± 2244 |
| T146G + H155L (SEQ ID NO: 218) | N/A | N/A | 3682 ± 1715 | 3008 ± 775 | 2176 ± 698 | 4022 ± 898 | 8712 ± 879 | 3284 ± 1803 |
| L257G + H155L (SEQ ID NO: 219) | N/A | N/A | 3566 ± 1693 | 2974 ± 781 | 956 ± 1073 | 2988 ± 772 | 7046 ± 1660 | 3072 ± 1631 |
| S283N + H155L (SEQ ID NO: 220) | N/A | N/A | 2670 ± 1807 | 2554 ± 444 | 2430 ± 1647 | 3874 ± 1837 | 9450 ± 3268 | 2758 ± 1204 |

Example 9: Further Characterization of UGT76G1 H155L Variant

UGT76G1 H155L (SEQ ID NO:184) was expressed in the steviol glycoside-producing *S. cerevisiae* strain described in Examples 2 and 8. As shown in FIG. 6A, the strain expressing UGT76G1 H155L (gray bars) produced higher levels of RebM, RebA, RebB, 13-SMG, and rubusoside, compared to the control strain expressing wild-type UGT76G1 (black bars). The steviol glycoside-producing strain expressing UGT76G1 H155L produced higher titers of RebM than RebD (FIG. 6A).

The strain expressing UGT76G1 H155L (SEQ ID NO:184) produced greater total levels of steviol glycosides (13-SMG+1,2-bioside+rubusoside+RebG+RebB+RebA+RebE+RebD+RebM) and RebD+RebM (gray bars), compared to the control strain expressing wild-type UGT76G1 (black bars) (FIG. 6B). Thus, the steviol glycoside-producing strain expressing UGT76G1 H155L (gray bars) demonstrated a 20% increase in steviol glycoside production and a 10% increase in RebD and RebM titers, compared to the control strain expressing wild-type UGT76G1 (black bars) (FIG. 6C).

Figure 6D:
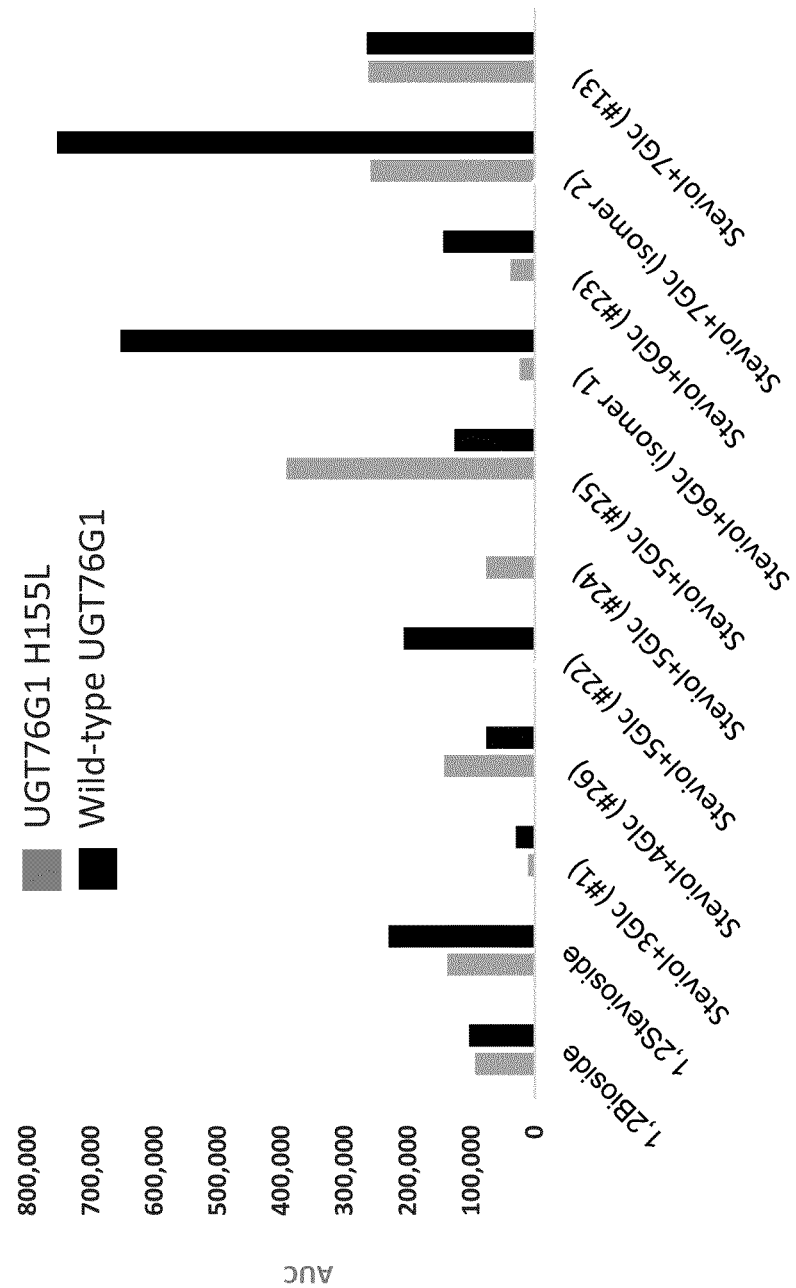
FIG. 6D shows production of a tri-glycosylated steviol molecule (steviol+3Glc (#1)), a tetra-glycosylated steviol molecule (steviol+4Glc (#26)), three penta-glycosylated steviol molecules (steviol+5Glc (#22), steviol+5Glc (#24), and steviol+5Glc (#25)), two hexa-glycosylated steviol molecules (steviol+6Glc (isomer 1) and steviol+6Glc (#23)), and two hepta-glycosylated steviol molecules (steviol+7Glc (isomer 2) and steviol+7Glc (#13)) in a steviol glycoside-producing strain expressing UGT76G1 H155L (gray bars), compared to a control strain expressing wild-type UGT76G1 (black bars). See Example 9.

The strain expressing UGT76G1 H155L (gray bars) also produced lesser amounts of a 1,2-bioside, 1,2-stevioside, a tri-glycosylated steviol molecule (steviol+3Glc (#1)), a penta-glycosylated steviol molecule (steviol+5Glc (#22), two hexa-glycosylated steviol molecules (steviol+6Glc (isomer 1 and #23)), and a hepta-glycosylated steviol molecule (steviol+7Glc (isomer 2)) but increased amounts of a tetra-glycosylated molecule (steviol+4Glc (#26)) and two penta-glycosylated steviol molecules (Steviol+5Glc (#24 and #25)), compared to the control strain expressing wild-type UGT76G1 (black bars) (FIG. 6D). See FIGS. 1, 7, and 8 for structures of particular steviol glycosides detected.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

TABLE 10

Sequences disclosed herein.

```
SEQ ID NO: 1
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG LVLKGSDCLL SKCYHEFGTQ WLPLLETLHQ   240
VPVVPVGLLP PEIPGDEKDE TWVSIKKWLD GKQKGSVVYV ALGSECLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473

SEQ ID NO: 2
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG LVLKGSDCLL SKCYHEFGTQ WLPLLETLHQ   240
VPVVPVGLLP PEIPGDEKDE TWVSIKKWLD GKQKGSVVYV ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFWDQPLNA RLLEDKQVGI EIPRNEEDGC LTKESVARSL   420
RSVVVEKEGE IYKANARELS KIYNDTKVEK EYVSQFVDYL EKNARAVAID HES          473

SEQ ID NO: 3
atggcagagc aacaaaagat caaaaagtca cctcacgtct tacttattcc atttcctctg    60
caaggacata tcaacccatt catacaattt gggaaaagat tgattagtaa gggtgtaaag   120
acaacactgg taaccactat ccacactttg aattctactc tgaaccactc aaatactact   180
actacaagta tagaaattca agctatatca gacggatgcg atgagggtgg ctttatgtct   240
gccggtgaat cttacttgga aacattcaag caagtgggat ccaagtctct ggccgatcta   300
atcaaaaagt tacagagtga aggcaccaca attgacgcca taatctacga ttctatgaca   360
gagtgggttt tagacgttgc tatcgaattt ggtattgatg gaggttcctt tttcacacaa   420
gcatgtgttg tgaattctct atactaccat gtgcataaag ggttaatctc tttaccattg   480
ggtgaaactg tttcagttcc aggttttcca gtgttacaac gttgggaaac cccattgatc   540
ttacaaaatc atgaacaaat acaatcacct tggtcccaga tgttgtttgg tcaattcgct   600
aacatcgatc aagcaagatg ggtctttact aattcattct ataagttaga ggaagaggta   660
attgaatgga ctaggaagat ctggaatttg aaagtcattg gtccaacatt gccatcaatg   720
tatttggaca aaagacttga tgatgataaa gataatggtt tcaatttgta caaggctaat   780
catcacgaat gtatgaattg gctggatgac aaaccaaagg aatcagttgt atatgttgct   840
ttcggctctc ttgttaaaca tggtccagaa caagttgagg agattacaag agcacttata   900
gactctgacg taaacttttt gtgggtcatt aagcacaaag aggaggggaa actgccagaa   960
aaccttttctg aagtgataaa gaccggaaaa ggtctaatcg ttgcttggtg taaacaattg  1020
gatgttttag ctcatgaatc tgtaggctgt tttgtaacac attgcggatt caactctaca  1080
ctagaagcca tttccttagg cgtacctgtc gttgcaatgc ctcagttctc cgatcagaca  1140
accaacgcta aacttttgga cgaaatacta ggggtgggtg tcagagttaa agcagacgag  1200
aatggtatcg tcagaagagg gaacctagct tcatgtatca aaatgatcat ggaagaggaa  1260
agaggagtta tcataaggaa aaacgcagtt aagtggaagg atcttgcaaa ggttgccgtc  1320
catgaaggcg gctcttcaga taatgatatt gttgaatttg tgtccgaact aatcaaagcc  1380
taa                                                                 1383

SEQ ID NO: 4
MAEQQKIKKS PHVLLIPFPL QGHINPFIQF GKRLISKGVK TTLVTTIHTL NSTLNHSNTT    60
TTSIEIQAIS DGCDEGGFMS AGESYLETFK QVGSKSLADL IKKLQSEGTT IDAIIYDSMT   120
EWVLDVAIEF GIDGGSFFTQ ACVVNSLYYH VHKGLISLPL GETVSVPGFP VLQRWETPLI   180
LQNHEQIQSP WSQMLFGQFA NIDQARWVFT NSFYKLEEEV IEWTRKIWNL KVIGPTLPSM   240
YLDKRLDDDK DNGFNLYKAN HHECMNWLDD KPKESVVYVA FGSLVKHGPE QVEEITRALI   300
DSDVNFLWVI KHKEEGKLPE NLSEVIKTGK GLIVAWCKQL DVLAHESVGC FVTHCGFNST   360
LEAISLGVPV VAMPQFSDQT TNAKLLDEIL GVGVRVKADE NGIVRRGNLA SCIKMIMEEE   420
RGVIIRKNAV KWKDLAKVAV HEGGSSDNDI VEFVSELIKA                          460

SEQ ID NO: 5
atggatgcaa tggctacaac tgagaagaaa ccacacgtca tcttcatacc atttccagca    60
caaagccaca ttaaagccat gctcaaacta gcacaacttc tccaccacaa aggactccag   120
ataaccttcg tcaacaccga cttcatccac aaccagtttc ttgaatcatc gggcccacat   180
tgtctagacg gtgcaccggg tttccggttc gaaaccattc cggatggtgt ttctcacgtt   240
ccggaagcga gcatcccaat cagagaatca ctcttgagat ccattgaaac caacttcttg   300
gatcgtttca ttgatcttgt aaccaaactt ccggatcctc cgacttgtat tatctcagat   360
gggttcttgt cggttttcac aattgacgct gcaaaaaagc ttggaattcc ggtcatgatg   420
tattggacac ttgctgcctg tgggttcatg ggttttttacc atattcattc tctcattgag   480
aaaggatttg caccacttaa agatgcaagt tacttgacaa atgggtattt ggacaccgtc   540
```

TABLE 10-continued

Sequences disclosed herein.

```
attgattggg ttccgggaat ggaaggcatc cgtctcaagg atttcccgct ggactggagc      600
actgacctca atgacaaagt tttgatgttc actacggaag ctcctcaaag gtcacacaag      660
gtttcacatc atattttcca cacgttcgat gagttggagc ctagtattat aaaaactttg      720
tcattgaggt ataatcacat ttacaccatc ggcccactgc aattacttct tgatcaaata      780
cccgaagaga aaaagcaaac tggaattacg agtctccatg gatacagttt agtaaaagaa      840
gaaccagagt gttttccagtg gcttcagtct aaagaaccaa attccgtcgt ttatgtaaat      900
tttggaagta ctacagtaat gtctttagaa gacatgacgg aatttggttg gggacttgct      960
aatagcaacc attatttcct tggatcatc cgatcaaact tggtgatagg ggaaaatgca     1020
gttttgcccc ctgaacttga ggaacatata agaaaagag gctttattgc tagctggtgt     1080
tcacaagaaa aggtcttgaa gcacccttcg gttggagggt tcttgactca ttgtgggtgg     1140
ggatcgacca tcgagagctt gtctgctggg gtgccaatga tatgctggcc ttattcgtgg     1200
gaccagctga ccaactgtag gtatatatgc aaagaatggg aggttgggct cgagatggga     1260
accaaagtga aacgagatga agtcaagagg cttgtacaag agttgatggg agaaggaggt     1320
cacaaaatga ggaacaaggc taaagattgg aaagaaaagg ctcgcattgc aatagctcct     1380
aacggttcat cttctttgaa catagacaaa atggtcaagg aaatcaccgt gctagcaaga     1440
aactagttac aaagttgttt cacattgtgc tttctattta agatgtaact ttgttctaat     1500
ttaatattgt ctagatgtat tgaaccataa gtttagttgg tctcaggaat tgatttttaa     1560
tgaaataatg gtcattaggg gtgagt                                         1586

SEQ ID NO: 6
atggatgcaa tggcaactac tgagaaaaag cctcatgtga tcttcattcc atttcctgca       60
caatctcaca taaaggcaat gctaaagtta gcacaactat tacaccataa gggattacag      120
ataactttcg tgaataccga cttcatccat aatcaatttc tggaatctga tggccctcat      180
tgtttggacg gagccccagg gtttagattc gaaacaattc ctgacggtgt ttcacattcc      240
ccagaggcct ccatcccaat aagagagagt ttactgaggt caatagaaac caacttttg       300
gatcgtttca ttgacttggt cacaaaactt ccagacccac caacttgcat aatctctgat      360
ggctttctgt cagtgtttac tatcgacgct gccaaaaagt tgggtatccc agttatgatg      420
tactggactc ttgctgcatg cggtttcatg ggtttctatc acatccattc tcttatcgaa      480
aagggttttg ctccactgaa agatgcatca tacttaacca acggctacct ggatactgtt      540
attgactggg taccaggtat ggaaggtata agacttaaag attttccttt ggattggtct      600
acagaccta atgataaagt attgatgttt actacagaag ctccacacaag atctcataag      660
gtttcacatc atatctttca caccttgat gaattggaac catcaatcat caaaaccttg       720
tctctaagat acaatcatat ctacactatt ggtccattca aattacttct agatcaaatt      780
cctgaagaga aaaagcaaac tggtattaca tccttacacg gctactcttt agtgaaagag      840
gaaccagaat gttttcaatg gctacaaagt aaagagccta attctgtggt ctacgtcaac      900
ttcggaagta caacagtcat gtccttggaa gatatgactg aatttggttg gggccttgct      960
aattcaaatc attactttct atggattatc aggtccaatt tggtaatagg ggaaaacgcc     1020
gtattacctc cagaattgga ggaacacatc aaaagagag gtttcattgc ttcctggtgt     1080
tctcaggaaa aggtattgaa acatccttct gttggtggtt tccttactca ttgcggttgg     1140
ggctctcaa tcgaatcact aagtgcagga gttccaatga tttgttggcc atattcatgg     1200
gaccaactta caaattgtag gtatatctgt aaagagtggg aagttggatt agaaatggga     1260
acaaaggtta aacgtgatga agtgaaaaga ttggttcagg agttgatggg ggaaggtggc     1320
cacaagatga gaaacaaggc caaagattgg aaggaaaaag ccagaattgc tattgctcct     1380
aacggggtcat cctctctaaa cattgataag atggtcaaag attacagt cttagccaga     1440
aactaa                                                              1446

SEQ ID NO: 7
MDAMATTEKK PHVIFIPFPA QSHIKAMLKL AQLLHHKGLQ ITFVNTDFIH NQFLESSGPH       60
CLDGAPGFRF ETIPDGVSHS PEASIPIRES LLRSIETNFL DRFIDLVTKL PDPPTCIISD      120
GFLSVFTIDA AKKLGIPVMM YWTLAACGFM GFYIHSLIE KGFAPLKDAS YLTNGYLDTV       180
IDWVPGMEGI RLKDFPLDWS TDLNDKVLMF TTEAPQRSHK VSHHIFHTFD ELEPSIIKTL      240
SLRYNHIYTI GPLQLLLDQI PEEKKQTGIT SLHGYSLVKE EPECFQWLQS KEPNSVVYVN      300
FGSTTVMSLE DMTEFGWGLA NSNHYFLWII RSNLVIGENA VLPPELEEHI KKRGFIASWC      360
SQEKVLKHPS VGGFLTHCGW GSTIESLSAG VPMICWPYSW DQLTNCRYIC KEWEVGLEMG      420
TKVKRDEVKR LVQELMGEGG HKMRNKAKDW KEKARIAIAP NGSSSLNIDK MVKEITVLAR      480
N                                                                    481

SEQ ID NO: 8
atggaaaaca agaccgaaac aacagttaga cgtaggcgta gaatcattct gtttccagta       60
ccttttcaag ggcacatcaa tccaatacta caactagcca acgttttgta ctctaaaggt      120
ttttctatta caatctttca ccaaatttc aacaaaccaa aacatccaa tacccacat         180
ttcacattca gattcatact tgataatgat ccacaagatg aacgtatttc aaacttacct      240
acccacggtc ctttagctgg aatgagaatt ccaatcatca atgaacatgg tgccgatgag      300
cttagaagag aattagagtt actattgttg gcatccgaag aggacgagga agtctcttgt      360
ctgattactg acgctctatg gtactttgcc caatctgtcg ctgataagtt gaatttgagg      420
agattggtac taatgacatc cagtctgttt aactttcacg ctcatgttag tttaccacaa      480
tttgacgaat tgggatactt ggaccctgat gacaagacta ggttagagga caggcctct       540
ggttttccta tgttgaaagt caaagatatc aagtctgcct attctaattg gcaaatcttg      600
aaagagatct taggaaagat gatcaaacag acaaaggctt catctggagt gatttggaac      660
agtttcaaag agttagaaga gtctgaattg gagactgtaa tcagagaaat tccagcacct      720
tcattcctga taccattacc aaaaacatttg actgcttcct cttcctcttt gttggatcat      780
gacagaacag ttttttcaatg gttggaccaa caaccaccta gttctgtttt gtacgtgtca      840
tttgtagta cttctgaagt cgatgaaaag gacttccttg aaatcgcaag gcttagtc         900
gatagtaagc agtcattcct ttgggtcgtg cgtccaggtt tcgtgaaagg ctcaacatgg      960
gtcgaaccac ttccagatgg ttttctaggc gaaagaggta gaatagtcaa atgggttcct     1020
caacaggaag ttttagctca tggcgctatt ggggcattct ggactcattc cggatggaat     1080
tcaacttag aatcagtatg cgaaggggta cctatgatct ttcagatttt ggtcttgat        1140
caaccactga acgcaagata catgtctgat gttttgaaag tgggtgtata tctagaaaat     1200
```

TABLE 10-continued

Sequences disclosed herein.

```
ggctgggaaa ggggtgaaat agctaatgca ataagacgtg ttatggttga tgaagagggg    1260
gagtatatca gacaaaacgc aagagtgctg aagcaaaagg ccgacgtttc tctaatgaag    1320
ggaggctctt catacgaatc cttagaatct cttgtttcct acatttcatc actgtaa      1377

SEQ ID NO: 9
MENKTETTVR RRRRIILFPV PFQGHINPIL QLANVLYSKG FSITIFHTNF NKPKTSNYPH      60
FTFRFILDND PQDERISNLP THGPLAGMRI PIINEHGADE LRRELELLML ASEEDEEVSC    120
LITDALWYFA QSVADSLNLR RLVLMTSSLF NFHAHVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFQWLDQ QPPSSVLYVS FGSTSEVDEK DFLEIARGLV    300
DSKQSPLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458

SEQ ID NO: 10
atggctacat ctgattctat tgttgatgac aggaagcagt tgcatgtggc tactttccct     60
tggcttgctt tcggtcatat actgccttac ctacaactat caaaactgat agctgaaaaa    120
ggacataaag tgtcattcct ttcaacaact agaaacattc aaagattatc ttcccacata    180
tcaccattga ttaacgtcgt tcaattgaca ctttccaaga tacaggaatt accagaagat    240
gctgaagcta caacagatgt gcatcctgaa gatatccctt acttgaaaaa ggcatccgat    300
ggattacagc ctgaggtcac tagattcctt gagcaacaca gtccagattg gatcatatac    360
gactacactc actattggtt gccttcaatt gcagcatcac taggcatttc tagggcacat    420
ttcagtgtaa ccacaccttg gccattgct tacatgggtc catccgctga tgctatgatt     480
aacggcagtg atggtagaac taccgttgaa gatttgacaa ccccaccaaa gtggtttcca    540
tttccaacta aagtctgttg gagaaaacac gacttagcaa gactggttcc atacaaggca    600
ccaggaatct cagacggcta gaatgggt ttagtcctta aagggtctga ctgcctattg      660
tctaagtgtt accatgagtt tgggacacaa tggctaccac ttttggaaac attacaccaa    720
gttcctgtcg taccagttgg tctattacct ccagaaatcc ctggtgatga aggacgag      780
acttgggttt caatcaaaaa gtggttagac gggaagcaaa aaggctcagt ggtatatgtg    840
gcactgggtt ccgaagtttt agtatctcaa acagaagttg tggaacttgc cttaggtttg    900
gaactatctg gattgccatt tgtctgggcc tacagaaaac caaaaggccc tgcaaagtcc    960
gattcagttg aattgccaga cggctttgtc gagagaacta gagataragg ttggtatgg    1020
acttcatggg ctccacaatt gagaatcctg agtcacgaat ctgtgtgcgg tttcctaaca    1080
cattgtggtt ctggttctat agttgaagga ctgatgtttg gtcatccact tatcatgttg    1140
ccaatctttg gtgaccagcc tttgaatgca cgtctgttag aagataaaca agttggaatt    1200
gaaatcccac gtaatgagga agatggatgt ttaaccaagg agtctgtggc cagatcatta    1260
cgttccgttg tcgttgaaaa ggaaggcgaa atctacaagg ccaatgcccg tgaactttca    1320
aagatctaca tgacacaaa gtagagaag gaatatgttt ctcaatttgt agattaccta   1380
gagaaaaacg ctagagccgt agctattgat catgaatcct aa                     1422

SEQ ID NO: 11
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTDRGLVW TSWAPQLRIL SHESVCGFLT     360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 12
atggctactt ctgattccat cgttgacgat agaaagcaat tgcatgttgc tactttccca     60
tggttggctt tcggtcatat tttgccatac ttgcaattgt ccaagttgat tgctgaaaag    120
ggtcacaagg tttcattctt gtctaccacc agaaacatcc aaagattgtc ctctcatatc    180
tccccattga tcaacgttgt tcaattgact ttgccaagag tccaagaatt gccagaagat    240
gctgaagcta ctactgatgt tcatccagaa gatatccctt acttgaaaaa ggcttccgat    300
ggtttacaac cagaagttac tagattcttg aacaacattt ccccagattg gatcatctac    360
gattatactc attactggtt gccatccatt gctgcttcat tgggtatttc tagagcccat    420
ttctctgtta ctactccatg ggctattgct tatatgggtc catctgctga tgctatgatt    480
aacggttctg atggtagaac taccgttgaa gatttgacta ctccaccaaa gtggtttcca    540
tttccaacaa aagtctgttg gagaaaacac gatttggcta gatttgttcc atacaaagct    600
ccaggtattt ctgatggtta cagaatgggt atggttttga aggttccga ttgcttgttg     660
tctaagtgct atcatgaatt cggtactcaa tggttgcctt tgttgaaaac attgcatcaa    720
gttccagttg ttccagtagg tttgttgcca ccagaaattc caggtgacga aaaagacgaa    780
acttgggttt ccatcaaaaa gtggttggat ggtaagcaaa agggttctgt tgtttatgtt    840
gctttgggtt ccgaagtttt ggtttctcaa accgaagttg ttgaattgc tttgggtttg    900
gaattgtctg gtttgccatt tgtttgggcc tacagaaaac taaaggtcc agctaagtct    960
gattctgttg aattgccaga tggtttcgtt gaaagaacta gagataragg tttggtttgg    1020
acttcttggg ctccacaatt gagaattttg tctcatgaat ccgtctgtgg tttcttgact    1080
cattgtggtt ctggttctat cgttgaaggt ttgatgtttg gtcacccatt gattatgttg    1140
ccaatctttg gtgaccaacc attgaacgct agattattgg aagataagca agtcggtatc    1200
gaaatcccaa gaaatgaaga agatggttgc ttgaccaaag aatctgttgc tagatctttg    1260
agatccgttg tcgttgaaaa agaaggtgaa atctacaagg ctaacgctag agaattgtcc    1320
```

TABLE 10-continued

Sequences disclosed herein.

```
aagatctaca acgataccaa ggtcgaaaaa gaatacgttt cccaattcgt tgactacttg    1380
gaaaagaatg ctagagctgt tgccattgat catgaatctt ga                       1422

SEQ ID NO: 13
MATSDSIVDD RKQLHVATFP WLAFGHILPY LQLSKLIAEK GHKVSFLSTT RNIQRLSSHI      60
SPLINVVQLT LPRVQELPED AEATTDVHPE DIPYLKKASD GLQPEVTRFL EQHSPDWIIY     120
DYTHYWLPSI AASLGISRAH FSVTTPWAIA YMGPSADAMI NGSDGRTTVE DLTTPPKWFP     180
FPTKVCWRKH DLARLVPYKA PGISDGYRMG MVLKGSDCLL SKCYHEFGTQ WLPLLETLHQ     240
VPVVPVGLLP PEIPGDEKDE TWVSIKKWLD GKQKGSVVYV ALGSEALVSQ TEVVELALGL     300
ELSGLPFVWA YRKPKGPAKS DSVELPDGFV ERTRDRGLVW TSWAPQLRIL SHESVCGFLT     360
HCGSGSIVEG LMFGHPLIML PIFGDQPLNA RLLEDKQVGI EIPRNEEDGC LTKESVARSL     420
RSVVVEKEGE IYKANARELS KIYNDTKVEK EYVSQFVDYL EKNARAVAID HES            473

SEQ ID NO: 14
atggactccg gctactcctc ctcctacgcc gccgccgccg ggatgcacgt cgtgatctgc      60
ccgtggctcg ccttcggcca cctgctcccg tgcctcgacc tcgcccagcg cctcgcgtcg     120
cggggccacc gcgtgtcgtt cgtctccacg ccgcggaaca tatcccgcct cccgccggtg     180
cgccccgcgc tcgcgccgct cgtcgccttc gtggcgctgc cgctcccgcg cgtcgagggg     240
ctccccgacg gcgccgagtc caccaacgac gtcccccacg acaggccgga catggtcgag     300
ctccaccgga gggccttcga cgggctcgcc gcgcccttct cggagttctt gggcaccgcg     360
tgcgccgact gggtcatcgt cgacgtcttc caccactggg ccgcagccgc cgctctcgag     420
cacaaggtgc catgtgcaat gatgttgttg ggctctgcac atatgatcgc ttccatagca     480
gacagacggc tcgagcgcgc ggagacagag tcgcctgcgg ctgccgggca gggacgccca     540
gcggcggcgc caacgttcga ggtggcgagg atgaagttga tacgaaccaa aggctcatcg     600
ggaatgtccc tcgccgagcg cttctccttg acgctctcga ggagcagcct cgtcgtcggg     660
cggagctgcg tggagttcga gccggagacc gtcccgctcc tgtcgacgct ccgcggtaag     720
cctattacct tccttggcct tatgccgccg ttgcatgaag gccgccgga ggacggcgag     780
gatgccaccg tccgctggct cgacgcgcag ccggccaagt ccgtcgtgta cgtcgcgcta     840
ggcagcgagg tgccactggg agtggagaag gtccacgagc tcgcgctcgg gctggagctc     900
gccgggacgc gcttcctctg ggctcttagg aagcccactg gcgtctccga cgccgacctc     960
ctccccgccg gcttcgagga gcgcacgcgc ggccgcggcg tcgtggcgac gagatgggtt    1020
cctcagatga gcatactggc gcacgcgcc gtgggcgcgt tcctgaccca ctgcggctgg    1080
aactcgacca tcgagggcgct catgttcggc caccgctta tcatgctgcc gatcttcggc    1140
gaccaggga cgaacgcgcg gctaatcgag gcgaagaacg ccggattgca ggtggcaaga    1200
aacgacgcg atggatcgtt cgaccgagaa ggcgtcgcgg cggcgattcg tgcagtcgcg    1260
gtggaggaag aaagcagcaa agtgtttcaa gccaaagcca agaagctgca ggagatcgtc    1320
gcggacatgg cctgccatga gaggtacatc gacgcattca ttcagcaatt gagatcttac    1380
aaggattga                                                            1389

SEQ ID NO: 15
atggatagtg gctactcctc atcttatgct gctgccgctg gtatgcacgt tgtgatctgc      60
ccttggttgg cctttggtca cctgttacca tgtctggatt tagcccaaag actgcctca     120
agaggccata gagtatcatt tgtgtctact cctagaaata tctctcgttt accaccagtc     180
agacctgctc tagctcctct agttgcattc gttgctcttc cacttccaag agtagaagga     240
ttgccagacg gcgctgaatc tactaatgac gtaccacatg atagacctga catggtcgaa     300
ttgcatagaa gagcctttga tggattggca gctccatttt ctgagttcct gggcacagca     360
tgtgcagact gggttatagt cgatgtattt catcactggg ctgctgcagc cgcattggaa     420
cataaggtgc cttgtgctat gatgttgtta gggtcagcac acatgatcgc atccatagct     480
gatagaagat tggaaagagc tgaaacagaa tccccagccg cagcaggaca aggtaggcca     540
gctgccgccc aacctttga agtggctaga atgaaattga ttcgtactaa aggtagttca     600
gggatgagtc ttgctgaaag gttttctctg acattatcta gatcatcatt agttgtaggt     660
agatcctgcg tcgagttcga acctgaaaca gtaccttttac tatctacttt gagaggcaaa     720
cctattactt tccttggtct aatgcctcca ttacatgaag gaaggagaga agatggtgaa     780
gatgctactg ttaggtggtt agatgcccaa cctgctaagt ctgttgttta cgttgcattg     840
ggttctgagg taccactagg ggtggaaaag gtgcatgaat tagcattagg acttgagctg     900
gccggaacaa gattcctttg ggctttgaga aaaccaaccg gtgtttctga cgccgacttg     960
ctaccagctg gttcgaaga gagaacaaga ggccgtggtg tcgttgctac tagatgggtc    1020
ccacaaatga gtattctagc tcatgcagct gtaggggcc ttctaaccca ttgcggttgg    1080
aactcaacaa tagaaggact gatgtttggt catccactta ttatgttacc aatctttggc    1140
gatcaggac ctaacgcaag attgattgag gcaagaacg caggtctgca ggttgcacgt    1200
aatgatggtg atgttccctt tgatagagaa ggcgttgcag ctgccatcag agcagtcgcc    1260
gttgaggaag agtcatctaa agtttttcaa gctaaggcca aaaaattaca agagattgtg    1320
gctgacatgg cttgtcacga aagatacatc gatggtttca tccaacaatt gagaagttat    1380
aaagactaa                                                             1389

SEQ ID NO: 16
MDSGYSSSYA AAGMHVVIC PWLAFGHLLP CLDLAQRLAS RGHRVSFVST PRNISRLPPV      60
RPALAPLVAF VALPLPRVEG LPDGAESTND VPHDRPDMVE LHRRAFDGLA APFSEFLGTA     120
CADWVIVDVF HHWAAAAALE HKVPCAMMLL GSAHMIASIA DRRLERAETE SPAAAGQGRP     180
AAAPTFEVAR MKLIRTKGSS GMSLAERFSL TLSRSSLVVG RSCVEFEPET VPLLSTLRGK     240
PITFLGLMPP LHEGRREDGE DATVRWLDAQ PAKSVVYVAL GSEVPLGVEK VHELALGLEL     300
AGTRFLWALR KPTGVSDADL LPAGFEERTR GRGVVATRWV PQMSILAHAA VGAFLTHCGW     360
NSTIEGLMFG HPLIMLPIFG DQGPNARLIE AKNAGLQVAR NDGDGSFDRE GVAAAIRAVA     420
VEEESSKVFQ AKAKKLQEIV ADMACHERYI DGFIQQLRSY KD                        462

SEQ ID NO: 17
MDSGYSSSYA AAGMHVVIC PWLAFGHLLP CLDLAQRLAS RGHRVSFVST PRNISRLPPV      60
RPALAPLVAF VALPLPRVEG LPDGAESTND VPHDRPDMVE LHRRAFDGLA APFSEFLGTA     120
```

TABLE 10-continued

Sequences disclosed herein.

```
CADWVIVDVF HHWAAAAALE HKVPCAMMLL GSAHMIASIA DRRLERAETE SPAAAGQGRP    180
AAAPTFEVAR MKLIRTKGSS GMSLAERFSL TLSRSSLVVG RSCVEFEPET VPLLSTLRGK    240
PITFLGLLPP EIPGDEKDET WVSIKKWLDG KQKGSVVYVA LGSEALVSQT EVVELALGLE    300
LSGLPFVWAY RKPKGPAKSD SVELPDGFVE RTRDRGLVWT SWAPQLRILS HESVCGFLTH    360
CGSGSIVEGL MFGHPLIMLP IFGDQPLNAR LLEDKQVGIE IARNDGDSF DREGVAAAIR     420
AVAVEEESSK VFQAKAKKLQ EIVADMACHE RYIDGFIQQ RSYKD                    465

SEQ ID NO: 18
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE ARAVAIDHES    180
FPTKVCWRKH DLARLVPYKA PGISDGYRMG MVLKGSDCLL SKCYHEFGTQ WLPLLETLHQ    240
VPVVPVGLMP PLHEGRREDG EDATVRWLDA QPAKSVVYVA LGSEVPLGVE KVHELALGLE    300
LAGTRFLWAL RKPTGVSDAD LLPAGFEERT RGRGVVATRW VPQMSILAHA AVGAGLTHCG    360
WNSTIEGLMF GHPLIMLPIF GDQGPNARLI EAKNAGLQVP RNEEDGCLTK ESVARSLRSV    420
VVEKEGEIYK ANARELSKIY NDTKVEKEYV SQFVDYLEKN ARAVAIDHES              470

SEQ ID NO: 19
atggctttgg taaacccaac cgctctttc tatggtacct ctatcagaac aagacctaca     60
aacttactaa atccaactca aaagctaaga ccagtttcat catccttcct accttctttc    120
tcatcagtta gtgcgattct tactgaaaaa catcaatcta atccttctga aacaacaat     180
ttgcaaactc atctagaaac tccttttcaac tttgatagtt atatgttgga aaaagtcaac   240
atggttaacg aggcgcttga tgcatctgtc ccactaaaag cccaatcaa aatccatgaa    300
tccatgagat actctttatt ggcaggcggt aagagaatca gaccaatgat gtgtattgca    360
gcctgcgaaa tagtcggagg taatatcctt aacgccatgc cagccgcatg tgccgtggaa    420
atgattcata ctatgtcttt ggtgcatgac gatcttccat gtatggataa tgatgacttc    480
agaagaggta aacctatttc acacaaggtc tacggggagg aaatggcagt attgaccggc    540
gatgctttac taagtttatc tttcgaacat atagctactg ctacaaaggg tgtatcaaag    600
gataagaatcg tcagagctat aggggagttg gcccgttcag ttggctccga aggtttagtg    660
gctgacaag ttgtagatat cttgtcgag ggtgctgatg ttggattaga tcacctagaa       720
tacattcaca tccacaaaac agcaatgttg cttgagtcct cagtagttat tggcgctatc    780
atgggaggag gatctgatca gcagatcgaa aagttgaaga aattcgctag atctattggt    840
ctactattcc aagttgtgga tgacatttg gatgttacaa aatctaccga agagtttggg      900
aaaacagctg gtaaggattt gttgacagat aagacaactt acccaaagtt gttaggtata    960
gaaaagtcca gagaatttgc cgaaaaactt aacaaggaag cacaagagca attaagtggc    1020
tttgatagac gtaaggcagc tcctttgatc gcgttagcca actacaatgc gtaccgtcaa    1080
aattga                                                              1086

SEQ ID NO: 20
MALVNPTALF YGTSIRTRPT NLLNPTQKLR PVSSSSLPSF SSVSAILTEK HQSNPSENNN    60
LQTHLETPFN FDSYMLEKVN MVNEALDASV PLKDPIKIHE SMRYSLLAGG KRIRPMMCIA    120
ACEIVGNIL NAMPAACAVE MIHTMSLVHD DLPCMDNDDF RRGKPISHKV YGEEMAVLTG     180
DALLSLSFEH IATATKGVSK DRIVRAIGEL ARSVGSEGLV AGQVVDILSE GADVGLDHLE    240
YIHIHKTAML LESSVVIGAI MGGGSDQQIE KLRKFARSIG LLFQVVDDIL DVTKSTEELG    300
KTAGKDLLTD KTTYPKLLGI EKSREFAEKL NKEAQEQLSG FDRRKAAPLI ALANYNAYRQ    360
N                                                                   361

SEQ ID NO: 21
atggctgagc aacaaatatc taacttgctg tctatgtttg atgcttcaca tgctagtcag    60
aaattagaaa ttactgtcca aatgatggac acataccatt acagagaaac gcctccagat    120
tcctcatctt ctgaaggcgg ttcattgtct agatacgacg agaagagt ctctttgcct     180
ctcagtcata atgctgcctc tccagatatt gtatcacaac tatgtttttc cactgcaatg    240
tcttcagagt tgaatcacag atggaaatct caaagattaa aggtggccga ttctccttac    300
aactatatcc taacattacc atcaaaagga attagaggtg cctttatcga ttccctgaac    360
gtatggttgg aggttccaga ggatgaaaca tcagtcatca aggaagttat ggtatgctc     420
cacaactctt cattaatcat tgatgacttc caagataatt ctccacttag aagaggaaag    480
ccatctaccc atacagtctt cggccctgcc caggctataa atactgctac ttacgtttata   540
gttaaagcaa tcgaaaagat acaagacata gtgggacacg atgcattggc agatgttacg    600
ggtactatta caactatttt ccaaggtcag gccatggact gtggtggac agcaaatgca    660
atcgttccat caatacagga atacttactt atggtaaaca ataaaaccgg tgctctcttt    720
agactgagtt tggagttgtt agctctgaat tccgaagcca gtatttctga tctctgcttta   780
gaaagtttat ctagtgctgt ttccttgcta ggtcaatact tccaaatcag agacgactat    840
atgaacttga tcgataacaa gtatacagat cagaaaggct tctgcgaaga tcttgatgaa    900
ggcaagtact cactaacact tattcatgcc ctccaaactg attcatccga tctactgacc    960
aacatccttt caatgagaag agtgcaagga aagttaacgg cacaaagag atgttggttc    1020
tggaaatga                                                           1029

SEQ ID NO: 22
MAEQQISNLL SMFDASHASQ KLEITVQMMD TYHYRETPPD SSSSEGGSLS RYDERRVSLP    60
LSHNAASPDI VSQLCFSTAM SSELNHRWKS QRLKVADSPY NYILTLPSKG IRGAFIDSLN    120
VWLEVPEDET SVIKEVIGML HNSSLIIDDF QDNSPLRRGK PSTHTVFGPA QAINTATYVI    180
VKAIEKIQDI VGHDALADVT GTITTIFQGQ AMDLWWTANA IVPSIQEYLL MVNDKTGALF    240
RLSLELLALN SEASISDSAL ESLSSAVSLL GQYFQIRDDY MNLIDNKYTD QKGFCEDLDE    300
GKYSLTLIHA LQTDSSDLLT NILSMRRVQG KLTAQKRCWF WK                      342

SEQ ID NO: 23
atggaaaaga ctaaggagaa agcagaacgt atcttgctgg agccatacag atacttatta    60
caactaccag gaaagcaagt ccgttctaaa ctatcacaag cgttcaatca ctggtaaaaa    120
```

TABLE 10-continued

Sequences disclosed herein.

```
gttcctgaag ataagttaca aatcattatt gaagtcacag aaatgctaca caatgcttct    180
ttactgatcg atgatataga ggattcttcc aaactgagaa gaggttttcc tgtcgctcat    240
tccatatacg gggtaccaag tgtaatcaac tcagctaatt acgtctactt cttgggattg    300
gaaaaagtat tgacattaga tcatccgagc gctgtaaagc tattcaccag acaacttctt    360
gaattgcatc aaggtcaagg tttggatatc tattggagag acacttatac ttgcccaaca    420
gaagaggagt acaaagcaat ggttctacaa aagactggcg gtttgttcgg acttgccgtt    480
ggtctgatgc aacttttctc tgattacaag gaggacttaa agcctctgtt ggatacccttg   540
ggcttgtttt tccagattag agatgactac gctaacttac attcaaagga atattcagaa    600
aacaaatcat tctgtgaaga tttgactgaa gggaagttta gttttccaac aatccacgcc    660
atttggtcaa gaccagaatc tactcaagtg caaaacattc tgcgtcagag aacagagaat    720
attgacatca aaaagtattg tgttcagtac ttggaagatg ttggttcttt tgcttacaca    780
agacatacac ttagagaatt agaggcaaaa gcataaaagc aaatagaagc ctgtggaggc    840
aatccttctc tagtggcatt ggttaaacat ttgtccaaaa tgttcaccga ggaaaacaag    900
taa                                                                  903

SEQ ID NO: 24
MEKTKEKAER ILLEPYRYLL QLPGKQVRSK LSQAFNHWLK VPEDKLQIII EVTEMLHNAS     60
LLIDDIEDSS KLRRGFPVAH SIYGVPSVIN SANYVYFLGL EKVLTLDHPD AVKLFTRQLL    120
ELHQGQGLDI YWRDTYTCPT EEEYKAMVLQ KTGGLFGLVN GLMQLFSDYK EDLKPLLDTL    180
GLFFQIRDDY ANLHSKEYSE NKSFCEDLTE GKFSFPTIHA IWSRPESTQV QNILRQRTEN    240
IDIKKYCVQY LEDVGSFAYT RHTLRELEAK AYKQIEACGG NPSLVALVKH LSKMFTEENK    300

SEQ ID NO: 25
atggcaagat tctattttct taacgcacta ttgatggtta tctcattaca atcaactaca     60
gccttcactc cagctaaact tgcttatcca acaacaacaa cagctctaaa tgtcgcctcc    120
gccgaaactt ctttcagtct agatgaatac ttggcctcta agataggacc tatagagtct    180
gccttggaag catcagtcaa aatccagaatt ccacagaccg ataagatctg cgaatctatg    240
gcctactctt tgatggcagg aggcaagaga attagaccag tgttgtgtat cgctgcatgt    300
gagatgttcg gtggatccca agatgtcgct atgcctactg ctgtggcatt agaaatgata    360
cacacaatgt ctttgattca tgatgatttg ccatccatgg ataacgatga cttgagaaga    420
ggtaaaccaa caaaccatgt cgttttcggc gaagatgtag ctattcttgc aggtgactct    480
ttattgtcaa cttccttcga gcacgtcgct agagaaacaa aaggagtgtc agcagaaaag    540
atcgtggatg ttatcgctag attaggcaaa tctgttggtg ccgagggcct tgctggcggt    600
caagtttatg acttagaatg tgaagctaaa ccaggtacca cattagacga cttgaaatgg    660
attcatatcc ataaaaccgc tacattgtta caagttgctg tagcttctgg tgcagttcta    720
ggtggtgcaa ctcctgaaga ggttgctgca tgcgagtttgt ttgctatgaa tataggtctt    780
gcctttcaag ttgccgacga tatccttgat gtaaccgctt catcagaaga tttgggtaaa    840
actgcaggca aagatgaagc tactgataag caaacttacc caaagttatt aggattagaa    900
gagagtaagg catacgcaag acaactaatc gatgaagcca ggaaagtttt ggctcctttt    960
ggagatagag ctgcccttt attggccatt gcagatttca ttattgatag aaagaattga   1020

SEQ ID NO: 26
MARFYFLNAL LMVISLQSTT AFTPAKLAYP TTTTALNVAS AETSFSLDEY LASKIGPIES     60
ALEASVKSRI PQTDKICESM AYSLMAGGKR IRPVLCIAAC EMFGGSQDVA MPTAVALEMI    120
HTMSLIHDDL PSMDNDDLRR GKPTNHVVFG EDVAILAGDS LLSTSFEHVA RETKGVSAEK    180
IVDVIARLGK SVGAEGLAGG QVMDLECEAK PGTTLDDLKW IHIHKTATLL QVAVASGAVL    240
GGATPEEVAA CELFAMNIGL AFQVADDILD VTASSEDLGK TAGKDEATDK TTYPKLLGLE    300
ESKAYARQLI DEAKESLAPF GDRAAPLLAI ADFIIDRKN                           339

SEQ ID NO: 27
atgcacttag caccacgtag agtccctaga ggtagaagat caccacctga cagagttcct     60
gaaagacaag gtgccttggg tagaagacgt ggagctggct ctactggctg tgcccgtgct    120
gctgctggtg ttcaccgtag aagaggagga ggcgaggctg atccatcagc tgctgtgcat    180
agaggctggc aagccggtgg tggcaccggt ttgcctgatg aggtggtgtc taccgcagcc    240
gccttagaaa tgtttcatgc ttttgcttta atccatgatg atatcatgga tgatagtgca    300
actagaagag gctccccaac tgttcacaga gccctagctg atcgtttagg cgctgctctg    360
gacccagatc aggccggtca actaggagtt tctactgcta tcttggttgg agatctggct    420
ttgacatggt ccgatgaatt gttatacgct ccattgactc cacatagact ggcagcagta    480
ctaccattgg taacagctat gagagctgaa accgttcatg gccaatatct tgatataact    540
agtgctagaa gacctgggac cgatacttct cttgcattga gaatagccag atataagaca    600
gcagcttaca caatggaacg tccactgcac atggtgcag ccctggctgg ggcaagacca    660
gaactattag cagggctttc agcatacgcc ttgccagctg agaagccttc ccaattggca    720
gatgacctgc taggcgtctt cggtgatcca agacgtacag ggaaacctga cctagatgat    780
cttagaggtg gaaagcatac tgtcttagtc gccttggcaa gaacatgc cactccagaa    840
cagagacaca cattggatac attattgggt acaccaggtc ttgatagaca aggcgcttca    900
agactaagat gcgtattggt agcaactggt gcaagagccg aagccgaaag acttattaca    960
gagagaagag atcaagcatt aactgcattg aacgcattaa cactgccacc tcctttagct   1020
gaggcattag caagattgac attagggtct acagctcatc ctgcctaa               1068

SEQ ID NO: 28
MHLAPRRVPR GRRSPPDRVP ERQGALGRRR GAGSTGCARA AAGVHRRRGG GEADPSAAVH     60
RGWQAGGGTG LPDEVVSTAA ALEMFHAFAL IHDDIMDDSA TRRGSPTVHR ALADRLGAAL    120
DPDQAGQLGV STAILVGDLA LTWSDELLYA PLTPHRLAAV LPLVTAMRAE TVHGQYLDIT    180
SARRPGTDTS LALRIARYKT AAYTMERPLH IGAALAGARP ELLAGLSAYA LPAGEAFQLA    240
DDLLGVFGDP RRTGKPDLDD LRGGKHTVLV ALAREHATPE QRHTLDTLLG TPGLDRQGAS    300
RLRCVLVATG ARAEAERLIT ERRDQALTAL NALTLPPPLA EALARLTLGS TAHPA         355
```

TABLE 10-continued

Sequences disclosed herein.

SEQ ID NO: 29
```
atgtcatatt tcgataacta cttcaatgag atagttaatt ccgtgaacga catcattaag    60
tcttacatct ctggcgacgt accaaaacta tacgaagcct cctaccattt gtttacatca   120
ggaggaaaga gactaagacc attgatcctt acaatttctt ctgatctttt cggtggacag   180
agagaaagag catactatgc tggcgcagca atcgaagttt tgcacacatt cactttggtt   240
cacgatgata tcatggatca agataacatt cgtagaggtc ttcctactgt acatgtcaag   300
tatggcctac ctttggccat tttagctggt gacttattgc atgcaaaagc ctttcaattg   360
ttgactcagg cattgagagg tctaccatct gaaactatca tcaaggcgtt tgatatcttt   420
acaagatcta tcattatcat atcagaaggt caagctgtcg atatgaatt cgaagataga    480
attgatatca aggaacaaga gtatttggat atgatatctc gtaaaaccgc tgccttattc   540
tcagcttctt cttccattgg ggcgttgata gctggagcta gataacga tgtgagatta    600
atgtccgatt tcgtacaaa tcttgggatc gcatttcaaa ttgtagatga tatacttggt   660
ttaacagctg atgaaaaaga gctaggaaaa cctgttttca gtgatatcag agaaggtaaa   720
aagaccatat tagtcattaa gactttagaa ttgtgtaagg aagacgagaa aaagattgtg   780
ttaaaagcgc taggcaacaa gtcagcatca aaggaagagt tgatgagttc tgctgacata   840
atcaaaaagt actcattgga ttacgcctac aacttagctg agaaatacta caaaaacgcc   900
atcgattctc taaatcaagt ttcaagtaaa agtgatattc cagggaaggc attgaaatat   960
cttgctgaat tcaccatcag aagacgtaag taa                                993
```

SEQ ID NO: 30
```
MSYFDNYFNE IVNSVNDIIK SYISGDVPKL YEASYHLFTS GGKRLRPLIL TISSDLFGGQ    60
RERAYYAGAA IEVLHTFTLV HDDIMDQDNI RRGLPTVHVK YGLPLAILAG DLLHAKAFQL   120
LTQALRGLPS ETIIKAFDIF TRSIIISEG QAVDMEFEDR IDIKEQEYLD MISRKTAALF    180
SASSSIGALI AGANDNDVRL MSDFGTNLGI AFQIVDDILG LTADEKELGK PVFSDIREGK   240
KTILVIKTLE LCKEDEKKIV LKALGNKSAS KEELMSSADI IKKYSLDYAY NLAEKYYKNA   300
IDSLNQVSSK SDIPGKALKY LAEFTIRRRK                                    330
```

SEQ ID NO: 31
```
atggtcgcac aaactttcaa cctggatacc tacttatccc aaagacaaca acaagttgaa    60
gaggccctaa gtgctgctct tgtgccagct tatcctgaga aatatacga agctatgaga   120
tactccctcc tggcaggtgg caaaagatta agacctatct tatgtttagc tgcttgcgaa   180
ttggcaggtg gttctgttga acaagccatg ccaactgcgt gtgcacttga aatgatccat   240
acaatgtcac taattcatga tgacctgcca gccatgatga acgatgattt cagaagagga   300
aagccaacta atcacaaggt gttcggggaa gatatagcca tcttagcggg tgatgcgctt   360
ttagcttacg cttttgaaca tattgcttct caaacaagag gagtaccacc tcaattggtg   420
ctacaagtta ttgctagaat cggacacgcc gttgctgcaa caggcctcgt tgtgaggccaa   480
gtcgtagacc ttgaatctga aggtaaagct atttccttag aaacattgga gtatattcac   540
tcacataaga ctggagcctt gctggaagca tcagttgtct caggcggtat tctcgcaggg   600
gcagatgaag agcttttggc cagattgtct cattacgcta gagatatagg cttggctttt   660
caaatcgtcg atgatatcct ggatgttact gctacatctg aacagttggg gaaaaccgct   720
ggtaaagacc aggcagccgc aaaggcaact tatccaagtc tattgggttt agaagcctct   780
agacagaaag cggaagagtt gattcaatct gctaaggaag ccttaagacc ttacggttca   840
caagcagagc cactcctagc gctggcagac ttcatcacac gtcgtcagca ttaa          894
```

SEQ ID NO: 32
```
MVAQTFNLDT YLSQRQQQVE EALSAALVPA YPERIYEAMR YSLLAGGKRL RPILCLAACE    60
LAGGSVEQAM PTACALEMIH TMSLIHDDLP AMDNDDFRRG KPTNHKVFGE DIAILAGDAL   120
LAYAFEHIAS QTRGVPPQLV LQVIARIGHA VAATGLVGGQ VVDLESEGKA ISLETLEYIH   180
SHKTGALLEA SVVSGGILAG ADEELLARLS HYARDIGLAF QIVDDILDVT ATSEQLGKTA   240
GKDQAAAKAT YPSLLGLEAS RQKAEELIQS AKEALRPYGS QAEPLLALAD FITRRQH      297
```

SEQ ID NO: 33
```
atgaaaaccg ggtttatctc accagcaaca gtatttcatc acagaatctc accagcgacc    60
actttcagac atcactttatc acctgctact acaaactcta caggcattgt cgccttaaga   120
gacatcaact tcgatgtaa agcagttcct aaagagtact ctgatctgtt gcagaaagat   180
gaggcttctt tcacaaaatg ggacgatgac aaggtgaaag atcatcttga taccaacaaa   240
aacttatacc caaatgatga gattaaggaa tttgttgaat cagtaaaggc tatgttcggt   300
agtatgaatg acggggagat aaacgtctct gcatacgata ctgcatgggt tgcttttggtt   360
caagatgtcg atggatcagg tagtcctcag ttcccttctt ctttagaatg gattgccaac   420
aatcaattgt cagatggatc atgggagat catttgctgt tctcagctca cgatagaatc   480
atcaacacat tagcatgcgt tattcactt acaagttgga atgttcatcc ttctaagtgt   540
gaaaaaggtt tgaattttct gagagaaaac atttgcaaat tagaagatga aaacgcagaa   600
catatgccaa ttggttttga agtaacattc ccatcactaa ttgatatcgc gaaaagttg    660
aacattgaag tacctgagga tactccagca cttaaagaga tctacgcacg tagagatatc   720
aagttaacta agatcccaat ggaagttctt cacaaggtac ctactacttt gttacattct   780
ttggaaggaa tgcctgattt ggagtgggaa aaactgttaa agctacaatg taaagatggt   840
agtttcttgt ttccccatc tagtaccgca ttcgccctaa tgcaaacaaa agatgagaaa   900
tgcttacagt atctaacaaa tatcgtcact aagttcaacg gtggcgtgcc taatgtgtac   960
ccagtcgatt tgtttgaaca tatttgggtt gttgatagac tgcagagatt ggggattgcc  1020
agatacttca aatcagagat aaaagattgt gtagagtata tcaataagta ctggaccaaa  1080
aatgaatttt gttgggctag aaatactcac gttcaagata tcgatgatac agccatggga  1140
ttcagagtgt tgagagcgca cggttatgac gtcactccag atgtttttag acaatttgaa  1200
aaagatggta aattcgtttg ctttgcaggg caatcaacaa agccgtcagc aggaatgttt  1260
aacgtttaca gagcctctca aatgttgttc ccaggggaga gaattttgga agatgccaaa  1320
aagttctctt acaattactt aaaggaaaag caaagtacca acgaattgct ggataaatgg  1380
ataatcgcta aagatctacc tggtgaagtt ggttatgctc tggatatccc atggtatgct  1440
tccttaccaa gattggaaac tcgttattac cttgaacaat acggcggtga agatgatgtc  1500
tggataggca agacattata cagaatgggt tacgtgtcca ataacacata tctagaaatg  1560
```

TABLE 10-continued

Sequences disclosed herein.

```
gcaaagctgg attacaataa ctatgttgca gtccttcaat tagaatggta cacaatacaa   1620
caatggtacg tcgatattgg tatagagaag ttcgaatctg acaacatcaa gtcagtcctg   1680

SEQ ID NO: 34
MKTGFISPAT VFHHRISPAT TFRHHLSPAT TNSTGIVALR DINFRCKAVS KEYSDLLQKD     60
EASFTKWDDD KVKDHLDTNK NLYPNDEIKE FVESVKAMFG SMNDGEINVS AYDTAWVALV    120
QDVDGSGSPQ FPSSLEWIAN NQLSDGSWGD HLLFSAHDRI INTLACVIAL TSWNVHPSKC    180
EKGLNFLREN ICKLEDENAE HMPIGFEVTF PSLIDIAKKL NIEVPEDTPA LKEIYARRDI    240
KLTKIPMEVL HKVPTTLLHS LEGMPDLEWE KLLKLQCKDG SFLFSPSSTA FALMQTKDEK    300
CLQYLTNIVT KFNGGVPNVY PVDLFEHIWV VDRLQRLGIA RYFKSEIKDC VEYINKYWTK    360
NGICWARNTH VQDIDDTAMG FRVLRAHGYD VTPDVFRQPE KDGKFVCFAG QSTQAVTGMF    420
NVYRASQMLF PGERILEDAK KFSYNYLKEK QSTNELLDKW IIAKDLPGEV GYALDIPWYA    480
SLPRLETRYY LEQYGGEDDV WIGKTLYRMG YVSNNTYLEM AKLDYNNYVA VLQLEWYTIQ    540
QWYVDIGIEK FESDNIKSVL VSYYLAAASI FEPERSKERI AWAKTTILVD KITSIFDSSQ    600
SSKEDITAFI DKFRNKSSSK KHSINGEPWH EVMVALKKTL HGFALDALMT HSQDIHPQLH    660
QAWEMWLTKL QDGVDVTAEL MVQMINMTAG RWVSKELLTH PQYQRLSTVT NSVCHDITKL    720
HNFKENSTTV DSKVQELVQL VFSDTPDDLD QDMKQTFLTV MKTFYYKAWC DPNTINDHIS    780
KVFEIVI                                                              787

SEQ ID NO: 35
atgcctgatg cacacgatgc tccacctcca caaataagac agagaacact agtagatgag     60
gctacccaac tgctaactga gtccgcagaa gatgcatggg gtgaagtcag tgtgtcagaa    120
tacgaaacag caaggctagt tgcccatgct acatggttag gtggacacgc cacaagagtg    180
gccttccttc tggagagaca acacgaagac gggtcatggg gtccaccagg tggatatagg    240
ttagtcccta cattatctgc tgttcacgca ttattgacat gtcttgcctc tcctgctcag    300
gatcatggcg ttccacatga tagacttttta agagctgttg acgcaggctt gactgccttg    360
agaagattgg ggacatctga ctcccccacct gatactatca cagttgagct ggttatccca    420
tcttttgctag agggcattca acacttactg gaccctgctc atcctcatag tagaccagcc    480
ttctctcaac atagaggctc tcttgtttgt cctggtggac tagatgggag aactctagga    540
gctttgagat cacacgccgc agcaggtaca ccagtaccag gaaaagtctg gcacgcttcc    600
gagactttgg gcttgagtac cgaagctgct tctcacttgc aaccagccca aggtataatc    660
ggtggctctg ctgctgccac agcaacatgg ctaaccaggg ttgcaccatc tcaacagtca    720
gattctgcca gaagatacct tgaggaatta caacacagat actctgccc agttccttcc     780
attacccta tcacatactt cgaaagcaca tggttattga caattttgc agcagccggt      840
gttccttgtg aggctccagc tgctttgttg gattccttag aagcagcact tacaccacaa    900
ggtgctcctg ctggagcagg attgcctcca gatgctgata tacagccgtc tgtgttgctt    960
gcattggcaa cacatgggag aggtagaaga ccagaagtac tgatggatta caggactgac   1020
gggtatttcc aatgctttat tggggaaagg actccatcaa tttcaacaaa cgctcacgta   1080
ttggaaacat tagggcatca tgtggcccaa catccacaag atagagccag atacggatca   1140
gccatggata ccgcatcagc ttggctgctg gcagctcaaa agcaagatgg ctcttggtta   1200
gataaatggc atgcctcacc atactacgct actgtttgtt gcacacaagc cctagccgct   1260
catgcaagtc ctgcaactgc accagctaga cagagagctg tcagatgggt tttagccaca   1320
caaagatccg atggcggttg gggtctatgg cattcaactg ttgaagagac tgcttatgcc   1380
ttacagatct tggccccacc ttctggtggt ggcaatatcc cagtccaaca agcacttact   1440
agaggcagag caagattgtg tggagccttg ccactgactc ctttatggca tgataaggat   1500
ttgtatactc cagtaagagt agtcagagct gccagagctg ctgctctgta cactaccaga   1560
gatctattgt taccaccatt gtaa                                           1584

SEQ ID NO: 36
MPDAHDAPPP QIRQRTLVDE ATQLLTESAE DAWGEVSVSE YETARLVAHA TWLGGHATRV     60
AFLLERQHED GSWGPPGGYR LVPTLSAVHA LLTCLASPAQ DHGVPHDRLL RAVDAGLTAL    120
RRLGTSDSPP DTIAVELVIP SLLEGIQHLL DPAHPHSRPA FSQHRGSLVC PGGLDGRTLG    180
ALRSHAAAGT PVPGKVWHAS ETLGLSTEAA SHLQPAQGII GGSAAATATW LTRVAPSQQS    240
DSARRYLEEL QHRYSGPVPS ITPITYFERA WLLNNFAAAG VPCEAPAALL DSLEAALTPQ    300
GAPAGAGLPP DADDTAAVLL ALATHGRGRR PEVLMDYRTD GYFQCFIGER TPSISTNAHV    360
LETLGHHVAQ HPQDRARYGS AMDTASAWLL AAQKQDGSWL DKWHASPYYA TVCCTQALAA    420
HASPATAPAR QRAVRWVLAT QRSDGGWGLW HSTVEETAYA LQILAPPSGG GNIPVQQALT    480
RGRARLCGAL PLTPLWHDKD LYTPVRVVRA ARAAALYTTR DLLLPPL                  527

SEQ ID NO: 37
atgaacgccc tatccgaaca cattttgtct gaattgagaa gattattgtc tgaaatgagt     60
gatggcggat ctgttggtcc atctgtgtat gatacggccc aggccctaag attccacggt    120
aacgtaacag gtagacaaga tgcatatgct tggttgatcg cccagcaaca agcagatgga    180
ggttgggggct ctgccgactt tccactcttt agacatgctc aacatgggc tgcacttctc    240
gcattacaaa gagctgatcc acttcctggc gcagcagacg cagttcagac cgcaacaaga    300
ttcttgcaaa gacaaccaga tccatacgct catgccgttc ctgaggatgc ccctattggt    360
gctgaactga tcttgcctca gttttgtgga gaggctgctt ggttgttggg aggtgtggcc    420
ttccctagac acccagccct attaccatta agacaggctt gtttagtcaa actgggtgca    480
gtcgccatgt tgccttcagg cacccccattg ttccactcct gggaggcattg gggtacttct    540
ccaacaacag cctgtccaga cgatgatggt tctataggta tctcaccagc agctacagcc    600
gcctggagag cccaggctgt gaccagaggc tcaactcctc aagtgggcag agctgacgca    660
tacttacaaa tggcttcaag agcaacgaga tcaggcatag aaggagtctt ccctaatgtt    720
tggcctataa acgtattcga accatgctgg tcactgtaca ctctccatct tgccggtctg    780
ttcgcccatc cagcactggc tgaggctgta agagttatcg ttgctcaact tgaacgaaga    840
ttgggagtgc atggcctcgg accagcttta cattttgctg ccgacgctga tgatactgca    900
gttgccttat gcgttctgca tttggctggc agagatcctg cagttgacgc attgagacat    960
tttgaaattg gtgagctctt tgttacattc ccaggagaga gaaatgctag tgtctctacg   1020
aacattcacg ctcttcatgc tttgagattg ttaggtaaac cagctgccgg agcaagtgca   1080
```

TABLE 10-continued

Sequences disclosed herein.

```
tacgtcgaag caaatagaaa tccacatggt ttgtgggaca acgaaaaatg gcacgtttca    1140
tggctttatc caactgcaca cgccgttgca gctctagctc aaggcaagcc tcaatggaga    1200
gatgaaagag cactagccgc tctactacaa gctcaaagag atgatggtgg ttggggagct    1260
ggtagaggat ccactttcga ggaaaccgcc tacgctcttt tcgctttaca cgttatggac    1320
ggatctgagg aagccacagg cagaagaaga atcgctcaag tcgtcgcaag agccttagaa    1380
tggatgctag ctagacatgc cgcacatgga ttaccacaaa caccactctg gattggtaag    1440
gaattgtact gtcctactag agtcgtaaga gtagctgagc tagctggcct gtggttagca    1500
ttaagatggg gtagaagagt attagctgaa ggtgctggtg ctgcacctta a            1551

SEQ ID NO: 38
MNALSEHILS ELRRLLSEMS DGGSVGPSVY DTAQALRFHG NVTGRQDAYA WLIAQQQADG      60
GWGSADFPLF RHAPTWAALL ALQRADPLPG AADAVQTATR FLQRQPDPYA HAVPEDAPIG     120
AELILPQFCG EAAWLLGGVA FPRHPALLPL RQACLVKLGA VAMLPSGHPL LHSWEAWGTS     180
PTTACPDDDG SIGISPAATA AWRAQAVTRG STPQVGRADA YLQMASRATR SGIEGVFPNV     240
WPINVFEPCW SLYTLHLAGL FAHPALAEAV RVIVAQLEAR LGVHGLGPAL HFAADADDTA     300
VALCVLHLAG RDPAVDALRH FEIGELFVTF PGERNASVST NIHALHALRL LGKPAAGASA     360
YVEANRNPHG LWDNEKWHVS WLYPTAHAVA ALAQGKPQWR DERALAALLQ AQRDDGGWGA     420
GRGSTFEETA YALFALHVMD GSEEATGRRR IAQVVARALE WMLARHAAHG LPQTPLWIGK     480
ELYCPTRVVR VAELAGLWLA LRWGRRVLAE GAGAAP                              516

SEQ ID NO: 39
atggttttgt cttcttcttg tactacagta ccacacttat cttcattagc tgtcgtgcaa      60
cttggtcctt ggagcagtag gattaaaaag aaaaccgata ctgttgcagt accagccgct     120
gcaggaaggt ggagaagggc cttggctaga gcacagcaca catcagaatc cgcagctgtc     180
gcaaagggca gcagtttgac ccctatagtg agaactgacg ctgagtcaag agaacaaga     240
tggccaaccg atgacgatga cgccgaacct ttagtggatg agatcaggc aatgcttact     300
tccatgtctg atggtgacat ttccgtgagc gcatacgata cagcctggtc cggattggtt     360
ccaagattag acggcggtga aggtcctcaa tttccagcag ctgtgagatg gataagaaat     420
aaccagttgc ctgacggaag ttggggcgat gccgcattat tctctgccta tgacaggctt     480
atcaatacccc ttgcctgcgt tgtaacttg acaaggtggt ccctagaacc agagatgaga     540
ggtagaggac tatctttttt gggtaggaac atgtggaaat tagcaactga agatgaagag     600
tcaatgccta ttggcttcga attagcattt ccatctttga tagagcttgc taagagccta    660
ggtgtccatg acttccctta tgatcaccag gccctacaag aatctactc ttcaagagag      720
atcaaaatga gaggattcc aaaagaagtg atgcataccg ttccaacatc aatattgcac      780
agtttggagg gtatgcctgg cctagattgg gctaaactac ttaaactaca gagcagcgac     840
ggaagttttt tgttctcacc agctgccact gcatatgctt taatgaatac cggagatgac     900
aggtgtttta gctacatcga tagaacagta aagaaattca acggcggcgt ccctaatgtt    960
tatccagtgg atctatttga acatatttgg gccgttgata gacttgaaag attaggaatc   1020
tccaggtact tccaaaagga gatcgaacaa tgcatggatt atgtaaacag gcattggact   1080
gaggacggta tttgttgggc aaggaactct gatgtcaaag aggtgaacga cacagctatg   1140
gcctttgagc ttcttaggtt gcacggctac agcgtcagtc ctgatgtgtt taaaaacttc   1200
gaaaaggacg gtgaattttt cgcatttgtc ggacagtcta atcaagctgt taccggtatg   1260
tacaacttaa acagagcaag ccagatatcc ttcccaggcg aggatgtgct tcatagagct   1320
ggtgccttct catatgagtt cttgaggaga aaagaagcag agggagcttt gagggacaag   1380
tggatcattt ctaaagatct acctggtgaa gttgtgtata cttgggattt tccatggtac   1440
ggcaacttac ctagagtcga ggccagagac tacctagagc aatacggagg tggtgatgac   1500
gtttggattg gcaagacatt gtataggatg ccacttgtaa acaatgatgt atatttggaa   1560
ttggcaagaa tggatttcaa ccactgccag gctttgcatc agttagagtg gcaaggacta   1620
aaaagatggt atactgaaaa taggttgatg gactttggtg tcgcccaaga agatgccctt   1680
agcttatt ttcttgcagc cgcatctgtt tacgagcctt gtagagctgc cgagaggctt    1740
gcatgggcta gagccgcaat actagctaac gccgtgagca cccacttaag aaatagccca   1800
tcattcagag aaaggttaga gcattctctt aggtgtagac ctagtgaaga gacagatggc   1860
tcctggttta actcctcaag tggctctgat gcagtttag taaaggctgt cttaagactt   1920
actgattcat tagccaggga agcacagcca atccatggag gtgacccaga agatattata   1980
cacaagttgt taagatctgc ttgggccgag tgggttaggg aaaaggcaga cgctgccgat   2040
agcgtgtgca atggtagttc tgcagtagaa caagagggat caagaatggt ccatgataaa   2100
cagacctgtc tattattggc tagaatgatc gaaatttctg ccggtagggc agctggtgaa   2160
gcagccagtg aggacggcga tagaagaata attcaattaa ggctccat ctgcgacagt    2220
cttaagcaaa aaatgctagt ttcacaggac cctgaaaaaa atgaagagat gatgctctac   2280
gtggatgacg aattgaagtt gaggattaga gagttcgttc aatatttgct tagactaggt   2340
gaaaaaaga ctggatctag cgaaaccagg caaacatttt taagtatagt gaaatcatgt   2400
tactatgctg ctcattgccc acctcatgtc gttgatagac acattagtag agtgattttc   2460
gagccagtaa gtgccgcaaa gtaaccgcgg                                    2490

SEQ ID NO: 40
MVLSSSCTTV PHLSSLAVVQ LGPWSSRIKK KTDTVAVPAA AGRWRRALAR AQHTSESAAV      60
AKGSSLTPIV RTDAESRRTR WPTDDDDAEP LVDEIRAMLT SMSDGDISVS AYDTAWVGLV     120
PRLDGGEGPQ FPAAVRWIRN NQLPDGSWGD AALFSAYDRL INTLACVVTL TRWSLEPEMR     180
GRGLSFLGRN MWKLATEDEE SMPIGFELAP PSLIELAKSL GVHDFPYDHQ ALQGIYSSRE     240
IKMKRIPKEV MHTVPTSILH SLEGMPGLDW AKLLKLQSSD GSFLFSPAAT AYALMNTGDD     300
RCFSYIDRTV KKFNGGVPNV YPVDLFEHIW AVDRLERLGI SRYFQKEIEQ CMDYVNRHWT     360
EDGICWARNS DVKEVDDTAM AFRLLRLHGY SVSPDVFKNF EKDGEFFAFV GQSNQAVTGM     420
YNLNRASQIS FPGEDVLHRA GAFSYEFLRR KEAEGALRDK WIISKDLPGE VVYTLDFPWY     480
GNLPRVEARD YLEQYGGGDD VWIGKTLYRM PLVNNDVYLE LARMDFNHCQ ALHQLEWQGL     540
```

TABLE 10-continued

Sequences disclosed herein.

```
KRWYTENRLM DFGVAQEDAL RAYFLAAASV YEPCRAAERL AWARAAILAN AVSTHLRNSP    600
SFRERLEHSL RCRPSEETDG SWFNSSSGSD AVLVKAVLRL TDSLAREAQP IHGGDPEDII    660
HKLLRSAWAE WVREKADAAD SVCNGSSAVE QEGSRMVHDK QTCLLLARMI EISAGRAAGE    720
AASEDGDRRI IQLTGSICDS LKQKMLVSQD PEKNEEMMSH VDDELKLRIR EFVQYLLRLG    780
EKKTGSSETR QTFLSIVKSC YYAAHCPPHV VDRHISRVIF EPVSAAK                 827

SEQ ID NO: 41
cttcttcact aaatacttag acagagaaaa cagagctttt taaagccatg tctcttcagt     60
atcatgttct aaactccatt ccaagtacaa cctttctcag ttctactaaa acaacaatat    120
cttcttcttt cctaccatc tcaggatctc ctctcaatgt cgctagagac aaatccagaa    180
gcggttccat acattgttca aagcttcgaa ctcaagaata cattaattct caagaggttc    240
aacatgattt gcctctaata catgagtggc aacagcttca aggagaagat gctcctcaga    300
ttagtgttgg aagtaatagt aatgcattca aagaagcagt gaagagtgtg aaaacgatct    360
tgagaaacct aacggacggg gaaattacga tatcggctta cgatacagct tgggttgcat    420
tgatcgatgc cggagataaa actccggcgt ttccctccgc cgtgaaatgg atcgccgaga    480
accaactttc cgatggttct tggggagatg cgtatctctt ctcttatcat gatcgtctca    540
tcaatacct tgcatgcgtc gttgctctaa gatcatggaa tctctttcct catcaatgca    600
acaaaggaat cacgttttc cgggaaaata ttgggaagct agaagacgaa aatgatgagc    660
atatgccaat cggattcgaa gtagcattcc catcgttgct tgagatagct cgaggaataa    720
acattgatgt accgtacgat tctccggtct taaaagatat atacgccaag aaagagctaa    780
agcttacaag gataccaaaa gagataatgc acaagatacc aacaacattg ttgcatagtt    840
tggagggat gcgtgattta gattgggaaa agctcttgaa acttcaatct caagacggat    900
ctttcctctt ctctccttcc tctaccgctt ttgcattcat gcagacccga gacagtaact    960
gcctcgagta tttgcgaaat gccgtcaaac gtttcaatgg aggagttccc aatgtctttc   1020
ccgtggatct tttcgagcac atatggatag tggatcggtt acaacgttta gggatatcga   1080
gatactttga agaagagatt aaagagtgtc ttgactatgt ccacagatat tggaccgaca   1140
atggcatatg ttgggctaga tgttcccatg tccaagacat cgatgataca gccatggcat   1200
ttaggctctt aagacaacat ggataccaag tgtccgcaga tgtattcaag aactttgaga   1260
aagagggaga gttttctgc tttgtggggc aatcaaacca agcagtaacc ggtatgttca   1320
acctataccg ggcatcacaa ttggcgtttc caagggaaga gatattgaaa aacgccaaag   1380
agttttctta taattatctg ctagaaaaac gggagagaga ggagttgatt gataagtgga   1440
ttataatgaa agacttacct ggcgagattg ggtttgcgtt agagattcca tggtacgcaa   1500
gcttgcctcg agtagagacg agattctata ttgatcaata tggtggagaa aacgacgttt   1560
ggattggcaa gactctttat aggatgccat acgtgaacaa taatggatat ctggaattag   1620
caaaacaaga ttacaacaat tgccaagctc agcatcagct cgaatgggac atattccaaa   1680
agtggtatga agaaaatagg ttaagtgagt ggggtgtgcg cagaagtgag cttctcgagt   1740
gttactactt agcggctgca actatatttg aatcagaaag gtcacatgag agaatggttt   1800
gggctaagtc aagtgtattg gttaaagcca tttcttcttc ttttgggaa tcctctgact   1860
ccagaagaag cttctccgat cagtttcatg aatacattgc caatgctcga cgaagtgatc   1920
atcacttaa tgacaggaac atgagattgg accgaccagg atcggttcag gccagtcggc   1980
ttgccggagt gttaatcggg actttgaatc aaatgtcttt tgaccttttc atgtctcatg   2040
gccgtgacgt taacaatctc ctctatctat cgtggggaga ttggatggaa aaatggaaac   2100
tatatggaga tgaaggagaa ggagagctca tggtgaagat gataattcta atgaagaaca   2160
atgacctaac taacttcttc acccacactc acttcgttcg tctcgcggaa atcatcaatc   2220
gaatctgtct tcctcgccaa tacttaaagg caaggagaaa cgatgagaag gagaagacaa   2280
taaagagtat ggaaggag atggggaaaa tggttgagtt agcattgtcg gagagtgaca   2340
catttcgtga cgtcagcatc acgtttcttg atgtagcaaa agcattttac tactttgctt   2400
tatgtggcga tcatctccaa actcacatct ccaaagtctt gtttcaaaaa gtctagtaac   2460
ctcatcatca tcatcgatcc attaacaatc agtggatcga tgtatccata gatgcgtgaa   2520
taatatttca tgtagagaag gagaacaaat tagatcatgt agggttatca                2570

SEQ ID NO: 42
MSLQYHVLNS IPSTTFLSST KTTISSSFLT ISGSPLNVAR DKSRSGSIHC SKLRTQEYIN     60
SQEVQHDLPL IHEWQQLQGE DAPQISVGSN SNAFKEAVKS VKTILRNLTD GEITISAYDT    120
AWVALIDAGD KTPAFPSAVK WIAENQLSDG SWGDAYLFSY HDRLINTLAC VVALRSWNLF    180
PHQCNKGITF FRENIGKLED ENDEHMPIGF EVAFPSLLEI ARGINIDVPY DSPVLKDIYA    240
KKELKLTRIP KEIMHKIPTT LLHSLEGMRD LDWEKLLKLQ SQDGSFLFSP SSTAFAFMQT    300
RDSNCLEYLR NAVKRFNGGV PNVFPVDLFE HIWIVDRLQR LGISRYFEEE IKECLDYVHR    360
YWTDNGICWA RCSHVQDIDD TAMAFRLLRQ HGYQVSADVF KNFEKEGEFF CFVGQSNQAV    420
TGMFNLYRAS QLAFPREEIL KNAKEFSYNY LLEKREREEL IDKWIIMKDL PGEIGFALEI    480
PWYASLPRVE TRFYIDQYGG ENDVWIGKTL YRMPYVNNNG YLELAKQDYN NCQAQHQLEW    540
DIFQKWYEEN RLSEWGVRRS ELLECYYLAA ATIFESERSH ERMWAKSSV LVKAISSSFG    600
ESSDSRRSFS DQFHEYIANA RRSDHHFNDR NMRLDRPGSV QASRLAGVLI GTLNQMSFDL    660
FMSHGRDVNN LLYLSWGDWM EKWKLYGDEG EGELMVKMII LMKNNDLTNF FTHTHFVRLA    720
EIINRICLPR QYLKARRNDE KEKTIKSMEK EMGKMVELAL SESDTFRDVS ITFLDVAKAF    780
YYFALCGDHL QTHISKVLFQ KV                                              802

SEQ ID NO: 43
atgaatttga gtttgtgtat agcatctcca ctattgacca aatctaatag accagctgct     60
ttatcagcaa ttcatacagc tagtacatcc catggtggcc aaaccaaccc tacgaatctg    120
ataatcgata cgaccaagga gagaataaca aaacaattca aaaatgttga aatttcagtt    180
tcttcttatg atactgcgtg ggttgccatg gttccatcac ctaattctcc aaagtctcca    240
tgtttcccag taatgtttga ttggctgatt aacaaccagt tgaatgatgg atcttgggat    300
ttagtcaatc acacgcacaa tcacaaccat ccacttttga aagattcttt atcctcaact    360
ttggcttgca tcgtgccct aaagagatgg aacgtaggtg aggatcagat taacaagggg    420
cttagtttca ttgaatctaa cttggcttcc gcgactgaaa atctcaacc atctccaata    480
ggattcgata tcatctttcc aggtctgtta gagtacgcca aaaatctaga tcaacttta    540
ctgtctaagc aaactgattt ctcactaatg ttacacaaga gagaattaga acaaaagaga    600
```

TABLE 10-continued

Sequences disclosed herein.

```
tgtcattcaa acgaaatgga tggttaccta gcttatatct ctgaaggtct tggtaatctt    660
tacgattgga atatggtgaa aaagtaccag atgaaaaatg gctcagtttt caattcccct    720
tctgcaactg cggcagcatt cattaaccat caaaatccag gatgcctgaa ctatttgaat    780
tcactactag acaaattcgg caacgcagtt ccaactgtat accctcacga tttgtttatc    840
agattgagta tggtggatac aattgaaaga cttggtatat cccaccactt tagagtcgag    900
atcaaaaatg ttttggatga gacataccgt tgttgggtgg agagagatga acaaatcttt    960
atggatgttg tgacgtgcgc gttggccttt agattgttgc gtattaacgg ttacgaagtt   1020
agtccagatc cacttgccga aattacaaac gaattagctt taaaggatga atacgccgct   1080
cttgaaacat atcatgcgtc acatatcctt taccaagagg acttatcatc tggaaaacaa   1140
attcttaaat ctgctgattt cctgaaggaa atcatatcca ctgatagtaa tagactgtcc   1200
aaactgatcc ataaagaggt tgaaaatgca cttaagttcc ctattaacac cggcttagaa   1260
cgtattaaca caagacgtaa catccagctt tacaacgtag acaatactag aatcttgaaa   1320
accacttacc attcttccaa catatcaaac actgattacc taagattagc tgttgaagat   1380
ttctacacat gtcagtctat ctatagagaa gagctgaaag gattagagag atgggtcgtt   1440
gagaataagc tagatcaatt gaaatttgcc agacaaaaga cagcttattg ttacttctca   1500
gttgccgcca ctttatcaag tccagaattg tcagatgcac gtatttcttg ggctaaaaac   1560
ggaattttga caactgttgt tgatgatttc tttgatattg gcgggacaat cgacgaattg   1620
acaaacctga ttcaatgcgt tgaaaagtgg aatgtcgatg tcgataaaga ctgttgctca   1680
gaacatgtta gaatactgtt cttggctctg aaagtatgcta tctgttggat cggggatgag   1740
gctttcaaat ggcaagctag agatgtgacg tctcacgtca ttcaaacctg gctagaactg   1800
atgaactcta tgttgagaga agcaatttgg actagagatg catacgttcc tacattaaac   1860
gagtatatgg aaaacgctta tgtctccttt gctttgggtc ctatcgttaa gcctgccata   1920
tactttgtag gaccaaagct atccgaggaa atcgtcgaat catcagaata ccataacttg   1980
ttcaagttaa tgtccacaca aggcagatta cttaatgata ttcattcttt caaaagagag   2040
tttaaggaag gaaagttaaa tgctgttgct ctgcatcttt ctaatggcga agtggtaaa    2100
gtcgaagagg aagtagttga ggaaatgatg atgatgatca aaaacaagag aaaggagttg   2160
atgaaactaa tcttcgaaga gaacggttca attgttccta gagcatgtaa ggatgcattt   2220
tggaacatgt gtcatgtgct aaactttttc tacgcaaacg acgatggttt tactgggaac   2280
acaatactag atacagtgaa agacatcata tacaacccct tggtcttagt aaacgaaaac   2340
gaggagcaaa gataa                                                    2355
```

SEQ ID NO: 44
```
MNLSLCIASP LLTKSNRPAA LSAIHTASTS HGGQTNPTNL IIDTTKERIQ KQFKNVEISV     60
SSYDTAWVAM VPSPNSPKSP CFPECLNWLI NNQLNDGSWG LVNHTHNHNH PLLKDSLSST    120
LACIVALKRW NVGEDQINKG LSFIESNLAS ATEKSQPSPI GFDIIFPGLL EYAKNLDINL    180
LSKQTDFSLM LHKRELEQKR CHSNEMDGYL AYISEGLGNL YDWNMVKKYQ MKNGSVFNSP    240
SATAAAFINH QNPGCLNYLN SLLDKFGNAV PTVYPHDLFI RLSMVDTIER LGISHHFRVE    300
IKNVLDETYR CWVERDEQIF MDVVTCALAF RLLRINGYEV SPDPLAEITN ELALKDEYAA    360
LETYHASHIL YQEDLSSGKQ ILKSADFLKE IISTDSNRLS KLIHKEVENA LKFPINTGLE    420
RINTRRNIQL YNVDNTRILK TTYHSSNISN TDYLRLAVED FYTCQSIYRE ELKGLERWVV    480
ENKLDQLKFA RQKTAYCYFS VAATLSSPEL SDARISWAKN GILTTVVDDF FDIGGTIDEL    540
TNLIQCVEKW NVDVDKDCCS EHVRILFLAL KDAICWIGDE AFKWQARDVT SHVIQTWLEL    600
MNSMLREAIW TRDAYVPTLN EYMENAYVSF ALGPIVKPAI YFVGPKLSEE IVESSEYHNL    660
FKLMSTQGRL LNDIHSFKRE FKEGKLNAVA LHLSNGESGK VEEEVVEEMM MMIKNKRKEL    720
MKLIFEENGS IVPRACKDAF WNMCHVLNFF YANDDGFTGN TILDTVKDII YNPLVLVNEN    780
EEQR                                                                784
```

SEQ ID NO: 45
```
atgaatctgt ccctttgtat agctagtcca ctgttgacaa atcttctag accaactgct      60
cttttctgcaa ttcatactgc cagtactagt catggaggtc aaacaaaccc aacaaatttg   120
ataatcgata ctactaagga gagaatccaa aagctattca aaaatgttga atctcagta    180
tcatcttatg acacccgcatg ggttgcaatg gtgccatcac ctaattcccc aaaaagtcca   240
tgttttccag agtgcttgaa ttggttaatc aataatcagt taaacgatggg ttcttggggt   300
ttagtcaacc acactcataa ccacaatcat ccattattga aggactcttt atcatcaaca   360
ttagcctgta ttgttgcatt gaaaagatgg aatgtaggtg aagatcaaat caacaagggt   420
ttatcattca tagaatccaa tctagcttct gctaccgaca atcacaaacc atctccaatc   480
gggttcgaca taatccttccc tggttttgctg gagtatgcca aaaaccttga tatcaactta   540
ctgtctaaac aaaacagattt ctctttgatg ctacacaaaa gagagttaga gcagaaaaga   600
tgccattcta acgaaattga cgggtactta gcatatatct cagaagtttt gggtaatttg   660
tatgactgga acatggtcaa aaagtatcag atgaaaaatg gatccgtatt caattctcct   720
tctgcaactg ccgcagcatt cattaatcat caaaacccctg ggtgtcttaa ctactttgaa   780
tcactattag ataagtttgg aaatgcagtt ccaacagttg atcctttgga cttgtacatc   840
agattatcta tggttgacac tatagagaga ttaggtattt ctcatcattt cagagttgag   900
atcaaaaatg ttttggacga gacatacaga tgttgggtcg aaagagatga gcaaatcttt   960
atggatgtcg tgacctgcgc tctggctttt agattgctaa ggatacacgg atacaaagta  1020
tctcctgatc aactggctga gattacaaac gaactggctt tcaaagacga atacgccgca  1080
ttagaaacat accatgcatc ccaaatacttt taccaggaag acctaagttc aggaaaacaa  1140
atcttgaagt ctgcagattt cctgaaaggc attctgtcta cagatagtaa taggttgtct  1200
aaattgatac acaaggaagt agaaaacgca ctaaagtttc ctattaacac tggttttagag  1260
agaatcaata ctaggagaaa cattcagctg tacaacgtag ataatacaag gattcttaag  1320
accacctacc atagttcaaa catttccaac acctattact taagattagc tgtcgaagac  1380
ttttacactt gtcaatcaat ctacagagag gagttaaagg gcctagaaag atgggtagtt  1440
caaaacttgg atcaactt gaagtttgct agacagaaga cagcatactg ttatttctct   1500
gttgctgcta cccttttcatc cccagaattg tctgatgcca gaataagttg gcgcaaaaat  1560
ggtattctta caactgtagt cgatgatttc tttgatattg gaggtactat tgatgaactg  1620
acaaatctta ttcaatgtgt tgaaaagtgg aacgtggatg tagataagga ttgctgcagt  1680
gaacatgtga gaatactttt cctggctcta aaagatgcaa tatgttggat tggcgacgag  1740
gccttcaagt ggcaagctag agatgttaca tctcatgtca tccaaacttg gcttgaactg  1800
```

TABLE 10-continued

Sequences disclosed herein.

```
atgaactcaa tgctaagaga agcaatctgg acaagagatg catacgttcc aacattgaac    1860
gaatacatgg aaaacgctta cgtctcattt gccttgggtc ctattgttaa gccagccata    1920
tactttgttg ggccaaagtt atccgaagag attgttgagt cttccgaata tcataaccta    1980
ttcaagttaa tgtcaacaca aggcagactt ctgaacgata tccactcctt caaaagagaa    2040
ttcaaggaag gtaagctaaa cgctgttgct ttgcacttgt ctaatggtga atctggcaaa    2100
gtggaagagg aagtcgttga ggaaatgatg atgatgatca aaaacaagag aaaggaattg    2160
atgaaattga ttttcgagga aaatggttca atcgtaccta gagcttgtaa agatgcttat    2220
tggaatatgt gccatgttct taacttcttt tacgctaatg atgatggctt cactggaaat    2280
acaatattgg atacagttaa agatatcatc tacaacccac ttgttttggt caatgagaac    2340
gaggaacaaa gataa                                                    2355

SEQ ID NO: 46
MNLSLCIASP LLTKSSRPTA LSAIHTASTS HGGQTNPTNL IIDTTKERIQ KLFKNVEISV     60
SSYDTAWVAM VPSPNSPKSP CFPECLNWLI NNQLNDGSWG LVNHTHNHNH PLLKDSLSST    120
LACIVALKRW NVGEDQINKG LSFIESNLAS ATDKSQPSPI GFDIIFPGLL EYAKNLDINL    180
LSKQTDFSLM LHKRELEQKR CHSNEIDGYL AYISEGLGNL YDWNMVKKYQ MKNGSVFNSP    240
SATAAAFINH QNPGCLNYLN SLLDKFGNAV PTVYPLDLYI RLSMVDTIER LGISHHFRVE    300
IKNVLDETYR CWVERDEQIF MDVVTCALAF RLLRIHGYKV SPDQLAEITN ELAFKDEYAA    360
LETYHASQIL YQEDLSSGKQ ILKSADFLKG ILSTDSNRLS KLIHKEVENA LKFPINTGLE    420
RINTRRNIQL YNVDNTRILK TTYHSSNISN TYYLRLAVED FYTCQSIYRE ELKGLERWVI    480
QNKLDQLKFA RQKTAYCYFS VAATLSSPEL SDARISWAKN GILTTVVDDF FDIGGTIDEL    540
TNLIQCVEKW NVDVDKDCCS EHVRILFLAL KDAICWIGDE AFKWQARDVT SHVIQTWLEL    600
MNSMLREAIW TRDAYVPTLN EYMENAYVSF ALGPIVKPAI YFVGPKLSEE IVESSEYHNL    660
FKLMSTQGRL LNDIHSFKRE FKEGKLNAVA LHLSNGESGK VEEEVVEEMM MMIKNKRKEL    720
MKLIFEENGS IVPRACKDAF WNMCHVLNFF YANDDGFTGN TILDTVKDII YNPLVLVNEN    780
EEQR                                                                784

SEQ ID NO: 47
atggctatgc cagtgaagct aacacctgcg tcattatcct taaaagctgt gtgctgcaga     60
ttctcatccg gtggccatgc tttgagattc gggagtagtc tgccatgttg gagaaggacc    120
cctacccaaa gatctacttc ttcctctact actagaccag ctgccgaagt gtcatcaggt    180
aagagtaaac aacatgatca ggaagctagt gaagcgacta tcagacaaca attacaactt    240
gtggatgtcc tggagaatat gggaatatcc agacattttg ctgcagagat aaagtgcata    300
ctagacagaa cttacagatc ttggttacaa agacacgagg aaatcatgct ggacactatg    360
acatgtgcta tggcttttag aatcctaaga ttgaacggat acaacgtttc atcagatgaa    420
ctataccacg ttgtagaggc atctggtctg cataattcct tgggtgggta tcttaacgat    480
accagaacac tacttgaatt acacaaggct tcaacagtta gtatctctga ggatgaatct    540
atcttagatt caattggctc tagatccaga acattgctta gaacaattt ggagtctggt    600
ggcgcactga gaaagccttc tttattcaaa gaggttgaac atgcactgga tggacctttt    660
tacaccacac ttgatagact tcatcatagg tggaatattg aaaacttcaa cattattgag    720
caacacatgt tggagactcc atactttatct aaccagcata catcaaggga tatcctagca    780
ttgtcaatta gagatttttc ctcctccaaa ttcacttatc aacaagagct acagcatctg    840
gagagttggg ttaaggaatg tagattagat caactacagt tcgcaagaca gaaattagcg    900
tacttttacc tatcagccgc aggcaccatg tttttctcctg agctttctga tgcgagaaca    960
ttatgggcca aaaacggggt gttgacaact attgttgatg atttctttga tgttgccggt   1020
tctaaagagg aattggaaaa cttagtcatg ctggtcgaaa tgtgggatga acatcacaaa   1080
gttgaattct attctgagca ggtcgaaatc atcttctctt ccatctacga ttctgtcaac   1140
caattgggtg agaaggcctc tttggttcaa gacagatcaa ttacaaaaca ccttgttgaa   1200
atatggttag acttgttaaa gtccatgatg acgaagttg aatggagact gtcaaaatac   1260
gtgcctacag aaaaggaata catgattaat gcctctctta tcttcggcct aggtccaatc   1320
gttttaccag cttttgtattt cgttggtcca aagattcag aaagtatagt aaaggaccca   1380
gaatatgatg aattgttcaa actaatgtca acatgtggta gattgttgaa tgacgtgcaa   1440
acgttcgaaa gagaataacaa tgagggtaaa ctgaattctg tcagtctatt ggttcttcac   1500
ggaggcccaa tgtctatttc agacgcaaag aggaaattac aaaagcctat tgatacgtgt   1560
agaagagatc ttcttttcttt ggtccttaga gaagagtctg tagtaccaag accatgtaag   1620
gaactattct ggaaaatgtg taagtgtgc tatttctttt actcaacaac tgatgggttt   1680
tctagtcaag tcgaaagagc aaaagaggta gacgctgtca taaatgagcc actgaagttg   1740
caaggttctc atacactggt atctgatgtt taa                                1773

SEQ ID NO: 48
MAMPVKLTPA SLSLKAVCCR FSSGGHALRF GSSLPCWRRT PTQRSTSSST TRPAAEVSSG     60
KSKQHDQEAS EATIRQQLQL VDVLENMGIS RHFAAEIKCI LDRTYRSWLQ RHEEIMLDTM    120
TCAMAFRILR LNGYNVSSDE LYHVVEASGL HNSLGGYLND TRTLLELHKA STVSISEDES    180
ILDSIGSRSR TLLREQLESG GALRKPSLFK EVEHALDGPF YTTLDRLHHR WNIENFNIIE    240
QHMLETPYLS NQHTSRDILA LSIRDFSSSQ FTYQQELQHL ESWVKECRLD QLQFARQKLA    300
YFYLSAAGTM FSPELSDART LWAKNGVLTT IVDDFFDVAG SKEELENLVM LVEMWDEHHK    360
VEFYSEQVEI IFSSIYDSVN QLGEKASLVQ DRSITKHLVE IWLDLLKSMM TEVEWRLSKY    420
VPTEKEYMIN ASLIFGLGPI VLPALYFVGP KISESIVKDP EYDELFKLMS TCGRLLNDVQ    480
TFEREYNEGK LNSVSLLVLH GGPMSISDAK RKLQKPIDTC RRDLLSLVLR EESVVPRPCK    540
ELFWKMCKVC YFFYSTTDGF SSQVERAKEV DAVINEPLKL QGSHTLVSDV               590

SEQ ID NO: 49
atgcagaact tccatggtac aaaggaaagg atcaaaaaga tgtttgcaca gattgaattg     60
tccgttttctt cttatgatac agcctggggtt gcaatggtcc catcccctga ttgcccagaa    120
acaccttgtt ttccagaatg tactaaatgg atcctagaaa atcagtttggg tgatggtagt    180
tggtcacttc tcatggcaa tccacttcta gttaaagatg cattatcttc cactcttgct    240
tgtattctgg ctcttaaaag atggggaatc ggtgaggaac agattaacaa aggactgaga    300
ttcatagaac tcaactctgc tagtgtaacc gataacgaac aacacaaacc aattggattt    360
```

TABLE 10-continued

Sequences disclosed herein.

```
gacattatct ttccaggtat gattgaatac gctatagact tagacctgaa tctaccacta    420
aaaccaactg acattaactc catgttgcat cgtagagccc ttgaattgac atcaggtgga    480
ggcaaaaatc tagaaggtag aagagcttac ttggcctacg tctctgaagg aatcggtaag    540
ctgcaagatt gggaaatggc tatgaaatac aacgtaaaaa acggatctct gttcaatagt    600
ccatcaacaa ctgcagctgc attcatccat atacaagatg ctgaatgcct ccactatatt    660
cgttctcttc tccagaaatt tggaaacgca gtccctacaa tatacctct cgatatctat     720
gccagacttt caatggtaga tgccctggaa cgtcttggta ttgatagaca tttcagaaag    780
gagagaaagt tcgttctgga tgaaacatac agattttggt tgcaaggaga agaggagatt    840
ttctccgata acgcaacctg tgctttggcc ttcagaatat tgagacttaa tggttacgat    900
gtctctcttg aagatcactt ctctaactct ctgggcggtt acttaaagga ctcaggagca    960
gctttagaac tgtacagagc cctccaattg tcttacccag acgagtccct cctggaaaag   1020
caaaattcta gaacttctta cttcttaaaa caaggtttat ccaatgtctc cctctgtggt   1080
gacagattgc gtaaaaacat aattggagag gtgcatgatg ctttaaactt ttccgaccac   1140
gctaacttac aaagattagc tattcgtaga aggattaagc attacgctac tgacgataca   1200
aggattctaa aaacttccta cagatgctca acaatcggta accaagattt tctaaaactt   1260
gcagtggaag atttcaatat ctgtcaatca atacaaagag aggaattcaa gcatattgaa   1320
agatgggtcg ttgaaagacg tctagacaag ttaaagttcg ctagacaaaa agaggcctat   1380
tgctatttct cagccgcagc aacattgttt gcccctgaat tgtctgatgc tagaatgtct   1440
tgggccaaaa atggtgtatt gacaactgtg gttgatgatt tcttcgatgt cggaggctct   1500
gaagaggaat tagttaactt gatagaattg atcgagcgtt gggatgtgaa tggcagtgca   1560
gattttgta gtgaggaagt tgagattatc tattctgcta tccactcaac tatctctgaa    1620
ataggtgata agtcatttgg ctggcaaggt agagatgtaa agtctcaagt tatcaagatc   1680
tggctggact tattgaaatc aatgttaact gaagctcaat ggtcttcaaa caagtctgtt   1740
cctaccctag atgagtatat gacaaccgcc catgtttcat tcgcacttgg tccaattgta   1800
cttcagcct tatacttcgt tggcccaaag ttgtcagaag aggttgcagg tcatcctgaa    1860
ctactaaacc tctacaaagt cacatctact tgtggcagac tactgaatga ttggagaagt   1920
tttaagagag aatccgagga aggtaagctc aacgctatca gtttatacat gatccactcc   1980
ggtggtgctt ctacagaaga ggaaacaatc gaacatttca aaggtttgat tgattctcag   2040
agaaggcaac tgttacaatt ggtgttgcaa gagaaggata gtatcatacc tagaccatgt   2100
aaagatctat tttggaatat gattaagtta ttacacactt tctacatgaa agatgatggc   2160
ttcacctcaa atgagatgag gaatgtagtt aaggcaatca ttaacgaacc aatctcactg   2220
gatgaattat ga                                                       2232

SEQ ID NO: 50
MSCIRPWFCP SSISATLTDP ASKLVTGEFK TTSLNFHGTK ERIKKMFDKI ELSVSSYDTA     60
WVAMVPSPDC PETPCFPECT KWILENQLGD GSWSLPHGNP LLVKDALSST LACILALKRW    120
GIGEEQINKG LRFIELNSAS VTDNEQHKPI GFDIIFPGMI EYAKDLDLNL PLKPTDINSM    180
LHRRALELTS GGGKNLEGRR AYLAYVSEGI GKLQDWEMAM KYQRKNGSLF NSPSTTAAAF    240
IHIQDAECLH YIRSLLQKFG NAVPTIYPLD IYARLSMVDA LERLGIDRHF RKERKFVLDE    300
TYRFWLQGEE EIFSDNATCA LAFRILRLNG YDVSLEDHFS NSLGGYLKDS GAALELYRAL    360
QLSYPDESLL EKQNSRTSYF LKQGLSNVSL CGDRLRKNII GEVHDALNFP DHANLQRLAI    420
RRRIKHYATD DTRILKTSYR CSTIGNQDFL KLAVEDFNIC QSIQREEFKH IERWVVERRL    480
DKLKFARQKE AYCYFSAAAT LFAPELSDAR MSWAKNGVLT TVVDDFFDVG GSEEELVNLI    540
ELIERWDVNG SADFCSEEVE IIYSAIHSTI SEIGDKSFGW QGRDVKSHVI KIWLDLLKSM    600
LTEAQWSSNK SVPTLDEYMT TAHVSFALGP IVLPALYFVG PKLSEEVAGH PELLNLYKVM    660
STCGRLLNDW RSFKRESEEG KLNAISLYMI HSGGASTEEE TIEHFKGLID SQRRQLLQLV    720
LQEKDSIIPR PCKDLFWNMI KLLHTFYMKD DGFTSNEMRN VVKAIINEPI SLDEL         775

SEQ ID NO: 51
atgtctatca accttcgctc ctccggttgt tcgtctccga tctcagctac tttggaacga     60
ggattggact cagaagtaca gacaagagct aacaatgtga gctttgagca acaaaggag    120
aagattagga agatgttgga gaaagtggag cttttctgttt cggcctacga tactagttgg    180
gtagcaatgg ttccatcacc gagctcccaa aatgctccac ttttcccaca gtgtgtgaaa    240
tggttattgg ataatcaaca tgaagatgga tcttggggac ttgataacca tgaccatcaa    300
tctcttaaga aggatgtgtt atcatctaca ctggctagta tcctcgcgtt aaagaagtgg    360
ggaattggtg aaagacaaat aaacaagggt ctccagttta ttgagctgaa ttctgcatta    420
gtcactgatg aaaccataca gaaaccaaca gggtttgata ttatatttcc tgggatgatt    480
aaatatgcta gagatttgaa tctgacgatt ccattgggct cagaagtggt ggatgacatg    540
atacgaaaaa gagatctgga tcttaaatgt gatagtgaaa gttttcaaa gggaagagaa    600
gcatatctgg cctatgtttt agaggggaca agaaacctaa aagattggga tttgatagtc    660
aaatatcaaa ggaaaaatgg gtcactgttt gattctccag ccacaacagc agctgctttt    720
actcagtttg gaatgatgg ttgtctccgt tatctctgtt ctctccttca gaaattcgag    780
gctgcagttc cttcagttta tccatttgat caatatgcac gccttagtat aattgtcact    840
cttgaaagct taggaattga tagagatttc aaaaccgaaa tcaaaagcat attggatgaa    900
acctatagat attggcttcg tggggatgaa gaaatatgtt tggacttggc cacttgtgct    960
ttggcttttcc gattattgct tgctcatggc tatgatgtgt cttacgatcc gctaaaacca   1020
tttgcagaag aatctggttt ctctgatact ttggaaggat atgttaagaa tacgttttct   1080
gtgttagaat tatttaaggc tgctcaaagt tatccacatg aatcagcttt gaagaagcag   1140
tgttgttgga ctaaacaata tctggagatg gaattgttgt gatggggttaa gacctctgtt   1200
cgagataaat accctcaagaa agaggtcgag gatgctcttg cttttccctc ctatgcaagc   1260
ctagaaagat cagatcacag gagaaaaata tcaatggttt ctgctgtgga aacaccaga   1320
gttacaaaaa cctcatatcg tttgcacaat atttgcacct ctgatatcct gaagttagct   1380
gtggatgact tcaatttctg ccagtccata caccgtgaag aaatggaacg tcttgataga   1440
tggattgtgg agaatagatt gcaggaactg aaatttgcca gacagaagct ggcttactgt   1500
tatttctctg ggctgcaaac tttatttct ccagaactat ctgatgctcg tatatcgtgg    1560
gccaaaggtg gagtacttac aacgttgtat gacgacttct ttgatgttgg agggtccaaa   1620
gaagaactgg aaaccctcat acacttggtc gaaaagtggg atttgaacgg tgttcctgag   1680
tacagctcag aacatgttga gatcatattc tcagttctaa gggacaccat tctcgaaaca   1740
```

TABLE 10-continued

Sequences disclosed herein.

| | | | | | |
|---|---|---|---|---|---|
| ggagacaaag | cattcaccta | tcaaggacgc | aatgtgacac | accacattgt | gaaaatttgg | 1800 |
| ttggatctgc | tcaagtctat | gttgagagaa | gccgagtggt | ccagtgacaa | gtcaacacca | 1860 |
| agcttggagg | attacatgga | aaatgcgtac | atatcatttg | cattaggacc | aattgtcctc | 1920 |
| ccagctacct | atctgatcgg | acctccactt | ccagagaaga | cagtcgatag | ccaccaatat | 1980 |
| aatcagctct | acaagctcgt | gagcactatg | ggtcgtcttc | taaatgacat | acaaggtttt | 2040 |
| aagagagaaa | gcgcggaagg | gaagctgaat | gcggtttcat | tgcacatgaa | acacgagaga | 2100 |
| gacaatcgca | gcaaagaagt | gatcatagaa | tcgatgaaag | gtttagcaga | gagaaagagg | 2160 |
| gaagaattgc | ataagctagt | tttggaggag | aaaggaagtg | tggttccaag | ggaatgcaaa | 2220 |
| gaagcgttct | tgaaaatgag | caaagtgttg | aacttatttt | acaggaagga | cgatggattc | 2280 |
| acatcaaatg | atctgatgag | tcttgttaaa | tcagtgatct | acgagcctgt | tagcttacag | 2340 |
| aaagaatctt | taacttga | | | | | 2358 |

SEQ ID NO: 52

| | | | | | |
|---|---|---|---|---|---|
| MSINLRSSGC | SSPISATLER | GLDSEVQTRA | NNVSFEQTKE | KIRKMLEKVE | LSVSAYDTSW | 60 |
| VAMVPSPSSQ | NAPLFPQCVK | WLLDNQHEDG | SWGLDNHDHQ | SLKKDVLSST | LASILALKKW | 120 |
| GIGERQINKG | LQFIELNSAL | VTDETIQKPT | GFDIIFPGMI | KYARDLNLTI | PLGSEVVDDM | 180 |
| IRKRDLDLKC | DSEKFSKGRE | AYLAYVLEGT | RNLKDWDLIV | KYQRKNGSLF | DSPATTAAAF | 240 |
| TQFGNDGCLR | YLCSLLQKFE | AAVPSVYPFD | QYARLSIIVT | LESLGIDRDF | KTEIKSILDE | 300 |
| TYRYWLRGDE | EICLDLATCA | LAFRLLLAHG | YDVSYDPLKP | FAEESGFSDT | LEGYVKNTFS | 360 |
| VLELFKAAQS | YPHESALKKQ | CCWTKQYLEM | ELSSWVKTSV | RDKYLKKEVE | DALAFPSYAS | 420 |
| LERSDHRRKI | LNGSAVENTR | VTKTSYRLHN | ICTSDILKLA | VDDFNFCQSI | HREEMERLDR | 480 |
| WIVENRLQEL | KFARQKLAYC | YFSGAATLFS | PELSDARISW | AKGGVLTTVV | DDFFDVGGSK | 540 |
| EELENLIHLV | EKWDLNGVPE | YSSEHVEIIF | SVLRDTILET | GDKAFTYQGR | NVTHHIVKIW | 600 |
| LDLLKSMLRE | AEWSSDKSTP | SLEDYMENAY | ISFALGPIVL | PATYLIGPPL | PEKTVDSHQY | 660 |
| NQLYKLVSTM | GRLLNDIQGF | KRESAEGKLN | AVSLHMKHER | DNRSKEVIIE | SMKGLAERKR | 720 |
| EELHKLVLEE | KGSVVPRECK | EAFLKMSKVL | NLFYRKDDGF | TSNDLMSLVK | SVIYEPVSLQ | 780 |
| KESLT | | | | | | 785 |

SEQ ID NO: 53

| | | | | | |
|---|---|---|---|---|---|
| atggaatttg | atgaaccatt | ggttgacgaa | gcaagatctt | tagtgcagcg | tactttacaa | 60 |
| gattatgatg | acagatacgg | cttcggtact | atgtcatgtg | ctgcttatga | tacagcctgg | 120 |
| gtgtctttag | ttacaaaaac | agtcgatggg | agaaaacaat | ggcttttccc | agagtgtttt | 180 |
| gaatttctac | tagaaacaca | atctgatgcc | ggaggatggg | aaatcgggaa | ttcagcacca | 240 |
| atcgacggta | tattgaatac | agctgcatcc | ttacttgctc | taaaacgtca | cgttcaaact | 300 |
| gagcaaatca | tccaacctca | acatgaccat | aaggatctag | caggtagagc | tgaacgtgcc | 360 |
| gctgcatctt | tgagagcaca | attggctgca | ttggatgtgt | ctacaactga | acacgtcggt | 420 |
| tttgagataa | ttgttcctgc | aatgctagac | ccattagaag | ccgaagatcc | atctctagtt | 480 |
| ttcgattttc | cagctaggaa | acctttgatg | aagattcatg | atgctaagat | gagtagattc | 540 |
| aggccagaat | acttgtatgg | caaacaacca | atgaccgcct | acattcatt | agaggctttc | 600 |
| ataggcaaaa | tcgacttcga | taaggtaaga | caccaccgta | cccatgggtc | tatgatgggt | 660 |
| tctccttcat | ctaccgcagc | ctacttaatg | cacgcttcac | aatgggatgg | tgactcagag | 720 |
| gcttaccttta | gacacgtgat | taaacacgca | gcagggcagg | gaactggtgc | tgtaccatct | 780 |
| gctttcccat | caacacattt | tgagtcatct | tggattctta | ccacattgtt | tagagctgga | 840 |
| ttttcagctt | ctcatcttgc | ctgtgatgag | ttgaacaagt | tggtcgagat | acttgagggc | 900 |
| tcattcgaga | aggaaggtgg | ggcaatcggt | tacgctccag | ggtttcaagc | agatgttgat | 960 |
| gatactgcta | aaacaataag | tacattagca | gtccttggaa | gagatgctac | accaagacaa | 1020 |
| atgatcaagg | tatttgaagc | taatacacat | tttagaacat | accctggtga | agagatcct | 1080 |
| tctttgacag | ctaattgtaa | tgctctatca | tttgtctgtg | actattggtg | gaagtctgat | 1200 |
| ggtaagatta | aagataagtg | gaacacttgc | tacttgtacc | catctgtctt | attagttgag | 1260 |
| gttttggttg | atcttgttag | tttattggag | cagggtaaat | tgcctgatgt | tttgatcaa | 1320 |
| gagcttcaat | acagagtcgc | catcacattg | ttccaagcat | gtttaaggcc | attactagac | 1380 |
| caagatgccg | aaggatcatg | gaacaagtct | atcgaagcca | cagcctacgg | catccttatc | 1440 |
| ctaactgaag | ctaggagagt | ttgtttcttc | gacagattgt | ctgagccatt | gaatgaggca | 1500 |
| atccgtagag | gtatcgcttt | cgccgactct | atgtctggaa | ctgaagctca | gttgaactac | 1560 |
| atttggatcg | aaaaggttag | ttacgcacct | gcattattga | ctaaatccta | tttgttagca | 1620 |
| gcaagatggg | ctgctaagtc | tcctttaggc | gcttccgtag | gctcttcttt | gtggactcca | 1680 |
| ccaagaagaa | gattggataa | gcatgtcaga | ttattccata | aagctgagtt | attcagatcc | 1740 |
| cttccagaat | gggaattaag | agcctccatg | attgaagcag | ctttgttcac | accacttcta | 1800 |
| agagcacata | gactagacgt | tttccctaga | caagatgtag | gtgaagacaa | atatcttgat | 1860 |
| gtagttccat | tcttttggac | tgccgctaac | aacagagata | gaacttacgc | ttccactcta | 1920 |
| ttccttacg | atatgttt | tatcgcaatg | ttaaacttcc | agttagacga | attcatgagg | 1980 |
| gccacagccg | gtatcttatt | cagagatcat | atggatgatt | tgaggcaatt | gattcatgat | 2040 |
| cttttggcag | agaaaacttc | cccaaagagt | tctggtagaa | gtagtcaggg | cacaaaagat | 2100 |
| gctgactcag | gtatagagga | agacgtgtca | atgtccgatt | cagcttcaga | ttcccaggat | 2160 |
| agaagtccag | aatacgactt | ggttttcagt | gcattagata | cctttacaaa | acatgtcttg | 2220 |
| caacacccat | ctatacaaag | tgcctctgta | tgggatagaa | aactacttgc | tagagagatg | 2280 |
| aaggcttact | tacttgctca | tatccaacaa | gcagaagatt | caactccatt | gtctgaattg | 2340 |
| aaagatgtgc | ctcaaaagac | tgatgtaaca | agagtttcta | catctactac | taccttcttt | 2400 |
| aactgggtta | gaacaacttc | cgcagaccat | atatcctgcc | catactcctt | ccactttgta | 2460 |
| gcatgccatc | taggcgcagc | attgtcacct | aaagggtcta | acggtgattg | ctatccttca | 2520 |
| gctggtgaga | agttcttggc | agctgcagtc | tgcagacatt | tggccaccat | gtgtagaatg | 2580 |
| tacaacgatc | ttggatcagc | tgaacgtgat | tctgatgaag | gtaatttgaa | ctccttggac | 2640 |
| gaatttgaat | tcgccgattc | tgcaggaaac | ggagggatag | aaattcagaa | ggcgctcta | 2700 |
| ttaaggttag | ctgagtttga | gagagattca | tacttagagg | ccttccgtcg | tttacaagat | 2760 |
| gaatccaata | gagttcacgg | tccagccggt | ggtgatgaag | ccagattgtc | cagaaggaga | 2820 |
| atggcaatcc | ttgaattctt | cgcccagcag | gtagatttgt | acggtcaagt | atacgtcatt | 2880 |
| agggatattt | ccgctcgtat | tcctaaaaac | gaggttgaga | aaaagagaaa | attggatgat | 2940 |
| gctttccaatt | ga | | | | | 2952 |

TABLE 10-continued

Sequences disclosed herein.

```
SEQ ID NO: 54
MEFDEPLVDE ARSLVQRTLQ DYDDRYGFGT MSCAAYDTAW VSLVTKTVDG RKQWLFPECF        60
EFLLETQSDA GGWEIGNSAP IDGILNTAAS LLALKRHVQT EQIIQPQHDH KDLAGRAERA       120
AASLRAQLAA LDVSTTEHVG FEIIVPAMLD PLEAEDPSLV FDFPARKPLM KIHDAKMSRF       180
RPEYLYGKQP MTALHSLEAF IGKIDFDKVR HHRTHGSMMG SPSSTAAYLM HASQWDGDSE       240
AYLRHVIKHA AGQGTGAVPS AFPSTHFESS WILTTLFRAG FSASHLACDE LNKLVEILEG       300
SFEKEGGAIG YAPGFQADVD DTAKTISTLA VLGRDATPRQ MIKVFEANTH FRTYPGERDP       360
SLTANCNALS ALLHQPDAAM YGSQIQKITK FVCDYWWKSD GKIKDKWNTC YLYPSVLLVE       420
VLVDLVSLLE QGKLPDVLDQ ELQYRVAITL FQACLRPLLD QDAEGSWNKS IEATAYGILI       480
LTEARRVCFF DRLSEPLNEA IRRGIAFADS MSGTEAQLNY IWIEKVSYAP ALLTKSYLLA       540
ARWAAKSPLG ASVGSSLWTP PREGLDKHVR LFHQAELFRS LPEWELRASM IEAALFTPLL       600
RAHRLDVFPR QDVGEDKYLD VVPFFWTAAN NRDRTYASTL FLYDMCFIAM LNFQLDEFME       660
ATAGILFRDH MDDLRQLIHD LLAEKTSPKS SGRSSQGTKD ADSGIEEDVS MSDSASDSQD       720
RSPEYDLVFS ALSTFTKHVL QHPSIQSASV WDRKLLAREM KAYLLAHIQQ AEDSTPLSEL       780
KDVPQKTDVT RVSTSTTTFF NWVRTTSADH ISCPYSFHFV ACHLGAALSP KGSNGDCYPS       840
AGEKFLAAAV CRHLATMCRM YNDLGSAERD SDEGNLNSLD FPEFADSAGN GGIEIQKAAL       900
LRLAEFERDS YLEAFRRLQD ESNRVHGPAG GDEARLSRRR MAILEFFAQQ VDLYGQVYVI       960
RDISARIPKN EVEKKRKLDD AFN                                               983

SEQ ID NO: 55
atggcttcta gtacacttat ccaaaacaga tcatgtggcg tcacatcatc tatgtcaagt        60
tttcaaatct tcagaggtca accactaaga tttcctggca ctagaacccc agctgcagtt       120
caatgcttga aaaagaggag atgcttaggc caaccgaat ccgtactaga atcatctcct        180
ggctctggtt catatagaat agtaactggc ccttctggaa ttaacccctag ttctaacggg      240
cacttgcaag agggttcctt gactcacagg ttaccaatac caatggaaaa atctatcgat       300
aacttccaat ctactctata tgtgtcagat atttggtctg aaacactaca gagaactgaa       360
tgtttgctac aagtaactga aaacgtccag atgaatgagt ggattgagga aattagaatg       420
tactttagaa atatgacttt aggtgaaatt tccatgtccc cttacgacac tgcttgggtg       480
gctagagttc cagcgttgga cggttctcat gggcctcaat tccacagatc tttgcaatgg       540
attatcgaca accaattacc agatggggac tggggcgaac cttctcttt cttgggttac        600
gatagagttt gtaatacttt agcctgtgtg attgcgttga aaacatgggg tgttggggca       660
caaaacgttg aaaagaggaa tcagttccta caatctaaca tatacaagat ggaggaagat       720
gacgctaatc atatgccaat aggattcgaa atcgtattcc ctgctatgat ggaagatgcc       780
aaagcattag gtttggattt gccatacgat gctactattt tgcaacagat ttcagccgaa       840
agagagaaaa agatgaaaaa gatcccaatg gcaatggtgt acaaataccc aaccacttta       900
cttcactcct tagaaggctt gcatagagaa gttgattgga ataagttgtt acaattacaa       960
tctgaaaatg gtagttttct ttattcacct gcttcaaccg catgcgcctt aatgtacact       1020
aaggacgtta aatgttttga ttacttaaac cagttgttga tcaagttcga ccacgcatgc      1080
ccaaatgtat atccagtcga tctattcgaa agattatgga tggttgacag attgcagaga      1140
ttagggatct ccagatactt tgaaagagag attagagatt gtttacaata cgtctacaga      1200
tattggaaag attgtggaat cggatgggct tctaactctt ccgtacaaga tgttgatgat      1260
acagccatgg cgtttagact tttaaggact catggtttcg acgtaaagga agattgcttt      1320
agacagtttt tcaaggacgg agaattcttc tgcttcgcag gccaatcatc tcaagcagtt      1380
acaggcatgt ttaatctttc aagagccagt caaacattgt ttccaggaga atctttattg      1440
aaaaaggcta gaaccttctc tagaaacttc ttgagaacaa agcatgagaa caacgaatgt      1500
ttcgataaat ggatcattac taaagatttg gctggtgaag tcgagtataa cttgaccttc      1560
ccatggtatg cctctttgcc tagattagaa cataggacat acttagatca atatggaatc      1620
gatgatatct ggataggcaa atctttatac aaaatgcctg ctgttaccaa cgaagttttc      1680
ctaaagttgg caaaggcaga ctttaacatg tgtcaagctc tacacaaaaa ggaattggaa      1740
caagtgataa agtggaacgc gtcctgtcaa ttcagagatc ttgaattcgc cagacaaaaa      1800
tcagtagaat gctattttgc tggtcagcc acaatgttca aaccagaaat ggttcaagct       1860
agattagtct gggcaagatg ttgtgtattg acaactgtct tagacgatta ctttgaccac      1920
gggacacctg ttgaggaact tagagtgttt gttcaagctg tcagaacatg gaatccagag      1980
ttgatcaacg gtttgccaga gcaagctaaa atcttgttta tgggcttata caaaacagtt      2040
aacacaattg cagaggaagc attcatggca cagaaaagag acgtccatca tcatttgaaa      2100
cactattggg acaagttgat aacaagtgcc ctaaaggagg ccgaatgggc agagtcaggt      2160
tacgtcccaa catttgatga atacatggaa gtagctgaaa tttctgttgc tctagaacca      2220
attgtctgta gtaccttgtt ctttgcgggt catagactag atgaggatgt tctagatagt      2280
tacgattacc atctagttat gcatttggta aacagagtcg gtagaatctt gaatgatata      2340
caaggcagga gagggaggc ttcacaaggt aagatctcat cagttcaaat ctacatggag       2400
gaacatccat ctgttccatc tgaggccatg gcgatcgctc atcttcaaga gttagttgat      2460
aattcaatgc agcaattgac atacgaagtt cttaggttca ctgcggttcc aaaaagttgt      2520
aagagaatcc acttgaatat ggctaaaatc atgcatgcct tctacaagga tactgatgga      2580
ttctcatccc ttactgcaat gacaggattc gtcaaaaagg ttcttttcga acctgtgcct      2640
gagtaa                                                                 2646

SEQ ID NO: 56
MASSTLIQNR SCGVTSSMSS FQIFRGQPLR FPGTRTPAAV QCLKKRRCLR PTESVLESSP        60
GSGSYRIVTG PSGINPSSNG HLQEGSLTHR LPIPMEKSID NFQSTLYVSD IWSETLQRTE       120
CLLQVTENVQ MNEWIEEIRM YFRNMTLGEI SMSPYDTAWV ARVPALDGSH GPQFHRSLQW       180
IIDNQLPDGD WGEPSLFLGY DRVCNTLACV IALKTWGVGA QNVERGIQFL QSNIYKMEED      240
DANHMPIGFE IVFPAMMEDA KALGLDLPYD ATILQQISAE REKKMKKIPM AMVYKYPTTL       300
LHSLEGLHRE VDWNKLLQLQ SENGSFLYSP ASTACALMYT KDVKCFDYLN QLLIKFDHAC      360
PNVYPVDLFE RLWMVDRLQR LGISRYFERE IRDCLQYVYR YWKDCGIGWA SNSSVQDVDD      420
TAMAFRLLRT HGFDVKEDCF RQFFKDGEFF CFAGQSSQAV TGMFNLSRAS QTLFPGESLL      480
KKARTFSRNF LRTKHENNEC FDKWIITKDL AGEVEYNLTF PWYASLPRLE HRTYLDQYGI      540
DDIWIGKSLY KMPAVTNEVF LKLAKADFNM CQALHKKELE QVIKWNASCQ FRDLEFARQK      600
```

TABLE 10-continued

Sequences disclosed herein.

| | | | | | |
|---|---|---|---|---|---|
| SVECYFAGAA | TMFEPEMVQA | RLVWARCCVL | TTVLDDYFDH | GTPVEELRVF | VQAVRTWNPE | 660
| LINGLPEQAK | ILFMGLYKTV | NTIAEEAFMA | QKRDVHHHLK | HYWDKLITSA | LKEAEWAESG | 720
| YVPTFDEYME | VAEISVALEP | IVCSTLFFAG | HRLDEDVLDS | YDYHLVMHLV | NRVGRILNDI | 780
| QGMKREASQG | KISSVQIYME | EHPSVPSEAM | AIAHLQELVD | NSMQQLTYEV | LRFTAVPKSC | 840
| KRIHLNMAKI | MHAFYKDTDG | FSSLTAMTGF | VKKVLFEPVP | E | | 881

SEQ ID NO: 57

| | | | | | |
|---|---|---|---|---|---|
| atgcctggta | aaattgaaaa | tggtacccca | aaggacctca | agactggaaa | tgattttgtt | 60
| tctgctgcta | agagtttact | agatcgagct | ttcaaaagtc | atcattccta | ctacggatta | 120
| tgctcaactt | catgtcaagt | ttatgataca | gcttgggttg | caatgattcc | aaaaacaaga | 180
| gataatgtaa | aacagtggtt | gtttccagaa | tgtttccatt | acctcttaaa | aacacaagcc | 240
| gcagatggct | catggggttc | attgcctaca | acacagacag | cgggtatcct | agatacagcc | 300
| tcagctgtgc | tggcattatt | gtgccacgca | caagagcctt | tacaaatatt | ggatgtatct | 360
| ccagatgaaa | tggggttgag | aatagaacac | ggtgtccacat | ccttgaaacg | tcaattagca | 420
| gtttggaatg | atgtggagga | caccaaccat | attggcgtg | agtttatcat | accagcctta | 480
| ctttccatgc | tagaaaagga | attagatgtt | ccatctttg | aatttccatg | taggtccatc | 540
| ttagagagaa | tgcacgggga | gaaattaggt | catttcgacc | tggaacaagt | ttacggcaag | 600
| ccaagctcat | tgttgcactc | attggaagca | tttctcggta | agctagattt | tgatcgacta | 660
| tcacatcacc | tataccacgg | cagtatgatg | gcatctccat | cttcaacggc | tgcttatctt | 720
| attgggcta | caaatggga | tgacgaagcc | gaagattacc | taagacatgt | aatgcgtaat | 780
| ggtgcaggac | atgggaatgg | aggtattctt | ggtacatttc | caactactca | tttcgaatgt | 840
| agctggatta | tagcaacgtt | gttaaaggtt | ggctttactt | tgaagcaaat | tgacggcgat | 900
| ggcttaagag | gtttatcaac | catcttactt | gaggcgcttc | gtgatgagaa | tggtgtcata | 960
| ggctttgccc | ctagaacagc | agatgtagat | gacacagcca | aagctctatt | ggccttgtca | 1020
| ttggtaaacc | agccagtgtc | acctgatatc | atgattaagg | tctttgaggg | caaagaccat | 1080
| tttaccactt | ttggttcaga | aagagatcca | tcattgactt | ccaacctgca | cgtcctttta | 1140
| tctttactta | aacaatctaa | cttgtctcaa | taccatccta | aaatcctaaa | aacaacatta | 1200
| ttcacttgta | gatggtggtg | gggttccgat | cattgtgtca | aagacaaatg | gaatttgagt | 1260
| cacctatatc | caactatgtt | gttggttgaa | gccttcactg | aagtgctcca | tctcattgac | 1320
| ggtggtgaat | tgtctagtct | gtttgatgaa | tcctttaagt | gtaagattgg | tcttagcatc | 1380
| tttcaagcgg | tacttagaat | aatcctcacc | caagacaacg | acggctcttg | gagaggatac | 1440
| agagaacgaa | cgtgttacgc | aatattggct | ttagttcaaa | cgagacatgt | atgctttttc | 1500
| actcacatgt | ttgacagact | gcaatcatgt | gttgatcgag | gtttctcatg | gttgaaatct | 1560
| tgctcttttc | attctcaaga | cctgacttgg | acctctaaaa | cagcttatga | agtgggtttc | 1620
| gtagctgaag | catataaact | agctgcttta | caatctgctt | ccctgagggt | tcctgctgcc | 1680
| accattggac | attctgtcac | gtctgccgtt | ccatcaagtg | atcttgaaaa | atacatgaga | 1740
| ttggtgagaa | aaactgcgtt | attctctcca | ctggatgagt | ggggtctaat | ggcttctatc | 1800
| atcgaatctt | cattttttcgt | accattactg | caggcacaaa | gagttgaaat | atacccctaga | 1860
| gataatatca | aggtggacga | agataagtac | ttgtctatta | tcccattcac | atgggtcgga | 1920
| tgcaataata | ggtctagaac | tttcgcaagt | aacagatgat | tatacgatat | gatgtacctt | 1980
| tcattactcg | gctatcaaac | cgacgagtac | atggaagctg | tagctgggcc | agtgtttggg | 2040
| gatgtttcct | tgttacatca | aacaattgat | aaggtgattg | ataatacaat | gggtaacctt | 2100
| gcgagagcca | atgaacagt | acacagtggt | aatggacatc | agcacgaatc | tcctaatata | 2160
| ggtcaagtcg | aggacacctt | gactcgtttc | acaaattcaa | tcttgaatca | caaagacgta | 2220
| cttaactcta | gctcatctga | tcaagatact | ttgagaagag | agtttagaac | attcatgcac | 2280
| gctcatataa | cacaaatcga | agataactca | cgattcagta | agcaagcctc | atccgatgcg | 2340
| ttttcctctc | ctgaacaatc | ttactttcaa | tgggtgaact | caactggtgg | ctcacatgtc | 2400
| gcttcgcct | attcatttgc | cttctctaat | tgcctcatgt | ctgcaaattt | gttgcagggt | 2460
| aaagacgcat | ttccaagcgg | aacgcaaaag | tacttaatct | ccctctgttat | gagacatgcc | 2520
| acaaacatgt | gtagaatgta | taacgacttt | ggctctattg | ccagagacaa | cgctgagaga | 2580
| aatgttaata | gtattcattt | tcctgagttt | actctctgta | acggaacttc | tcaaaaccta | 2640
| gatgaaggga | aggaaagact | tctgaaaatc | gcaacttacg | aacaagggta | tttggataga | 2700
| gcactagagg | ccctggaaag | agagagtaga | gatgatgccg | gagacagagc | tggatctaaa | 2760
| gatatgagaa | agttgaaaat | cgttaagtta | ttctgtgatg | ttacggactt | atacgatcag | 2820
| ctctacgtta | tcaaagattt | gtcatcctct | atgaagtaa | | | 2859

SEQ ID NO: 58

| | | | | | |
|---|---|---|---|---|---|
| MPGKIENGTP | KDLKTGNDFV | SAAKSLLDRA | FKSHHSYYGL | CSTSCQVYDT | AWVAMIPKTR | 60
| DNVKQWLFPE | CFHYLLKTQA | ADGSWGSLPT | TQTAGILDTA | SAVLALLCHA | QEPLQILDVS | 120
| PDEMGLRIEH | GVTSLKRQLA | VWNDVEDTNH | IGVEFIIPAL | LSMLEKELDV | PSFEFPCRSI | 180
| LERMHGEKLG | HFDLEQVYGK | PSSLLHSLEA | FLGKLDFDRL | SHHLYHGSMM | ASPSSTAAYL | 240
| IGATKWDDEA | EDYLRHVMRN | GAGHGNGGIS | GTFPTTHFEC | SWIIATLLKV | GFTLKQIDGD | 300
| GLRGLSTILL | EALRDENGVI | GFAPRTADVD | DTAKALLALS | LVNQPVSPDI | MIKVFEGKDH | 360
| FTTFGSERDP | SLTSNLHVLL | SLLKQSNLSQ | YHPQILKTTL | FTCRWWWGSD | HCVKDKWNLS | 420
| HLYPTMLLVE | AFTEVLHLID | GGELSSLFDE | SFKCKIGLSI | FQAVLREIILT | QDNDGSWRGY | 480
| REQTCYAILA | LVQARHVCFF | THMVDRLQSC | VDRGFSWLKS | CSFHSQDLTW | TSKTAYEVGF | 540
| VAEAYKLAAL | QSASLEVPAA | TIGHSVTSAV | PSSDLEKYMR | LVRKTALFSP | LDEWGLMASI | 600
| IESSFFVPLL | QAQRVEIYPR | DNIKVDEDKY | LSIIPFTWVG | CNNRSRTFAS | NRWLYDMMYL | 660
| SLLGYQTDEY | MEAVAGPVFG | DVSLLHQTID | KVIDNTMGNL | ARANGTVHSG | NGHQHESPNI | 720
| GQVEDTLTRF | TNSVLNHKDV | LNSSSSDQDT | LRREFRTFMH | AHITQIEDNS | RFSKQASSDA | 780
| FSSPEQSYFQ | WVNSTGGSHV | ACAYSFAFSN | CLMSANLLQG | KDAFPSGTQK | YLISSVMRHA | 840
| TNMCRMYNDF | GSIARDNAER | NVNSIHFPEF | TLCNGTSQNL | DERKERLLKI | ATYEQGYLDR | 900
| ALEALERQSR | DDAGDRAGSK | DMRKLKIVKL | FCDVTDLYDQ | LYVIKDLSSS | MK | 952

SEQ ID NO: 59

| | | | | | |
|---|---|---|---|---|---|
| atggatgctg | tgacgggttt | gttaactgtc | ccagcaaccg | ctataactat | tggtggaact | 60
| gctgtagcat | tggcggtagc | gctaatcttt | tggtacctga | atcctacac | atcagctaga | 120
| agatcccaat | caaatcatct | tccaagagtg | cctgaagtca | caggtgttcc | attgttagga | 180

TABLE 10-continued

Sequences disclosed herein.

```
aatctgttac aattgaagga gaaaaagcca tacatgactt ttacgagatg ggcagcgaca    240
tatggaccta tctatagtat caaaactggg gctacaagta tggttgtggt atcatctaat    300
gagatagcca aggaggcatt ggtgaccaga ttccaatcca tatctacaag gaacttatct    360
aaagccctga agtacttac agcagataag acaatggtcg caatgtcaga ttatgatgat     420
tatcataaaa cagttaagag acacatactg accgccgtct tgggtcctaa tgcacagaaa    480
aagcatagaa ttcacagaga tatcatgatg gataacatat ctactcaact tcatgaattc    540
gtgaaaaaca acccagaaca ggaagaggta gaccttagaa aaatcttttca atctgagtta   600
ttcggcttag ctatgagaca agccttagga aaggatgttg aaagtttgta cgttgaagac    660
ctgaaaatca ctatgaatag agcgaaatc tttcaagtcc ttgttgttga tccaatgatg     720
ggagcaatcg atgttgattg gagagacttc tttccatacc taaagtgggt cccaaacaaa    780
aagttcgaaa atactattca acaaatgtac atcagaagag aagctgttat gaaatcttta    840
atcaaagagc acaaaagag aatagcgtca ggcgaaaagc taaatagtta tatcgattac     900
cttttatctg aagctcaaac tttaaccgat cagcaactat tgatgtcctt gtgggaacca    960
atcattgaat cttcagatac aacaatggtc acaacgaat gggcaatgta cgaattagct    1020
aaaaaaccta aattgcaaga taggttgtac agagacatta agtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag gaatggaacc cagaaagatt catgaaagag   1320
aatgagacaa ttgattttca aaagacgatg gccttcggtg gtggtaagag agtttgtgct   1380
ggttccttgc aagccctttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                      1542

SEQ ID NO: 60
MDAVTGLLTV PATAITIGGT AVALAVALIF WYLKSYTSAR RSQSNHLPRV PEVPGVPLLG    60
NLLQLKEKKP YMTFTRWAAT YGPIYSIKTG ATSMVVVSSN EIAKEALVTR FQSISTRNLS   120
KALKVLTADK TMVAMSDYDD YHKTVKRHIL TAVLGPNAQK KHRIHRDIMM DNISTQLHEF   180
VKNNPEQEEV DLRKIFQSEL FGLAMRQALG KDVESLYVED LKITMNRDEI FQVLVVDPMM   240
GAIDVDWRDF FPYLKWVPNK KFENTIQQMY IRREAVMKSL IKEHKKRIAS GEKLNSYIDY   300
LLSEAQTLTD QQLLMSLWEP IIESSDTTMV TTEWAMYELA KNPKLQDRLY RDIKSVCGSE   360
KITEEHLSQL PYITAIFHET LRRHSPVPII PLRHVHEDTV LGGYHVPAGT ELAVNIYGCN   420
MDKNVWENPE EWNPERFMKE NETIDFQKTM AFGGGKRVCA GSLQALLTAS IGIGRMVQEF   480
EWKLKDMTQE EVNTIGLTTQ MLRPLRAIIK PRI                                 513

SEQ ID NO: 61
aagcttacta gtaaaatgga cggtgtcatc gatatgcaaa ccattccatt gagaaccgct    60
attgctattg gtggtactgc tgttgctttg gttgttgcat tatactttg gttcttgaga    120
tcctacgctt ccccatctca tcattctaat catttgccac cagtacctga agttccaggt   180
gttccagttt tgggtaattt gttgcaattg aagaaaaaa agccttacat gaccttcacc    240
aagtgggctg aaatgtatgg tccaatctac tctattgaaa ctggtgctac ttccatgatt   300
gttgtctctt ctaacgaaat cgccaaagaa gttgttgtta ccagattccc atctatctct   360
accagaaaat tgtcttacgc cttgaaggtt ttgaccgaag ataagtctat ggttgccatg   420
tctgattatc acgattacca taagaccgtc aagagacata ttttgactgc tgttttgggt   480
ccaaacgccc aaaaaagtt tagagcacat agagacacca tgatggaaaa cgtttccaat   540
gaattgcatg ccttcttcga aaagaaccca aatcaagaag tcaacttgag aaagatcttc   600
caatcccaat tattcggttt ggctatgaag caagccttgg gtaaagatgt tgaatccatc   660
tacgttaagg atttggaaac caccatgaag agagaagaaa tcttcgaagt tttggttgtc   720
gatccaatga tgggtgctat tgaagttgat tggagagact tttttcccata cttgaaatgg   780
gttccaaaca agtccttcga aaacatcatc catagaatgt acactagaag agaagctgtt   840
atgaaggcct tgatccaaga acacaagaaa agaattgcct ccgtgaaaa cttgaactcc    900
tacattgatt acttgttgtc tgaagcccaa accttgacta taagcaatt attgatgtct   960
ttgtgggaac ctattatcga atcttctgat accactatgg ttactactga atgggctatg  1020
tacgaattgg ctaagaatcc aaacatgcaa gacagattat acgaagaaat ccaatccgtt  1080
tgcggttccg aaaagattac tgaagaaaac ttgtcccaat gccatactt gtacgctgtt   1140
ttccaagaaa ctttgagaaa gcactgtcca gttcctatta tgccattgag atatgttcac  1200
gaaaacaccg ttttgggtgg ttatcatgtt ccagctgcta ctgaagttgc tattaacatc  1260
tacggttgca acatggataa gaaggtctgg gaaatccag aagatggaa tccagaaaga    1320
ttcttgtccg aaaaagaatc catggacttg tacaaaacta tggcttttgg tggtggtaaa  1380
agagtttgcg ctggttcttt acaagccatg gttatttctt gcattggtat cggtagattg  1440
gtccaagatt ttgaatggaa gttgaaggat gatgccgaag aagatgttaa cactttgggt  1500
ttgactaccc aaaagttgca tccattattg gccttgatta cccaagaaa gtaactcgag  1560
ccgcgg                                                             1566

SEQ ID NO: 62
MDGVIDMQTI PLRTAIAIGG TAVALVVALY FWFLRSYASP SHHSNHLPPV PEVPGVPVLG    60
NLLQLKEKKP YMTFTKWAEM YGPIYSIRTG ATSMVVVSSN EIAKEVVVTR FPSISTRKLS   120
YALKVLTEDK SMVAMSDYHD YHKTVKRHIL TAVLGPNAQK KFRAHRDTMM ENVSNELHAF   180
FEKNPNQEVN LRKIFQSQLF GLAMKQALGK DVESIYVKDL ETTMKREEIF EVLVVDPMMG   240
AIEVDWRDFF PYLKWVPNKS FENIIHRMYT RREAVMKALI QEHKKRIASG ENLNSYIDYL   300
LSEAQTLTDK QLLMSLWEPI IESSDTTMVT TEWAMYELAK NPNMQDRLYE EIQSVCGSEK   360
ITEENLSQLP YLYAVFQETL RKHCPVPIMP LRYVHENTVL GGYHVPAGTE VAINIYGCNM   420
DKKVWENPEE WNPERFLSEK ESMDLYKTMA FGGGKRVCAG SLQAMVISCI GIGRLVQDFE   480
WKLKDDAEED VNTLGLTTQK LHPLLALINP RK                                  512

SEQ ID NO: 63
atggccaccc tccttgagca tttccaagct atgccctttg ccatccctat tgcactggct    60
gctctgtctt ggctgttcct cttttacatc aaagtttcat tcttttccaa caagagtgct   120
```

TABLE 10-continued

Sequences disclosed herein.

```
caggctaagc tccctcctgt gccagtggtt cctgggctgc cggtgattgg gaatttactg     180
caactcaagg agaagaaacc ctaccagact tttacaaggt gggctgagga gtatggacca     240
atctattcta tcaggactgg tgcttccacc atggtcgttc tcaataccac ccaagttgca     300
aaagaggcca tggtgaccag atatttatcc atctcaacca gaaagctatc aaacgcacta     360
aagattctta ctgctgataa atgtatggtt gcaataagtg actacaacga ttttcacaag     420
atgataaagc gatacatact ctcaaatgtt cttggaccta gtgctcagaa gcgtcaccgg     480
agcaacagag ataccttgag agctaatgtc tgcagccgat tgcattctca agtaaagaac     540
tctcctcgag aagctgtgaa tttcagaaga gtttttgagt gggaactctt tggaattgca     600
ttgaagcaag cctttggaaa ggacatagaa aagcccattt atgtgaggaa acttggcact     660
acactgtcaa gagatgagat ctttaaggtt ctagtgcttg acataatgga gggtgcaatt     720
gaggttgatt ggagagattt cttcccttac ctgagatgga ttccgaatac gcgcatggaa     780
acaaaaattc agcgactcta tttccgcagg aaagcagtga tgactgccct gatcaacgag     840
cagaagaagc gaattgcttc aggagaggaa atcaactgtt atatcgactt cttgcttaag     900
gaagggaaga cactgacaat ggaccaaata gtatgttgc  tttgggagac ggttattgaa     960
acagcagata ctacaatggt aacgacagaa tgggctatgt atgaagttgc taaagactca    1020
aagcgtcagg atcgtctcta tcaggaaatc caaaagtttt gtggatcgga gatggttaca    1080
gaggaatact tgtcccaact gccgtacctg aatgcagttt tccatgaaac gctaaggaag    1140
cacagtccgg ctgcgttagt tccttttaaga tatgcacatg aagataccca actaggaggt    1200
tactacattc cagctggaac tgagattgct ataaacatat acgggtgtaa catggacaag    1260
catcaatggg aaagccctga ggaatggaaa ccggagagat ttttggaccc gaaatttgat    1320
cctatggatt tgtacaagac catggctttt ggggctggaa agagggtatg tgctggttct    1380
cttcaggcaa tgttaatagc gtgcccgacg attggtaggc tggtgcagga gtttgagtgg    1440
aagctgagag atggagaaga agaaaatgta gatactgttg ggctcaccac tcacaaacgc    1500
tatccaatgc atgcaatcct gaagccaaga agtta                                1535

SEQ ID NO: 64
atggctacct tgttggaaca ttttcaagct atgccattcg ctattccaat tgctttggct       60
gctttgtctt ggttgttttt gttctacatc aaggtttctt tcttctccaa caaatccgct      120
caagctaaat tgccaccagt tccagttgtt ccaggtttgc cagttattgg taatttgttg      180
caattgaaag aaaagaagcc ataccaaacc ttcactagat gggctgaaga atatggtcca      240
atctactcta ttagaactgg tgcttctact atggttgtct tgaacactac tcaagttgcc      300
aagaagcta tggttaccag atacttgtct atctctacca gaaagttgtc caacgccttg      360
aaaattttga ccgctgataa gtgcatggtt gccatttctg attacaacga tttccacaag      420
atgatcaaga gatatatctt gtctaacgtt ttgggtccat ctgccaaaa  aagacataga      480
tctaacagag ataccttgag agccaacgtt tgttctagat gcattccca  agttaagaac      540
tctccaagag aagctgtcaa cttagaaga gttttcgaat gggaattatt cggtatcgct       600
ttgaaacaag ccttcggtaa ggatattgaa aagccaatct acgtcgaaga attgggtact      660
actttgtcca gagatgaaat cttcaaggtt ttggtcttgg acattatgga aggtgccatt      720
gaagttgatt ggagagattt tttcccatac ttgcgttgga ttccaaacac cagaatggaa      780
actaagatcc aaagattata ctttagaaga aaggccgtta tgaccgcctt gattaacgaa      840
caaaagaaaa gaattgcctc cggtgaagaa atcaactgct acatcgattt cttgttgaaa      900
gaaggtaaga ccttgaccat ggaccaaatc tctatgttgt tgtgggaaac cgttattgaa      960
actgctgata ccacaatggt tactactgaa tgggctatgt acgaagttgc taaggattct     1020
aaaagacaag acagattata ccaagaaatc caaaagttct gcggttctga aatggttaca     1080
gaagaatact tgtcccaatt gccatacttg aatgctgttt tccacgaaac tttgagaaaa     1140
cattctccag ctgctttggt tccattgaga tatgctcatg aagatactca attgggtggt     1200
tattacattc cagccggtac tgaaattgcc attaacatct acggttgcaa catggacaaa     1260
caccaatggg aatctccaga agaatggaag ccagaaagat ttttggatcc taagtttgaa     1320
ccaatggact tgtacaaaac tatggccttt ggtgctggaa aaagagtttg cgctggttct     1380
ttacaagcta tgttgattgc ttgtccaacc atcggtagat tggttcaaga atttgaatgg     1440
aagttgagag atggtgaaga agaaaacgtt gatactgttg gtttgaccac ccataagaga     1500
tatccaatgc atgctatttt gaagccaaga tcttaa                              1536

SEQ ID NO: 65
aagcttacta gtaaaatggc ctccatcacc catttcttac aagattttca agctactcca       60
ttcgctactg cttttgctgt tggtggtgtt tctttgttga tattcttctt cttcatccgt      120
ggtttccact ctactaagaa aaacgaatat tacaagttgc caccagttcc agttgttcca      180
ggtttgccag ttgttggtaa tttgttgcaa ttgaaagaaa agaagccata caagactttc      240
ttgagatggg ctgaaattca tggtccaatc tactctatta gaactggtgc ttctaccatg      300
gttgttgtta actctactca tgttgccaaa gaagctatgg ttaccagatt ctcttcaatc      360
tctaccagaa agttgtccaa ggctttggaa ttattgacct ccaacaaatc tatggttgcc      420
acctctgatt acaacgaatt tcacaagatg gtcaagaagt acatcttggc cgaattattg      480
ggtgctaatg ctcaaagag  acacagaatt catagagaca cctgatcga  aaacgtcttg      540
aacaaattgc atgcccatac caagaattct ccattgcaag ctgttaactt cagaaagatc      600
ttcgaatctg aattattcgg tttggctatg agcaagcct  tgggttatga tgttgattcc      660
ttgttcgttg aagaattggg tactaccttg tccagagca  aaatctacaa cgttttggtc      720
agtgacatgt tgaagggtgc tattgaagtt gattggagag acttttttccc atacttgaaa      780
tggatcccaa acagtccctt cgaaatgaag attcaaagat tggcctctag aagacaagcc      840
gttatgaact ctattgtcaa agaacaaaag aagtccattg cctctggtaa gggtgaaaac      900
tgttacttga attacttgtt gtccgaagct aagactttga ccgaaaagca aatttccatt      960
ttggctgggg aaaccattat tgaaactgct gatacaactg ttgttaccac tgaatgggct     1020
atgtacgaat tggctaaaaa cccaaagcaa caagacagat tatacaacga atccaaaac      1080
gtctggcgta ctgataagat taccgaagaa catttgtcca agttgcctta cttgtctgct     1140
gtttttcacg aaaccttgag aaagtattct ccatctccat tggttccatt gagatacgct     1200
catgaagata tcaattggg  tggttattat gttccagccg gtactgaaat tgctgttaat     1260
atctacggtt gcaacatgga caagaatcaa tgggaaactc cagaagaatg gaagccagaa     1320
agattttgg  acgaaagta  cgatccaatg gacatgtaca agactatgtc ttttggttcc     1380
ggtaaaagag tttgcgctgg ttctttacaa gctagtttga ttgcttgtac ctccatcggt     1440
```

| | | | | |
|---|---|---|---|---|
| agattggttc | aagaatttga | atggagattg | aaagacggtg | aagttgaaaa cgttgatacc | 1500 |
| ttgggtttga | ctacccataa | gttgtatcca | atgcaagcta | tcttgcaacc tagaaactga | 1560 |
| ctcgagccgc | gg | | | | 1572 |

SEQ ID NO: 66
```
MASITHFLQD FQATPFATAF AVGGVSLLIF FFFIRGFHST KKNEYYKLPP VPVVPGLPVV    60
GNLLQLKEKK PYKTFLRWAE IHGPIYSIRT GASTMVVVNS THVAKEAMVT RFSSISTRKL   120
SKALELLTSN KSMVATSDYN EFHKMVKKYI LAELLGANAQ KRHRIHRDTL IENVLNKLHA   180
HTKNSPLQAV NFRKIFESEL FGLAMKQALG YDVDSLFVEE LGTTLSREEI YNVLVSDMLK   240
GAIEVDWRDF FPYLKWIPNK SFEMKIQRLA SRRQAVMNSI VKEQKKSIAS GKGENCYLNY   300
LLSEAKTLTE KQISILAWET IIETADTTVV TTEWAMYELA KNPKQQDRLY NEIQNVCGTD   360
KITEEHLSKL PYLSAVFHET LRKYSPSPLV PLRYAHEDTQ LGGYYVPAGT EIAVNIYGCN   420
MDKNQWETPE EWKPERFLDE KYDPMDMYKT MSFGSGKRVC AGSLQASLIA CTSIGRLVQE   480
FEWRLKDGEV ENVDTLGLTT HKLYPMQAIL QPRN                               514
```

SEQ ID NO: 67
| | | | | |
|---|---|---|---|---|
| atgatttcct | tgttgttggg | ttttgttgtc | tcctccttct | tgtttatctt cttcttgaaa |   60 |
| aaaattgttg | tcttcttcag | tcgtcacaaa | atgtccgaag | tttctagatt gccatctgtt |  120 |
| ccagttccag | gttttccatt | gattggtaac | ttgttgcaat | tgaaagaaaa gaagccacac |  180 |
| aagactttca | ccaagtggtc | tgaattatat | ggtccaatct | actctatcaa gatgggttcc |  240 |
| tcttctttga | tcgtcttgaa | ctctattgaa | accgccaaag | aagctatggt cagtagattc |  300 |
| tcttcaatct | ctaccagaaa | gttgtctaac | gctttgactg | ttttgacctg caacaaatct |  360 |
| atggttgcta | cctctgatta | cgatgacttt | cataagttcg | tcaagagatg cttgttgaac |  420 |
| ggtttgttgg | gtgctaatgc | tcaagaaaga | aaaagacatt | acagagatgc cttgatcgaa |  480 |
| aacgttacct | ctaaattgca | tgcccatacc | agaaatcatc | cacaagaacc agttaacttc |  540 |
| agagccattt | tcgaacacga | attattcggt | ttgctttga  | aacaagcctt cggtaaagat |  600 |
| gtcgaatcca | tctatgtaaa | agaattgggt | gtcaccttgt | ccagagatga aattttcaag |  660 |
| gttttggtcc | acgacatgat | ggaaggtgct | attgatgttg | attggagaga tttcttccca |  720 |
| tacttgaaat | ggatcccaaa | caactctttc | gaagccagaa | ttcaacaaaa gcacaagaga |  780 |
| agattggctg | ttatgaacgc | cttgatccaa | gacagattga | atcaaaacga ttccgaatcc |  840 |
| gatgatgact | gctacttgaa | tttcttgatg | tctgaagcta | agaccttgac catggaacaa |  900 |
| attgctattt | tggtttggga | aaccattatc | gaaactgctg | ataccacttt ggttactact |  960 |
| gaatgggcta | tgtacgaatt | ggccaaacat | caatctgttc | aagatagatt attcaaagaa | 1020 |
| atccaatccg | tctgcggtgg | tgaaaagatc | aagaagaac  | aattgccaag attgccttac | 1080 |
| gtcaatggtg | ttttttcacga | aaccttgaga | aagtattctc | cagctccatt ggttccaatt | 1140 |
| agatacgctc | atgaagatac | ccaaattggt | ggttatcata | ttccagccgg ttctgaaatt | 1200 |
| gccattaaca | tctacggttg | caacatggat | aagaagagat | gggaaagacc tgaagaatgg | 1260 |
| tggccagaaa | gattttttgga | agatagatac | gaatcctccg | acttgcataa gactatggct | 1320 |
| tttggtgctg | gtaaaagagt | ttgtgctggt | gcttacaag  | ctagtttgat ggctggtatt | 1380 |
| gctatcggta | gattggttca | agaattcgaa | tggaagttga | gagatggtga agaagaaaac | 1440 |
| gttgatactt | acggtttgac | tcccaaaag  | ttgtatccat | tgatggccat tatcaaccca | 1500 |
| agaagatctt | aa | | | | 1512 |

SEQ ID NO: 68
```
MASMISLLLG FVVSSFLFIF FLKKLLFFFS RHKMSEVSRL PSVPVPGFPL IGNLLQLKEK    60
KPHKTFTKWS ELYGPIYSIK MGSSSLIVLN SIETAKEAMV SRFSSISTRK LSNALTVLTC   120
NKSMVATSDY DDFHKMVKRC LLNGLLGANA QERKRHYRDA LIENVTSKLH AHTRNHPQEP   180
VNFRAIFEHE LFGVALKQAF GKDVESIYVK ELGVTLSRDE IFKVLVHDMM EGAIDVDWRD   240
FFPYLKWIPN NSFEARIQQK HKRRLAVMNA LIQDRLNQND SESDDDCYLN FLMSEAKTLT   300
MEQIAILVWE TIIETADTTL VTTEWAMYEL AKHQSVQDRL FKEIQSVCGG EKIKEEQLPR   360
LPYVNGVFHE TLRKYSPAPL VPIRYAHEDT QIGGYHIPAG SEIAINIYGC NMDKKRWERP   420
EEWWPERFLE DRYESSDLHK TMAFGAGKRV CAGALQASLM AGIAIGRLVQ EFEWKLRDGE   480
EENVDTYGLT SQKLYPLMAI INPRRS                                       506
```

SEQ ID NO: 69
| | | | | |
|---|---|---|---|---|
| aagcttacta | gtaaaatgga | catgatgggt | attgaagctg | ttccatttgc tactgctgtt |   60 |
| gttttgggtg | gtatttcctt | ggttgttttg | atcttcatca | agagattcgt ttccaacaga |  120 |
| aagagatccg | ttgaaggttt | gccaccagtt | ccagatattc | caggtttacc attgattggt |  180 |
| aacttgttgc | aattgaaaga | aaagaagcca | cataagacct | tgctagatg ggctgaaact |  240 |
| tacggtccaa | ttttctctat | tagaactggt | gcttctacca | tgatcgtctt gaattcttct |  300 |
| gaagttgcca | agaagctat  | ggtcactaga | ttctcttcaa | tctctaccag aaagttgtcc |  360 |
| aacgccttga | gattttgac  | cttcgataag | tgtatggttg | ccactctga ttacaacgat |  420 |
| tttcacaaaa | tggtcaaggg | tttcatcttg | agaaacgttt | aggtgctcc agcccaaaaa |  480 |
| agacatagat | gtcatagaga | taccttgatc | gaaaacatct | ctaagtactt gcatgcccat |  540 |
| gttaagactt | ctccattgga | accagttgtc | ttgaagaaga | ttttcgaatc cgaaattttc |  600 |
| ggtttggctt | tgaaacaagc | cttgggtaag | gatatcgaat | ccatctatgt tgaagaattg |  660 |
| ggtactacct | tgtccagaga | agaaattttt | gccgttttgg | ttgttgatcc aatggctggt |  720 |
| gctattgaag | ttgattggag | agattttttc | ccatacttgt | cctggattcc aaacaagtct |  780 |
| atggaaatga | agatccaaag | aatggatttt | agaagaggtg | ctttgatgaa ggccttgatt |  840 |
| ggtgaacaaa | agaaaagaat | cggttccggt | gaagaaaaga | actcctacat tgatttcttg |  900 |
| ttgtctgaag | ctaccacttt | gaccgaaaag | caaattgcta | tgttgatctg ggaaaccatc |  960 |
| atcgaaattt | ccgatacaac | tttggttacc | tctgaatggg | ctatgtacga attggctaaa | 1020 |
| gacccaaata | gacaagaaat | cttgtacaga | gaaatccaca | agggtttgcgg ttctaacaag | 1080 |
| ttgactgaag | aaaaacttgtc | caagttgcca | tacttgaact | ctgttttcca cgaaaccttg | 1140 |
| agaaagtatt | ctccagctcc | aatggttcca | gttagatatg | ctcatgaaga tactcaattg | 1200 |
| ggtggttacc | atattccagc | tggttctcaa | attgccatta | acatctacgg ttgcaacatg | 1260 |
| aacaaaaagc | aatgggaaaa | tcctgaagaa | tggaagccag | aaagattctt ggacgaaaag | 1320 |
| tatgacttga | tggacttgca | taagactatg | gcttttggtg | gtggtaaaag agtttgtgct | 1380 |

TABLE 10-continued

Sequences disclosed herein.

| | | | | | |
|---|---|---|---|---|---|
| ggtgcttac | aagcaatgtt | gattgcttgc | acttccatcg | gtagattcgt | tcaagaattt | 1440 |
| gaatggaagt | tgatgggtgg | tgaagaagaa | aacgttgata | ctgttgcttt | gacctcccaa | 1500 |
| aaattgcatc | caatgcaagc | cattattaag | gccagagaat | gactcgagcc | gcgg | 1554 |

SEQ ID NO: 70

```
MDMMGIEAVP FATAVVLGGI SLVVLIFIRR FVSNRKRSVE GLPPVPDIPG LPLIGNLLQL      60
KEKKPHKTFA RWAETYGPIF SIRTGASTMI VLNSSEVAKE AMVTRFSSIS TRKLSNALKI     120
LTFDKCMVAT SDYNDFHKMV KGFILRNVLG APAQKRHRCH RDTLIENISK YLHAHVKTSP     180
LEPVVLKKIF ESEIFGLALK QALGKDIESI YVEELGTTLS REEIFAVLVV DPMAGAIEVD     240
WRDFFPYLSW IPNKSMEMKI QRMDFRRGAL MKALIGEQKK RIGSGEEKNS YIDFLLSEAT     300
TLTEKQIAML IWETIIEISD TTLVTSEWAM YELAKDPNRQ EILYREIHKV CGSNKLTEEN     360
LSKLPYLNSV FHETLRKYSP APMVPVRYAH EDTQLGGYHI PAGSQIAINI YGCNMNKKQW     420
ENPEEWKPER FLDEKYDLMD LHKTMAFGGG KRVCAGALQA MLIACTSIGR FVQEFEWKLM     480
GGEEENVDTV ALTSQKLHPM QAIIKARE                                       508
```

SEQ ID NO: 71

| | | | | | |
|---|---|---|---|---|---|
| aagcttaaaa | tgagtaagtc | taatagtatg | aattctacat | cacacgaaac | ccttttttcaa | 60 |
| caattggtct | tgggtttgga | ccgtatgcca | ttgatggatg | ttcactggtt | gatctacgtt | 120 |
| gctttcggcg | catgttatg | ttcttatgtg | atacatgttt | tatcatcttc | ctctacagta | 180 |
| aaagtgccag | ttgttggata | caggtctgta | ttcgaaccta | catggttgct | tagacttaga | 240 |
| ttcgtctggg | aaggtggctc | tatcataggt | caagggtaca | ataagtttaa | agactctatt | 300 |
| ttccaagtta | ggaaattggg | aactgatatt | gtcattatac | cacctaacta | tattgatgaa | 360 |
| gtgagaaaat | tgtcacagga | caagactaga | tcagttgaac | ctttcattaa | tgattttgca | 420 |
| ggtcaataca | caagaggcat | ggttttcttg | caatctgact | tacaaaaccg | tgttatacaa | 480 |
| caaagactaa | ctccaaaatt | ggtttccttg | accaaggtca | tgaaggaaga | gttggattat | 540 |
| gctttaacaa | aagagatgcc | tgatatgaaa | aatgacgaat | gggtagaagt | agatatcagt | 600 |
| agtataatgg | tgagattgat | ttccaggatc | tccgccagag | tctttctagg | gcctgaacac | 660 |
| tgtcgtaacc | aggaatggtt | gactactaca | gcagaatatt | cagaatcact | tttcattaca | 720 |
| gggtttatct | taagagttgt | acctcatatc | ttaagaccat | tcatcgcccc | tctattacct | 780 |
| tcatacagga | ctctacttag | aaacgtttca | agtggtagaa | gagtcatcgg | tgacatcata | 840 |
| agatctcagc | aaggggatgg | taacgaagat | atactttcct | ggatgagaga | tgctgccaca | 900 |
| ggagaggaaa | agcaaatcga | taacattgct | cagagaatgt | taattctttc | tttagcatca | 960 |
| atccacacta | ctgcgatgac | catgacacat | gccatgtacg | atctatgtgc | ttgccctgag | 1020 |
| tacattgaac | cattaagaga | tgaagttaaa | tctgttgttg | gggcttctgg | ctgggacaag | 1080 |
| acagcgttaa | acagatttca | taagttggac | tccttcctaa | aagagtcaca | aagattcaac | 1140 |
| ccagtattct | tattgacatt | caatagaatc | taccatcaat | ctatgaccctt | atcagatgcc | 1200 |
| actaacattc | catctggaac | acgtattgct | gttccatcac | acgcaatgtt | gcaagattct | 1260 |
| gcacatgtcc | caggtccaac | cccacctact | gaatttgatg | gattcagata | tagtaagata | 1320 |
| cgttctgata | gtaactacgc | acaaaagtac | ctattctcca | tgaccgattc | ttcaaacatg | 1380 |
| gctttcggat | acggcaagta | tgcttgtcca | ggtagatttt | acgcgtctaa | tgagatgaaa | 1440 |
| ctaacattag | ccattttgtt | gctacaattt | gagttcaaac | taccagatgg | taaaggtcgt | 1500 |
| cctagaaata | tcactatcga | ttctgatatg | attccagacc | caagagctag | actttgcgtc | 1560 |
| agaaaaagat | cacttagaga | tgaatgaccg | cgg | | | 1593 |

SEQ ID NO: 72

```
MSKSNSMNST SHETLFQQLV LGLDRMPLMD VHWLIYVAFG AWLCSYVIHV LSSSSTVKVP      60
VVGYRSVFEP TWLLRLRFVW EGGSIIGQGY NKFKDSIFQV RKLGTDIVII PPNYIDEVRK     120
LSQDKTRSVE PFINDFAGQY TRGMVFLQSD LQNRVIQQRL TPKLVSLTKV MKEELDYALT     180
KEMPDMKNDE WVEVDISSIM VRLISRISAR VFLGPEHCRN QEWLTTTAEY SESLFITGFI     240
LRVVPHILRP FIAPLLPSYR TLLRNVSSGR RVIGDIIRSQ QGDGNEDILS WMRDAATGEE     300
KQIDNIAQRM LILSLASIHT TAMTMTHAMY DLCACPEYIE PLRDEVKSVV GASGWDKTAL     360
NRFHKLDSFL KESQRFNPVF LLTFNRIYHQ SMTLSDGTNI PSGTRIAVPS HAMLQDSAHV     420
PGPTPPTEFD GFRYSKIRSD SNYAQKYLFS MTDSSNMAFG YGKYACPGRF YASNEMKLTL     480
AILLLQFEFK LPDGKGRPRN ITIDSDMIPD PRARLCVRKR SLRDE                     525
```

SEQ ID NO: 73

| | | | | | |
|---|---|---|---|---|---|
| aagcttaaaa | tggaagatcc | tactgtctta | tatgcttgtc | ttgccattgc | agttgcaact | 60 |
| ttcgttgtta | gatggtacag | agatccattg | agatccatcc | caacagttgg | tggttccgat | 120 |
| ttgcctattc | tatcttacat | cggcgcacta | agatggacaa | gacgtggcag | agagatactt | 180 |
| caagagggat | atgatggcta | cagaggatct | acattcaaaa | tcgcgatgtt | agaccgttgg | 240 |
| atcgtgatcg | caaatggtcc | taaactagct | gatgaagtca | gacgtagacc | agtgaagag | 300 |
| ttaaacttta | tggacggatt | aggagccattc | gtccaaacta | agtacacctt | aggtgaagct | 360 |
| attcataacg | atccataca | tgtcgatatc | ataagagaaa | aactaacaag | aggccttcca | 420 |
| gccgtgcttc | ctgatgtcat | tgaagagttg | acacttgcgg | ttagacagta | cattccaaca | 480 |
| gaaggtgatg | aatgggtgtc | cgtaaactgt | tcaaaggccg | caagagatat | tgttgctaga | 540 |
| gcttctaata | gagtctttgt | aggtttgcct | gcttgcagaa | accaaggtta | cttagatttg | 600 |
| gcaatagact | ttacattgtc | tgttgtcaag | gatagagcca | tcatcaatat | gttttccagaa | 660 |
| ttgttgaagc | caatagttgg | cagagttgta | ggtaacgcca | ccagaaatgt | tcgtagagct | 720 |
| gttccttttg | ttgctccatt | ggtggaggaa | agacgtagac | ttatggaaga | gtacggtgaa | 780 |
| gactggtctg | aaaaacctaa | tgatatgtta | cagtggataa | tggatgaagc | tgcatccaga | 840 |
| gatagttcag | tgaaggcaat | cgcagagaga | ttgttaatgg | tgaacttcgc | ggctattcat | 900 |
| acctcatcaa | acactatcac | tcatgctttg | taccaccttg | ccgaaatgcc | tgaaactttg | 960 |
| caaccactta | gagaagagat | cgaaccatta | gtcaaagagg | agggctggac | caaggctgct | 1020 |
| atgggaaaaa | tgtggtggtt | agattcattt | ctaagagaat | caaagata | caatggcatt | 1080 |
| aacatcgtat | ctttaactag | aatgctgac | aaagatatta | cattgagtga | tggcacatttt | 1140 |
| ttgccaaaag | gtactctagt | ggccgttcca | gcgtattcta | ctcatagaga | tgatgctgtc | 1200 |
| tacgctgatg | ccttagtatt | cgatccttcc | agattctcac | gtatgagagc | gagagaaggt | 1260 |
| gaaggtacaa | agcaccagtt | cgttaatact | tcagtcgagt | acgttccatt | tggtcacgga | 1320 |

TABLE 10-continued

Sequences disclosed herein.

```
aagcatgctt gtccaggaag attcttcgcc gcaaacgaat tgaaagcaat gttggcttac   1380
attgttctaa actatgatgt aaagttgcct ggtgacggta aacgtccatt gaacatgtat   1440
tggggtccaa cagttttgcc tgcaccagca ggccaagtat tgttcagaaa gagacaagtt   1500
agtctataac cgcgg                                                    1515

SEQ ID NO: 74
MEDPTVLYAC LAIAVATFVV RWYRDPLRSI PTVGGSDLPI LSYIGALRWT RRGREILQEG     60
YDGYRGSTFK IAMLDRWIVI ANGPKLADEV RRRPDEELNF MDGLGAFVQT KYTLGEAIHN    120
DPYHVDIIRE KLTRGLPAVL PDVIEELTLA VRQYIPTEGD EWVSVNCSKA ARDIVARASN    180
RVFVGLPACR NQGYLDLAID FTLSVVKDRA IINMFPELLK PIVGRVVGNA TRNVRRAVPF    240
VAPLVEERRR LMEEYGEDWS EKPNDMLQWI MDEAASRDSS VKAIAERLLM VNFAAIHTSS    300
NTITHALYHL AEMPETLQPL REEIEPLVKE EGWTKAAMGK MWWLDSFLRE SQRYNGINIV    360
SLTRMADKDI TLSDGTFLPK GTLVAVPAYS THRDDAVYAD ALVFDPFRFS RMRAREGEGT    420
KHQFVNTSVE YVPFGHGKHA CPGRFFAANE LKAMLAYIVL NYDVKLPGDG KRPLNMYWGP    480
TVLPAPAGQV LFRKRQVSL                                                499

SEQ ID NO: 75
atggcatttt tctctatgat ttcaattttg ttgggatttg ttatttcttc tttcatcttc     60
atcttttttct tcaaaaagtt acttagtttt agtaggaaaa acatgtcaga agtttctact   120
ttgccaagtg ttccagtagt gcctggtttt ccagttattg ggaatttgtt gcaactaaag    180
gagaaaaagc ctcataaaac tttcactaga tggtcagaga tatatggacc tatctactct    240
ataaagatgg gttcttcatc tcttattgta ttgaacagta cagaaactgc taaggaagca    300
atggtcacta gattttcatc aatatctacc agaaaattgt caaacgccct aacagttcta    360
acctgcgata agtctatggt cgccacttct gattatgatg acttccacaa attagttaag    420
agatgtttgc taaatggact tcttggtgct aatgctcaaa agagaaaaag acactacaga    480
gatgctttga ttgaaaatgt gagttccaag ctacatgcac acgctagaga tcatccacaa    540
gagccagtta actttagagc aattttcgaa cacgaattgt tggtgtagc attaaagcaa     600
gccttcggta aagacgtaga atccatatac gtcaaggagt taggcgtaac attatcaaaa    660
gatgaaatct ttaaggtgct tgtacatgat atgatggagg gtgcaattga tgtagattgg    720
agagatttct tcccatattt gaaatggatc cctaataagt cttttgaagc taggatacaa    780
caaaagcaca agagaagact agctgttatg aacgcactta tacaggacag attgaagcaa    840
aatgggtctg aatcagatga tgattgttac cttaacttct taatgtctga ggctaaaaca    900
ttgactaagg aacagatcgc aatccttgtc tgggaaacaa tcattgaaac agcagatact    960
accttagtca caactgaatg ggccatatac gagctagcca aacatccatc tgtgcaagat   1020
aggttgtgta aggagatcca aacgtgtgt ggtggagaga aattcaagga agagcagttg    1080
tcacaagttc cttaccttaa cggcgttttc catgaaacct tgagaaaata ctcacctgca   1140
ccattagttc ctattagata cgcccacgaa gatacacaaa tcggtggcta ccatgttcca   1200
gctgggtccg aaattgctat aaacatctac gggtgcaaca tggacaaaaa gagatgggaa   1260
agaccagaag attggtggcc agaaagattc ttagatgatg gcaaatatga aacatctgat   1320
ttgcataaaa caatggcttt cggagctggc aaaagagtgt gtgccggtgc tctacaagcc   1380
tccctaatgg ctggtatcgc tattggtaga ttggtccaag agttcgaatg gaaacttaga   1440
gatggtgaag aggaaaatgt cgatacttat gggttaacat ctcaaaagtt atacccacta   1500
atggcaatca tcaatcctag aagatcctaa                                    1530

SEQ ID NO: 76
MAFFSMISIL LGFVISSFIF IFFFKKLLSF SRKNMSEVST LPSVPVVPGF PVIGNLLQLK     60
EKKPHKTFTR WSEIYGPIYS IKMGSSSLIV LNSTETAKEA MVTRFSSIST RKLSNALTVL    120
TCDKSMVATS DYDDFHKLVK RCLLNGLLGA NAQKRKRHYR DALIENVSSK LHAHARDHPQ    180
EPVNFRAIFE HELFGVALKQ AFGKDVESIY VKELGVTLSK DEIFKVLVHD MMEGAIDVDW    240
RDFFPYLKWI PNKSFEARIQ QKHKRRLAVM NALIQDRLKQ NGSESDDDCY LNFLMSEAKT    300
LTKEQIAILV WETIIETADT TLVTTEWAIY ELAKHPSVQD RLCKEIQNVC GGEKFKEEQL    360
SQVPYLNGVF HETLRKYSPA PLVPIRYAHE DTQIGGYHVP AGSEIAINIY GCNMDKKRWE    420
RPEDWWPERF LDDGKYETSD LHKTMAFGAG KRVCAGALQA SLMAGIAIGR LVQEFEWKLR    480
DGEEENVDTY GLTSQKLYPL MAIINPRRS                                     509

SEQ ID NO: 77
atgcaatcag attcagtcaa agtctctcca tttgatttgg tttccgctgc tatgaatggc     60
aaggcaatgg aaaagttgaa cgctagtgaa tctgaagatc caacaacatt gcctgcacta    120
aagatgctag ttgaaaatag agaattgttg acactgttca caacttcctt cgcagttctt    180
attgggtgtc ttgtatttct aatgtggaga cgttcatcct ctaaaaagct ggtacaagat    240
ccagttccac aagttatcgt tgtaaagaag aaagagaagg agtcagaagt tgatgacggg    300
aaaaaagaaag tttctatttt ctacggcaca caaacaggaa ctgccgaagg ttttgctaaa    360
gcattagtcg aggaagcaaa agtgagatat gaaaagacct cttttcaaggt tatcgatcta    420
gatgactacg ctgcagatga tgatgaatat gaggaaaaac tgaaaaagga atccttagcc    480
ttcttcttct tggccacata cggtgatggt gaacctactg ataatgctgc taacttctac    540
aagtggttca cagaaggcga cgataaaggt gaatggctga aaaagttaca atacggagta    600
tttggtttag gtaacagaca atatgaacat tcaacaagaa tcgctattgt agttgatgat    660
aaacttactg aaatgggagc caaaagatta gtaccagtag gattagggga tgatgatcag    720
tgtatagaag atgacttcac cgcctggaag gaattgatta ggcagaatt ggatcaactt     780
ttaagggacg aagatgatac ttctgtgact accccataca ctgcagccgt attggagtac    840
agagtggttt accatgataa accagcagac tcatatgctg aagatcaaac ccatacaaac    900
ggtcatgttg tcatgatgc acagcatcct tcaagatcta atgtggcttt caaaaaggaa     960
ctacacacct ctcaatcaga taggtcttgt actcacttag aattcgatat ttctcacaca   1020
tgactgtctt acgaaactgg cgatcacgtt ggcgttatt ccgagaactt gtccgaagtt    1080
gtcgatgaag cactaaaact gttagggtta tcaccagaca catacttctc agtccatgct   1140
gataaggagg atgggacacc tatccggtggt gcttcactac caccacctt tcctccttgc   1200
acattggaga acgctctaac cagatacgca gatgtcttat cctcacctaa aaaggtagct   1260
ttgctggcat tggctgctca tgctagtgat cctagtgaag ccgataggtt aaagttcctg   1320
```

TABLE 10-continued

Sequences disclosed herein.

```
gcttcaccag ccggaaaaga tgaatatgca caatggatcg tcgccaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtt tacgagacta ctccagcagg cagaattcac   1560
agaggattgt gttcaacctg gatgaaaaat gctgtccctt aacagagtc acctgattgc    1620
tctcaagcat ccatttcgt tagaacatca aatttcagac ttccagtgga tccaaaagtt    1680
ccagtcatta tgataggacc aggcactggt cttgccccat caggggctt tcttcaagag    1740
agattggcct tgaaggaatc tggtacagaa ttgggtcctt ctatcttttt ctttggttgc   1800
cgtaatagaa aagttgactt tatctacgag gacgagctta acaattttgt tgagacagga   1860
gcattgtcag aattgatcgt cgcattttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133
```

SEQ ID NO: 78
```
MQSDSVKVSP FDLVSAAMNG KAMEKLNASE SEDPTTLPAL KMLVENRELL TLFTTSFAVL    60
IGCLVFLMWR RSSSKKLVQD PVPQVIVVKK KEKESEVDDG KKKVSIFYGT QTGTAEGFAK   120
ALVEEAKVRY EKTSFKVIDL DDYAADDDEY EEKLKKESLA FFFLATYGDG EPTDNAANFY   180
KWFTEGDDKG EWLKKLQYGV FGLGNRQYEH FNKIAIVVDD KLTEMGAKRL VPVGLGDDDQ   240
CIEDDFTAWK ELVWPELDQL LRDEDDTSVT TPYTAAVLEY RVVYHDKPAD SYAEDQTHTN   300
GHVVHDAQHP SRSNVAFKKE LHTSQSDRSC THLEFDISHT GLSYETGDHV GVYSENLSEV   360
VDEALKLLGL SPDTYFSVHA DKEDGTPIGG ASLPPPFPGY TLRDALTRYA DVLSSPKKVA   420
LLALAAHASD PSEADRLKFL ASPAGKDEYA QWIVANQRSL LEVMQSFPSA KPPLGVFFAA   480
VAPRLQPRYY SISSSPKMSP NRIHVTCALV YETTPAGRIH RGLCSTWMKN AVPLTESPDC   540
SQASIFVRTS NFRLPVDPKV PVIMIGPGTG LAPFRGFLQE RLALKESGTE LGSSIFFFGC   600
RNRKVDFIYE DELNNFVETG ALSELIVAFS REGTAKEYVQ HKMSQKASDI WKLLSEGAYL   660
YVCGDAKGMA KDVHRTLHTI VQEQGSLDSS KAELYVKNLQ MSGRYLRDVW              710
```

SEQ ID NO: 79
```
atgaaggtca gtccattcga attcatgtcc gctattatca agggtagaat ggacccatct     60
aactcctcat ttgaatctac tggtgaagtt gcctccgtta tctttgaaaa cagagaattg   120
gttgccatct tgaccacttc tattgctgtt atgattggtt gcttcgttgt cttgatgtgg   180
agaagagctg gttctagaaa ggttaagaat gtcgaattgc caaagccatt gattgtccat   240
gaaccagaac ctgaagttga agatggtaag aagaaggttt ccatcttctt cggtactcaa   300
actggtactg ctgaaggttt tgctaaggct ttggctgata agctaaagc tagatacgaa   360
aaggctacct tcagagttgt tgatttggat gattatgctg ccgatgatga ccaatacgaa   420
gaaaaattga gaacgaatc cttcgccgtt ttccttgttgg ctacttatgg tgatggtgaa   480
cctactgata atgctgctag attttacaag tggttcgccg aaggtaaaga aagaggtgaa   540
tggttgcaaa acttgcacta tgctgttttt ggtttgggta acagacaata cgaacacttc   600
aacaagattg ctaaggttgc cgacgaatta ttggaagctc aaggtggtaa tagattggtt   660
aaggttggtt taggtgatga cgatcaatgc atcgaagatg atttttctgc ttggagagaa   720
tctttgtggc cagaattgga tatgttgttg agagatgaag atgatgctac tactgttact   780
actccatata ctgctgctgt cttggaatac agagttgtct ttcatgattc tgctgatgtt   840
gctgctgaag ataagtcttg gattaacgct aatggtcatg ctgttcatga tgctcaacat   900
ccattcagat ctaacgttgt cgtcagaaaa gaattgcata cttctgcctc tgatagatcc   960
tgttctcatt tggaattcaa catttccggt tccgctttga attacgaaac tggtgatcat  1020
gttggtgtct actgtgaaaa cttgactgaa actgttgatg aagccttgaa cttgttgggt  1080
ttgtctccag aaacttactt ctctatctac accgataacg aagatggtac tccattgggt  1140
ggttcttcat tgccaccacc atttccatca tgtactttga aactgctttt gaccagatac  1200
gctgattgt tgaactctcc aaaaaagtct gctttgttgg ctttagctgc tcatgcttct  1260
aatccagttg aagctgatag attgaagtac ttggcttctc cagctggtaa agatgaatat  1320
gcccaatctg ttatcggttc ccaaaagtct ttggttggaag ttatggctga attcccatct  1380
gctaaaccac cattaggtgt ttttttttgct gctgttgctc caagattgca acctagattc  1440
tactccattt catcctctcc aagaatggct ccatctagaa tccatgttac ttgtgctttg  1500
gtttacgata agatgccaac tggtagaatt cataaggggt tttgttctac ctggatgaag  1560
aattctgttc caatggaaaa gtcccatgaa tgttcttggg ctccaatttt cgttagacaa  1620
tccaattta agttgccagc cgaatccaag gttccaatta tcatggttgg tccaggtact  1680
ggtttggctc cttttagagg ttttttacaa gaaagattgg ccttgaaaga atccggtgtt  1740
gaattgggtc catccatttt gttttttcggt tgcagaaaca aagaatgga ttacatctac  1800
gaagatgaat tgaacaactt cgttgaaacc ggtgcttttgt ccgaattggt tattgctttt  1860
tctagagaag gtcctaccaa agaatacgtc aacataaga tggctgaaaa ggcttctgat  1920
atctggaact tgatttctga aggtgcttac ttgtacgttt gtggtgatgc taaaggtatg  1980
gctaaggatg ttcatagaac cttgcatacc atcatgcaag aacaaggttc tttggattct  2040
tccaaagctg aatccatggt caagaacttg caaatgaatg gtagatactt aagagatgtt  2100
tggtaa                                                              2106
```

SEQ ID NO: 80
```
MKVSPFEFMS AIIKGRMDPS NSSFESTGEV ASVIFENREL VAILTTSIAV MIGCFVVLMW    60
RRAGSRKVKN VELPKPLIVH EPEPEVEDGK KKVSIFFGTQ TGTAEGFAKA LADEAKARYE   120
KATFRVVDLD DYAADDDQYE EKLKNESFAV FLLATYGDGE PTDNAARFYK WFAEGKERGE   180
WLQNLHYAVF GLGNRQYEHF NKIAKVADEL LEAQGGNRLV KVGLGDDDQC IEDDFSAWRE   240
SLWPELDMLL RDEDDATTVT TPYTAAVLEY RVVPHDSADV AAEDKSWINA NGHAVHDAQH   300
PFRSNVVVRK ELHTSASDRS CSHLEFNISG SALNYETGDH VGVYCENLTE TVDEALNLLG   360
LSPETYFSIY TDNEDGTPLG GSSLPPPFPS CTLRTALTRY ADLLNSPKKS ALLALAAHAS   420
NPVEADRLRY LASPAGKDEY AQSVIGSQKS LLEVMAEFPS AKPPLGVFFA AVAPRLQPRF   480
YSISSSPRMA PSRIHVTCAL VYDKMPTGRI HKGVCSTWMK NSVPMEKSHE CSWAPIFVRQ   540
SNFKLPAESK VPIIMVGPGT GLAPFRGFLQ ERLALKESGV ELGPSILFFG CRNRRMDYIY   600
```

TABLE 10-continued

Sequences disclosed herein.

```
EDELNNFVET GALSELVIAF SREGPTKEYV QHKMAEKASD IWNLISEGAY LYVCGDAKGM    660
AKDVHRTLHT IMQEQGSLDS SKAESMVKNL QMNGRYLRDV W                        701

SEQ ID NO: 81
atggcagaat tagatacact tgatatagta gtattaggtg ttatctttttt gggtactgtg    60
gcatacttta ctaagggtaa attgtggggt gttaccaagg atccatacgc taacggattc   120
gctgcaggtg gtgcttccaa gcctggcaga actagaaaca tcgtcgaagc tatggaggaa   180
tcaggtaaaa actgtgttgt tttctacggc agtcaaacag gtacagcgga ggattacgca   240
tcaagacttg caaaggaagg aaagtccaga ttcggtttga acactatgat cgccgatcta   300
gaagattatg acttcgataa cttagacact gttccatctg ataacatcgt tatgtttgta   360
ttggctactt acggtgaagg cgaaccaaca gataacgccg tggatttcta tgagttcatt   420
actggcgaag atgcctcttt caatgagggc aacgatcctc cactaggtaa cttgaattac   480
gttgcgttcg gtctgggcaa caatacctac gaacactaca actcaatggt caggaacgtt   540
aacaaggctc tagaaaagtt aggagctcat agaattggag aagcaggtga gggtgacgac   600
ggagctggaa ctatggaaga ggactttta gcttggaaga tccaatgtg ggaagccttg    660
gctaaaaaga tgggcttgga ggaaagagaa gctgtatatg aacctatttt cgctatcaat   720
gagagagatg atttgacccc tgaagcgaat gaggtatact gggagaacc taataagcta   780
cacttggaag gtacagcgaa aggtccattc aactcccaca acccatatat cgcaccaatt   840
gcagaatcat acgaactttt ctcagctaag gatagaaatt gtctgcatat ggaaattgat   900
atttctggta gtaatctaaa gtatgaaaca ggcgaccata tcgcgatctg gcctaccaac   960
ccaggtgaag aggtcaacaa atttcttgac attctagatc tgtctggtaa gcaacattcc  1020
gtcgtaacag tgaaagcctt agaacctaca gccaaagttc cttttccaaa tccaactacc  1080
tacgatgcta tattgagata ccatctggaa atatgcgctc cagtttctag acagtttgtc  1140
tcaacttttag cagcattcgc ccctaatgat gatatcaaag ctgagatgaa ccgtttggga  1200
tcagacaaag attactccca cgaaagaca ggaccacatt actacaatat cgctagattt   1260
ttggcctcag tctctaaagg tgaaaatgg acaaagatac catttctgc tttcatagaa   1320
ggccttacaa aactacaacc aagatactat tctatctctc cctctagttt agttcagcct  1380
aaaaagatta gtattactgc tgttgtcgaa tctcagcaaa ttccaggtag agatgaccca  1440
ttcagaggtg tagcgactaa ctacttgttc gctttgaagc agaaacaaaa cggtgatcca  1500
aatccagctc cttttggcca atcatacgag ttgacaggac caaggaataa gtatgatggt  1560
atacatgttc cagtccatgt aagacattct aactttaagc taccatctga tccaggcaaa  1620
cctattatca tgatcggtcc aggtaccggt gttgcccctt ttagaggctt cgtccaaagg  1680
agggcaaaac aagccagaga tggtgtagaa gttggtaaaa cactgctgtt ctttggatgt  1740
agaaagagta cagaagattt catgtatcaa aaagagtggc aagagtacaa ggaagctctt  1800
ggcgacaaat tcgaaatgat tacagctttt tcaagagaag gatctaaaaa ggtttatgtt  1860
caacacagac tgaaggaaag atcaaaggaa gtttctgatc ttctatccca aaaagcatac  1920
ttctacgttt gcggagacgc cgcacatatg gcacgtgaag tgaacactgt gttagcacag  1980
atcatagcag aaggccgtgg tgtatcagaa gccaagggtg aggaaattgt caaaaacatg  2040
agatcagcaa atcaatacca agtgtgttct gatttcgtaa ctttacactg taaagagaca  2100
acatacgcga attcagaatt gcaagaggat gtctggagtt aa                      2142

SEQ ID NO: 82
MAELDTLDIV VLGVIFLGTV AYFTKGKLWG VTKDPYANGF AAGGASKPGR TRNIVEAMEE    60
SGKNCVVFYG SQTGTAEDYA SRLAKEGKSR FGLNTMIADL EDYDFDNLDT VPSDNIVMFV   120
LATYGEGEPT DNAVDFYEFI TGEDASFNEG NDPPLGNLNY VAFGLGNNTY EHYNSMVRNV   180
NKALEKLGAH RIGEAGEGDD GAGTMEEDFL AWKDPMWEAL AKKMGLEERE AVYEPIFAIN   240
ERDDLTPEAN EVYLGEPNKL HLEGTAKGPF NSHNPYIAPI AESYELFSAK DRNCLHMEID   300
ISGSNLKYET GDHIAIWPTN PGEEVNKFLD ILDLSGKQHS VVTVKALEPT AKVPFNPTT    360
YDAILRYHLE ICAPVSRQFV STLAAFAPND DIKAEMNRLG SDKDYFHEKT GPHYYNIARF   420
LASVSKGEKW TKIPFSAFIE GLTKLQPRYY SISSSSLVQP KKISITAVVE SQQIPGRDDP   480
FRGVATNYLF ALKQKQNGDP NPAPFGQSYE LTGPRNKYDG IHVPVHVRHS NFKLPSDPGK   540
PIIMIGPGTG VAPFRGFVQE RAKQARDGVE VGKTLLFFGC RKSTEDFMYQ KEWQEYKEAL   600
GDKFEMITAF SREGSKKVYV QHRLKERSKE VSDLLSQKAY FYVCGDAAHM AREVNTVLAQ   660
IIAEGRGVSE AKGEEIVKNM RSANQYQVCS DFVTLHCKET TYANSELQED VWS          713

SEQ ID NO: 83
atgcaatcgg aatccgttga agcatcgacg attgatttga tgactgctgt tttgaaggac    60
acagtgatcg atacagcgaa cgcatctgat aacggagact caaagatgcc gccggcgttg   120
gcgatgatgt tcgaaattcg tgatctgttg ctgattttga ctacgtcagt tgctgttttg   180
gtcggatgtt tcgttgtttt ggtgtggaag agatcgtccg gaagaagtc cggcaaggaa    240
ttggagccgc cgaagatcgt tgtgccgaag aggcggctgg agcaggaggt tgatgatgat   300
aagaagaagg ttacgatttt cttcggaaca caaactggaa cggctgaagg tttcgctaag   360
gcacttttcg aagaagcgaa agcgcgatat gaaaaggcag cgtttaaagt gattgatttg   420
gatgattatg ctgctgattt ggatgagtat gcagagaagc tgaagaagga acatatgct    480
ttcttcttct tggctacata tggagatggt gagcaactga ataatgctgc caaattttat   540
aaatggttta ctgagggaga cgagaaaggc gtttggcttc aaaaacttca atatggagta   600
tttggtcttg gcaacagaca atatgaacat tcaacaagaa ttggaatagt ggttgatgat   660
ggtctcaccg agcagggtgc aaaacgcatt gttcccgttg tcttggaga cgacgatcaa   720
tcaattgaag acgattttttc ggcatggaaa gagttagtgt ggcccgaatt ggatctattg   780
cttcgcgatg aagatgacaa agctgctgca actccttaca cagctgcaat ccctgaatac   840
cgcgtcgtat tcatgacaaa acccgatgcg tttttctgatg atcatactca aaccaatggt   900
catgctgttc atgatgctca acatccatgc agatccaatg tggctgttaa aaagagctt    960
catactcctg aatccgatcg ttcatgcaca catcttgaat ttgacatttc tcacactgga  1020
ttatcttatg aaactggga tcatgtttggt gtatactgtg aaaacctaat tgaagtagtg   1080
gaagaagctg ggaaatttgtt aggattatca acagatactt atttctcgtt acatattgat  1140
aacgaagatg gttcaccact tggtggacct tcattacaac ctcctttcc tccttgtact  1200
ttaagaaaag cattgactaa ttatgcagat ctgttaagct ctcccaaaaa gtcaactttg   1260
cttgctctag ctgctcatgc ttccgatccc actgaagctg atcgtttaag atttcttgca  1320
```

TABLE 10-continued

Sequences disclosed herein.

```
tctcgcgagg gcaaggatga atatgctgaa tgggttgttg caaaccaaag aagtcttctt    1380
gaagtcatgg aagctttccc gtcagctaga ccgccacttg gtgtttttctt tgcagcggtt    1440
gcaccgcgtt tacagcctcg ttactactct atttcttcct ccccaaagat ggaaccaaac    1500
aggattcatg ttacttgcgc gttggtttat gaaaaaactc ccgcaggtcg tatccacaaa    1560
ggaatctgct caacctggat gaagaacgct gtacctttga ccgaaagtca agattgcagt    1620
tgggcaccga tttttgttag aacatcaaac ttcagacttc aattgaccc gaaagtcccg    1680
gttatcatga ttggtcctgg aaccggggttg gctccattca ggggttttct tcaagaaaga    1740
ttggctctta aagaatccgg aaccgaactc gggtcatcta ttttattctt cggttgtaga    1800
aaccgcaaag tggattacat atatgagaat gaactcaaca actttgttga aaatggtgcg    1860
cttctctgagc ttgatgttgc tttctcccgc gatggcccga cgaaagaata cgtgcaacat    1920
aaaatgaccc aaaaggcttc tgaaatatgg aatatgctct ctgagggagc atatttatat    1980
gtatgtggtg atgctaaagg catggctaaa gatgtacacc gtacacttca caccattgtg    2040
caagaacagg gaagtttgga ctcgtctaaa gcggagttgt atgtgaagaa tctacaaatg    2100
tcaggaagat acctccgtga tgtttggtaa                                     2130

SEQ ID NO: 84
MQSESVEAST IDLMTAVLKD TVIDTANASD NGDSKMPPAL AMMFEIRDLL LILTTSVAVL     60
VGCFVVLVWK RSSGKKSGKE LEPPKIVVPK RRLEQEVDDG KKKVTIFFGT QTGTAEGFAK    120
ALFEEAKARY EKAAFKVIDL DDYAADLDEY AEKLKKETYA FFFLATYGDG EPTDNAAKFY    180
KWFTEGDEKG VWLQKLQYGV FGLGNRQYEH FNKIGIVVDD GLTEQGAKRI VPVGLGDDDQ    240
SIEDDFSAWK ELVWPELDLL LRDEDDKAAA TPYTAAIPEY RVVFHDKPDA FSDDHTQTNG    300
HAVHDAQHPC RSNVAVKKEL HTPESDRSCT HLEFDISHTG LSYETGDHVG VYCENLIEVV    360
EEAGKLLGLS TDTYFSLHID NEDGSPLGGP SLQPPFPPCT LRKALTNYAD LLSSPKKSTL    420
LALAAHASDP TEADRLRFLA SREGKDEYAE WVVANQRSLL EVMEAFPSAR PPLGVFFAAV    480
APRLQPRYYS ISSSPKMEPN RIHVTCALVY EKTPAGRIHK GICSTWMKNA VPLTESQDCS    540
WAPIFVRTSN FRLPIDPKVP VIMIGPGTGL APFRGFLQER LALKESGTEL GSSILFFGCR    600
NRKVDYIYEN ELNNFVENGA LSELDVAFSR DGPTKEYVQH KMTQKASEIW NMLSEGAYLY    660
VCGDAKGMAK DVHRTLHTIV QEQGSLDSSK AELYVKNLQM SGRYLRDVW                709

SEQ ID NO: 85
atgcaatcta actccgtgaa gatttcgccg cttgatctgg taactgcgct gtttagcggc     60
aaggttttgg acacatcgaa cgcatcggaa tcgggagaat ctgctatgct gccgactata    120
gcgatgatta tggagaatcg tgagctgttg atgatactca aacgtcggt tgctgtattg     180
atcggatgcg ttgtcgtttt ggtgtggcgg agatcgtcta cgaagaagtc ggcgttggag    240
ccaccggtga ttgtggttcc gaagagagtg caagaggagg aagttgatga tggtaagaag    300
aagttacgg ttttcttcgg cacccaaact ggaacagctg aaggcttcgc taaggcactt    360
gttgaggaag ctaaagctcg atatgaaaag gctgtcttta aagtaattga tttggatgat    420
tatgctgctg atgacgatga gtatgaggag aaactaaaga aagaatcttt ggccttttc     480
tttttggcta cgtatggaga tggtgagcca acagataatg ctgccagatt ttataaatgg    540
tttactgagg gagatgcgaa aggagaatgg cttaataagc ttcaatatgg agtatttggt    600
ttgggtaaca gacaatatga acattttaac aagatcgcaa aagtggttga tgatggtctt    660
gtagaacagg gtgcaaagcg tcttgttcct gttggacttg gagatgatga tcaatgtatt    720
gaagatgact tcaccgcatg gaaagagtta gtatggccgg agttggatca attacttcgt    780
gatgaggaga acacaactgt tgctactcca tacacagctg ctgttgcaga atatcgcgtt    840
gtttttcatg aaaaaccaga cgcgcttttct gaagattata gttatacaaa tggccatgct    900
gttcatgatg ctcaacatcc atgcagatcc aacgtggctg tcaaaaagga acttcatagt    960
cctgaatctg accggtcttg cactcatctt gaatttgaca tctcgaacac cggactatca   1020
tatgaaactg gggaccatgt tggagtttac tgtgaaaact tgagtgaagt tgtgaatgat   1080
gctgaaagat tagtaggatt accaccagac acttactcct ccatccacac tgatagtgaa   1140
gacgggtcgc cacttggcgg agccttcattg ccgcctcctt tccgccatg cactttaagg   1200
aaaagcattga cgtgttatgc tgatgttttg agttctccca agaagtcggc tttgcttgca   1260
ctagctgctc atgccaccga tccccagtga actgataagt tgaaatttct tgcatcccgt   1320
gccgaaaagg atgaatattc tcaatggata gttgcaagcc aagaagtct ccttgaagtc    1380
atggaagcat tcccgtcagc taagccttca cttggtgttt tctttgcatc tgttgccccg   1440
cgcttacaac aagatacta ctctatttct tcctcaccca agatggcacc ggataggatt   1500
catgttacat gtgcattagt ctatgagaaa acacctgcag gccgcatcca caaggagtt   1560
tgttcaactt ggatgaagaa cgcagtgcct atgaccggga gtcaagattg cagttgggcc   1620
ccaatatacg tccgaacatc caatttcaga ctaccatctg accctaaggt cccggttatc   1680
atgattggac ctggcactgg tttggctcct tttagaggtt tccttcaaga gcggttagct   1740
ttaaaggaag ccggaactga cctcggttta tccatttttat tcttcggatg taggaatcgc   1800
aaagtggatt tcatatatga aaacgagctt aacaacttttg tggagactgg tgctctttct   1860
gagcttattg ttgcttttctc ccgtgaaggc ccgactaagg aatatgtgca acacaagatg   1920
agtgagaagg cttcggatat ctggaacttg ctttctgaag agcatatttt atacgtatgt   1980
ggtgatgcca aaggcatggc caagatgta catcgaaccc tccacacaat tgtgcaagaa   2040
cagggatctc ttgactcgtc aaaggcagaa ctctacgtga gaatctaca aatgtcagga   2100
agatacctcc gtgacgtttg gtaa                                          2124

SEQ ID NO: 86
MQSNSVKISP LDLVTALFSG KVLDTSNASE SGESAMLPTI AMIMENRELL MILTTSVAVL     60
IGCVVVLVWR RSSTKKSALE PPVIVVPKRV QEEEVDDGKK KVTVFFGTQT GTAEGFAKAL    120
VEEEAKARYEK AVFKVIDLDD YAADDDEYEE KLKKESLAFF FLATYGDGEP TDNAARFYKW    180
FTEGDAKGEW LNKLQYGVFG LGNRQYEHFN KIAKVVDDGL VEQGAKRLVP VGLGDDDQCI    240
EDDFTAWKEL VWPELDQLL DEDDTTVATP YTAAVAEYRV VPHEKPDALS EDYSYTNGHA    300
VHDAQHPCRS NVAVKKELHS PESDRSCTHL EFDISNTGLS YETGDHVGVY CENLSEVVND    360
AERLVGLPPD TYSSIHTDSE DGSPLGGASL PPPFPPCTLR KALTCYADVL SSPKKSALLA    420
LAAHATDPSE ADRLKFLASP AGKDEYSQWI VASQRSLLEV MEAFPSAKPS LGVFFASVAP    480
RLQPRYYSIS SSPKMAPDRI HVTCALVYEK TPAGRIHKGV CSTWMKNAVP MTESQDCSWA    540
PIYVRTSNFR LPSDPKVPVI MIGPGTGLAP FRGFLQERLA LKEAGTDLGL SILFFGCRNR    600
```

| | | | | | |
|---|---|---|---|---|---|
| KVDFIYENEL | NNFVETGALS | ELIVAFSREG | PTKEYVQHKM | SEKASDIWNL | LSEGAYLYVC | 660 |
| GDAKGMAKDV | HRTLHTIVQE | QGSLDSSKAE | LYVKNLQMSG | RYLRDVW | | 707 |

SEQ ID NO: 87

| | | | | |
|---|---|---|---|---|
| atgtcctcca | actccgattt | ggtcagaaga | ttggaatctg | ttttgggtgt | ttctttcggt | 60 |
| ggttctgtta | ctgattccgt | tgttgttatt | gctaccacct | ctattgcttt | ggttatcggt | 120 |
| gttttggttt | tgttgtggag | aagatcctct | gacagatcta | gagaagttaa | gcaattggct | 180 |
| gttccaaagc | cagttactat | cgttgaagaa | gaagatgaat | tcgaagttgc | ttctggtaag | 240 |
| accagagttt | ctattttcta | cggtactcaa | actggtactg | ctgaaggttt | tgctaaggct | 300 |
| ttggctgaag | aaatcaaagc | cagatacgaa | aaagctgccg | ttaaggttat | tgatttggat | 360 |
| gattacacag | ccgaagatga | caaatacggt | gaaaagttaa | agaaagaaac | tatggccttc | 420 |
| ttcatgttgg | ctacttatgg | tgatggtgaa | cctactgata | atgctgctag | attttacaag | 480 |
| tggttcaccg | aaggtactga | tagaggtgtt | tggttggaac | atttgagata | cggtgtattc | 540 |
| ggtttgggta | acagacaata | cgaacacttc | aacaagattg | ccaaggttgt | tgatgatttg | 600 |
| ttggttgaac | aaggtgccaa | gagattggtt | actgttggtt | tgggtgatga | tgatcaatgc | 660 |
| atcgaagatg | atttctccgc | ttggaaagaa | gccttgtggc | cagaattgga | tcaattattg | 720 |
| caagatgata | ccaacaccgt | ttctactcca | tacactgctg | ttattccaga | atacagagtt | 780 |
| gttatccacg | atccatctgt | tacctcttat | gaagatccat | actctaacat | ggctaacggt | 840 |
| aatgcctctt | acgatattca | tcatccatgt | agagctaacg | ttgccgtcca | aaaagaattg | 900 |
| cataagccag | aatctgacag | aagttgcatc | catttggaat | tcgatatttt | cgctactggt | 960 |
| ttgacttacg | aaaccggtga | tcatgttggt | gtttacgctg | ataattgtga | tgatactgta | 1020 |
| gaagaagccg | ctaagttgtt | gggtcaacca | ttggatttgt | tgttctccat | tcataccgat | 1080 |
| aacaacgacg | gtacttcttt | gggttcttct | ttgccaccac | catttccagg | tccatgtact | 1140 |
| ttgagaactg | cttttggctag | atatgccgat | ttgttgaatc | caccaaaaaa | ggctgctttg | 1200 |
| attgctttag | ctgctcatgc | tgatgaacca | tctgaagctg | aaagattgaa | gttcttgtca | 1260 |
| tctccacaag | gtaaggacga | atattctaaa | tgggttgtcg | gttcccaaag | atccttggtt | 1320 |
| gaagttatgg | ctgaatttcc | atctgctaaa | ccaccattgg | gtgtattttt | tgctgctgtt | 1380 |
| gttcctagat | tgcaacctag | atattactcc | atctcttcca | gtccaagatt | tgctccacat | 1440 |
| agagttcatg | ttacttgcgc | ttttggttat | ggtccaactc | caactggtag | aattcacaga | 1500 |
| ggtgtatgtt | cattctggat | gaagaatgtt | gtcccattgg | aaaagtctca | aaactgttct | 1560 |
| tgggccccaa | ttttcatcag | acaatctaat | ttcaagttgc | cagccgatca | ttctgttcca | 1620 |
| atagttatgg | ttggtccagg | tactggttta | gctccttta | gaggtttctt | acaagaaaga | 1680 |
| ttggccttga | aagaagaagg | tgctcaagtt | ggtcctgctt | tgttgttttt | tggttgcaga | 1740 |
| aacagacaaa | tggacttcat | ctacgaagtc | gaattgaaca | actttgtcga | acaaggtgct | 1800 |
| ttgtccgaat | tgatcgttgc | tttttcaaga | gaaggtccat | ccaaagaata | cgtccaacat | 1860 |
| aagatggttg | aaaaggcagc | ttacatgtgg | aacttgattt | ctcaaggtgg | ttacttctac | 1920 |
| gtttgtggtg | atgctaaagg | tatggctaga | gatgttcata | gaacattgca | taccatcgtc | 1980 |
| caacaagaag | aaaaggttga | ttctaccaag | gccgaatcca | tcgttaagaa | attgcaaatg | 2040 |
| gacggtagat | acttgagaga | tgtttggtga | | | | 2070 |

SEQ ID NO: 88

| | | | | | |
|---|---|---|---|---|---|
| MSSNSDLVRR | LESVLGVSFG | GSVTDSVVVI | ATTSIALVIG | VLVLLWRRSS | DRSREVKQLA | 60 |
| VPKPVTIVEE | EDEFEVASGK | TRVSIFYGTQ | TGTAEGFAKA | LAEEIKARYE | KAAVKVIDLD | 120 |
| DYTAEDDKYG | EKLKKETMAF | FMLATYGDGE | PTDNAARFYK | WFTEGTDRGV | WLEHLRYGVF | 180 |
| GLGNRQYEHF | NKIAKVVDDL | LVEQGAKRLV | TVGLGDDDQC | IEDDFSAWKE | ALWPELDQLL | 240 |
| QDDTNTVSTP | YTAVIPEYRV | VIHDPSVTSY | EDPYSNMANG | NASYDIHHPC | RANVAVQKEL | 300 |
| HKPESDRSCI | HLEFDIFATG | LTYETGDHVG | VYADNCDDTV | EEAAKLLGQP | LDLLFSIHTD | 360 |
| NNDGTSLGSS | LPPPPFPGPCT | LRTALARYAD | LLNPPKKAAL | IALAAHADEP | SEAERLKFLS | 420 |
| SPQGKDEYSK | WVVGSQRSLV | EVMAEFPSAK | PPLGVFFAAV | VPRLQPRYYS | ISSSPRFAPH | 480 |
| RVHVTCALVY | GPTPTGRIHR | GVCSFWMKNV | VPLEKSQNCS | WAPIFIRQSN | FKLPADHSVP | 540 |
| IVMVGPGTGL | APFRGFLQER | LALKEEGAQV | GPALLFFGCR | NRQMDFIYEV | ELNNFVEQGA | 600 |
| LSELIVAFSR | EGPSKEYVQH | KMVEKAAYMW | NLISQGGYFY | VCGDAKGMAR | DVHRTLHTIV | 660 |
| QQEEKVDSTK | AESIVKKLQM | DGRYLRDVW | | | | 689 |

SEQ ID NO: 89

| | | | | | |
|---|---|---|---|---|---|
| atgacttctg | cactttatgc | ctccgatctt | ttcaaacaat | tgaaagtat | catgggaacg | 60 |
| gattctttgt | ccgatgatgt | tgtattagtt | attgctacaa | cttctctggc | actggttgct | 120 |
| ggtttcgttg | tctattatgtg | gaaaaagacc | acggcagatc | gttccggcga | gctaaagcca | 180 |
| ctaatgatcc | ctaagtctct | gatggcgaaa | gatgaggat | atgacttaga | tctaggttct | 240 |
| ggaaaaacga | gagtctctat | cttcttcggc | acacaaaccg | gaacagccga | aggattcgct | 300 |
| aaagcacttt | cagaaagagt | caaagcaaga | tacgaaaagg | cggctgtaaa | agtaatcgat | 360 |
| ttggatgatt | acgctgccga | tgatgaccaa | tatgaggaaa | agttgaaaaa | ggaaacattg | 420 |
| gcttctttt | gtgtagccac | gtatggtgat | ggtgaaccaa | ccgataacgc | cgcaagattc | 480 |
| tacaagtggt | ttactgaaga | gaacgaaaga | gatatcaagt | gcagcaact | tgcttacggc | 540 |
| gttttgcct | taggtaacag | acaatacgag | cactttaaca | agataggtat | tgtcttagat | 600 |
| gaagagttat | gcaaaaaggg | tgcgaagaga | ttgattgaag | tcggtttagg | agatgatgat | 660 |
| caatctatcg | aggatgactt | taatgcatgg | aaggaatctt | tgtggtctga | attagataag | 720 |
| ttacttaagg | acgaagatga | taaatccgtt | gccactccat | acacagccgt | cattccagaa | 780 |
| tatagagtag | ttactcatga | tccaagattc | acaacacaga | aatcaatgga | aagtaatgtg | 840 |
| gctaatggta | atactaccat | cgatattcat | catccatgta | gagtagacgt | tgcagttcaa | 900 |
| aaggaattgc | acactcatga | atcagacaga | tcttgcatac | atcttgaatt | tgatatatca | 960 |
| cgtactggta | tcacttacga | aacaggtgat | cacgtgggtg | tctacgctga | aaaccatgtt | 1020 |
| gaaattgtag | aggaagctgg | aaagttgttg | ggccatgtt | tagatcttgt | tttctcaatt | 1080 |
| catgccgata | aagaggatgg | ctcaccacta | gaaagtcagc | tgcctccacc | atttccagga | 1140 |
| ccatgcaccc | taggtaccgg | tttagctcgt | tacgcggatc | tgttaaatcc | tccacgtaaa | 1200 |
| tcagctctag | tggccttggc | tgcgtacgcc | acagaacctt | ctgaggcaga | aaaactgaaa | 1260 |
| catctaactt | caccagatgg | taaggatgaa | tactcacaat | ggatagtagc | tagtcaacgt | 1320 |
| tctttactag | aagttatggc | tgcttcccca | tccgctaaac | ctcctttggg | tgttttcttc | 1380 |

TABLE 10-continued

Sequences disclosed herein.

```
gccgcaatag cgcctagact gcaaccaaga tactattcaa tttcatcctc acctagactg   1440
gcaccatcaa gagttcatgt cacatccgct ttagtgtacg gtccaactcc tactggtaga   1500
atccataagg gcgtttgttc aacatggatg aaaaacgcgg ttccagcaga gaagtctcac   1560
gaatgttctg gtgctccaat ctttatcaga gcctccaact tcaaactgcc ttccaatcct   1620
tctactccta ttgtcatggt cggtcctggt acaggtcttg ctccattcag aggtttctta   1680
caagagagaa tggccttaaa ggaggatggt gaagagttgg gatcttcttt gttgttttc    1740
ggctgtagaa acagacaaat ggatttcatc tacgaagatg aactgaataa ctttgtagat   1800
caaggagtta tttcagagtt gataatggct ttttctagaa aaggtgctca gaaggagtac   1860
gtccaacaca aaatgatgga aaaggccgca caagtttggg acttaatcaa agaggaaggc   1920
tatctatatg tctgtggtga tgcaaagggt atggcaagag atgttcacag aacacttcat   1980
actatagtcc aggaacagga aggcgttagt tcttctgaag cggaagcaat tgtgaaaaag   2040
ttacaaacag agggaagata cttgagagat gtgtggtaa                         2079

SEQ ID NO: 90
MTSALYASDL FKQLKSIMGT DSLSDDVVLV IATTSLALVA GFVVLLWKKT TADRSGELKP    60
LMIPKSLMAK DEDDDLDLGS GKTRVSIFFG TQTGTAEGFA KALSEEIKAR YEKAAVKVID   120
LDDYAADDDQ YEEKLKKETL AFFCVATYGD GEPTDNAARF YKWFTEENER DIKLQQLAYG   180
VFALGNRQYE HFNKIGIVLD EELCKKGAKR LIEVGLGDDD QSIEDDFNAW KESLWSELDK   240
LLKDEDDKSV ATPYTAVIPE YRVVTHDPRF TTQKSMESNV ANGNTTIDIH HPCRVDVAVQ   300
KELHTHESDR SCIHLEFDIS RTGITYETGD HVGVYAENHV EIVEEAGKLL GHSLDLVFSI   360
HADKEDGSPL ESAVPPPFPG PCTLGTGLAR YADLLNPPRK SALVALAAYA TEPSEAEKLK   420
HLTSPDGKDE YSQWIVASQR SLLEVMAAFP SAKPPLGVFF AAIAPRLQPR YYSISSSPRL   480
APSRVHVTSA LVYGPTPTGR IHKGVCSTWM KNAVPAEKSH ECSGAPIFIR ASNFKLPSNP   540
STPIVMVGPG TGLAPFRGFL QERMALKEDG EELGSSLLFF GCRNRQMDFI YEDELNNFVD   600
QGVISELIMA FSREGAQKEY VQHKMMEKAA QVWDLIKEEG YLYVCGDAKG MARDVHRTLH   660
TIVQEQEGVS SSEAEAIVKK LQTEGRYLRD VW                                 692

SEQ ID NO: 91
atgtcttcct cttcctcttc cagtacctct atgattgatt tgatggctgc tattattaaa     60
ggtgaaccag ttatcgtctc cgacccagca aatgcctctg cttatgaatc agttgctgca   120
gaattgtctt caatgttgat cgaaaacaga caattcgcca tgatcgtaac tacatcaatc   180
gctgttttga tcggttgtat tgtcatgttg gtatggagaa gatccggtag tggtaattct   240
aaaagagtcg aacctttgaa accattagta attaagccaa gagaagaaga aatagatgac   300
ggtagaaaga aagttacaat attttttcggt acccaaactg gtacagctga aggttttgca   360
aaagcccttag gtgaagaagc taaggcaaga tacgaaaaga ctagattcaa gatagtcgat   420
ttggatgact atgccgctga tgacgatgaa tacgaagaaa agttgaagaa agaagatgtt   480
gcatttttct ttttggcaac ctatggtgac ggtgaaccaa ctgacaatgc agccagattc   540
tacaaatggt ttacagaggg taatgatcgt ggtgaatggt tgaaaaactt aaagtacggt   600
gtttttcggtt tgggtaacag acaatacgaa catttcaaca aagttgcaaa ggttgtcgac   660
gatattttgg tcgaacaagg tgctcaaaga ttagtccaag tggttttggg tgacgatgac   720
caatgtatag aagatgactt tactgcctgg agagaagctt tgtggcctga attagacaca   780
atcttgagag aagaagtgaa caccgccgtt gctacccccat atactgctgc agtattagaa   840
tacagagttt ccatccatga tagtgaagac gcaaagttta atgatatcac tttgccaat    900
ggtaacggtt acagttttt cgatgcacaa caccttaca agctaacgt tgcagtcaag     960
agagaattac ataccagga tccgacaga agttgtatac acttggaatt tgatatcgct   1020
ggttccggtt taaccatgaa gttggtgac catgtaggtg ttatgcga caatttgtct    1080
gaaactgttg atgaagcatt gagattgttg atatgtccc ctgacactta ttttagtttg   1140
cacgctgaaa aagaagatgg tacaccaatt tccagttctt taccacctcc attccctcca   1200
tgtaacttaa gaacagccctt gaccagatac gcttgcttgt tatcatcccc taaaagtcc    1260
gccttggttg ctttagccgc tcatgctagt gatcctactg aagcagaaag attgaaacac   1320
ttagcatctc cagccggtaa agatgaatat tcaaagtggg tagttgaatc tcaaagatca   1380
ttgttagaag ttatggcaga atttccatct gccaagcctc cattaggtgt cttcttttgct   1440
ggtgtagcac ctagattgca accaagatc tactcaatca gttcttcacc taagatcgct   1500
gaaactagaa ttcatgttac atgtgcatta gtctacgaaa agatgccaac cggtagaatt   1560
cacaagggtg tatgctctac ttggatgaaa aatgctgttc cttacgaaaa atcagaaaag   1620
ttgttcttag gtagaccaat cttcgtaaga caatcaaact tcaagttgcc ttctgattca   1680
aaggttccaa taatcatgat aggtcctggt acaggtttga ccccattcag aggtttcttg   1740
caagaaagat tggctttagt tgaatctggt gtcgaattag gtccttcagt tttgttcttt   1800
ggttgtagaa acagaagaat ggatttcatc tatgaagaag aattgcaaag attcgtcgaa   1860
tctggtgcat tggccgaatt atctgtagct ttttcaagag aaggtccaac taaggaatac   1920
gttcaacata agtgatgga taaggcatcc gacatatgga acgatcag tcaaggtgt    1980
tatttgtacg tttgcggtga cgcaaagggt atggccagag atgtccatag atctttgcac   2040
acaattgctc aagaacaagg ttccatggat agtaccaaag ctgaaggttt cgtaaagaac   2100
ttacaaactt ccggtagata cttgagagat gtctggtga                         2139

SEQ ID NO: 92
MSSSSSSSTS MIDLMAAIIK GEPVIVSDPA NASAYESVAA ELSSMLIENR QFAMIVTTSI    60
AVLIGCIVML VWRRSGSGNS KRVEPLKPLV IKPREEEIDD GRKKVTIFFG TQTGTAEGFA   120
KALGEEAKAR YEKTRPFKIVD LDDYAADDDE YEEKLKKEEP AFFFLATYGD GEPTDNAARF   180
YKWFTEGNDR GEWLKNLKYG VFGLGNRQYE HFNKVAKVVD DILVEQGAQR LVQVGLGDDD   240
QCIEDDFTAW REALWPELDT ILREEGDTAV ATPYTAAVLE YRVSIHDSED AKFNDITLAN   300
GNGYTVFDAQ HPYKANVAVK RELHTPESDR SCIHLEFDIA GSGLTMKLGD HVGVLCDNLS   360
ETVDEALRLL DMSPDTYFSL HAEKEDGTPI SSSLPPPFPP CNLRTALTRY ACLLSSPKKS   420
ALVALAAHAS DPTEAERLKH LASPAGKDEY SKWVVESQRS LLEVMAEFPS AKPPLGVFFA   480
GVAPRLQPRF YSISSSPKIA ETRIHVTCAL VYEKMPTGRI HKGVCSTWMK NAVPYEKSEK   540
LFLGRPIFVR QSNFKLPSDS KVPIIMIGPG TGLAPFRGFL QERLALVESG VELGPSVLFF   600
GCRNRRMDFI YEEELQRFVE SGALAELSVA FSREGPTKEY VQHKMMDKAS DIWNMISQGA   660
YLYVCGDAKG MARDVHRSLH TIAQEQGSMD STKAEGFVKN LQTSGRYLRD VW           712
```

TABLE 10-continued

Sequences disclosed herein.

SEQ ID NO: 93
```
atggaagcct cttacctata catttctatt ttgcttttac tggcatcata cctgttcacc      60
actcaactta gaaggaagag cgctaatcta ccaccaaccg tgtttccatc aataccaatc     120
attggacact tatacttact caaaaagcct ctttatagaa ctttagcaaa aattgccgct     180
aagtacggac caatactgca attacaactc ggctacagac gtgttctggt gatttcctca     240
ccatcagcag cagaagagtg cttttaccaat aacgatgtaa tcttcgcaaa tagacctaag    300
acattgtttg gcaaaatagt gggtggaaca tcccttggca gtttatccta cggcgatcaa     360
tggcgtaatc taaggagagt agcttctatc gaaatcctat cagttcatag gttgaacgaa     420
tttcatgata tcagagtgga tgagaacaga ttgttaatta gaaaacttag aagttcatct    480
tctcctgtta ctcttataac agtcttttat gctctaacat tgaacgtcat tatgagaatg    540
atctctggca aaagatattt cgacagtggg gatagagaat tggaggagga aggtaagaga    600
tttcgagaaa tcttagacga aacgttgctt ctagccggtg cttctaatgt tggcgactac    660
ttaccaatat tgaactggtt gggagttaag tctcttgaaa agaaattgat cgctttgcag    720
aaaaagagag atgactttt ccaggtttg attgaacagg ttagaaaatc tcgtggtgct     780
aaagtaggca aaggtagaaa acgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat   960
gtattgaaga aagctcaagc tgaaatcgat agagttatcg gtaataacag attgattgac  1020
gagtcagaca ttggaaatat cccttacatc gggtgtatta tcaatgaaac tctaagactc  1080
tatccagcag ggccattgtt gttcccacat gaaagttctg ccgactcgt tatttccggt   1140
tacaatatac ctagaggtac aatgttaatc gtaaaccaat gggcgattca tcacgatcct  1200
aaagtctggg atgatcctga aaccttttaaa cctgaaaagt ttcaaggatt agaaggaact  1260
agagatggtt tcaaacttat gccattcggt tctgggagaa gaggatgtcc aggtgaaggt  1320
ttggcaataa ggctgttagg gatgacacta ggctcagtga tccaatgttt tgattgggag  1380
agagtaggag atgagatggt tgacatgaca gaaggtttgg gtgtcacact tcctaaggcc  1440
gttccattag ttgccaaatg taagccacgt tccgaaatga ctaatctcct atccgaactt  1500
taa                                                                 1503
```

SEQ ID NO: 94
```
MEASYLYISI LLLLASYLFT TQLRRKSANL PPTVFPSIPI IGHLYLLKKP LYRTLAKIAA      60
KYGPILQLQL GYRRVLVISS PSAAEECFTN NDVIFANRPK TLFGKIVGGT SLGSLSYGDQ    120
WRNLRRVASI EILSVHRLNE FHDIRVDENR LLIRKLRSSS SPVTLITVFY ALTLNVIMRM    180
ISGKRYFDSG DRELEEEGKR FREILDETLL LAGASNVGDY LPILNWLGVK SLEKKLIALQ    240
KKRDDFFQGL IEQVRKSRGA KVGKGRKTMI ELLLSLQESE PEYYTDAMIR SFVLGLLAAG    300
SDTSAGTMEW AMSLLVNHPH VLKKAQAEID RVIGNNRLID ESDIGNIPYI GCIINETLRL    360
YPAGPLLFPH ESSADCVISG YNIPRGTMLI VNQWAIHHDP KVWDDPETFK PERFQGLEGT    420
RDGFKLMPFG SGRRGCPGEG LAIRLLGMTL GSVIQCFDWE RVGDEMVDMT EGLGVTLPKA    480
VPLVAKCKPR SEMTNLLSEL                                                500
```

SEQ ID NO: 95
```
atggaagtaa cagtagctag tagtgtagcc ctgagcctgg tctttattag catagtagta      60
agatgggcat ggagtgtggt gaattgggtg tggtttaagc cgaagaagct ggaaagattt     120
ttgaggagc aaggccttaa aggcaattcc tacaggtttt tatatggaga catgaaggag     180
aactctatcc tgctcaaaca agcaagatcc aaacccatga acctctccac ctcccatgac    240
atagcacctc aagtcacccc tttttgtcgac caaaccgtga agcttacgg taagaactct    300
tttaattggg ttggccccat accaaggtgt aacataatga atccagaaga tttgaaggac   360
gtcttaacaa aaaatgttga cttttgttaag ccaatatcaa acccacttat caagttgtca   420
gctacaggta ttgcaatcta tgaaggtagg aaatggacta aacacagaag gattatcaac    480
ccaacattcc attcggagag gctaaagcgt atgttacctt catttcacca aagttgtaat    540
gagatggtca aggaatggga gagcttggtg tcaaaagagg gttcatcatg tgagttggat    600
gtctggcctt ttcttgaaaa tatgtcggca gatgtgatct cgagaacagc atttggaact    660
agctacaaaa aaggacagaa aatctttgaa ctcttgagag agcaagtaat atatgtaacg    720
aaaggctttc aaagttttta cattccagga tggaggtttc tcccaactaa gatgaacaag    780
aggatgaatg agattaacga agaaataaaa ggattaatca ggggtattat aattgacaga    840
gagcaaatca ttaaggcagg tgaagaaacc aacgatgact tattaggtgc acttatggag    900
tcaaacttga aggacattcg ggaactgggg aaaaacaaca aaaatgttgg gatgagtatt    960
gaagatgtaa ttcaggagtg taagctgttt tactttgctg gcaagaaac cacttcagtg    1020
ttgctggctt ggacaatggt tttacttggt caaaatcaga actggcaaga tcgagcaaga  1080
caagaggttt tgcaagtctt tggaagcagc aagccagatt tgatggtct agctcacctt  1140
aaagtcgtaa ccatgatttt gcttgaagtt cttcgattat acccaccagt cattgaactt  1200
attcgaacca ttcacaagaa aacaacaactt gggaagctcc cactaccaga aggagttgaa  1260
gtccgcttac caacactgct cattcaccat gacaaggaac tgtggggtga tgatgcaaac  1320
cagttcaatc cagagaggtt tcggaagga gtttccaaag caacaaagaa ccgactctca  1380
ttcttcccct tcggagccgg tccacgcatt gcattggac agaacttttc tatgatggaa  1440
gcaaagttgg cctagcatt gatcttgcaa cacttcacct ttgagctttc tccatctcat  1500
gcacatgctc cttcccatcg tataaccctt caaccacagt atggtgttcg tatcatttta  1560
catcgacgtt ag                                                        1572
```

SEQ ID NO: 96
```
atggaagtca ctgtcgcctc ttctgtcgct ttatccttag tcttcatttc cattgtcgtc      60
agatgggctt ggtcgttgt caactgggtt tggttcaaac caagaagtt ggaaagattc     120
ttgagagagc aaggtttgaa gggtaattct tatagtatct tgtacggtga catgaaggaa    180
aattctattt tgttgaagca agccagatcc aaaccaatga acttgtctac ctctcatgat    240
attgctccac aagttactcc attcgtcgat caaactgtta agcctacgg taagaactct    300
ttcaattggg ttggtccaat tcctagagtt aacatcatga acccagaaga tttgaaggat   360
gtcttgacca gaacgttga cttcgttaag ccaatttcca acccattgat taaattgttg    420
gctactggta ttgccatttta cgaaggtgaa aagtggacta agcatagaag aatcatcaac   480
```

TABLE 10-continued

Sequences disclosed herein.

```
cctaccttcc actctgaaag attgaagaga atgttaccat ctttccatca atcctgtaat      540
gaaatggtta aggaatggga atccttgtt tctaaagaag gttcttcttg cgaattggat       600
gtttggccat tcttggaaaa tatgtctgct gatgtcattt ccagaaccgc tttcggtacc      660
tcctacaaga agggtcaaaa gattttcgaa ttgttgagag agcaagttat ttacgttacc      720
aagggtttcc aatccttcta catcccaggt tggagattct tgccaactaa aatgaacaag      780
cgtatgaacg agatcaacga agaaattaaa ggtttgatca gaggtattat tatcgacaga      840
gaacaaatta ttaaagctgg tgaagaaacc aacgatgatt tgttgggtgc tttgatggag      900
tccaacttga aggatattag agaacatggt aagaacaaca agaatgttgg tatgtctatt      960
gaagatgtta ttcaagaatg taagttattc tacttcgctg gtcaagagac cacttctgtt     1020
ttgttagcct ggactatggt cttgttaggt caaaaccaaa attggcaaga tagagctaga     1080
caagaagttt tgcaagtctt cggttcttcc aagccagact tgatggttt ggcccacttg      1140
aaggttgtta ctatgatttt gttagaagtt ttgagattgt acccaccagt cattgagtta     1200
atcagaacca ttcataaaaa gactcaattg ggtaaattat ctttgccaga aggtgttgaa     1260
gtcagattac caaccttgtt gattcaccac gataaggaat tatgggggtga cgacgctaat     1320
caatttaatc cagaaagatt ttccgaaggt gtttccaagg ctaccaaaaa ccgtttgtct     1380
ttcttcccat ttggtgctgg tccacgtatt tgtatcggtc aaaacttttc catgatggaa     1440
gccaagttgg ctttggcttt aatcttgcaa cacttcactt tcgaattgtc tccatcccat     1500
gcccacgctc cttctcatag aatcacttta caaccacaat acggtgtcag aatcatctta     1560
cacagaagat aa                                                         1572

SEQ ID NO: 97
MEVTVASSVA LSLVFISIVV RWAWSVVNWV WFKPKKLERF LREQGLKGNS YRFLYGDMKE       60
NSILLKQARS KPMNLSTSHD IAPQVTPFVD QTVKAYGKNS FNWVGPIPRV NIMNPEDLKD      120
VLTKNVDFVK PISNPLIKLL ATGIAIYEGE KWTKHRRIIN PTFHSERLKR MLPSFHQSCN      180
EMVKEWESLV SKEGSSCELD VWPFLENMSA DVISRTAFGT SYKKGQKIFE LLREQVIYVT      240
KGFQSFYIPG WRFLPTKMNK RMNEINEEIK GLIRGIIIDR EQIIKAGEET NDDLLGALME      300
SNLKDIREHG KNNKNVGMSI EDVIQECKLF YFAGQETTSV LLAWTMVLLG QNQNWQDRAR      360
QEVLQVFGSS KPDFDGLAHL KVVTMILLEV LRLYPPVIEL IRTIHKKTQL GKLSLPEGVE      420
VRLPTLLIHH DKELWGDDAN QFNPERFSEG VSKATKNRLS FPPFGAGPRI CIGQNFSMME      480
AKLALALILQ HFTFELSPSH AHAPSHRITL QPQYGVRIIL HRR                        523

SEQ ID NO: 98
atggaagcat caagggctag ttgtgttgcg ctatgtgttg tttgggtgag catagtaatt       60
acattggcat ggagggtgct gaattgggtg tggttgaggc caagaaaact agaaagatgc      120
ttgagggagc aaggccttac aggcaattct tacaggcttt gtttggagac accaaggat      180
ctctcgaaga tgctggaaca aacacaatcc aaacccatca aactctccac ctccccatgat      240
atagcgccac gagtcaccc atttttccat cgaactgtga actctaatgg caagaattct      300
tttgtttgga tgggccctat accaagagtg cacatcatga atccagaaga tttgaaagat      360
gccttcaaca gacatgatga ttttcataag acagtaaaaa atcctatcat gaagtctcca      420
ccaccgggca ttgtaggcat tgaaggtgag caatgggcca aacacagaaa gattatcaac      480
ccagcattcc atttagagaa gctaaagggt atggtaccaa tattttacca aagttgtagc      540
gagatgatta caaatgggag agctcttgtg tccaaagaga gttcatgtga gttggatgtg      600
tggccttatc ttgaaaattt taccagcgat gtgatttccc gagctgcatt tggaagtagc      660
tatgaagagg gaaggaaaat atttcaacta ctaagagagg agcaaaagt ttattcggta       720
gctctacgaa gtgtttacat tccaggatgg aggtttctac caaccaagca gaacaagaag      780
acgaaggaaa ttcacaatga aattaaaggc ttacttaagg gcattataaa taaagggaa       840
gaggcgatga aggcagggga agccactaaa gatgacttac taggaatact tatggagtcc      900
aacttcaggg aaattcagga acatgggaac aacaaaaatg ctggaatgag tattgaagat      960
gtaattggag agtgtaagtt gttttacttt gctgggcaag agaccacttc ggtgttgctt     1020
gtttggacaa tgattttact aagccaaaat caggattggc aagctcgtgc aagagaagag     1080
gtcttgaaag tctttggaag caacatccca acctatgaag agctaagtca cctaaaagtt     1140
gtgaccatga ttttacttga agttcttcga ttatacccat cagtcgttgc gcttcctcga     1200
accactcaca agaaaacaca gcttggaaaa ttatcattac cagctggagt ggaagtctcc     1260
ttgcccatac tgcttgttca ccatgacaaa gagttgtggg gtgaggatgc aaatgagttc     1320
aagccagaga ggttttcaga gggagtttca aaggcaacaa agaacaaatt tacatactta     1380
cctttcgag ggggtccaag gatttgcatt ggacaaaact tgccatggt ggaagctaaa       1440
ttggccttgg ccctgatttt acaacacttt gcctttgagc tttctccatc ctatgctcat     1500
gctccttctg cagttataac ccttcaacct caatttggtg ctcatatcat tttgcataaa     1560
cgttga                                                                1566

SEQ ID NO: 99
atggaagctt ctagagcatc ttgtgttgct tgtgtgttg tttgggttttc catcgttatt       60
actttggctt ggagagttt gaattgggtc tggttaagac caaaaaagtt ggaaagatgc      120
ttgagagaac aaggtttgac tggtaactct acagattgt gttcggtga taccaaggac       180
ttgtctaaga tgttggaaca aactcaatcc aagcctatca agtgtctac ctctcatgat        240
attgctccaa gagttactcc attcttccat agaactgtta actccaacgg taagaactct      300
tttgtttgga tgggtccaat tccaagagtc catattatga accctgaaga tttgaaggac      360
gctttcaaca gacatgatga tttccataag accgtcaaga cccaattat gaagtctcca        420
ccaccaggta tagttggtat tgaaggtgaa caatgggcca aacatagaaa gattattaac      480
ccagccttcc acttggaaaa gttgaaaggt atggttccaa tcttctacca atcctgctct      540
gaaatgatta caagtgggga atccttggtt tccaaagaat cttcctgtga attggatgtc      600
tggccatatt tggaaaactt cacctccgat gttatttcca gagctgcttt tggttcttct      660
tacgaagag gtagaaagat cttccaatta ttgagagaag agcaaagttg ttactccgtt       720
gctttgat ctgtttacat tccaggttgg agattcttgc caactagca aaacaaaaag         780
accaagaaa tccacaacga aatcaagggt ttgttaaagg gtatcatcaa caagagagaa       840
gaagctatga aggctggtga agctacaaaa gatgatttgt tgggtatctt gatggaatcc      900
aacttcagag aaatccaaga acacggtaac aacaagaatg ccggtatgtc tattgaagat      960
gttatcggtg aatgcaagtt gttctacttt gctggtcaag aaactacctc cgttttgttg     1020
```

TABLE 10-continued

Sequences disclosed herein.

```
gtttggacca tgattttgtt gtcccaaaat caagattggc aagctagagc tagagaagaa    1080
gtcttgaaag ttttcggttc taacatccca acctacgaag aattgtctca cttgaaggtt    1140
gtcactatga tcttgttgga agtattgaga ttatacccat ccgttgttgc attgccaaga    1200
actactcata agaaaactca attgggtaaa ttgtccttgc cagctggtgt tgaagtttct    1260
ttgccaattt tgttagtcca ccacgacaaa gaattgtggg gtgaagatgc taatgaattc    1320
aagccagaaa gattctccga aggtgtttct aaagctacca agaacaagtt cacttacttg    1380
ccatttggtg gtggtccaag aatatgtatt ggtcaaaatt tcgctatggt cgaagctaaa    1440
ttggctttgg ctttgatctt gcaacatttc gctttcgaat tgtcaccatc ttatgctcat    1500
gctccatctg ctgttattac attgcaacca caatttggtg cccatatcat cttgcataag    1560
agataac                                                              1567

SEQ ID NO: 100
MEASRASCVA LCVVWVSIVI TLAWRVLNWV WLRPKKLERC LREQGLTGNS YRLLFGDTKD     60
LSKMLEQTQS KPIKLSTSHD IAPRVTPFFH RTVNSNGKNS FVWMGPIPRV HIMNPEDLKD    120
AFNRHDDFHK TVKNPIMKSP PPGIVGIEGE QWAKHRKIIN PAFHLEKLKG MVPIFYQSCS    180
EMINKWESLV SKESSCELDV WPYLENFTSD VISRAAFGSS YEEGRKIFQL LREEAKVYSV    240
ALRSVYIPGW RFLPTKQNKK TKEIHNEIKG LLKGIINKRE EAMKAGEATK DDLLGILMES    300
NFREIQEHGN NKNAGMSIED VIGECKLFYF AGQETTSVLL VWTMILLSQN QDWQARAREE    360
VLKVFGSNIP TYEELSHLKV VTMILLEVLR LYPSVVALPR TTHKKTQLGK LSLPAGVEVS    420
LPILLVHHDK ELWGEDANEF KPERFSEGVS KATKNKFTYL PFGGGPRICI GQNFAMVEAK    480
LALALILQHF AFELSPSYAH APSAVITLQP QFGAHIILHK R                        521

SEQ ID NO: 101
ASWVAVLSVV WVSMVIAWAW RVLNWVWLRP KKLEKCLREQ GLAGNSYRLL FGDTKDLSKM     60
LEQTQSKPIK LSTSHDIAPH VTPFFHQTVN SYGKNSFVWM GPIPRVHIMN PEDLKDTFNR    120
HDDFHKVVKN PIMKSLPQGI VGIEGEQWAK HRKIINPAFH LEKLKGMVPI FYRSCSEMIN    180
KWESLVSKES SCELDVWPYL ENFTSDVISR AAFGSSYEEG RKIFQLLREE AKIYTVAMRS    240
VYIPGWRFLP TKQNKKAKEI HNEIKGLLKG IINKREEAMK AGEATKDDLL GILMESNFRE    300
IQEHGNNKNA GMSIEDVIGE CKLFYFAGQE TTSVLLVWTM VLLSQNQDWQ ARAREEVLQV    360
FGSNIPTYEE LSQLKVVTMI LLEVLRLYPS VVALPRTTHK KTQLGKLSLP AGVEVSLPIL    420
LVHHDKELWG EDANEFKPER FSEGVSKATK NQFTYFPFGG GPRICIGQNF AMMEAKLALS    480
LILRHFALEL SPLYAHAPSV TITLQPQYGA HIILHKR                             517

SEQ ID NO: 102
MEASRPSCVA LSVVLVSIVI AWAWRVLNWV WLRPNKLERC LREQGLTGNS YRLLFGDTKE     60
ISMMVEQAQS KPIKLSTTHD IAPRVIPFSH QIVYTYGRNS FVWMGPTPRV TIMNPEDLKD    120
AFNKSDEFQR AISNPIVKSI SQGLSSLEGE KWAKHRKIIN PAFHLEKLKG MLPTFYQSCS    180
EMINKWESLV FKEGSREMDV WPYLENLTSD VISRAAFGSS YEEGRKIFQL LREEAKFYTI    240
AARSVYIPGW RFLPTKQNKR MKEIHKEVRG LLKGIINKRE DAIKAGEAAK GNLLGILMES    300
NFREIQEHGN NKNAGMSIED VIGECKLFYF AGQETTSVLL VWTLVLLSQN QDWQARAREE    360
VLQVFGTNIP TYDQLSHLKV VTMILLEVLR LYPAVVELPR TTYKKTQLGK FLLPAGVEVS    420
LHIMLAHHDK ELWGEDAKEF KPERFSEGVS KATKNQFTYF PFGAGPRICI GQNFAMLEAK    480
LALSLILQHF TFELSPSYAH APSVTITLHP QFGAHFILHK R                        521

SEQ ID NO: 103
CVALSVVLVS IVIAWAWRVL NWVWLRPNKL ERCLREQGLT GNSYRLLFGD TKEISMMVEQ     60
AQSKPIKLST THDIAPRVIP FSHQIVYTYG RNSFVWMGPT PRVTIMNPED LKDAFNKSDE    120
FQRAISNPIV KSISQGLSSL EGEKWAKHRK IINPAFHLEK LKGMLPTFYQ SCSEMINKWE    180
SLVFKEGSRE MDVWPYLENL TSDVISRAAF GSSYEEGRKI FQLLREEAKF YTIAARSVYI    240
PGWRFLPTKQ NKRMKEIHKE VRGLLKGIIN KREDAIKAGE AAKGNLLGIL MESNFREIQE    300
HGNNKNAGMS IEDVIGECKL FYFAGQETTS VLLVWTLVLL SQNQDWQARA REEVLQVFGT    360
NIPTYDQLSH LKVVTMILLE VLRLYPAVVE LPRTTYKKTQ LGKFLLPAGV EVSLHIMLAH    420
HDKELWGEDA KEFKPERFSE GVSKATKNQF TYFPFGAGPR ICIGQNFAML EAKLALSLIL    480
QHFTFELSPS YAHAPSVTIT LHPQFGAHFI LHKR                                514

SEQ ID NO: 104
MGPIPRVHIM NPEDLKDTFN RHDDFHKVVK NPIMKSLPQG IVGIEGDQWA KHRKIINPAF     60
HLEKLKGMVP IFYQSCSEMI NIWKSLVSKE SSCELDVWPY LENFTSDVIS RAAFGSSYEE    120
GRKIFQLLRE EAKVYTVAVR SVYIPGWRFL PTKQNKKTKE IHNEIKGLLK GIINKREEAM    180
KAGEATKDDL LGILMESNFR EIQEHGNNKN AGMSIEDVIG ECKLFYFAGQ ETTSVLLVWT    240
MVLLSQNQDW QARAREEVLQ VFGSNIPTYE ELSHLKVVTM ILLEVLRLYP SVVALPRTTH    300
KKTQLGKLSL PAGVEVSLPI LLVHHDKELW GEDANEFKPE RFSEGVSKAT KNQFTYFPFG    360
GGPRICIGQN FAMMEAKLAL SLILQHFTFE LSPQYSHAPS VTITLQPQYG AHLILHKR     418

SEQ ID NO: 105
atgggtttgt tcccattaga ggattcctac gcgctggtct ttgaaggact agcaataaca     60
ctggctttgt actatctact gtctttcatc tacaaaacat ctaaaagac atgtacacct    120
cctaaagcat ctggtgaaat cattccaatt acaggaatca tattgaatct gctatctggc    180
tcaagtggtc tacctattat cttagcactt gcctcttttg cagacagatg tggtcctatt    240
ttcaccatta ggctgggtat taggagagtg ctagtagtaa caaattggga aatcgctaag    300
gagattttca ctacccacga tttgatagtt tctaatagac aaaatactt agccgctaag    360
attcttggtt tcaattatgt ttcattctct ttcgctccat acggcccata ttgggtcgga    420
atcagaaaga ttattgctac aaaactaatg tcttcttcta gacttcagaa gttcaattt    480
gtaagagttt ttgaactaga aaactctatg aaatctatca gagaatcatg gaaggagaaa    540
aaggatgaag agggaaaggt attagttgag atgaaaaagt ggttctggga actgaatatg    600
aacatagtgt taaggacagt tgctggtaaa caatacactg gtacagttga tgatgccgat    660
gcaaagcgta tctccgagtt attcagagaa tggtttcact acactggcag atttgtcgtt    720
ggagacgctt ttccttttct aggttggttg gacctgggcg atacaaaaaa gacaatggaa    780
```

TABLE 10-continued

Sequences disclosed herein.

```
ttagttgcta gtagattgga ctcaatggtc agtaaatggt tagatgagca tcgtaaaaag    840
caagctaacg atgacaaaaa ggaggatatg gatttcatgg atatcatgat ctccatgaca    900
gaagcaaatt caccacttga aggatacggc actgatacta ttatcaagac cacatgtatg    960
actttgattg tttcaggagt tgatacaacc tcaatcgtac ttacttgggc cttatcactt   1020
ttgttaaaca acagagatac tttgaaaaag gcacaagagg aattagatat gtgcgtaggt   1080
aaaggaagac aagtcaacga gtctgatctt gttaacttga tatacttgga agcagtgctt   1140
aaagaggctt taagacttta cccagcagcg ttcttaggcg gaccaagagc attcttggaa   1200
gattgtactg ttgctggtta tagaattcca aagggcacct gcttgttgat taacatgtgg   1260
aaactgcata gagatccaaa catttggagt gatccttgcg aattcaagcc agaaagattt   1320
ttgacaccta atcaaaagga tgttgatgtg atcggtatgg atttcgaatt gataccattt   1380
ggtgccggca gaagatattg tccaggtact agattggctt tacagatgct gcatatcgta   1440
ttagcgacat tgctgcaaaa cttcgaaatg tcaacaccaa acgatgcgcc agtcgatatg   1500
actgcttctg ttggcatgac aaatgccaaa gcatcacctt tagaagtctt gctatcacct   1560
cgtgttaaat ggtcctaa                                                 1578

SEQ ID NO: 106
MGLFPLEDSY ALVFEGLAIT LALYYLLSFI YKTSKKTCTP PKASGEHPIT GHLNLLSGSS    60
GLPHLALASL ADRCGPIFTI RLGIRRVLVV SNWEIAKEIF TTHDLIVSNR PKYLAAKILG   120
FNYVSFSFAP YGPYWVGIRK IIATKLMSSS RLQKLQFVRV FELENSMKSI RESWKEKKDE   180
EGKVLVEMKK WFWELNMNIV LRTVAGKQYT GTVDDADAKR ISELFREWFH YTGRFVVGDA   240
FPPFLGWLDLG GYKKTMELVA SRLDSMVSKW LDEHRKKQAN DDKKEDMDFM DIMISMTEAN   300
SPLEGYGTDT IIKTTCMTLI VSGVDTTSIV LTWALSLLLN NRDTLKKAQE ELDMCVGKGR   360
QVNESDLVNL IYLEAVLKEA LRLYPAAFLG GPRAFLEDCT VAGYRIPKGT CLLINMWKLH   420
RDPNIWSDPC EFKPERFLTP NQKDVDVIGM DFELIPFGAG RRYCPGTRLA LQMLHIVLAT   480
LLQNFEMSTP NDAPVDMTAS VGMTNAKASP LEVLLSPRVK WS                     522

SEQ ID NO: 107
atgatacaag ttttaactcc aattctactc ttcctcatct tcttcgtttt ctggaaagtc    60
tacaaacatc aaaagactaa aatcaatcta ccaccaggtt ccttcggctg gccattttg    120
ggtgaaacct tagccttact tagagcaggc tgggattctg agccagaaag attcgtaaga    180
gagcgtatca aaaagcatgg atctccactt gttttcaaga catcactatt ggagacaga    240
ttcgctgttc tttgcggtcc agctgctaat aagtttttgt tctgcaacga aaacaaatta    300
gtggcatctt ggtggccagt ccctgtaagg aagttgttcg gtaaaagttt actcacaata    360
agaggagatg aagcaaaatg gatgagaaaa atgctattgt cttacttggg tccagatgca    420
tttgccacac attatgccgt tactatggat gttgtaacac gtagacatat tgatgtccat    480
tggaggggca aggaggaagt taatgtattt caaacagtta agttgtacgc attcgaatta    540
gcttgtagat tattcatgaa cctagatgac ccaaaccaca tcgcgaaact cggtagtctt    600
ttcaacattt tcctcaaagg gatcatcgag cttcctatag acgttcctgg aactagattt    660
tactccagta aaaaggccgc agctgccatt agaattgaat tgaaaaagct cattaaagct    720
agaaaactcg aattgaagga gggtaaggcg tcttcttcac aggacttgct ttctcatcta    780
ttaacatcac ctgatgagaa tgggatgttc ttgacagaag aggaaatagt cgataacatt    840
ctactttgt tattcgctgg tcacgatacc tctgcactat caataacact tttgatgaaa    900
accttaggtg aacacagtga tgtgtacgac aaggttttga aggaacaatt agaaatttcc    960
aaaacaaagg aggcttggga atcactaaag tgggaagata tccagaagat gaagtactca   1020
tggtcagtaa tctgtgaagt catgagattg aatcctcctg tcataggac atacagagag   1080
gcgttggttg atatcgacta tgctggttac actatcccaa aaggatggaa gttgcattgg   1140
tcagctgttt ctactcaaag agacgaagcc aatttcgaag atgtaactag attcgatcca   1200
tccagatttg aaggggcagg ccctactcca ttcacatttg tgccttcgg tgggagtcct   1260
agaatgtgtt taggcaaaga gtttgccagg ttagaagtgt tagcatttct ccacaacatt   1320
gttaccaact ttaagtggga tcttctaatc cctgatgaga agatcgaata tgatccaatg   1380
gctactccag ctaagggctt gccaattaga cttcatccac accagtcta a             1431

SEQ ID NO: 108
MIQVLTPILL FLIFFVFWKV YKHQKTKINL PPGSFGWPFL GETLALLRAG WDSEPERFVR    60
ERIKKHGSPL VFKTSLFGDR FAVLCGPAGN KFLFCNENKL VASWWPVPVR KLFGKSLLTI   120
RGDEAKWMRK MLLSYLGPDA FATHYAVTMD VVTRRHIDVH WRGKEEVNVF QTVKLYAFEL   180
ACRLFMNLDD PNHIAKLGSL FNIFLKGIIE LPIDVPGTRF YSSKKAAAAI RIELKKLIKA   240
RKLELKEGKA SSSQDLLSHL LTSPDENGMF LTEEEIVDNI LLLLFAGHDT SALSITLLMK   300
TLGEHSDVYD KVLKEQLEIS KTKEAWESLK WEDIQKMKYS WSVICEVMRL NPPVIGTYRE   360
ALVDIDYAGY TIPKGWKLHW SAVSTQRDEA NFEDVTRFDP SRFEGAGPTP FTFVPFGGGP   420
RMCLGKEFAR LEVLAFLHNI VTNFKWDLLI PDEKIEYDPM ATPAKGLPIR LHPHQV       476

SEQ ID NO: 109
atggagtctt tagtggttca tacagtaaat gctatctggt gtattgtaat cgtcgggatt    60
ttctcagttg gttatcacgt ttacggtaga gctgtggtcg aacaatggga aatgagaaga   120
tcactgaagc tacaaggtgt taaaggccca ccaccatcca tcttcaatgg taacgtctca   180
gaaatgcaac gtatccaatc cgaagctaaa cactgctctg gcgataacat tatctcacat   240
gattattctt cttcattatt cccacacttc gatcactgga gaaaacagta cggcagaatc   300
tacacatact ctactggatt aaagcaacac ttgtacatca atcatccaga aatggtgaag   360
gagctatctc agactaacac attgaacttg gtagaatcaa cccatataac caaaagattg   420
aatcctatct taggtaacgg aatcataacc tctaatggtc ctcattgggc ccatcagcgt   480
agaattatcg cctacgagtt tactcatgat aagatcaagg gtatggttgg tttgatggtt   540
gagtcgctca tgcctatgtt gaataagtgg gaggagatgg taaagagagg cggagaaatg   600
ggatgcgaca taagagttga tgaggacttg agagatgttt cagcagatgt gattgcaaaa   660
gcctgtttcg gatcctcatt ttctaaaggt aaggctattt tctctatgat aagagattg   720
cttacagcta tcacaaagag aagtgttcta ttcagattca acggattcac tgatatggtc   780
tttgggagta aaaagcatgg tgacgttgat atagacgctt tagaaatgga attggaatca   840
tccatttggg aaactgtcaa ggaacgtgaa atagaatgta agatactca caaaaaggat   900
```

TABLE 10-continued

Sequences disclosed herein.

```
ctgatgcaat tgattttgga aggggcaatg cgttcatgtg acggtaacct ttgggataaa    960
tcagcatata gaagatttgt tgtagataat tgtaaatcta tctacttcgc agggcatgat   1020
agtacagctg tctcagtgtc atggtgtttg atgttactgg ccctaaaccc atcatggcaa   1080
gttaagatcc gtgatgaaat tctgtcttct tgcaaaaatg gtattccaga tgccgaaagt   1140
atcccaaacc ttaaaacagt gactatggtt attcaagaga caatgagatt ataccctcca   1200
gcaccaatcg tcgggagaga agcctctaaa gatatcgatt gggcgatct agttgttcct    1260
aaaggcgtct gtatatggac actaatacca gctttacaca gagatcctga gatttgggga   1320
ccagatgcaa acgatttcaa accagaaaga ttttctgaag aatttcaaa ggcttgtaag    1380
tatcctcaaa gttacattcc atttggtctg ggtcctagaa catgcgttgg taaaaacttt   1440
ggcatgatgg aagtaaaggt tcttgtttcc ctgattgtct ccaagttctc tttcactcta   1500
tctcctacct accaacatag tcctagtcac aaacttttag tagaaccaca acatgggggtg  1560
gtaattagag tggtttaa                                                 1578

SEQ ID NO: 110
MESLVVHTVN AIWCIVIVGI FSVGYHVYGR AVVEQWRMRR SLKLQGVKGP PPSIFNGNVS     60
EMQRIQSEAK HCSGDNIISH DYSSSLFPHF DHWRKQYGRI YTYSTGLKQH LYINHPEMVK    120
ELSQTNTLNL GRITHITKRL NPILGNGIIT SNGPHWAHQR RIIAYEFTHD KIKGMVGLMV    180
ESAMPMLNKW EEMVKRGGEM GCDIRVDEDL KDVSADVIAK ACFGSSFSKG KAIFSMIRDL    240
LTAITKRSVL FRFNGFTDMV FGSKKHGDVD IDALEMELES SIWETVKERE IECKDTHKKD    300
LMQLILEGAM RSCDGNLWDK SAYRRFVVDN CKSIYFAGHD STAVSVSWCL MLLALNPSWQ    360
VKIRDEILSS CKNGIPDAES IPNLKTVTMV IQETMRLYPP APIVGREASK DIRLGDLVVP    420
KGVCIWTLIP ALHRDPEIWG PDANDFKPER FSEGISKACK YPQSYIPFGL GPRTCVGKNF    480
GMMEVKVLVS LIVSKFSFTL SPTYQHSPSH KLLVEPQHGV VIRVV                    525

SEQ ID NO: 111
atgtacttcc tactacaata cctcaacatc acaaccgttg gtgtctttgc cacattgttt     60
ctctctattt gtttacttct ctggagaagt agagcgggta acaaaaagat tgccccagaa    120
gctgccgctg catggcctat tatcggccac ctccacttac ttgcaggtgg atcccatcaa    180
ctaccacata ttacattggg taacatggca gataagtacg gtcctgtatt cacaatcaga    240
ataggcttgc atagagctgt agttgtctca tcttgggaaa tggcaaagga atgttcaaca    300
gctaatgatc aagtgtcttc ttcaagacct gaactattag cttctaagtt gttgggttat    360
aactacgcca tgttttggttt tcaccatac ggttcatact ggagagaaat gagaaagatc    420
atctctctcg aattactatc taattccaga ttggaactat tgaaagatgt tagagcctca    480
gaagttgtca catctattaa ggaactatac aaattgtggg cggaaaagaa aatgagtca    540
ggattggttt ctgtcgagat gaaacaatgg ttcgagatt tgactttaaa cgtgatcttg    600
agaatggtgg ctggtaaaag atacttctcc gcgagtgacg cttcagaaaa caaacaggcc   660
cagcgttgta gaagagtctt cagagaattc ttccatctct ccggcttgtt tgtggttgct   720
gatgctatac cttttcttgg atggctcgat tggggaagac acgagaagac cttgaaaaag   780
accgccatag aaatggattc catcgcccag gagtggcttg aggaacatag acgtagaaaa   840
gattctgag atgataattc tacccaagat ttcatgacg ttatgcaatc tgtgctagat    900
ggcaaaaatc taggcggata cgatgctgat acgattaaca aggctacatg cttaactctt   960
atatcaggtg gcagtgatac tactgtagtt tctttgacat gggctcttag tcttgtgtta  1020
aacaatagag atacttgaa aaaggcacag gaagagttag acatccaagt cggtaaggaa   1080
agattggtta acgagcaaga catcagtaag ttagttact tgcaagcaat agtaaaagag   1140
acactcagac tttatccacc aggtcctttg ggtggtttga acaattcac tgaagattgt   1200
acactaggtg gctatcacgt tcaaaagga actagattaa tcatgaactt atccaagatt   1260
caaaaagatc cacgtatttg gtctgatcct actgaattcc aaccagagag attccttacg   1320
actcataaag atgtcgatcc acgtgggaaa cactttgaat tcattccatt cggtgcagga   1380
agacgtgcat gtcctggtat cacattcgga ttacaagtac tacatctaac attggcatct   1440
ttcttgcatg cgtttgaatt ttcaacacca tcaaatgagc aggttaacat gagagaatca   1500
ttaggtctta cgaatatgaa atctaccca ttagaagttt tgatttctcc aagactatcc    1560
cttaattgct tcaaccttat gaaaatttga                                    1590

SEQ ID NO: 112
MYFLLQYLNI TTVGVFATLF LSYCLLLWRS RAGNKKIAPE AAAAWPIIGH LHLLAGGSHQ     60
LPHITLGNMA DKYGPVFTIR IGLHRAVVVS SWEMAKECST ANDQVSSSRP ELLASKLLGY    120
NYAMFGFSPY GSYWREMRKI ISLELLSNSR LELLKDVRAS EVVTSIKELY KLWAEKKNES    180
GLVSVEMKQW FGDLTLNVIL RMVAGKRYFS ASDASENKQA QRCRRVFREF FHLSGLFVVA    240
DAIPFLGWLD WGRHEKTLKK TAIEMDSIAQ EWLEEHRRRK DSGDDNSTQD FMDVMQSVLD    300
GKNLGGYDAD TINKATCLTL ISGGSDTTVV SLTWALSLVL NNRDTLKKAQ EELDIQVGKE    360
RLVNEQDISK LVYLQAIVKE TLRLYPPGPL GGLRQFTEDC TLGGYHVSKG TRLIMNLSKI    420
QKDPRIWSDP TEFQPERFLT THKDVDPRGK HFEFIPFGAG RRACPGITFG LQVLHLTLAS    480
FLHAFEFSTP SNEQVNMRES LGLTNMKSTP LEVLISPRLS SCSLYN                   526

SEQ ID NO: 113
atggaaccta acttttactt gtcattacta ttgttgttcg tgaccttcat ttctttaagt     60
ctgttttca tcttttacaa acaaaagtcc ccattgaatt tgccaccagg aaaatgggt     120
taccctatca taggtgaaag tttagaattc ctatccacag gctggaaggg acatcctgaa    180
aagttcatat ttgataagaat tgcgtaagtac agtagtagtt tattcaagac ttctattgta    240
ggcgaatcca cagttgtttg ctgtggggca gctagtaaca aattccctatt ctctaacgaa    300
aacaaactgg taactgcctg gtggccagat tctgttaaca aaatcttccc aacaacttca    360
ctggattcta atttgaagga ggaatctata aagatgaaa agttgctgcc acagttcttc    420
aaaccagaag cacttcaaag atatcgtcggc gttatggatg taatcgcaca aagacattt    480
gtcactcact gggacaacaa aaatgagatc acagtttatc cacttgctaa agatacact    540
ttcttgcttc cgtgtagact gttcatgtct gttgaggatg aaaatcatgt ggcgaaattc    600
tcagaccct tccaactaat cgctgcaggc atcatttcac ttcctatcga tcttcctggt    660
actccattca acaaggccat aaaggcttca aatttcatta gaaagagct gataaagatt    720
atcaaacaaa gacgtgttga tctggcagag ggtacagcat ctccaaccca ggatatcttg    780
```

TABLE 10-continued

Sequences disclosed herein.

```
tcacatatgc tattaacatc tgatgaaaac ggtaaatcta tgaacgagtt gaacattgcc    840
gacaagattc ttggactatt gataggaggc cacgatacag cttcagtagc ttgcacattt    900
ctagtgaagt acttaggaga attaccacat atctacgata aagtctacca agagcaaatg    960
gaaattgcca agtccaaacc tgctggggaa ttgttgaatt gggatgactt gaaaaagatg   1020
aagtattcat ggaatgtggc atgtgaggta atgagattgt caccaccttt acaaggtggt   1080
tttagagagg ctataactga ctttatgttt aacggtttct ctattccaaa agggtggaag   1140
ttatactggt ccgccaactc tacacacaaa aatgcagaat gtttcccaat gcctgagaaa   1200
ttcgatccta ccagatttga aggtaatggt ccagcgcctt atacatttgt accattcggt   1260
ggaggcccta gaatgtgtcc tggaaaggaa tacgctagat tagaaatcct ggttttcatg   1320
cataatctgg tcaaacgttt taagtgggaa aaggttattc cagacgaaaa gattattgtc   1380
gatccattcc caatcccagc taaagatctt ccaatccgtt tgtatcctca caaagcttaa   1440
```

SEQ ID NO: 114
```
MEPNFYLSLL LLFVTFISLS LFFIFYKQKS PLNLPPGKMG YPIIGESLEF LSTGWKGHPE    60
KFIFDRMRKY SSELFKTSIV GESTVVCCGA ASNKFLFSNE NKLVTAWWPD SVNKIFPTTS   120
LDSNLKEESI KMRKLLPQFF KPEALQRYVG VMDVIAQRHF VTHWDNKNEI TVYPLAKRYT   180
FLLACRLFMS VEDENHVAKF SDPFQLIAAG IISLPIDLPG TPFNKAIKAS NFIRKELIKI   240
IKQRRVDLAE GTASPTQDIL SHMLLTSDEN GKSMNELNIA DKILGLLIGG HDTASVACTF   300
LVKYLGELPH IYDKVYQEQM EIAKSKPAGE LLNWDDLKKM KYSWNVACEV MRLSPPLQGG   360
FREAITDFMF NGFSIPKGWK LYWSANSTHK NAECFPMPEK FDPTRFEGNG PAPYTFVPFG   420
GGPRMCPGKE YARLEILVFM HNLVKRFKWE KVIPDEKIIV DPFPIPAKDL PIRLYPHKA    479
```

SEQ ID NO: 115
```
atggcctctg ttactttggg ttcctggatc gtcgtccacc accataacca tcaccatcca     60
tcatctatcc taactaaatc tcgttcaaga tcctgtccta ttacactaac caaaccaatc    120
tcttttcgtt caaagagaac agtttcctct agtagttcta tcgtgtcctc tagtgtcgtc    180
actaaggaag acaatctgag acagtctgaa ccttcttcct ttgatttcat gtcatatatc    240
attactaagg cagaactagt gaataaggct cttgattcag cagttccatt aagagagcca    300
ttgaaaatcc atgaagcaat gagatactct cttctagctg gcgggaagag agtcagacct    360
gtactctgca tagcagcgtg cgaattagtt ggtggcgagg aatcaaccgc tatgcctgcc    420
gcttgtgctg tagaaatgat tcatacaatg tcactgatac acgatgattt gccatgtatg    480
gataacgatg atctgagaag gggtaagcca actaaccata aggttttcgg cgaagatgtt    540
gccgtcttag ctggtgatgc tttgttatct ttcgcgttcg aacatttggc atccgcaaca    600
tcaagtgatg ttgtgtcacc agtaagagta gttagagcag ttggagaact ggctaaagct    660
attggaactg agggtttagt tgcaggtcaa gtcgtcgata tctcttccga aggtcttgat    720
ttgaatgata taggtcttga acatctcgaa ttcatccatc ttcacaagac agtcgcactt    780
ttagaagcca gtgcggttct cggcgcaatt gttggcggag ggagtgatga cgaaattgag    840
agattgagga agtttgctag atgtataagg ttactgttcc aagtagtaga cgatatacta    900
gatgtgacaa agtcttccaa agagttggga aaaacagctg gtaaagattt gattgccgac    960
aaattgacct accctaagat tatgggggcta gaaaaatcaa gagaatttgc cgagaaactc   1020
aatagagagg cgcgtgatca actgttgggt ttcgattctg ataaagttgc accactctta   1080
gccttagcca actacatcgc ttacagacaa aactaa                              1116
```

SEQ ID NO: 116
```
MASVTLGSWI VVHHNHHHP SSILTKSRSR SCPITLTKPI SFRSKRTVSS SSIVSSSVV     60
TKEDNLRQSE PSSFDFMSYI ITKAELVNKA LDSAVPLREP LKIHEAMRYS LLAGGKRVRP   120
VLCIAACELV GGEESTAMPA ACAVEMIHTM SLIHDDLPCM DNDDLRRGKP TNHKVFGEDV   180
AVLAGDALLS FAFEHLASAT SSDVVSPVRV VRAVGELAIA IGTEGLVAGQ VVDISSEGLD   240
LNDVGLEHLE FIHLHKTAAL LEASAVLGAI VGGGSDDEIE RLRKFARCIG LLFQVVDDIL   300
DVTKSSKELG KTAGKDLIAD KLTYPKIMGL EKSREFAEKL NREARDQLLG FDSDKVAPLL   360
ALANYIAYRQ N                                                        371
```

SEQ ID NO: 117
```
MATLLEHFQA MPFAIPIALA ALSWLFLFYI KVSFFSNKSA QAKLPPVPVV PGLPVIGNLL    60
QLKEKKPYQT FTRWAEEYGP IYSIRTGAST MVVLNTTQVA KEAMVTRYLS ISTRKLSNAL   120
KILTADKCMV AISDYNDFHK MIKRYILSNV LGPSAQKRHR SNRDTLRANV CSRLHSQVKN   180
SPREAVNFRR VFEWELFGIA LKQAFGKDIE KPIYVEELGT TLSRDEIFKV LVLDIMEGAI   240
EVDWRDFFPY LRWIPNTRME TKIQRLYFRR KAVMTALINE QKKRIASGEE INCYIDFLLK   300
EGKTLTMDQI SMLLWETVIE TADTTMVTTE WAMYEVAKDS KRQDRLYQEI QKVCGSEMVT   360
EEYLSQLPYL NAVFHETLRK HSPAALVPLR YAHEDTQLGG YYIPAGTEIA INIYGCNMDK   420
HQWESPEEWK PERFLDPKFD PMDLYKTMAF GAGKRVCAGS LQAMLIACPT IGRLVQEFEW   480
KLRDGEEENV DTVGLTTHKR YPMHAILKPR S                                  511
```

SEQ ID NO: 118
```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARLVPYKA PGISDGYRMG MVLKGSDCLL SKCYHEFGTQ WLPLLETLHQ   240
VPVVPVGLLP PEIPGDEKDE TWVSIKKWLD GKQKGSVVYV ALGSEVLVSQ TEVVELALGL   300
ELSGLPFVWA YRKPKGPAKS DSVELPDGFV ERTRDRGLVW TSWAPQLRIL SHESVCGFLT   360
HCGSGSIVEG LMFGHPLIML PIFGDQPLNA RLLEDKQVGI EIPRNEEDGC LTKESVARSL   420
RSVVVEKEGE IYKANARELS KIYNDTKVEK EYVSQFVDYL EKNARAVAID HES          473
```

SEQ ID NO: 119
```
MATSDSIVDD RKQLHVATFP WLAFGHILPY LQLSKLIAEK GHKVSFLSTT RNIQRLSSHI    60
SPLINVVQLT LPRVQELPED AEATTDVHPE DIPYLKKASD GLQPEVTRFL EQHSPDWIIY   120
DYTHYWLPSI AASLGISRAH FSVTTPWAIA YMGPSADAMI NGSDGRTTVE DLTTPPKWFP   180
FPTKVCWRKH DLARGVPYKA PGISDGYRMG LVLKGSDCLL SKCYHEFGTQ WLPLLETLHQ   240
```

TABLE 10-continued

Sequences disclosed herein.

```
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 120
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLPPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 121
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG HVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 122
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWAAAAALE HKVPCAMMLL GSAHMIASIA DRRLERAETE SPAAAGQGRP    180
AAAPTFEVAR MKLIRTKGSS GMSLAERFSL TLSRSSLVVG RSCVEFEPET VPLLSTLRGK    240
PITFLGLMPP LHEGRREDGE DATVRWLDAQ PAKSVVYYAL GSEVPLGVEK VHELALGLEL    300
AGTRFLWALR KPTGVSDADL LPAGFEERTR GRGVVATRWV PQMSILAHAA VGAFLTHCGW    360
NSTIEGLMFG HPLIMLPIFG DQGPNARLIE AKNAGLQVPR NEEDGCLTKE SVARSLRSVV    420
VEKEGEIYKA NARELSKIYN DTKVEKEYVS QFVDYLEKNA RAVAIDHES                469

SEQ ID NO: 123
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARCVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 124
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWLPSIAAS LGISRAHFSV TTPWAIAYMG PSADAMINGS DGRTTVEDLT    180
TPPKWFPFPT KVCWRKHDLA RLVPYKAPGI SDGYRMGMVL KGSDCLLSKC YHEFGTQWLP    240
LLETLHQPVV VPVGLMPPLH EGRREDGEDA TVRWLDAQPA KSVVYVALGS EVPLGVEKVH    300
ELALGLELAG TRFLWALRKP TGVSDADLLP AGFEERTRGR GVVATRWVPQ MSILAHAAVG    360
AFLTHCGWNS TIEGLMFGHP LIMLPIFGDQ GPNARLIEAK NAGLQVARND GDGSFDREGV    420
AAAIRAVAVE EESSKVFQAK AKKLQEIVAD MACHERYIDG FIQQLRSYKD               470

SEQ ID NO: 125
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWAAAA ALEHKVPCAM MLLGSAHMIA SIADRRLERA ETESPAAAGQ GRPAAAPTFE    180
VARMKLIRTK GSSGMSLAER FSLTLSRSSL VVGRSCVEFE PETVPLLSTL RGKPITFLGL    240
MPPLHEGRRE DGEDATVRWL DAQPAKSVVY VALGSEVPLG VEKVHELALG LELAGTRFLW    300
ALRKPTGVSD ADLLPAGFEE RTRGRGVVAT RWVPQMSILA HAAVGAFLTH CGWNSTIEGL    360
MFGHPLIMLP IFGDQGPNAR LIEAKNAGLQ VARNDGDGSF DREGVAAAIR AVAVEEESSK    420
VFQAKAKKLQ EIVADMACHE RYIDGFIQQL RSYKD                              455

SEQ ID NO: 126
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG MVLKGSDCLL SKCYHEFGTQ WLPLLETLHQ    240
VPVVPVGLLP PEIPGDEKDE TWVSIKKWLD GKQKGSVVYV ALGSEALVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIARNDGDGS FDREGVAAAI    420
RAVAVEEESS KVFQAKAKKL QEIVADMACH ERYIDGFIQQ LRSYKD                   466

SEQ ID NO: 127
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LLRSIETNFL DRFIDLVTKL PDPPTCIISD    120
```

TABLE 10-continued

Sequences disclosed herein.

```
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSSTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                   481

SEQ ID NO: 128
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWAAAA ALEHKVPCAM MLLGSAHMIA SIADRRLERA ETESPAAAGQ GRPAAAPTFE    180
VARMKLIRTK GSSGMSLAER FSLTLSRSSL VVGRSCVEFE PETVPLLSTL RGKPITFLGL    240
LPPEIPGDEK DETWVSIKKW LDGKQKGSVV YVALGSEALV SQTEVVELAL GLELSGLPFV    300
WAYRKPKGPA KSDSVELPDG FVERTRDRGL VWTSWAPQLR ILSHESVCGF LTHCGSGSIV    360
EGLMFGHPLI MLPIFGDQPL NARLLEDKQV GIEIPRNEED GCLTKESVAR SLRSVVVEKE    420
GEIYKANARE LSKIYNDTKV EKEYVSQFVD YLEKNARAVA IDHES                   465

SEQ ID NO: 129
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWLPSIAAS LGISRAHFSV TTPWAIAYMG PSADAMINGS DGRTTVEDLT    180
TPPKWFPFPT KVCWRKHDLA RLVPYKAPGI SDGYRMGMVL KGSDCLLSKC YHEFGTQWLP    240
LLETLHQVPV VPVGLLPPEI PGDEKDETWV SIKKWLDGKQ KGSVVYVALG SEALVSQTEV    300
VELALGLELS GLPFVWAYRK PKGPAKSDSV ELPDGFVERT RDRGLVWTSW APQLRILSHE    360
SVCGFLTHCG SGSIVEGLMF GHPLIMLPIF GDQPLNARLL EDKQVGIEIP RNEEDGCLTK    420
ESVARSLRSV VVEKEGEIYK ANARELSKIY NDTKVEKEYV SQFVDYLEKN ARAVAIDHES    480

SEQ ID NO: 130
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWAAAAALE HKVPCAMMLL GSAHMIASIA DRRLERAETE SPAAAGQGRP    180
AAAPTFEVAR MKLIRTKGSS GMSLAERFSL TLSRSSLVVG RSCVEFEPET VPLLSTLRGK    240
PITFLGLLPP EIPGDEKDET WVSIKKWLDG KQKGSVVYVA LGSEALVSQT EVVELALGLE    300
LSGLPFVWAY RKPKGPAKSD SVELPDGFVE RTRDRGLVWT SWAPQLRILS HESVCGFLTH    360
CGSGSIVEGL MFGHPLIMLP IFGDQPLNAR LLEDKQVGIE IPRNEEDGCL TKESVARSLR    420
SVVVEKEGEI YKANARELSK IYNDTKVEKE YVSQFVDYLE KNARAVAIDH ES            472

SEQ ID NO: 131
MDSGYSSSYA AAAGMHVVIC PWLAFGHLLP CLDLAQRLAS RGHRVSFVST PRNISRLPPV     60
RPALAPLVAF VALPLPRVEG LPDGAESTND VPHDRPDMVE LHRRAFDGLA APFSEFLGTA    120
CADWVIVDVF HHWLPSIAAS LGISRAHFSV TTPWAIAYMG PSADAMINGS DGRTTVEDLT    180
TPPKWFPFPT KVCWRKHDLA RLVPYKAPGI SDGYRMGMVL KGSDCLLSKC YHEFGTQWLP    240
LLETLHQVPV VPVGLLPPEI PGDEKDETWV SIKKWLDGKQ KGSVVYVALG SEALVSQTEV    300
VELALGLELS GLPFVWAYRK PKGPAKSDSV ELPDGFVERT RDRGLVWTSW APQLRILSHE    360
SVCGFLTHCG SGSIVEGLMF GHPLIMLPIF GDQPLNARLL EDKQVGIEIA RNDGDGSFDR    420
EGVAAAIRAV AVEEESSKVF QAKAKKLQEI VADMACHERY IDGFIQQLRS YKD           473

SEQ ID NO: 132
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG MVLKGSDCLL SKCYHEFGTQ WLPLLETLHQ    240
VPVVPVGLMP PLHEGRREDG EDATVRWLDA QPAKSVVYVA LGSEVPLGVE KVHELALGLE    300
LAGTRFLWAL RKPTGVSDAD LLPAGFEERT RGRGVVATRW VPQMSILAHA AVGAFLTHCG    360
WNSTIEGLMF GHPLIMLPIF GDQGPNARLI EAKNAGLQVA RNDGDGSFDR EGVAAAIRAV    420
AVEEESSKVF QAKAKKLQEI VADMACHERY IDGFIQQLRS YKD                     463

SEQ ID NO: 133
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWAAAA ALEHKVPCAM MLLGSAHMIA SIADRRLERA ETESPAAAGQ GRPAAAPTFE    180
VARMKLIRTK GSSGMSLAER FSLTLSRSSL VVGRSCVEFE PETVPLLSTL RGKPITFLGL    240
MPPLHEGRRE DGEDATVRWL DAQPAKSVVY VALGSEVPLG VEKVHELALG LELAGTRFLW    300
ALRKPTGVSD ADLLPAGFEE RTRGRGVVAT RWVPQMSILA HAAVGAFLTH CGWNSTIEGL    360
MFGHPLIMLP IFGDQGPNAR LIEAKNAGLQ VPRNEEDGCL TKESVARSLR SVVVEKEGEI    420
YKANARELSK IYNDTKVEKE YVSQFVDYLE KNARAVAIDH ES                      462

SEQ ID NO: 134
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWAAAA ALEHKVPCAM MLLGSAHMIA SIADRRLERA ETESPAAAGQ GRPAAAPTFE    180
VARMKLIRTK GSSGMSLAER FSLTLSRSSL VVGRSCVEFE PETVPLLSTL RGKPITFLGL    240
LPPEIPGDEK DETWVSIKKW LDGKQKGSVV YVALGSEALV SQTEVVELAL GLELSGLPFV    300
WAYRKPKGPA KSDSVELPDG FVERTRDRGL VWTSWAPQLR ILSHESVCGF LTHCGSGSIV    360
EGLMFGHPLI MLPIFGDQPL NARLLEDKQV GIEIARNDGD GSFDREGVAA AIRAVAVEEE    420
SSKVFQAKAK KLQEIVADMA CHERYIDGFI QQLRSYKD                           458
```

TABLE 10-continued

Sequences disclosed herein.

SEQ ID NO: 135
ggcaagccac gtttggtg                                                       18

SEQ ID NO: 136
ggagctgcat gtgtcagagg                                                     20

SEQ ID NO: 137
cgatgtattt catcactggt tgccatccat cgcggct                                  37

SEQ ID NO: 138
agccgcgatg gatggcaacc agtgatgaaa tacatcg                                  37

SEQ ID NO: 139
ttatgattat actcactact gggctgctgc agccgcattg                               40

SEQ ID NO: 140
agccgcgatg gatggcaacc agtgatgaaa tacatcg                                  37

SEQ ID NO: 141
caaacctatt actttccttg gtttactgcc accggaaata c                             41

SEQ ID NO: 142
gtatttccgg tggcagtaaa ccaaggaaag taataggttt g                             41

SEQ ID NO: 143
ccggtggttc cggtgggact aatgcctcca ttacatga                                 38

SEQ ID NO: 144
tcatgtaatg gaggcattag tcccaccgga accaccgg                                 38

SEQ ID NO: 145
gaacgcaggt ctgcaggttc caagaaatga ggaagatgg                                39

SEQ ID NO: 146
ccatcttcct catttcttgg aacctgcaga cctgcgttc                                39

SEQ ID NO: 147
MDAMATTEKK PHVIFIPFPA LSHIKAMLKL AQLLHHKGLQ ITFVNTDFIH NQFLESSGPH          60
CLDGAPGFRF ETIPDGVSHS PEASIPIRES LLRSIETNFL DRFIDLVTKL PDPPTCIISD         120
GFLSVFTIDA AKKLGIPVMM YWTLAACGFM GFYIHSLIE KGFAPLKDAS YLTNGYLDTV          180
IDWVPGMEGI RLKDFPLDWS TDLNDKVLMF TTEAPQRSHK VSHHIFHTFD ELEPSIIKTL         240
SLRYNHIYTI GPLQLLLDQI PEEKKQTGIT SLHGYSLVKE EPECFQWLQS KEPNSVVYVN         300
FGSTTVMSLE DMTEFGWGLA NSNHYFLWII RSNLVIGENA VLPPELEEHI KKRGFIASWC         360
SQEKVLKHPS VGGFLTHCGW GSTIESLSAG VPMICWPYSW DQLTNCRYIC KEWEVGLEMG         420
TKVKRDEVKR LVQELMGEGG HKMRNKAKDW KEKARIAIAP NGSSSLNIDK MVKEITVLAR         480
N                                                                        481

SEQ ID NO: 148
MDAMATTEKK PHVIFIPFPA TSHIKAMLKL AQLLHHKGLQ ITFVNTDFIH NQFLESSGPH          60
CLDGAPGFRF ETIPDGVSHS PEASIPIRES LLRSIETNFL DRFIDLVTKL PDPPTCIISD         120
GFLSVFTIDA AKKLGIPVMM YWTLAACGFM GFYIHSLIE KGFAPLKDAS YLTNGYLDTV          180
IDWVPGMEGI RLKDFPLDWS TDLNDKVLMF TTEAPQRSHK VSHHIFHTFD ELEPSIIKTL         240
SLRYNHIYTI GPLQLLLDQI PEEKKQTGIT SLHGYSLVKE EPECFQWLQS KEPNSVVYVN         300
FGSTTVMSLE DMTEFGWGLA NSNHYFLWII RSNLVIGENA VLPPELEEHI KKRGFIASWC         360
SQEKVLKHPS VGGFLTHCGW GSTIESLSAG VPMICWPYSW DQLTNCRYIC KEWEVGLEMG         420
TKVKRDEVKR LVQELMGEGG HKMRNKAKDW KEKARIAIAP NGSSSLNIDK MVKEITVLAR         480
N                                                                        481

SEQ ID NO: 149
MDAMATTEKK PHVIFIPFPA VSHIKAMLKL AQLLHHKGLQ ITFVNTDFIH NQFLESSGPH          60
CLDGAPGFRF ETIPDGVSHS PEASIPIRES LLRSIETNFL DRFIDLVTKL PDPPTCIISD         120
GFLSVFTIDA AKKLGIPVMM YWTLAACGFM GFYIHSLIE KGFAPLKDAS YLTNGYLDTV          180
IDWVPGMEGI RLKDFPLDWS TDLNDKVLMF TTEAPQRSHK VSHHIFHTFD ELEPSIIKTL         240
SLRYNHIYTI GPLQLLLDQI PEEKKQTGIT SLHGYSLVKE EPECFQWLQS KEPNSVVYVN         300
FGSTTVMSLE DMTEFGWGLA NSNHYFLWII RSNLVIGENA VLPPELEEHI KKRGFIASWC         360
SQEKVLKHPS VGGFLTHCGW GSTIESLSAG VPMICWPYSW DQLTNCRYIC KEWEVGLEMG         420
TKVKRDEVKR LVQELMGEGG HKMRNKAKDW KEKARIAIAP NGSSSLNIDK MVKEITVLAR         480
N                                                                        481

SEQ ID NO: 150
MDAMATTEKK PHVIFIPFPA QSHIKAMLKL AQLLHHKGLQ ITFVNTDSIH NQFLESSGPH          60
CLDGAPGFRF ETIPDGVSHS PEASIPIRES LLRSIETNFL DRFIDLVTKL PDPPTCIISD         120
GFLSVFTIDA AKKLGIPVMM YWTLAACGFM GFYIHSLIE KGFAPLKDAS YLTNGYLDTV          180
IDWVPGMEGI RLKDFPLDWS TDLNDKVLMF TTEAPQRSHK VSHHIFHTFD ELEPSIIKTL         240

| | |
|---|---:|
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 151
| | |
|---|---:|
| MDAMATTEKK PHVIFIPFPA QSHIKAMLKL AQLLHHKGLQ ITFVNTDHIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 152
| | |
|---|---:|
| MDAMATTEKK PHVIFIPFPA QSHIKAMLKL AQLLHHKGLQ ITFVNTDYIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 153
| | |
|---|---:|
| MDAMATTEKK PHVIFIPFPA QSHIKAMLKL AQLLHHKGLQ ITFVNTDRIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 154
| | |
|---|---:|
| MDAMATTEKK PHVIFIPFPA QSHIKAMLKL AQLLHHKGLQ ITFVNTDQIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 155
| | |
|---|---:|
| MDAMATTEKK PHVIFIPFPA QSHIKAMLKL AQLLHHKGLQ ITFVNTDWIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 156
| | |
|---|---:|
| MDAMATTEKK PHVIFIPFPA QSHIKAMLKL AQLLHHKGLQ ITFVNTDTIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNLVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 157
| | |
|---|---:|
| MDAMATTEKK PHVIFIPFPA QSHIKAMLKL AQLLHHKGLQ ITFVNTDFVH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYHIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |

TABLE 10-continued

Sequences disclosed herein.

```
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 158
MDAMATTEKK PHVIFIPFPA QSHIKAMLKL AQLLHHKGLQ ITFVNTDFIH NQFLESSGPH     60
CLDGAPGFRF ETIPDGVSHS PEAGIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 159
MDAMATTEKK PHVIFIPFPA QSHIKAMLKL AQLLHHKGLQ ITFVNTDFIH NQFLESSGPH     60
CLDGAPGFRF ETIPDGVSHS PEAAIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 160
MDAMATTEKK PHVIFIPFPA QSHIKAMLKL AQLLHHKGLQ ITFVNTDFIH NQFLESSGPH     60
CLDGAPGFRF ETIPDGVSHS PEATIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 161
MDAMATTEKK PHVIFIPFPA QSHIKAMLKL AQLLHHKGLQ ITFVNTDFIH NQFLESSGPH     60
CLDGAPGFRF ETIPDGVSHS PEACIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 162
MDAMATTEKK PHVIFIPFPA QSHIKAMLKL AQLLHHKGLQ ITFVNTDFIH NQFLESSGPH     60
CLDGAPGFRF ETIPDGVSHS PEAPIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 163
MDAMATTEKK PHVIFIPFPA QSHIKAMLKL AQLLHHKGLQ ITFVNTDFIH NQFLESSGPH     60
CLDGAPGFRF ETIPDGVSHS PEANIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 164
MDAMATTEKK PHVIFIPFPA QSHIKAMLKL AQLLHHKGLQ ITFVNTDFIH NQFLESSGPH     60
CLDGAPGFRF ETIPDGVSHS PEAVIPIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
```

TABLE 10-continued

Sequences disclosed herein.

```
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 165
MDAMATTEKK PHVIFIPFPA QSHIKAMLKL AQLLHHKGLQ ITFVNTDFIH NQFLESSGPH     60
CLDGAPGFRF ETIPDGVSHS PEASIRIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 166
MDAMATTEKK PHVIFIPFPA QSHIKAMLKL AQLLHHKGLQ ITFVNTDFIH NQFLESSGPH     60
CLDGAPGFRF ETIPDGVSHS PEASIGIRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 167
MDAMATTEKK PHVIFIPFPA QSHIKAMLKL AQLLHHKGLQ ITFVNTDFIH NQFLESSGPH     60
CLDGAPGFRF ETIPDGVSHS PEASIPHRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 168
MDAMATTEKK PHVIFIPFPA QSHIKAMLKL AQLLHHKGLQ ITFVNTDFIH NQFLESSGPH     60
CLDGAPGFRF ETIPDGVSHS PEASIPPRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 169
MDAMATTEKK PHVIFIPFPA QSHIKAMLKL AQLLHHKGLQ ITFVNTDFIH NQFLESSGPH     60
CLDGAPGFRF ETIPDGVSHS PEASIPMRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 170
MDAMATTEKK PHVIFIPFPA QSHIKAMLKL AQLLHHKGLQ ITFVNTDFIH NQFLESSGPH     60
CLDGAPGFRF ETIPDGVSHS PEASIPYRES LLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 171
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES KLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKKQTGIT SLHGYSLVKE EPECFQWLQS KEPNSVVYYN    300
```

TABLE 10-continued

Sequences disclosed herein.

```
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 172
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES RLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 173
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES TLRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 174
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LFRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 175
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LIRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 176
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LMRSIETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 177
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LLRSKETNFL DRFIDLVTKL PDPPTCIISD    120
GFLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
SQEKVLKHPS VGGFLTHCGW GSTIESLSAG VPMICWPYSW DQLTNCRYIC KEWEVGLEMG    420
TKVKRDEVKR LVQELMGEGG HKMRNKAKDW KEKARIAIAP NGSSSLNIDK MVKEITVLAR    480
N                                                                    481

SEQ ID NO: 178
MDAMATTEKK PHVIFIPFPA QSHIKAMLKL AQLLHHKGLQ ITFVNTDFIH NQFLESSGPH     60
CLDGAPGFRF ETIPDGVSHS PEASIPIRES LLRSIETNFL DRFIDLVTKL PDPPTCIISD    120
GSLSVFTIDA AKKLGIPVMM YWTLAACGFM GFYHIHSLIE KGFAPLKDAS YLTNGYLDTV    180
IDWVPGMEGI RLKDFPLDWS TDLNDKVLMF TTEAPQRSHK VSHHIFHTFD ELEPSIIKTL    240
SLRYNHIYTI GPLQLLLDQI PEEKQTGIT  SLHGYSLVKE EPECFQWLQS KEPNSVVYVN    300
FGSTTVMSLE DMTEFGWGLA NSNHYFLWII RSNLVIGENA VLPPELEEHI KKRGFIASWC    360
```

| | |
|---|---:|
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 179
| | |
|---|---:|
| MDAMATTEKK PHVIFIPFPA QSHIKAMLKL AQLLHHKGLQ ITFVNTDFIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNHYFLWII RSNSVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 180
| | |
|---|---:|
| MDAMATTEKK PHVIFIPFPA QSHIKAMLKL AQLLHHKGLQ ITFVNTDFIH NQFLESSGPH | 60 |
| CLDGAPGFRF ETIPDGVSHS PEASIPIRES LLRSIETNFL DRFIDLVTKL PDPPTCIISD | 120 |
| GFLSVFTIDA AKKLGIPVMM YWTLAACGFM GFYIHSLIE KGFAPLKDAS YLTNGYLDTV | 180 |
| IDWVPGMEGI RLKDFPLDWS TDLNDKVLMF TTEAPQRSHK VSHHIFHTFD ELEPSIIKTL | 240 |
| SLRYNHIYTI GPLQLLLDQI PEEKKQTGIT SLHGYSLVKE EPECFQWLQS KEPNSVVYVN | 300 |
| FGSTTVMSLE DMTEFGWGLA NSNMYFLWII RSNMVIGENA VLPPELEEHI KKRGFIASWC | 360 |
| SQEKVLKHPS VGGFLTHCGW GSTIESLSAG VPMICWPYSW DQLTNCRYIC KEWEVGLEMG | 420 |
| TKVKRDEVKR LVQELMGEGG HKMRNKAKDW KEKARIAIAP NGSSSLNIDK MVKEITVLAR | 480 |
| N | 481 |

SEQ ID NO: 181
| | |
|---|---:|
| MENKTETTVR RRRRIILFPV PFHGHINPIL QLANVLYSKG FSITIFHTNF NKPKTSNYPH | 60 |
| FTFRFILDND PQDERISNLP THGPLAGMRI PIINEHGADE LRRELELLML ASEEDEEVSC | 120 |
| LITDALWYFA QSVADSLNLR RLVLMTSSLF NFHAHVSLPQ FDELGYLDPD DKTRLEEQAS | 180 |
| GFPMLKVKDI KSAYSNWQIL KEILGKMIKQ TKASSGVIWN SFKELEESEL ETVIREIPAP | 240 |
| SFLIPLPKHL TASSSSLLDH DRTVFQWLDQ QPPSSVLYVS FGSTSEVDEK DFLEIARGLV | 300 |
| DSKQSFLWVV RPGFVKGSTW VEPLPDGFLG ERGRIVKWVP QQEVLAHGAI GAFWTHSGWN | 360 |
| STLESVCEGV PMIFSDFGLD QPLNARYMSD VLKVGVYLEN GWERGEIANA IRRVMVDEEG | 420 |
| EYIRQNARVL KQKADVSLMK GGSSYESLES LVSYISSL | 458 |

SEQ ID NO: 182
| | |
|---|---:|
| MENKTETTVR RRRRIILFPV PFQGHWNPIL QLANVLYSKG FSITIFHTNF NKPKTSNYPH | 60 |
| FTFRFILDND PQDERISNLP THGPLAGMRI PIINEHGADE LRRELELLML ASEEDEEVSC | 120 |
| LITDALWYFA QSVADSLNLR RLVLMTSSLF NFHAHVSLPQ FDELGYLDPD DKTRLEEQAS | 180 |
| GFPMLKVKDI KSAYSNWQIL KEILGKMIKQ TKASSGVIWN SFKELEESEL ETVIREIPAP | 240 |
| SFLIPLPKHL TASSSSLLDH DRTVFQWLDQ QPPSSVLYVS FGSTSEVDEK DFLEIARGLV | 300 |
| DSKQSFLWVV RPGFVKGSTW VEPLPDGFLG ERGRIVKWVP QQEVLAHGAI GAFWTHSGWN | 360 |
| STLESVCEGV PMIFSDFGLD QPLNARYMSD VLKVGVYLEN GWERGEIANA IRRVMVDEEG | 420 |
| EYIRQNARVL KQKADVSLMK GGSSYESLES LVSYISSL | 458 |

SEQ ID NO: 183
| | |
|---|---:|
| MENKTETTVR RRRRIILFPV PFQGHINPIL QLANVLYSKG FSITIFHTNF NKPKTSNYPH | 60 |
| FTFRFILDND PQDERISNLP THGPLAGMRI PIINEHGADE LRRELELLML ASEEDEEVSC | 120 |
| LITDALWYFA QSVADSLNLR RLVLMGSSLF NFHAHVSLPQ FDELGYLDPD DKTRLEEQAS | 180 |
| GFPMLKVKDI KSAYSNWQIL KEILGKMIKQ TKASSGVIWN SFKELEESEL ETVIREIPAP | 240 |
| SFLIPLPKHL TASSSSLLDH DRTVFQWLDQ QPPSSVLYVS FGSTSEVDEK DFLEIARGLV | 300 |
| DSKQSFLWVV RPGFVKGSTW VEPLPDGFLG ERGRIVKWVP QQEVLAHGAI GAFWTHSGWN | 360 |
| STLESVCEGV PMIFSDFGLD QPLNARYMSD VLKVGVYLEN GWERGEIANA IRRVMVDEEG | 420 |
| EYIRQNARVL KQKADVSLMK GGSSYESLES LVSYISSL | 458 |

SEQ ID NO: 184
| | |
|---|---:|
| MENKTETTVR RRRRIILFPV PFQGHINPIL QLANVLYSKG FSITIFHTNF NKPKTSNYPH | 60 |
| FTFRFILDND PQDERISNLP THGPLAGMRI PIINEHGADE LRRELELLML ASEEDEEVSC | 120 |
| LITDALWYFA QSVADSLNLR RLVLMTSSLF NFHALVSLPQ FDELGYLDPD DKTRLEEQAS | 180 |
| GFPMLKVKDI KSAYSNWQIL KEILGKMIKQ TKASSGVIWN SFKELEESEL ETVIREIPAP | 240 |
| SFLIPLPKHL TASSSSLLDH DRTVFQWLDQ QPPSSVLYVS FGSTSEVDEK DFLEIARGLV | 300 |
| DSKQSFLWVV RPGFVKGSTW VEPLPDGFLG ERGRIVKWVP QQEVLAHGAI GAFWTHSGWN | 360 |
| STLESVCEGV PMIFSDFGLD QPLNARYMSD VLKVGVYLEN GWERGEIANA IRRVMVDEEG | 420 |
| EYIRQNARVL KQKADVSLMK GGSSYESLES LVSYISSL | 458 |

SEQ ID NO: 185
| | |
|---|---:|
| MENKTETTVR RRRRIILFPV PFQGHINPIL QLANVLYSKG FSITIFHTNF NKPKTSNYPH | 60 |
| FTFRFILDND PQDERISNLP THGPLAGMRI PIINEHGADE LRRELELLML ASEEDEEVSC | 120 |
| LITDALWYFA QSVADSLNLR RLVLMTSSLF NFHAHVSLPQ FDELGYLDPD DKTRLEEQAS | 180 |
| GFPMLKVKDI KSAYSNWQIL KEILGKMIKQ TKASSGVIWN SFKELEESEL ETVIREIPAP | 240 |
| SFLIPLPKHL TASSSSGLDH DRTVFQWLDQ QPPSSVLYVS FGSTSEVDEK DFLEIARGLV | 300 |
| DSKQSFLWVV RPGFVKGSTW VEPLPDGFLG ERGRIVKWVP QQEVLAHGAI GAFWTHSGWN | 360 |
| STLESVCEGV PMIFSDFGLD QPLNARYMSD VLKVGVYLEN GWERGEIANA IRRVMVDEEG | 420 |
| EYIRQNARVL KQKADVSLMK GGSSYESLES LVSYISSL | 458 |

TABLE 10-continued

Sequences disclosed herein.

```
SEQ ID NO: 186
MENKTETTVR RRRRIILFPV PFQGHINPIL QLANVLYSKG FSITIFHTNF NKPKTSNYPH       60
FTFRFILDND PQDERISNLP THGPLAGMRI PIINEHGADE LRRELELLML ASEEDEEVSC      120
LITDALWYFA QSVADSLNLR RLVLMTSSLF NFHAHVSLPQ FDELGYLDPD DKTRLEEQAS      180
GPFMLKVKDI KSAYSNWQIL KEILGKMIKQ TKASSGVIWN SFKELEESEL ETVIREIPAP      240
SFLIPLPKHL TAWSSSLLDH DRTVFQWLDQ QPPSSVLYVS FGSTSEVDEK DFLEIARGLV      300
DSKQSFLWVV RPGFVKGSTW VEPLPDGFLG ERGRIVKWVP QQEVLAHGAI GAFWTHSGWN      360
STLESVCEGV PMIFSDFGLD QPLNARYMSD VLKVGVYLEN GWERGEIANA IRRVMVDEEG      420
EYIRQNARVL KQKADVSLMK GGSSYESLES LVSYISSL                             458

SEQ ID NO: 187
MENKTETTVR RRRRIILFPV PFQGHINPIL QLANVLYSKG FSITIFHTNF NKPKTSNYPH       60
FTFRFILDND PQDERISNLP THGPLAGMRI PIINEHGADE LRRELELLML ASEEDEEVSC      120
LITDALWYFA QSVADSLNLR RLVLMTSSLF NFHAHVSLPQ FDELGYLDPD DKTRLEEQAS      180
GPFMLKVKDI KSAYSNWQIL KEILGKMIKQ TKASSGVIWN SFKELEESEL ETVIREIPAP      240
SFLIPLPKHL TASSSLLDH DRTVFQWLDQ QPPSSVLYVS FGSGSEVDEK DFLEIARGLV       300
DSKQSFLWVV RPGFVKGSTW VEPLPDGFLG ERGRIVKWVP QQEVLAHGAI GAFWTHSGWN      360
STLESVCEGV PMIFSDFGLD QPLNARYMSD VLKVGVYLEN GWERGEIANA IRRVMVDEEG      420
EYIRQNARVL KQKADVSLMK GGSSYESLES LVSYISSL                             458

SEQ ID NO: 188
MENKTETTVR RRRRIILFPV PFQGHINPIL QLANVLYSKG FSITIFHTNF NKPKTSNYPH       60
FTFRFILDND PQDERISNLP THGPLAGMRI PIINEHGADE LRRELELLML ASEEDEEVSC      120
LITDALWYFA QSVADSLNLR RLVLMTSSLF NFHAHVSLPQ FDELGYLDPD DKTRLEEQAS      180
GPFMLKVKDI KSAYSNWQIL KEILGKMIKQ TKASSGVIWN SFKELEESEL ETVIREIPAP      240
SFLIPLPKHL TASSSLLDH DRTVFQWLDQ QPPSSVLYVS FGNTSEVDEK DFLEIARGLV       300
DSKQSFLWVV RPGFVKGSTW VEPLPDGFLG ERGRIVKWVP QQEVLAHGAI GAFWTHSGWN      360
STLESVCEGV PMIFSDFGLD QPLNARYMSD VLKVGVYLEN GWERGEIANA IRRVMVDEEG      420
EYIRQNARVL KQKADVSLMK GGSSYESLES LVSYISSL                             458

SEQ ID NO: 189
MENKTETTVR RRRRIILFPV PFQGHINPIL QLANVLYSKG FSITIFHTNF NKPKTSNYPH       60
FTFRFILDND PQDERISNLP THGPLAGMRI PIINEHGADE LRRELELLML ASEEDEEVSC      120
LITDALWYFA QSVADSLNLR RLVLMTSSLF NFHAHVSLPQ FDELGYLDPD DKTRLEEQAS      180
GPFMLKVKDI KSAYSNWQIL KEILGKMIKQ TKASSGVIWN SFKELEESEL ETVIREIPAP      240
SFLIPLPKHL TASSSLLDH DRTVFQWLDQ QPPSSVLYVS FGSTSEVDEK DFLEIARGLV       300
DSKQSFLWVV RPGFVKGSTW VEPLPDGFLG ERGRIVPWVP QQEVLAHGAI GAFWTHSGWN      360
STLESVCEGV PMIFSDFGLD QPLNARYMSD VLKVGVYLEN GWERGEIANA IRRVMVDEEG      420
EYIRQNARVL KQKADVSLMK GGSSYESLES LVSYISSL                             458

SEQ ID NO: 190
MENKTETTVR RRRRIILFPV PFQGHINPIL QLANVLYSKG FSITIFHTNF NKPKKSNYPH       60
FTFRFILDND PQDERISNLP THGPLAGMRI PIINEHGADE LRRELELLML ASEEDEEVSC      120
LITDALWYFA QSVADSLNLR RLVLMTSSLF NFHAHVSLPQ FDELGYLDPD DKTRLEEQAS      180
GPFMLKVKDI KSAYSNWQIL KEILGKMIKQ TKASSGVIWN SFKELEESEL ETVIREIPAP      240
SFLIPLPKHL TASSSLLDH DRTVFQWLDQ QPPSSVLYVS FGSTSEVDEK DFLEIARGLV       300
DSKQSFLWVV RPGFVKGSTW VEPLPDGFLG ERGRIVKWVP QQEVLAHGAI GAFWTHSGWN      360
STLESVCEGV PMIFSDFGLD QPLNARYMSD VLKVGVYLEN GWERGEIANA IRRVMVDEEG      420
EYIRQNARVL KQKADVSLMK GGSSYESLES LVSYISSL                             458

SEQ ID NO: 191
MATSDSIVDD RKQLHVATFP WLAFGHILPY LQLSKLIAEK GHKVSFLSTT RNIQRLSSHI       60
SPLINVVQLT LPRVQELPED AEATTDVHPE DIPYLKKASD GLQPEVTRFL EQHSPDWIIY      120
DYTHYWLPSI AASLGISRAH FSVTTPWAIA YMGPSADAMI NGSDGRTTVE DLTTPPKWFP      180
FPTKVCWRKH DLARLVPYKA PGISDGYRMG LVEKGSDCLL SKCYHEFGTQ WLPLLETLHQ      240
VPVVPVGLLP PEIPGDEKDE TWVSIKKWLD GKQKGSVVYV ALGSEVLVSQ TEVVELALGL      300
ELSGLPFVWA YRKPKGPAKS DSVELPDGFV ERTRDRGLVW TSWAPQLRIL SHESVCGFLT      360
HCGSGSIVEG LMFGHPLIML PIFGDQPLNA RLLEDKQVGI EIPRNEEDGC LTKESVARSL      420
RSVVVEKEGE IYKANARELS KIYNDTKVEK EYVSQFVDYL EKNARAVAID HES            473

SEQ ID NO: 192
MATSDSIVDD RKQLHVATFP WLAFGHILPY LQLSKLIAEK GHKVSFLSTT RNIQRLSSHI       60
SPLINVVQLT LPRVQELPED AEATTDVHPE DIPYLKKASD GLQPEVTRFL EQHSPDWIIY      120
DYTHYWLPSI AASLGISRAH FSVTTPWAIA YMGPSADAMI NGSDGRTTVE DLTTPPKWFP      180
FPTKVCWRKH DLARLVPYKA PGISDGYRMG LVLKGSDCLL YKCYHEFGTQ WLPLLETLHQ      240
```

TABLE 10-continued

Sequences disclosed herein.

```
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 193
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARHLS KIYNDTKVEK EYVSQFVDYL EKNARAVAID HES           473

SEQ ID NO: 194
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YTGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 195
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG CVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 196
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARSVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 197
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARVVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 198
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSESLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 199
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
```

TABLE 10-continued

Sequences disclosed herein.

```
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 200
MATSDSIVDD RKQLHVATFP WLAFGHILPY LQLSKLIAEK GHKVSFLSTT RNIQRLSSHI     60
SPLINVVQLT LPRVQELPED AEATTDVHPE DIVYLKKASD GLQPEVTRFL EQHSPDWIIY    120
DYTHYWLPSI AASLGISRAH FSVTTPWAIA YGGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 201
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKAID GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 202
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVKTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 203
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVLTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 204
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVMTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 205
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWKIA YMGPSADAMI NGSDGRTTVE DLTTPPKWFP    180
FPTKVCWRKH DLARLVPYKA PGISDGYRMG IVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 206
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARNVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES           473

SEQ ID NO: 207
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
```

TABLE 10-continued

Sequences disclosed herein.

```
FPTKVCWRKH DLARLVPYCA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 208
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG MVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVGKEGE IYKANARELS KIYNDTKVEK EYVSQFVDYL EKNARVVAID HES            473

SEQ ID NO: 209
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG TVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 210
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSENLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 211
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHFPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSESLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 212
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFKDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 213
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFYDQPLNA RLLEDKQVGI EIPRNEEDGC LTKESVARSL    420
RSVVVEKEGE IYKANARELS KIYNDTKVEK EYVSQFVDYL EKNARAVAID HES            473

SEQ ID NO: 214
MATSDSIVDD RKQLHVATFP WLAFGHILPY LQLSKLIAEK GHKVSFLSTT RNIQRLSSHI     60
SPLINVVQLT LPRVQELPED AEATTDVHPE DIPYLKKASD GLQPEVTRFL EQHSPDWIIY    120
DYTHYWLPSI AASLGISRAH FSVTTPWAIA YMGPSADAMI NGSDGRTTVE DLTTPPKWFP    180
FPTKVCWRKH DLARLVPYKA PGISDGYRMG LVLKGSDCLL SKCYHEFGTQ WLPLLETLHQ    240
```

TABLE 10-continued

Sequences disclosed herein.

```
VPVVPVGLLP PEIPGDEKDE TWVSIKKWLD GKQKGSVVYV ALGSEVLVSQ TEVVELALGL    300
ELSGLPFVWA YRKPKGPAKS DSVELPDGFV ERTRDRGLVW TSWAPQLRIL SHESVCGFLT    360
HCGSGSIVEG LMFGHPLIML PIFGDQPLNA RLLEDKQVGI EIPRNEEDGC LTKESVARSL    420
RSVVVEKEGE IYKANARMLS KIYNDTKVEK EYVSQFVDYL EKNARAVAID HES           473

SEQ ID NO: 215
ATCAACGGGUAAAATGGATGCTATGGCTACCACCG

SEQ ID NO: 216
CGTGCGAUTCAGTTTCTGGCCAAAACGGTGATT

SEQ ID NO: 217
MENKTETTVR RRRRIILFPV PFHGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMTSSLF NFHALVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFQWLDQ QPPSSVLYVS FGSTSEVDEK DFLEIARGLV    300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458

SEQ ID NO: 218
MENKTETTVR RRRRIILFPV PFQGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMGSSLF NFHALVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSLLDH DRTVFQWLDQ QPPSSVLYVS FGSTSEVDEK DFLEIARGLV    300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458

SEQ ID NO: 219
MENKTETTVR RRRRIILFPV PFQGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMTSSLF NFHALVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSSGLDH DRTVFQWLDQ QPPSSVLYVS FGSTSEVDEK DFLEIARGLV    300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458

SEQ ID NO: 220
MENKTETTVR RRRRIILFPV PFQGHINPIL QLANVLYSKG FSITIFHTNF NKPKTSNYPH     60
FTFRFILDND PQDERISNLP THGPLAGMRI PIINEHGADE LRRELELLML ASEEDEEVSC    120
LITDALWYFA QSVADSLNLR RLVLMTSSLF NFHALVSLPQ FDELGYLDPD DKTRLEEQAS    180
GFPMLKVKDI KSAYSNWQIL KEILGKMIKQ TKASSGVIWN SFKELEESEL ETVIREIPAP    240
SFLIPLPKHL TASSSLLDH DRTVFQWLDQ QPPSSVLYVS FGNTSEVDEK DFLEIARGLV     300
DSKQSFLWVV RPGFVKGSTW VEPLPDGFLG ERGRIVKWVP QQEVLAHGAI GAFWTHSGWN    360
STLESVCEGV PMIFSDFGLD QPLNARYMSD VLKVGVYLEN GWERGEIANA IRRVMVDEEG    420
EYIRQNARVL KQKADVSLMK GGSSYESLES LVSYISSL                           458
```

SEQUENCE LISTING

The patent contains a lengthy sequence listing. A copy of the sequence listing is available in electronic form from the USPTO web site (https://seqdata.uspto.gov/?pageRequest=docDetail&DocID=US11807888B2). An electronic copy of the sequence listing will also be available from the USPTO upon request and payment of the fee set forth in 37 CFR 1.19(b)(3).

The invention claimed is:
1. A steviol glycoside compound, wherein the compound is a tetra-glycosylated steviol compound 4.26 according to the following structure:
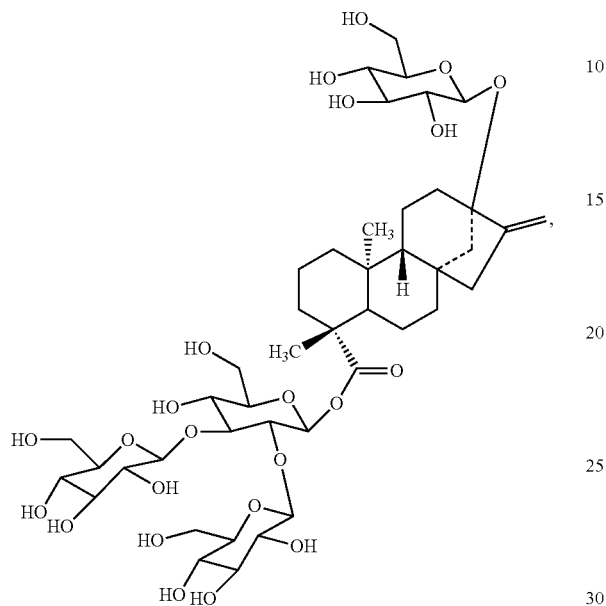
(compound 4.26)
or an isomer thereof.
* * * * *